(12) United States Patent
Lu

(10) Patent No.: US 7,566,803 B2
(45) Date of Patent: Jul. 28, 2009

(54) VITAMIN D RECEPTOR MODULATORS

(75) Inventor: Jianliang Lu, Fishers, IN (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 10/534,920

(22) PCT Filed: Nov. 20, 2003

(86) PCT No.: PCT/US03/35055

§ 371 (c)(1),
(2), (4) Date: May 20, 2008

(87) PCT Pub. No.: WO2004/048309

PCT Pub. Date: Jun. 10, 2004

(65) Prior Publication Data

US 2009/0018058 A1    Jan. 15, 2009

Related U.S. Application Data

(60) Provisional application No. 60/429,041, filed on Nov. 22, 2002.

(51) Int. Cl.
*C07C 229/00* (2006.01)
*A61K 31/59* (2006.01)
*A61K 31/195* (2006.01)

(52) U.S. Cl. ................... 562/441; 560/37; 514/167; 514/171; 514/563

(58) Field of Classification Search ................... None
See application file for complete search history.

(56) References Cited

U.S. PATENT DOCUMENTS

| | | | |
|---|---|---|---|
| 6,218,430 | B1 | 4/2001 | Allegretto |
| 2006/0094778 | A1 | 5/2006 | Nagpal et al. |
| 2006/0135484 | A1 | 6/2006 | Nagpal et al. |
| 2006/0287536 | A1 | 12/2006 | Dahnke et al. |
| 2006/0293385 | A1 | 12/2006 | Gajewski et al. |
| 2007/0105951 | A1 | 5/2007 | Gajewski et al. |
| 2007/0106095 | A1 | 5/2007 | Lu et al. |
| 2007/0149810 | A1 | 6/2007 | Lu et al. |

FOREIGN PATENT DOCUMENTS

| | | |
|---|---|---|
| WO | WO 2005/051893 | 6/2005 |
| WO | WO 2006/069153 | 6/2006 |
| WO | WO 2006/069154 | 6/2006 |

OTHER PUBLICATIONS

Roger Bouillion, et al., Structure-Function Relationships in the Vitamin D Endocrine System, Endocrine Review, Apr. 2005, pp. 200-257, vol. 16, No. 2.

Marcus F. Boehm, et al, Novel nonsecpsteroidal vitamin D mimics exert VDR-modulating activities with less calcium mobilization than 1,25-dihydroxyvitamin $D_3$, Chemistry & Biology, 1999, pp. 265-275, vol. 6, No. 5.

Sunil Nagpal, et al., Vitamin D Analogs: Mechanism of Action and Therapeutic Applications, Current Medicinal Chemistry, 2001, pp. 1661-1679, vol. 8, No. 13.

*Primary Examiner*—Sikarl A Witherspoon
(74) *Attorney, Agent, or Firm*—James B. Myers; MaCharri Vorndran-Jones

(57) ABSTRACT

The present invention relates to novel, non-secosteroidal, diaryl compounds with vitamin D receptor (VDR) modulating activity that are less hypercalcemic than $1\alpha,25$ dihydroxy vitamin D3. These compounds are useful for treating bone disease and psoriasis.

14 Claims, No Drawings

VITAMIN D RECEPTOR MODULATORS

CROSS REFERENCE TO RELATED APPLICATIONS

This patent application claims the benefit of priority under Title 35 United States Code, section 119(e), of Provisional Patent Application No. 60/429,041 filed Nov. 22, 2002, the disclosure of which is incorporated herein by reference and PCT Application Serial No. PCT/US2003/035055, filed Nov. 20, 2003.

BACKGROUND OF THE INVENTION

Vitamin $D_3$ Receptor (VDR) is a ligand dependent transcription factor that belongs to the superfamily of nuclear hormone receptors. The VDR protein is 427 amino acids, with a molecular weight of ~50 kDa. The VDR ligand, $1\alpha,25$-dihydroxyvitamin D3 (the hormonally active form of Vitamin D) has its action mediated by its interaction with the nuclear receptor known as Vitamin D receptor ("VDR"). The VDR ligand, $1\alpha,25$-dihydroxyvitamin D3 ($1\alpha,25(OH)_2D_3$) acts upon a wide variety of tissues and cells both related to and unrelated to calcium and phosphate homeostasis.

The activity $1\alpha,25$-dihydroxyvitamin D3 in various systems suggests wide clinical applications. However, use of conventional VDR ligands is hampered by their associated toxicity, namely hypercalcemia (elevated serum calcium). Currently, $1\alpha,25(OH)_2D_3$, marketed as Rocaltrol® pharmaceutical agent (product of Hoffmann-La Roche), is administered to kidney failure patients undergoing chronic kidney dialysis to treat hypocalcemia and the resultant metabolic bone disease. Other therapeutic agents, such as Calcipotriol® (synthetic analog of $1\alpha,25(OH)_2D_3$) show increased separation of binding affinity on VDR from hypercalcemic activity.

Chemical modifications of $1\alpha,25(OH)_2D_3$ have yielded analogs with attenuated calcium mobilization effects (R. Bouillon et. al., Endocrine Rev. 1995, 16, 200-257). One such analog, Dovonex® pharmaceutical agent (product of Bristol-Meyers Squibb Co.), is currently used in Europe and the United States as a topical treatment for mild to moderate psoriasis (K. Kragballe et. al., Br. J. Dermatol. 1988, 119, 223-230).

Other Vitamin $D_3$ mimics have been described in the publication, *Vitamin D Analogs: Mechanism of Action of Therapeutic Applications*, by Nagpal, S.; Lu, J.; Boehm, M. F., Curr. Med. Chem. 2001, 8, 1661-1679.

Although some degree of separation between the beneficial action and calcium raising (calcemic) effects has been achieved with these VDR ligands, to date the separation has been insufficient to allow for oral administration to treat conditions such as osteoporosis, cancers, leukemias, and severe psoriasis.

One example of a major class of disorder that could benefit from VDR mediated biological efficacy in the absence of hypercalcemia is osteoporosis. Osteoporosis is a systemic disorder characterized by decreased bone mass and microarchitectural deterioration of bone tissue leading to bone fragility and increased susceptibility to fractures of the hip, spine, and wrist (World Health Organization WHO 1994). Osteoporosis affects an estimated 75 million people in the United States, Europe, and Japan.

Within the past few years, several antiresorptive therapies have been introduced. These include bisphosphonates, hormone replacement therapy (HRT), a selective estrogen receptor modulator (SERM), and calcitonins. These treatments reduce bone resorption, bone formation, and increase bone density. However, none of these treatments increase true bone volume nor can they restore lost bone architecture.

Another major disorder that could benefits from VDR mediated biological activity is psoriasis. Psoriasis is one of the most common dermatologic diseases and is a chronic inflammatory skin condition characterized by erythematous, sharply demarcated papules and rounded plaques, covered by silvery micaceous scale.

Synthetic VDR ligands with reduced calcemic potential have been synthesized. For example, a class of bis-phenyl compounds stated to mimic $1\alpha,25$-dihydroxyvitamin $D_3$ is described in U.S. Pat. No. 6,218,430 and the article; "Novel nonsecosteroidal vitamin D mimics exert VDR-modulating activities with less calcium mobilization than $1\alpha,25$-Dihydroxyvitamin $D_3$" by Marcus F. Boehm, et. al., *Chemistry & Biology* 1999, Vol 6, No. 5, pgs. 265-275.

Synthetic VDR ligands having an aryl-thiophene nucleus are described in U.S. provisional patent application Ser. No. 60/384,151, filed 29 May 2002.

There remains a need for improved treatments using alternative or improved pharmaceutical agents that mimic $1\alpha,25$-dihydroxyvitamin $D_3$ to stimulate bone formation, restore bone quality, and treat other diseases without the attendant disadvantage of hypercalcemia.

SUMMARY OF THE INVENTION

Novel compounds having a nucleus of formula "(A)" have been found effective as Vitamin D Receptor (VDR) modulators:

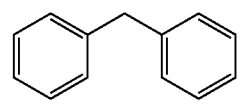

(A)

The compounds of the invention with VDR modulating activities are represented by formula (I)

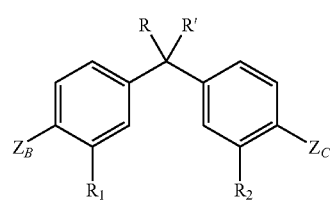

(I)

wherein the variables R, R', $R_1$, $R_2$, $Z_B$, and $Z_C$ are as hereinafter defined. It is a discovery of this invention that compounds described herein display the desirable cell differentiation and antiproliferative effects of $1,25(OH)_2D_3$ with reduced calcium mobilization (calcemic) effects if substituent $Z_C$ possesses a carbon atom linked group that is directly connected (i.e., with no intervening non-carbon atom) to the aryl nucleus.

In another aspect, the present invention is directed towards pharmaceutical compositions containing pharmaceutically effective amounts of compounds of formulae (I) or a pharmaceutically acceptable salt or prodrug thereof, either singly or in combination, together with pharmaceutically acceptable carriers and/or auxiliary agents.

Another aspect of the invention is a pharmaceutical formulation for treatment or prevention of osteoporosis containing pharmaceutically effective amounts of the vitamin D receptor modulator compound of formula (I) alone or together with pharmaceutically effective amounts of co-agents conventionally used for the treatment of osteoporosis.

Another aspect of the invention is a pharmaceutical formulation for treatment or prevention of psoriasis containing pharmaceutically effective amounts of the vitamin D receptor modulator compound of formula (I) alone or together with pharmaceutically effective amounts of co-agents conventionally used for the treatment of psoriasis.

Another aspect of the invention is a pharmaceutical formulation for treatment or prevention of prostate cancer containing pharmaceutically effective amounts of the vitamin D receptor modulator compound of formula (I) alone or together with pharmaceutically effective amounts of co-agents conventionally used for the treatment of prostate cancer.

Another aspect of the invention is to use the compounds of the invention to treat disease states responsive to Vitamin D receptor ligands.

Another aspect of the invention is the prevention and treatment of acne, actinic keratosis, alopecia, Alzheimer's disease, autoimmune induced diabetes, bone fracture healing, breast cancer, Crohn's disease, colon cancer, Type I diabetes, host-graft rejection, hypercalcemia, Type II diabetes, leukemia, multiple sclerosis, insufficient sebum secretion, osteomalacia, insufficient dermal firmness, insufficient dermal hydration, myelodysplastic syndrome, psoriatic arthritis, renal osteodystrophy, rheumatoid arthritis, scleroderma, seborrheic dermatitis, skin cancer, systemic lupus erythematosis, ulcerative colitis and wrinkles; by administering to a mammal in need thereof a pharmaceutically effective amount of a compound of Formula I.

DETAILED DESCRIPTION OF THE INVENTION

Definitions:

The term, "abscess" refers to adverse complications often associated with surgery, trama, or diseases that predispose the host to abscess formation from encapsulated bacteria lymphocytes, macrophages, and etc.

The term, "adhesion" refers to the adverse and abnormal union of surfaces normally separate by the formation of new fibrous tissue resulting from an inflammatory process.

The term, "Mustard" is inclusive of both sulfur mustards and nitrogen mustards, either alone or in any combination. Exemplary of such compounds are the vesicants; bis(2-chloroethyl) sulfide (Chemical Agent Symbol HD), $Cl(CH_2)_2S(CH_2)_2Cl$ 1,2-bis(2-chloroethylthio)ethane (Chemical Agent Symbol Q), $Cl(CH_2)_2S(CH_2)_2S(CH_2)_2Cl$; bis(2-chloroethylthioethyl)ether, $Cl(CH_2)_2S(CH_2)_2O(CH_2)_2S(CH_2)_2Cl$ (Chemical Agent Symbol T); tris(2-chloroethyl)amine (Chemical Agent Symbol HN3) $N(CH_2CH_2Cl)_3$; N-methyl-2,2'-dichlorodiethylamine (Chemical Agent Symbol NH2); and 2,2'-dichlorotriethylamine, $CH_3CH_2N(CH_2CH_2Cl)_2$ (Chemical Agent Symbol NH1).

The term "branched $C_3$-$C_5$ alkyl" is an alkyl group selected from 1-methylethyl; 1-methylpropyl; 2-methylpropyl; 1,1-dimethylethyl; 1,1-dimethylpropyl; 1,2-dimethylpropyl; or 2,2-dimethylpropyl. Preferred branched $C_3$-$C_5$ alkyl groups are 2-methylpropyl and 1,1-dimethylethyl, with the 1,1-dimethylethyl group being most preferred.

The term "branched alkyl terminal group" is used to identify the substituent $Z_B$ of Formula I of the Invention. The defining characteristic of the branched alkyl terminal group is that it is placed on the diphenyl nucleus other than on the phenyl ring bearing the substituent $Z_C$ as shown, for example, in the structural formula (B);

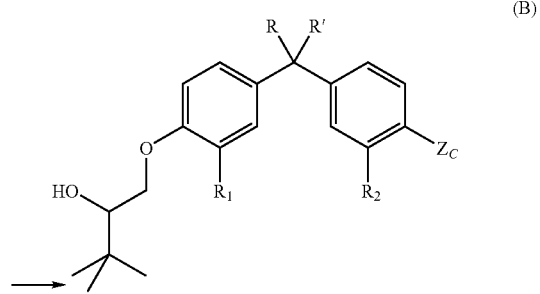

(B)

The term, "carbon atom linked group" is used to identify the chemical substituent $Z_C$ in the Formula I definition of compounds of the invention. Its defining characteristic is a carbon atom as the first atom and point of attachment to the aryl ring to which it is attached. For example in the structural formula (C):

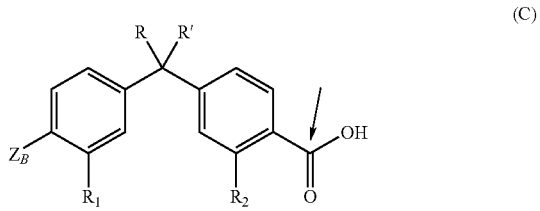

(C)

the arrow identifies the carbon atom linked directly to the aryl nucleus of formula (I). All compounds of the invention contain a carbon atom linked group as the $Z_C$ substituent.

The term "alkenyl" refers to aliphatic groups wherein the point of attachment is a carbon-carbon double bond, for example vinyl, 1-propenyl, and 1-cyclohexenyl. Alkenyl groups may be straight-chain, branched-chain, cyclic, or combinations thereof, and may be optionally substituted. Suitable alkenyl groups have from 2 to about 20 carbon atoms.

The term "$C_1$-$C_5$ alkyl" refers to saturated aliphatic groups including straight-chain, branched-chain, and cyclic groups and any combinations thereof. Alkyl groups may further be divided into "primary", "secondary", and "tertiary" alkyl groups. In primary alkyl groups, the carbon atom of attachment is substituted with zero (methyl) or one organic radical. In secondary alkyl groups, the carbon atom of attachment is substituted with two organic radicals. In tertiary alkyl groups, the carbon atom of attachment is substituted with three organic radicals. Examples of $C_1$-$C_5$ alkyl groups are methyl, ethyl, n-propyl, 1-methylethyl; n-butyl, 1-methylpropyl; 2-methylpropyl; 1,1-dimethylethyl; n-amyl, 1,1-dimethylpropyl; 1,2-dimethylpropyl; and 2,2-dimethylpropyl.

The term, "bond" when used to describe a divalent linking group indicates the absence of a divalent atom, for example in the group

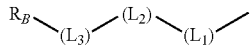

when $L_1$ is —O—, $L_2$ is a bond, $L_3$ is —CH$_2$—, and $R_B$ is tBu the structural formula is

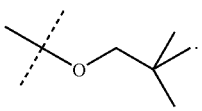

The term "cycloalkyl" includes organic radicals such as cyclopropyl, cyclobutyl, cyclopentyl and cyclohexyl.

The term, "cycloalkenyl" includes organic radicals such as cyclopropenyl, cyclobutenyl, cyclopentenyl and cyclohexenyl.

The term, "$C_1$-$C_5$ fluoroalkyl" is an alkyl group containing fluorine and includes organic radicals such as —CF$_3$, —CHF$_2$, —CH$_2$F, —CF$_2$CF$_3$, —CHFCF$_3$, —CH$_2$CF$_3$, —CH$_2$CHF$_2$, and —CH$_2$CH$_2$F, with —CF$_3$ being preferred.

The abbreviation, "Me" means methyl.
The abbreviation, "Et" means ethyl.
The abbreviation, "iPr" means 1-methylethyl.
The abbreviation, "tBu" means 1,1-dimethylethyl.
The abbreviation, "3Me3OH44DiMe-Pentyl" means 3-methyl-3-hydroxy-4,4-dimethylpentyl.
The abbreviation, "3Me3OH44DiMe-Pentenyl" means 3-methyl-3-hydroxy-4,4-dimethylpentenyl.
The abbreviation, "3Me3OH44DiMe-Pentynyl" means 3-methyl-3-hydroxy-4,4-dimethylpentynyl.
The abbreviation, "3Et3OH44DiMe-Pentyl" means 3-ethyl-3-hydroxy-4,4-dimethylpentyl.
The abbreviation, "3Et3OH44DiMe-Pentenyl" means 3-ethyl-3-hydroxy-4,4-dimethylpentenyl.
The abbreviation, "3Et3OH44DiMe-Pentynyl" means 3-ethyl-3-hydroxy-4,4-dimethylpentynyl.

The term, "—CH$_2$—C(O)—N-pyrrolidine" refers to the radical represented by the structural formula:

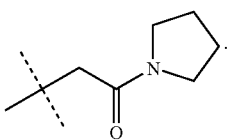

The term, "—CH$_2$—N-pyrrolidin-2-one" refers to the radical represented by the structural formula:

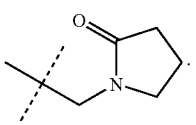

The term, "—CH$_2$-(1-methylpyrrolidin-2-one-3-yl)" refers to the organic radical represented by the structural formula:

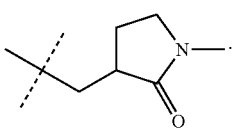

The term, "1,3,4-oxadiazolin-2-one-5-yl" refers to the organic radical represented by the structural formula:

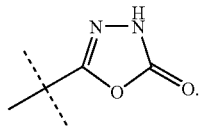

The term, "1,3,4-oxadiazolin-2-thione-5-yl" refers to the organic radical represented by the structural formula:

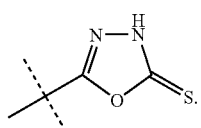

The term, "imidazolidine-2,4-dione-5-yl" refers to the organic radical represented by the structural formula:

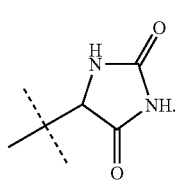

The term, "isoxazol-3-ol-5-yl" refers to the organic radical represented by the structural formula:

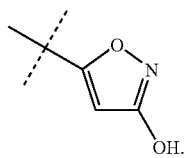

The term, "3-methyl-3-hydroxy-4,4-dimethylpentyl" refers to the radical having the structural formula:

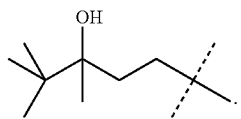

The term, "3-methyl-3-hydroxy-4,4-dimethylpentenyl." refers to the radical having the structural formula (both cis and trans isomers):

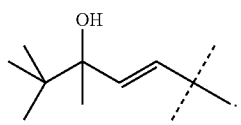

The term, "3-methyl-3-hydroxy-4,4-dimethylpentyl" refers to the radical having the structural formula:

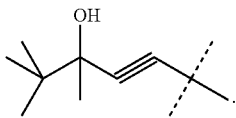

The term, "3-ethyl-3-hydroxy-4,4-dimethylpentynyl" refers to the radical having the structural formula:

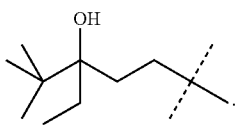

The term, "3-ethyl-3-hydroxy-4,4-dimethylpentenyl" refers to the radical having the structural formula (both cis and trans isomers):

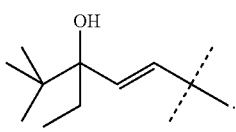

The term, "3-ethyl-3-hydroxy-4,4-dimethylpentynyl" refers to the radical having the structural formula:

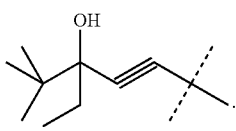

The term, "-5-ethylidene-1,3-thiazolidine-2,4-dione, refers to the radical represented by the structural formula:

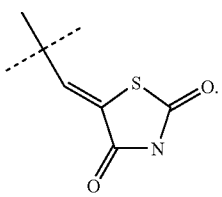

The dotted line symbol crossing a solid line representing a bond

means that the bond so marked is the bond of attachment.

The structural formula representing the compounds of the invention with or without open display of all pendant hydrogen atoms are equivalent, for example:

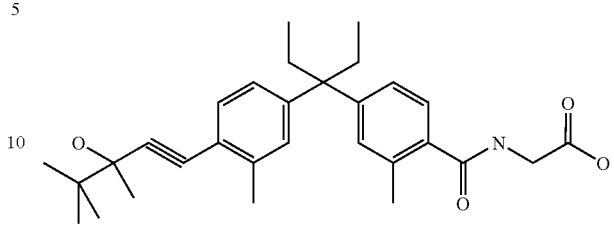

is the same compound as

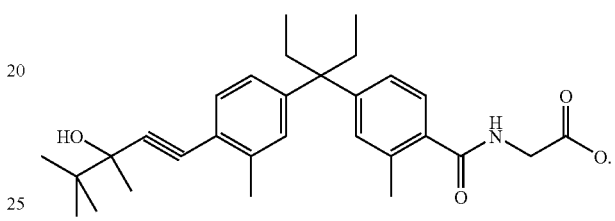

The term, "mammal" includes humans.

The term "ester" refers to compounds of the general formula; RO—C(O)R', prepared for example, where a hydroxy group of an acid is replaced with an alkoxide group. For example, a carboxylic ester is one in which the hydroxy group of a carboxylic acid is replaced with an alkoxide. Esters may derive from any acid comprising one or more hydroxy groups: for example, carbonic acid, carbamic acids, phosphonic acids, and sulfonic acids.

The term "halo" refer to fluorine, chlorine, bromine, and iodine.

The term, "$C_1$-$C_5$ fluoroalkyl" is an alkyl group containing fluorine and includes organic radicals such as —$CF_3$, —$CHF_2$, —$CH_2F$, —$CF_2CF_3$, —$CHFCF_3$, —$CH_2CF_3$, —$CH_2CHF_2$, and —$CH_2CH_2F$, with —$CF_3$ being preferred.

The term, "(Acidic Group)" means a carbon atom linked organic group that acts as a proton donor capable of hydrogen bonding. Illustrative of an (Acidic Group) is a group selected from the following:

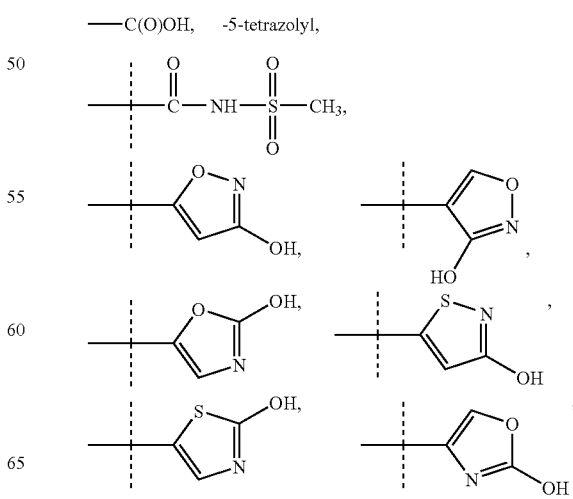

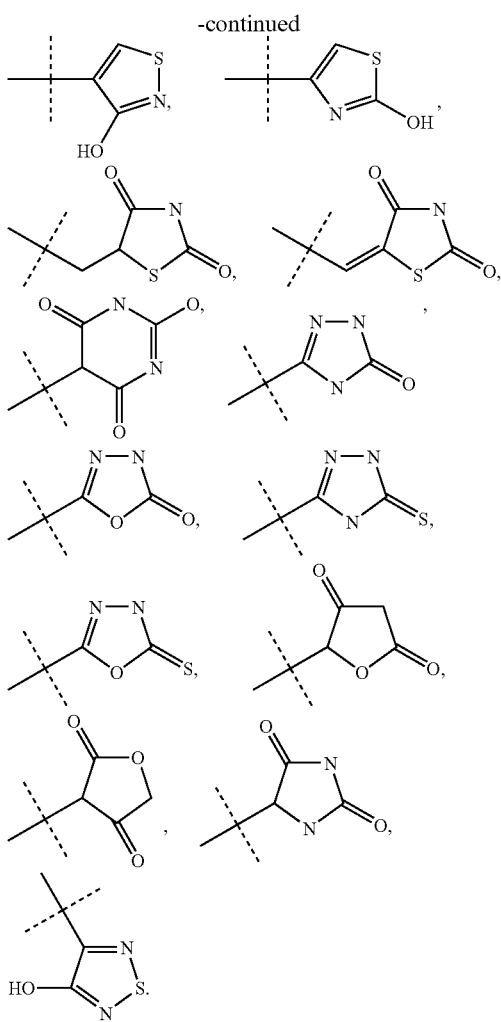

Compounds of the Invention:

The compounds of the invention with vitamin receptor modulating (VDRM) activities are represented by formula (I) or a pharmaceutically acceptable salt or a prodrug derivative thereof:

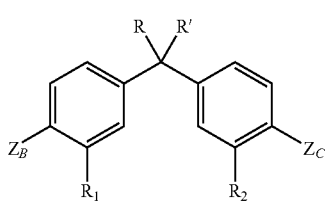

wherein;

R and R' are independently $C_1$-$C_5$ alkyl, $C_1$-$C_5$ fluoroalkyl, or together R and R' form a substituted or unsubstituted, saturated or unsaturated carbocyclic ring having from 3 to 8 carbon atoms;

$R_1$ and $R_2$ are independently selected from the group consisting of hydrogen, halo, $C_1$-$C_5$ alkyl, $C_1$-$C_5$ fluoroalkyl, —O—$C_1$-$C_5$ alkyl, —S—$C_1$-$C_5$ alkyl, —O—$C_1$-$C_5$ fluoroalkyl, —CN, —NO$_2$, acetyl, —S—$C_1$-$C_5$ fluoroalkyl, $C_2$-$C_5$ alkenyl, $C_3$-$C_5$ cycloalkyl, and $C_3$-$C_5$ cycloalkenyl;

$Z_B$ is a group represented by the formula:

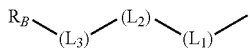

wherein

-($L_1$)-, -($L_2$)-, and -($L_3$)- is each a divalent linking groups independently selected from the group consisting of

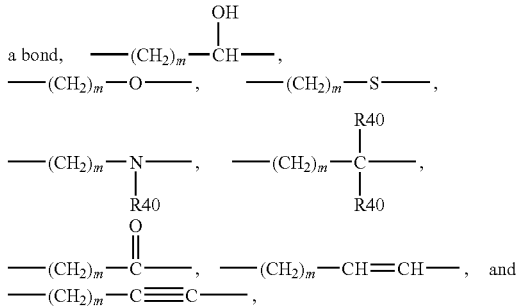

where m is 0, 1, or 2, and each R40 is independently hydrogen, $C_1$-$C_5$ alkyl, or $C_1$-$C_5$ fluoroalkyl;

$R_B$ is a branched $C_3$-$C_5$ alkyl;

$Z_C$ is a carbon atom linked group selected from

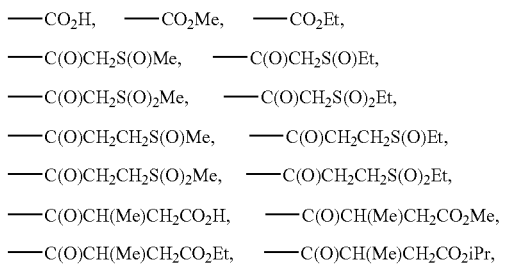

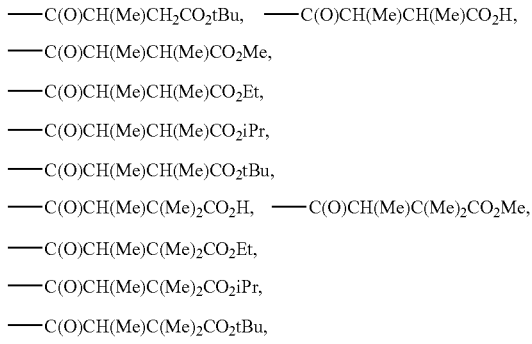

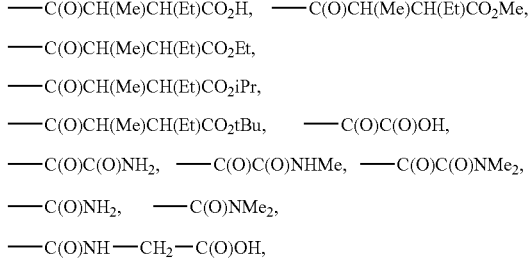

-continued

—C(O)NH—CH₂—C(O)OMe,
—C(O)NH—CH₂—C(O)OEt,
—C(O)NH—CH₂—C(O)OiPr,
—C(O)NH—CH₂—C(O)OtBu,
—C(O)NH—CH(Me)—C(O)OH,
—C(O)NH—CH(Me)—C(O)OMe,
—C(O)NH—CH(Me)—C(O)OEt,
—C(O)NH—CH(Me)—C(O)iPr,
—C(O)NH—CH(Me)—C(O)tBu,
—C(O)NH—CH(Et)—C(O)OH,
—C(O)NH—C(Me)₂—C(O)OH,
—C(O)NH—C(Me)₂—C(O)OMe,
—C(O)NH—C(Me)₂—C(O)OEt,
—C(O)NH—C(Me)₂—C(O)iPr,
—C(O)NH—C(Me)₂—C(O)tBu,
—C(O)NH—C(Me)(Et)—C(O)OH,
—C(O)NH—CH(F)—C(O)OH,
—C(O)NH—CH(CF₃)—C(O)OH,
—C(O)NH—CH(OH)—C(O)OH,
—C(O)NH—CH(cyclopropyl)-C(O)OH,
—C(O)NH—C(Me)₂—C(O)OH,
—C(O)NH—C(Me)₂—C(O)OH,
—C(O)NH—CF(Me)—C(O)OH,
—C(O)NH—C(Me)(CF₃)—C(O)OH,
—C(O)NH—C(Me)(OH)—C(O)OH,
—C(O)NH—C(Me)(cyclopropyl)CO₂H
—C(O)NMe—CH₂—C(O)OH,
—C(O)NMe—CH₂—C(O)OMe,
—C(O)NMe—CH₂—C(O)OEt,
—C(O)NMe—CH₂—C(O)OiPr,
—C(O)NMe—CH₂—C(O)tBu,
—C(O)NMe—CH₂—C(O)OH,
—C(O)NMe—CH(Me)—C(O)OH,
—C(O)NMe—CH(F)—C(O)OH,
—C(O)NMe—CH(CF₃)—C(O)OH,
—C(O)NMe—CH(OH)—C(O)OH,
—C(O)NMe—CH(cyclopropyl)-C(O)OH,
—C(O)NMe—C(Me)₂—C(O)OH,
—C(O)NMe—CF(Me)—C(O)OH,
—C(O)NMe—C(Me)(CF₃)—C(O)OH,
—C(O)NMe—C(Me)(OH)—C(O)OH,
—C(O)NMe—C(Me)(cyclopropyl)-C(O)OH,
—C(O)NHS(O)Me,
—C(O)NHSO₂Me,      —C(O)—NH-5-tetrazolyl,
—C(O)NHS(O)Me,     —C(O)NHS(O)Et,
—C(O)NHSO₂Me,      —C(O)NHSO₂Et,
—C(O)NHS(O)iPr,    —C(O)NHSO₂iPr,
—C(O)NHS(O)tBu,    —C(O)NHSO₂tBu,
—C(O)NHCH₂S(O)Me,  —C(O)NHCH₂S(O)Et,
—C(O)NHCH₂SO₂Me,   —C(O)NHCH₂SO₂Et,
—C(O)NHCH₂CH₂S(O)Me,  —C(O)NHCH₂CH₂S(O)Et,
—C(O)NHCH₂CH₂SO₂Me,   —C(O)NHCH₂CH₂SO₂Et,
—C(O)N(Me)S(O)Me,  —C(O)N(Me)SO₂Me,
—C(O)—N(Me)-5-tetrazolyl,  —C(O)N(Me)S(O)Me,
—C(O)N(Me)S(O)Et,  —C(O)N(Me)SO₂Me,
—C(O)N(Me)SO₂Et,   —C(O)N(Me)S(O)iPr,
—C(O)N(Me))SO₂iPr, —C(O)N(Me)S(O)tBu,
—C(O)N(Me)SO₂tBu,  —C(O)N(Me)CH₂S(O)Me,
—C(O)N(Me)CH₂S(O)Et,  —C(O)N(Me)CH₂SO₂Me,
—C(O)N(Me)CH₂SO₂Et,
—C(O)N(Me)CH₂CH₂S(O)Me,
—C(O)N(Me)CH₂CH₂S(O)Et,
—C(O)N(Me)CH₂CH₂SO₂Me,
—C(O)N(Me)CH₂CH₂SO₂Et,
—CH₂CO₂H,          —CH₂-5-tetrazolyl,
—CH₂CO₂Me,         —CH₂CO₂Et,
—CH₂NHS(O)Me,      —CH₂NHS(O)Et,
—CH₂NHSO₂Me,       —CH₂NHSO₂Et,
—CH₂NHS(O)iPr,     —CH₂NHSO₂iPr,
—CH₂NHS(O)tBu,     —CH₂NHSO₂tBu,
—CH₂NHCH₂CH₂SO₂CH₃,
—CH₂NH(CH₂CO₂H),
—CH₂N(C(O)Me)(CH₂CO₂H),
—CH₂—N-pyrrolidin-2-one,
—CH₂-(1-methylpyrrolidin-2-one-3-yl),
—CH₂S(O)Me,        —CH₂S(O)Et,
—CH₂S(O)₂Me,       —CH₂S(O)₂Et,
—CH₂S(O)iPr,       —CH₂S(O)₂iPr,
—CH₂S(O)tBu,       —CH₂S(O)₂tBu,
—CH₂CO₂H,   CH₂C(O)NH₂,
—CH₂C(O)NMe₂,      —CH₂C(O)NHMe₂,
—CH₂C(O)—N-pyrrolidine,
—CH₂S(O)₂Me,  CH₂S(O)Me,  —CH(OH)CO₂H,
—CH(OH)C(O)NH₂,    —CH(OH)C(O)NHMe,
—CH(OH)C(O)NMe₂,   —CH(OH)C(O)NEt₂,
—CH₂CH₂CO₂H,       —CH₂CH₂CO₂Me, -continued —CH₂CH₂CO₂Et, —CH₂CH₂C(O)NH₂,
—CH₂CH₂C(O)NHMe, —CH₂CH₂C(O)NMe₂,
—CH₂CH₂-5-tetrazolyl, —CH₂CH₂S(O)₂Me,
—CH₂CH₂S(O)Me, —CH₂CH₂S(O)₂Et,
—CH₂CH₂S(O)Et, —CH₂CH₂S(O)iPr,
—CH₂CH₂S(O)₂iPr, —CH₂CH₂S(O)tBu,
—CH₂CH₂S(O)₂tBu, —CH₂CH₂S(O)NH₂,
—CH₂CH₂S(O)NHMe, —CH₂CH₂S(O)NMe₂,
—CH₂CH₂S(O)₂NH₂, —CH₂CH₂S(O)₂NHMe,
—CH₂CH₂S(O)₂NMe₂, —CH₂CH₂CH₂S(O)Me,
—CH₂CH₂CH₂S(O)Et, —CH₂CH₂CH₂S(O)₂Me,
—CH₂CH₂CH₂S(O)₂Et, —C(O)OH,
-5-tetrazolyl, —C(O)—N(Me)-5-tetrazolyl,

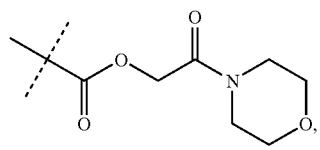

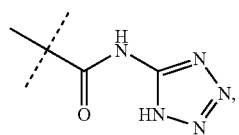

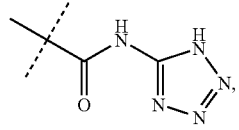

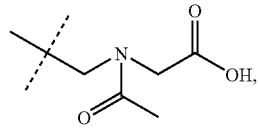

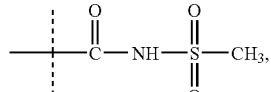

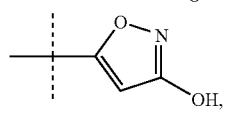

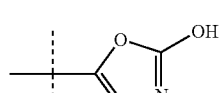

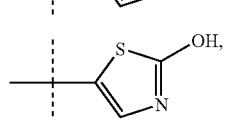

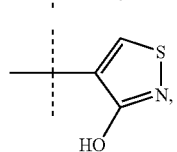

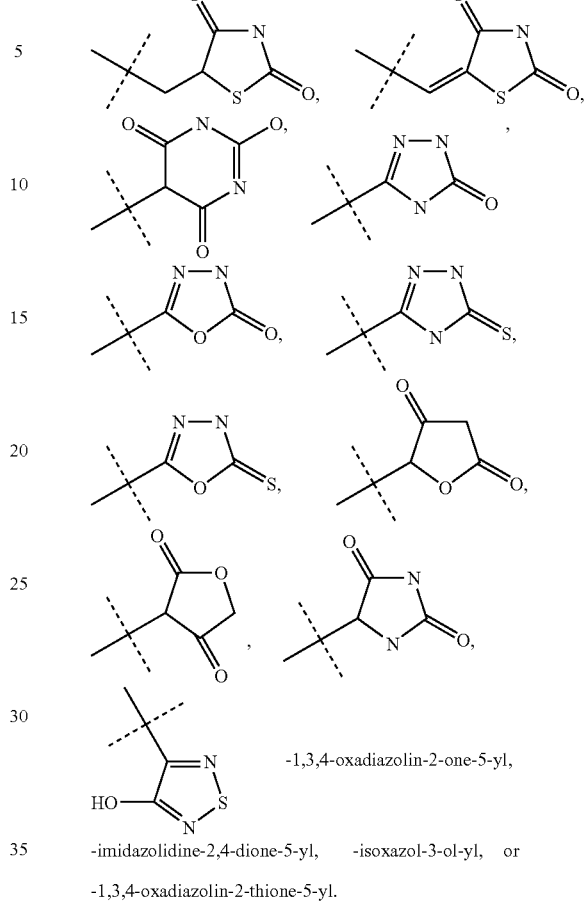

-1,3,4-oxadiazolin-2-one-5-yl,

-imidazolidine-2,4-dione-5-yl, -isoxazol-3-ol-yl, or

-1,3,4-oxadiazolin-2-thione-5-yl.

In the preceding formula (I) the divalent linking groups -(L1)- and -(L2)- and -(L3)- are understood (in the case of those having more than one substituent) to be oriented in either direction, for example, where divalent linker (L1) has the identity —(CH₂)ₘ—O—, it may be configured:

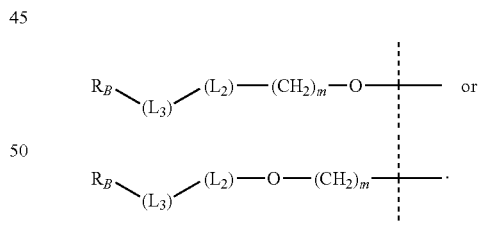

Preferred compounds of the invention with VDR modulating activities are represented by formula (I) or a pharmaceutically acceptable salt or a prodrug derivative thereof:

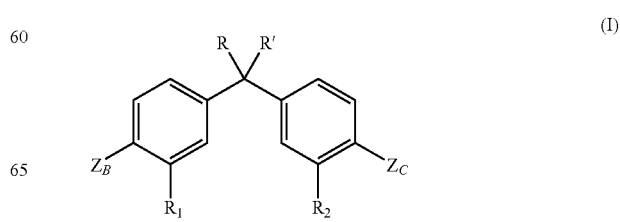

(I)

wherein;

R and R' are independently methyl, ethyl, propyl, or 1-methylethyl;

$R_1$ and $R_2$ are independently selected from the group consisting of hydrogen, fluoro, —Cl, —$CF_3$, —$CH_2F$, —$CHF_2$, methoxy, ethoxy, vinyl, methyl, ethyl, propyl, 1-methylethyl, 1,1-dimethylethyl, butyl, 1-methylpropyl, 2-methylpropyl, or cyclopropyl;

$Z_B$ is a branched alkyl terminated group represented by the formula:

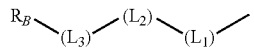

$R_B$ is 1-methylethyl; 1-methylpropyl; 2-methylpropyl; 1,1-dimethylethyl; 1,1-dimethylpropyl; 1,2-dimethylpropyl; 2,2-dimethylpropyl; 3-methyl-3-hydroxy-4,4-dimethylpentyl; 3-methyl-3-hydroxy-4,4-dimethylpentenyl; 3-methyl-3-hydroxy-4,4-dimethylpentyl; 3-ethyl-3-hydroxy-4,4-dimethylpentynyl; 3-ethyl-3-hydroxy-4,4-dimethylpentenyl; or 3-ethyl-3-hydroxy-4,4-dimethylpentynyl;

($L_1$) and ($L_2$) and ($L_3$) are independently divalent linking groups where $L_1$ is —O—, —$CH_2$—, —CHOH—, —CH(Me)—, —C(O)—, or —C(Me)OH—;

$L_2$ is —$CH_2$—, —CHOH—, —CH(Me)—, —C(O)—, or —C(Me)OH—; or $L_1$ and $L_2$ taken together is the group

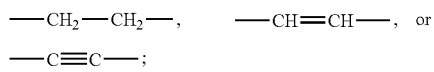

$L_3$ is a bond, —$CH_2$—, —CHOH—, —CH(Me)— —C(O)—, or —C(Me)OH—;

$Z_C$ is a group selected from
—C(O)$CH_2$S(O)Me,
—C(O)$CH_2$S(O)Et,
—C(O)$CH_2$S(O)$_2$Me,
—C(O)$CH_2$S(O)$_2$Et,
—C(O)$CH_2CH_2$S(O)Me,
—C(O)$CH_2CH_2$S(O)Et,
—C(O)$CH_2CH_2$S(O)$_2$Me,
—C(O)$CH_2CH_2$S(O)$_2$Et,
—C(O)CH(Me)$CH_2CO_2$H,
—C(O)CH(Me)$CH_2CO_2$Me,
—C(O)CH(Me)$CH_2CO_2$Et,
—C(O)CH(Me)$CH_2CO_2$iPr,
—C(O)CH(Me)$CH_2CO_2$tBu,
—C(O)CH(Me)CH(Me)$CO_2$H,
—C(O)CH(Me)CH(Me)$CO_2$Me,
—C(O)CH(Me)CH(Me)$CO_2$Et,
—C(O)CH(Me)CH(Me)$CO_2$iPr,
—C(O)CH(Me)CH(Me)$CO_2$tBu,
—C(O)CH(Me)C(Me)$_2CO_2$H,
—C(O)CH(Me)C(Me)$_2CO_2$Me,
—C(O)CH(Me)C(Me)$_2CO_2$Et,
—C(O)CH(Me)C(Me)$_2CO_2$iPr,
—C(O)CH(Me)C(Me)$_2CO_2$tBu,
—C(O)CH(Me)CH(Et)$CO_2$H,
—(O)CH(Me)CH(Et)$CO_2$Me,
—C(O)CH(Me)CH(Et)$CO_2$Et,
—C(O)CH(Me)CH(Et)$CO_2$iPr,
—C(O)CH(Me)CH(Et)$CO_2$tBu,
—C(O)C(O)OH,
—(C(O)C(O)$NH_2$,
—C(O)C(O)NHMe,
—C(O)C(O)$NMe_2$,
—C(O)$NH_2$,
—C(O)$NMe_2$,
—C(O)NH—$CH_2$—C(O)OH,
—C(O)NH—$CH_2$—C(O)OMe,
—C(O)NH—$CH_2$—C(O)OEt,
—C(O)NH—$CH_2$—C(O)OiPr,
—C(O)NH—$CH_2$—C(O)OtBu,
—C(O)NH—CH(Me)—C(O)OH,
—C(O)NH—CH(Me)—C(O)OMe,
—C(O)NH—CH(Me)—C(O)OEt,
—C(O)NH—CH(Me)—C(O)iPr,
—C(O)NH—CH(Me)—C(O)tBu,
—C(O)NH—CH(Et)C(O)OH,
—C(O)NH—C(Me)$_2$—C(O)OH,
—C(O)NH—C(Me)$_2$—C(O)OMe,
—C(O)NH—C(Me)$_2$—C(O)OEt,
—C(O)NH—C(Me)$_2$—C(O)iPr,
—C(O)NH—C(Me)$_2$—C(O)tBu,
—C(O)NH—CMe(Et)-C(O)OH,
—C(O)NH—CH(F)—C(O)OH,
—C(O)NH—CH($CF_3$)—C(O)OH,
—C(O)NH—CH(OH)—C(O)OH,
—C(O)NH—CH(cyclopropyl)-C(O)OH,
—C(O)NH—C(Me)$_2$—C(O)OH,
—C(O)NH—C(Me)$_2$—C(O)OH,
—C(O)NH—CF(Me)-C(O)OH,
—C(O)NH—C(Me)($CF_3$)—C(O)OH,
—C(O)NH—C(Me)(OH)—C(O)OH,
—C(O)NH—C(Me)(cyclopropyl)$CO_2$H,
—C(O)NMe-$CH_2$—C(O)OH,
—C(O)NMe-$CH_2$—C(O)OMe,
—C(O)NMe-$CH_2$—C(O)OEt,
—C(O)NMe-$CH_2$—C(O)OiPr,
—C(O)NMe-$CH_2$—C(O)tBu,
—C(O)NMe-CH(Me)-C(O)OH,
—C(O)NMe-CH(F)—C(O)OH,
—C(O)NMe-CH($CF_3$)—C(O)OH,
—C(O)NMe-CH(OH)—C(O)OH,
—C(O)NMe-CH(cyclopropyl)-C(O)OH,
—C(O)NMe-C(Me)$_2$—C(O)OH,
—C(O)NMe-CF(Me)-C(O)OH,
—C(O)NMe-C(Me)($CF_3$)—C(O)OH,
—C(O)NMe-C(Me)(OH)—C(O)OH,
—C(O)NMe-C(Me)(cyclopropyl)-C(O)OH, or
—C(O)—N(Me)-5-tetrazolyl.

Other preferred compounds of the invention are those represented by formula (I) or a pharmaceutically acceptable salt or a prodrug derivative thereof:

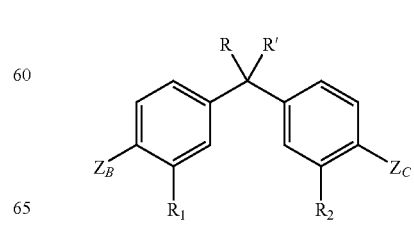

wherein;

R and R' are independently methyl or ethyl;

$R_1$ and $R_2$ are independently selected from the group consisting of hydrogen, fluoro, —Cl, —$CF_3$, —$CH_2F$, —$CHF_2$, methoxy, ethoxy, vinyl, methyl, or cyclopropyl;

$Z_B$ is a branched alkyl terminated selected from the formulae:

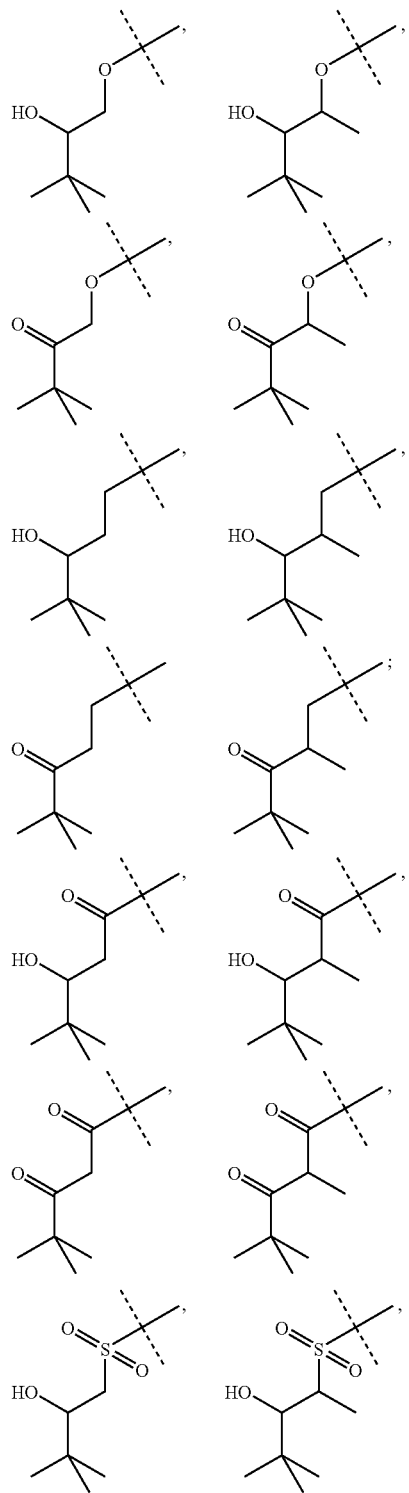

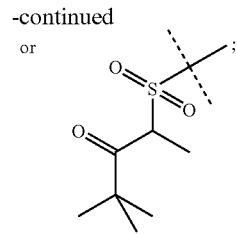

$Z_C$ is selected from

—C(O)$NH_2$,   —C(O)$NMe_2$,

—C(O)NH—$CH_2$—C(O)OH,

—C(O)NH—$CH_2$—C(O)OMe,

—C(O)NH—$CH_2$—C(O)OEt,

—C(O)NH—$CH_2$—C(O)OiPr,

—C(O)NH—$CH_2$—C(O)OtBu,

—C(O)NH—CH(Me)—C(O)OH,

—C(O)NH—CH(Me)—C(O)OMe,

—C(O)NH—CH(Me)—C(O)OEt,

—C(O)NH—CH(Me)—C(O)iPr,

—C(O)NH—CH(Me)—C(O)tBu,

—C(O)NH—CH(Et)—C(O)OH,

—C(O)NH—C(Me)$_2$—C(O)OH,

—C(O)NH—C(Me)$_2$—C(O)OMe,

—C(O)NH—C(Me)$_2$—C(O)OEt,

—C(O)NH—C(Me)$_2$—C(O)iPr,

—C(O)NH—C(Me)$_2$—C(O)tBu,

—C(O)NH—CMe(Et)—C(O)OH,

—C(O)NH—CH(F)—C(O)OH,

—C(O)NH—CH($CF_3$)—C(O)OH,

—C(O)NH—CH(OH)—C(O)OH,

—C(O)NH—CH(cyclopropyl)—C(O)OH,

—C(O)NH—C(Me)$_2$—C(O)OH,

—C(O)NH—C(Me)$_2$—C(O)OH,

—C(O)NH—CF(Me)—C(O)OH,

—C(O)NH—C(Me)($CF_3$)—C(O)OH,

—C(O)NH—C(Me)(OH)—C(O)OH,

—C(O)NH—C(Me)(cyclopropyl)$CO_2H$,

—C(O)NMe—$CH_2$—C(O)OH,

—C(O)NMe—$CH_2$—C(O)OMe,

—C(O)NMe—$CH_2$—C(O)OEt,

—C(O)NMe—$CH_2$—C(O)OiPr,

—C(O)NMe—$CH_2$—C(O)tBu,

—C(O)NMe—CH(Me)—C(O)OH,

—C(O)NMe—CH(F)—C(O)OH,

-continued

—C(O)NMe—CH(CF₃)—C(O)OH,

—C(O)NMe—CH(OH)—C(O)OH,

—C(O)NMe—CH(cyclopropyl)—C(O)OH,

—C(O)NMe—C(Me)₂—C(O)OH,

—C(O)NMe—CF(Me)—C(O)OH,

—C(O)NMe—C(Me)(CF₃)—C(O)OH,

—C(O)NMe—C(Me)(OH)—C(O)OH,

—C(O)NMe—C(Me)(cyclopropyl)—C(O)OH,

—C(O)—N(Me)-5-tetrazolyl,

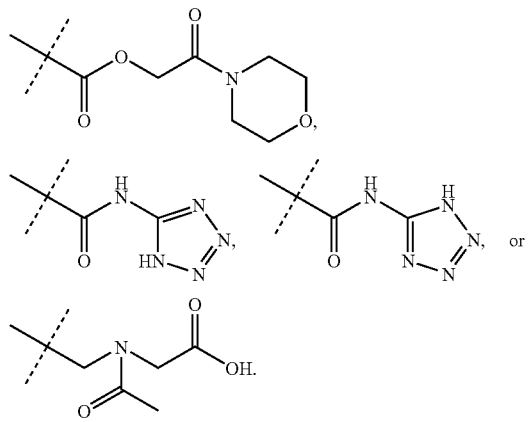

Particularly preferred is a compound or a pharmaceutically acceptable salt or ester prodrug derivative thereof represented by structural formulae (AA) to (DB) as follows:

AA)

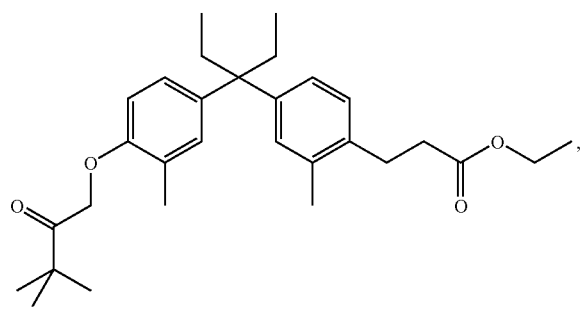

AF)

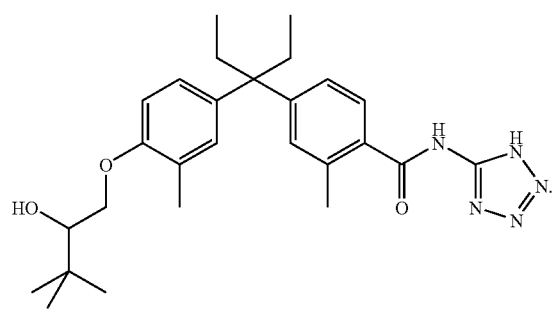

AJ)

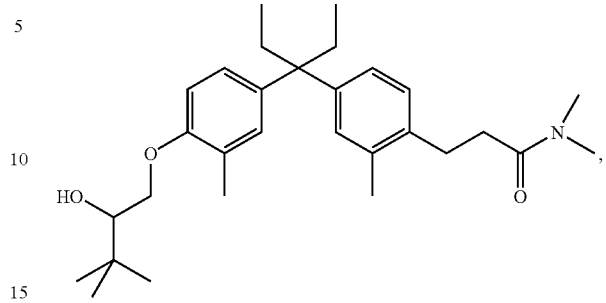

AP)

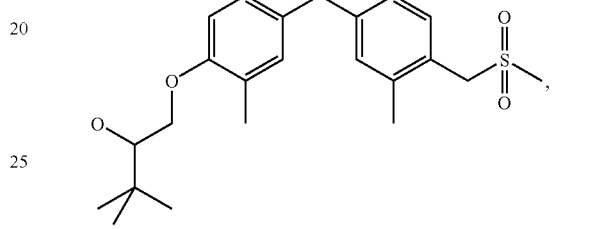

AR)

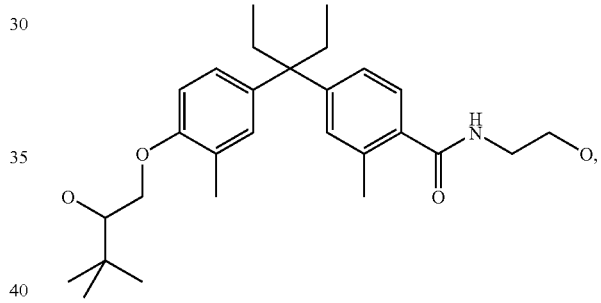

AS)

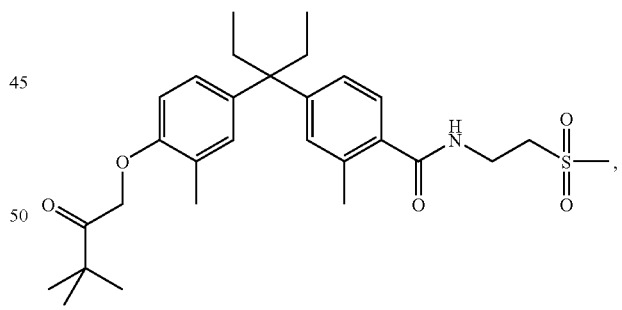

AT)

AW)
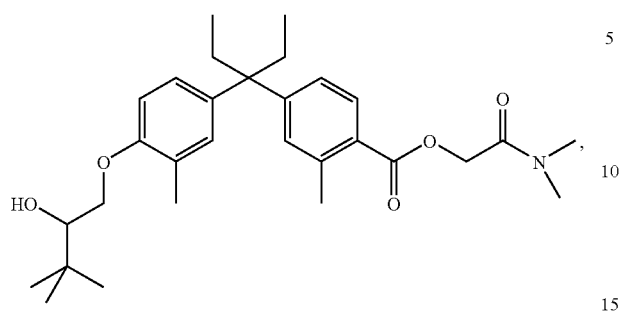
AZ)
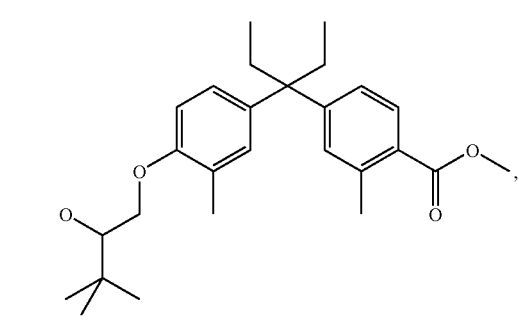
BA)
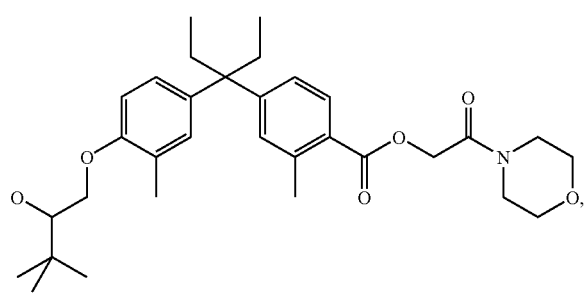
BE)
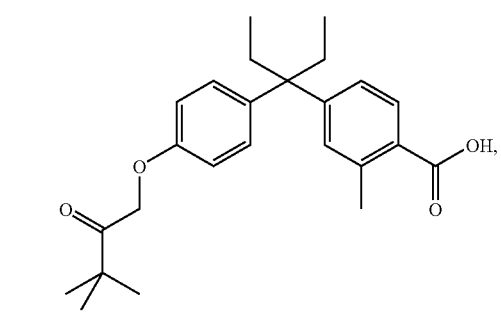
BF)
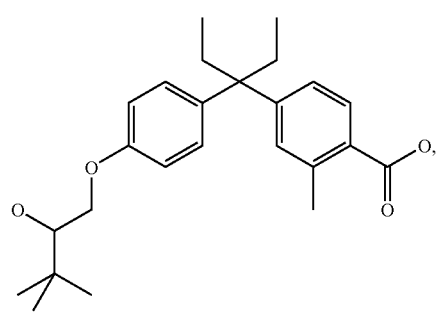
BH)
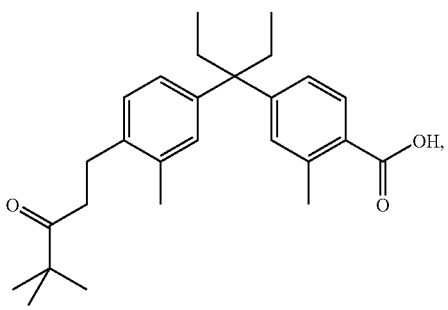
BI)
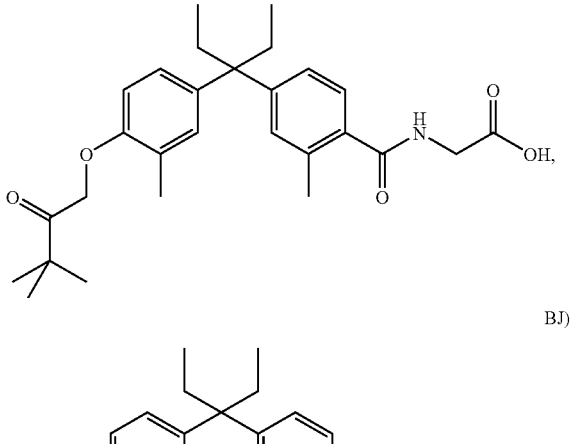
BJ)
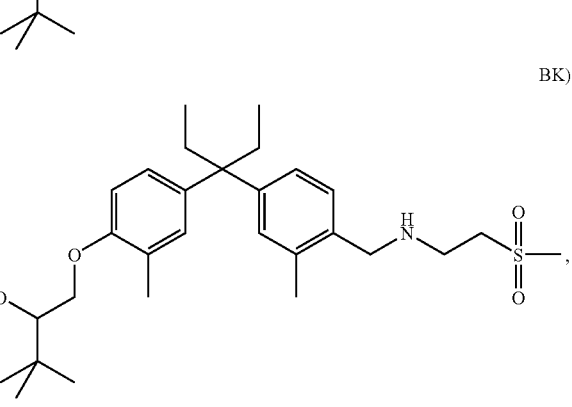
BK)
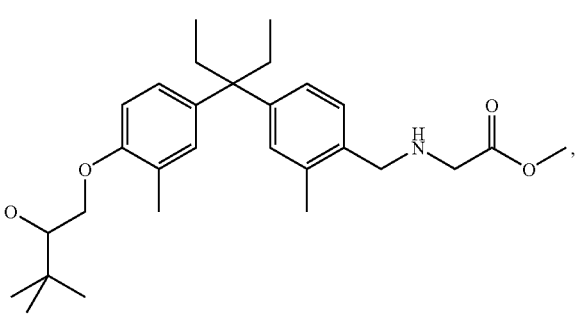
BN)

-continued
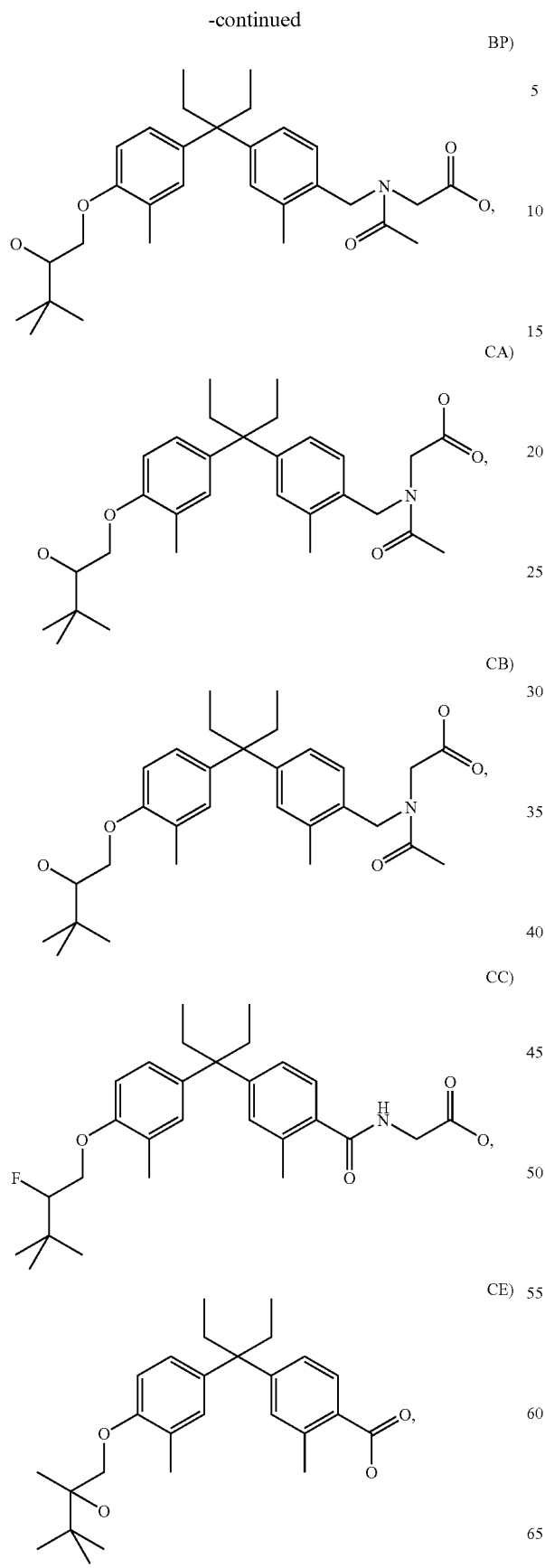
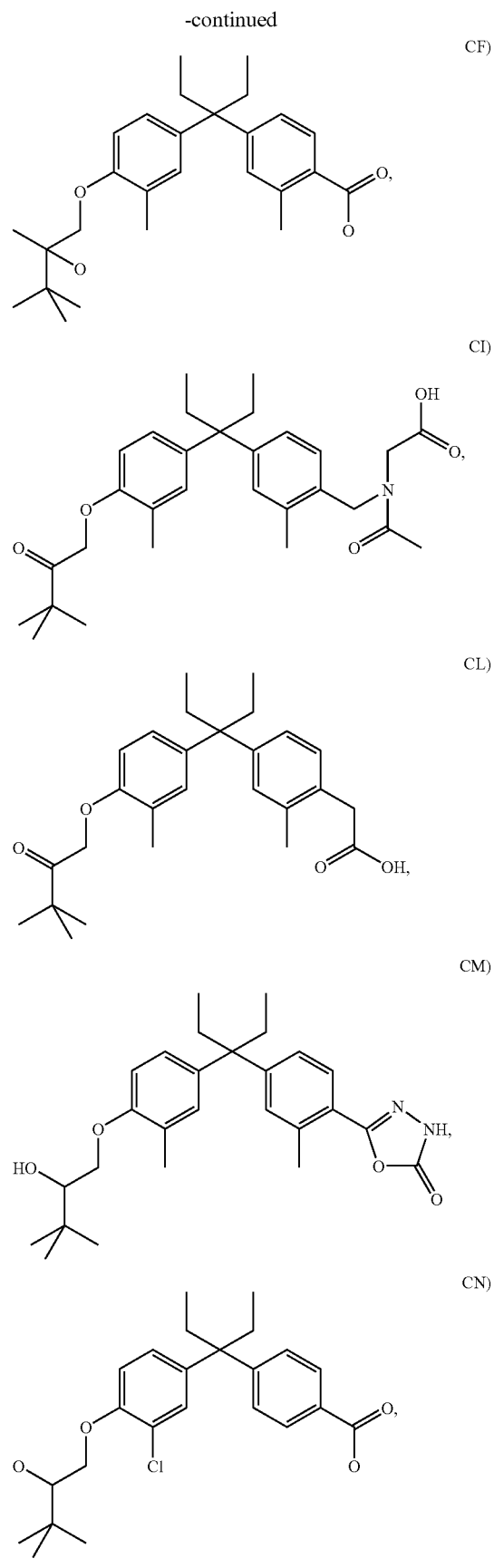

DA)
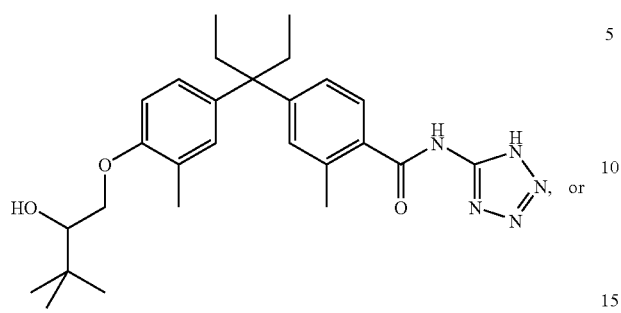
DB)
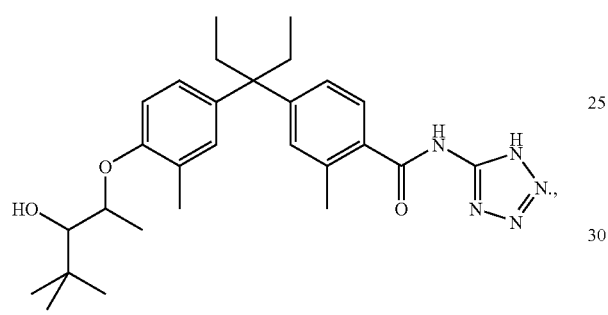
Other particularly preferred compounds of the invention are those shown by the structural formulae C-1 to C-54 set out below. Pharmaceutically acceptable salts for prodrug derivatives of these compounds are also preferred.
C-1)
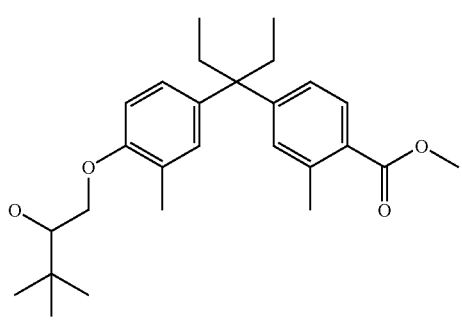
C-2)
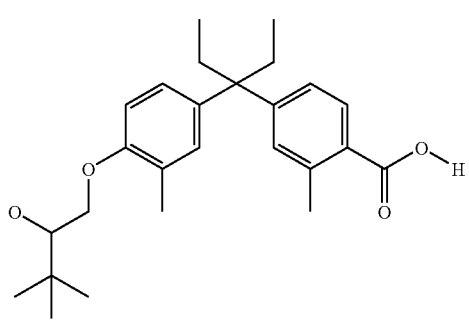
C-3)
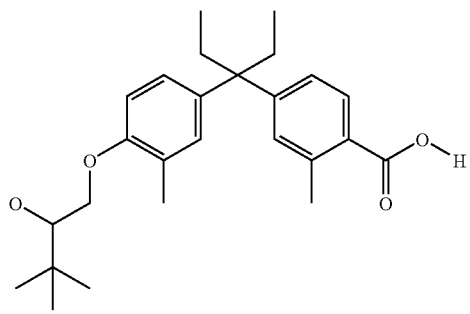
C-4)
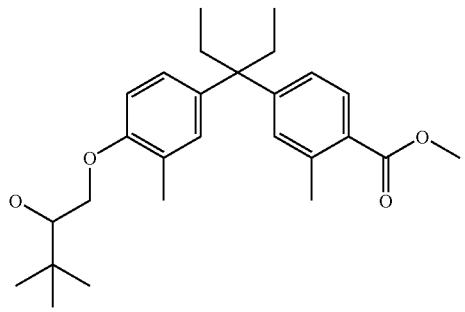
C-6)
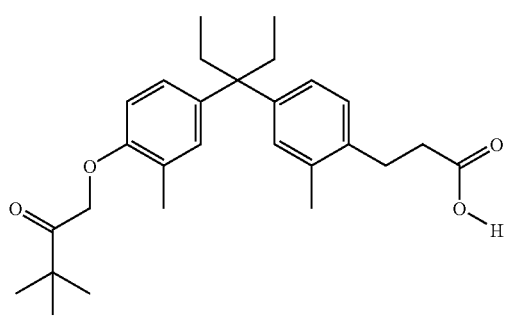
C-7)
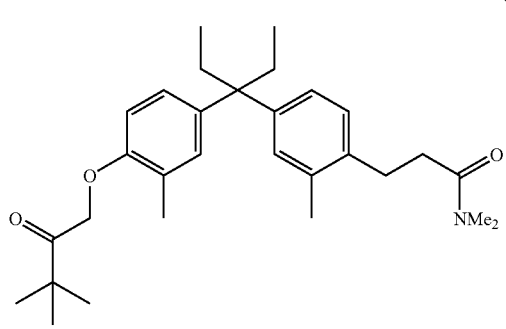
C-8)
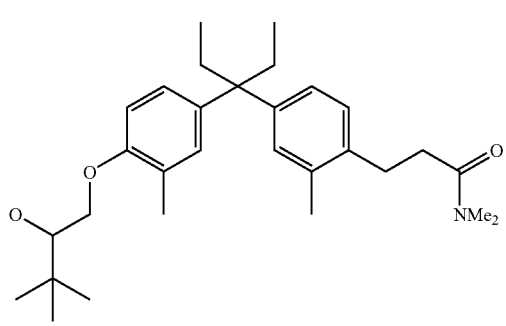

C-9)
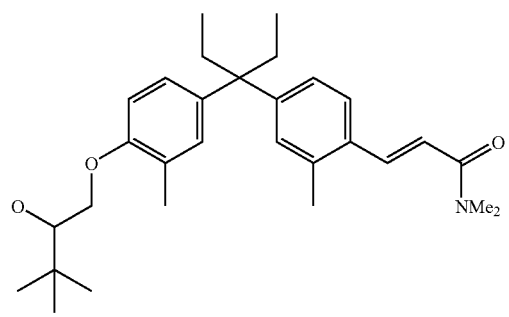
C-10)
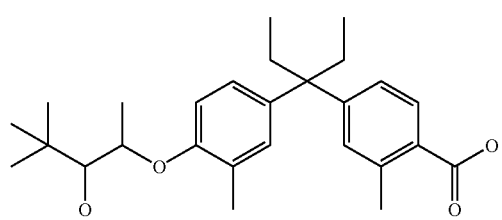
C-12)
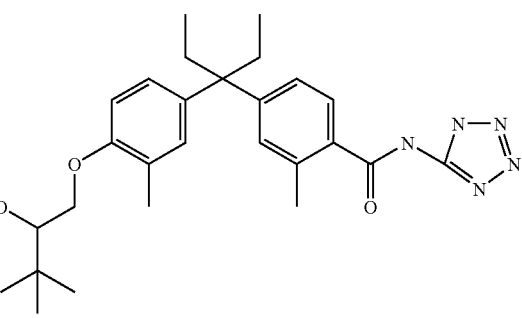
C-13)
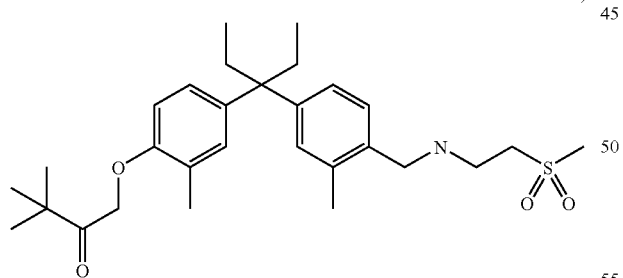
C-15)
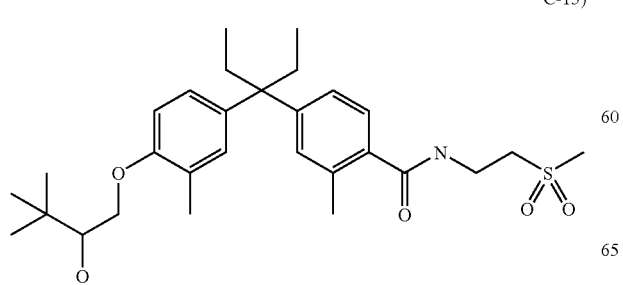
C-16)
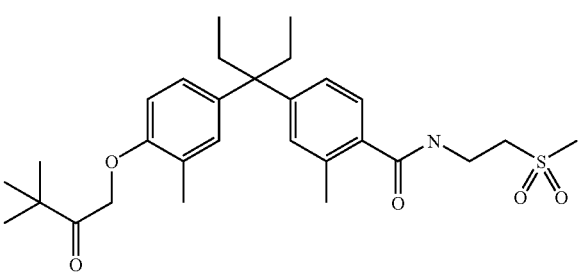
C-17)
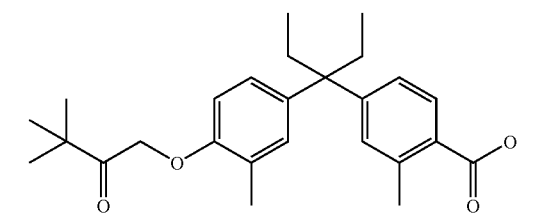
C-18)
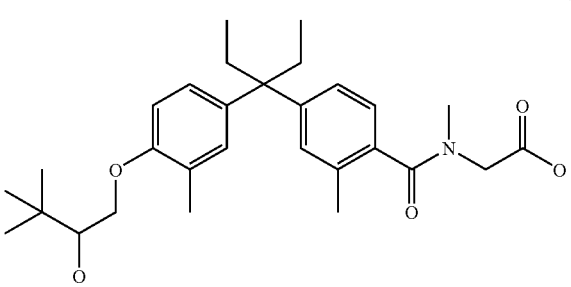
C-19)
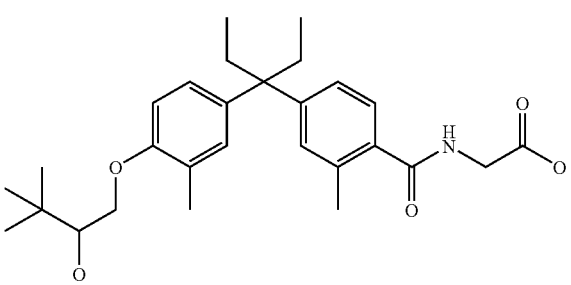
C-20)
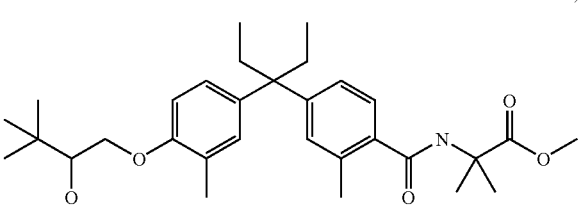
C-21)
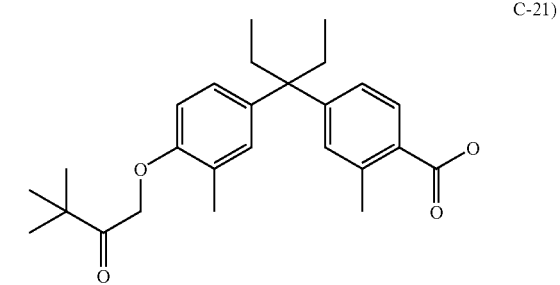

-continued
C-22)
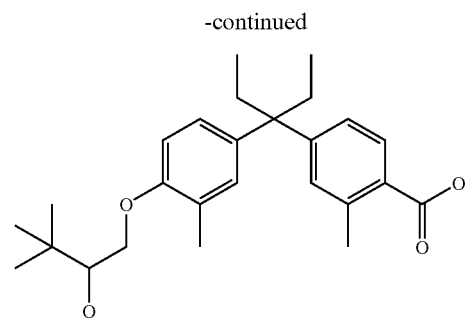
C-25)
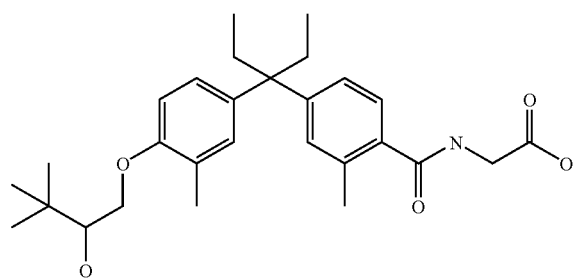
C-26)
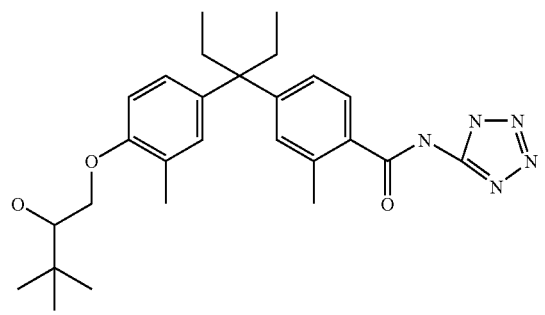
C-29)
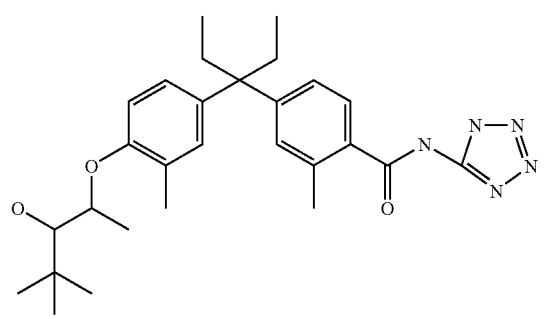
C-31)
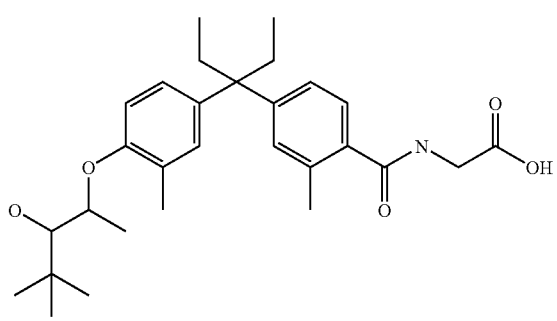
C-35)
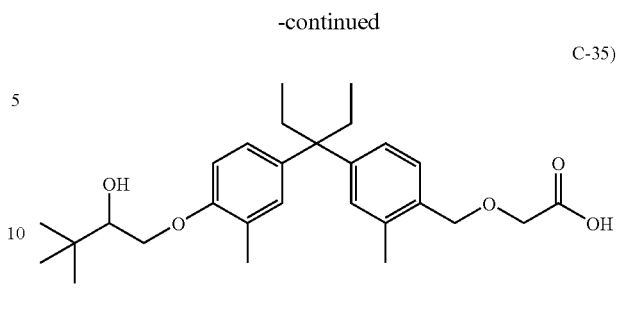
C-36)
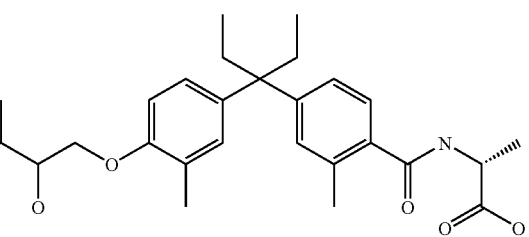
C-39)
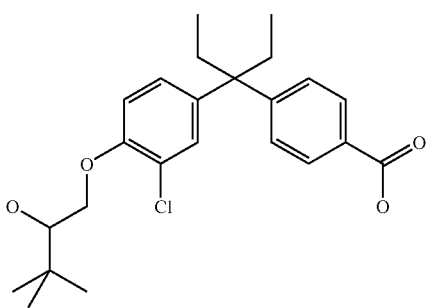
C-42)
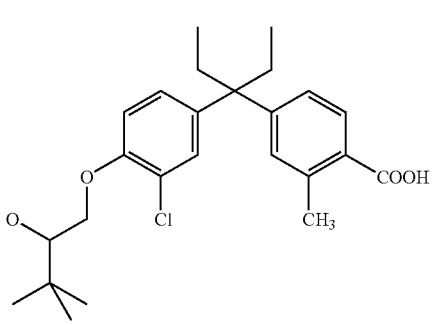
C-43)

-continued
C-44)
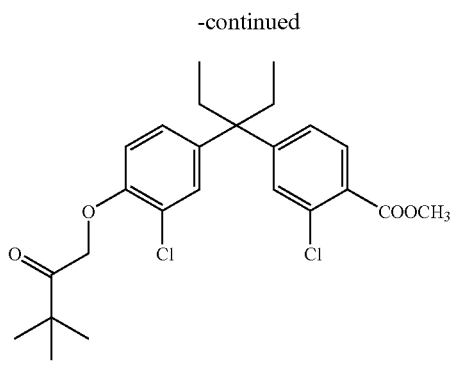
C-45)
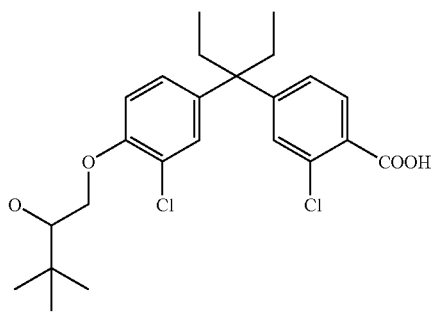
C-48)
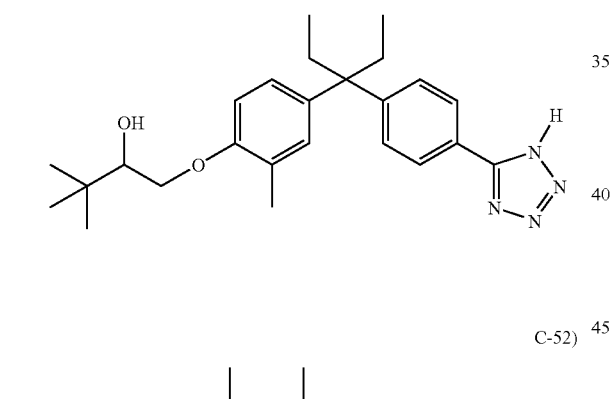
C-52)
C-54)
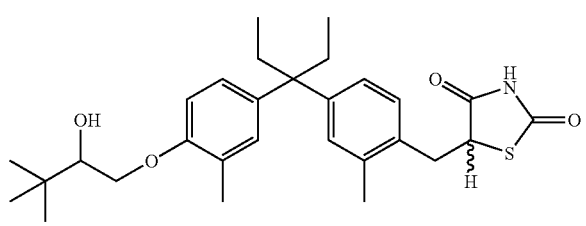
-continued
C-55)
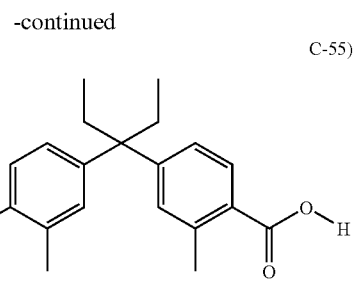
Most preferred are the individual enantiomers or a mixture of enantiomers represented by the formulae:
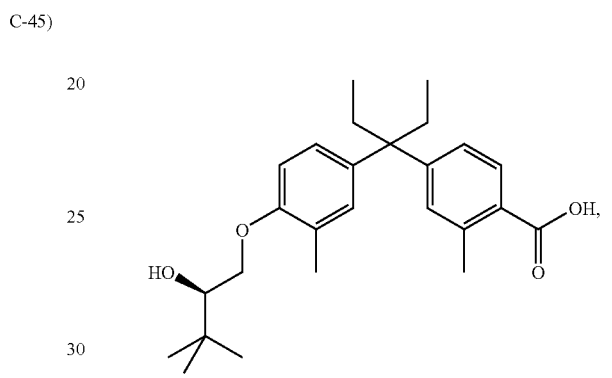
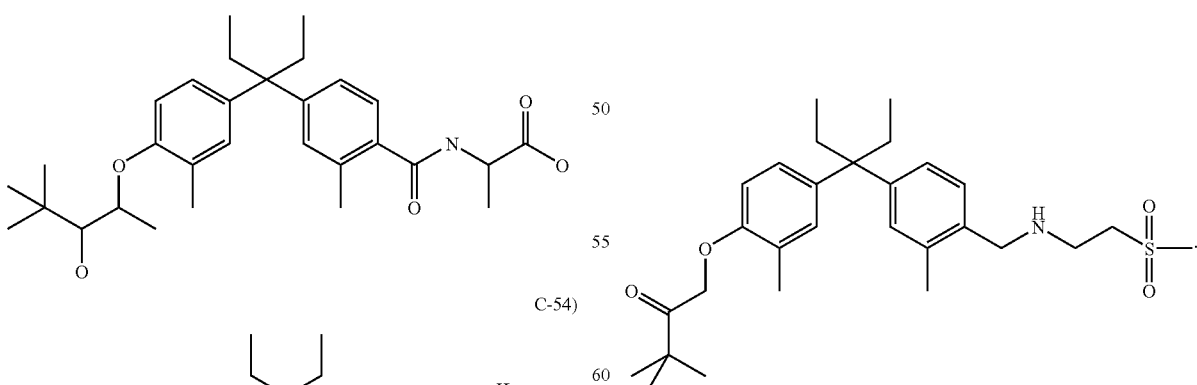
Additional particularly preferred are compounds or a pharmaceutically acceptable salt or prodrug derivative thereof selected from (TBU-1) to (TBU-86), as follows:

A compound or a pharmaceutically acceptable salt or an ester prodrug derivative thereof selected from (TBU-1) to (TBU-86), as follows:
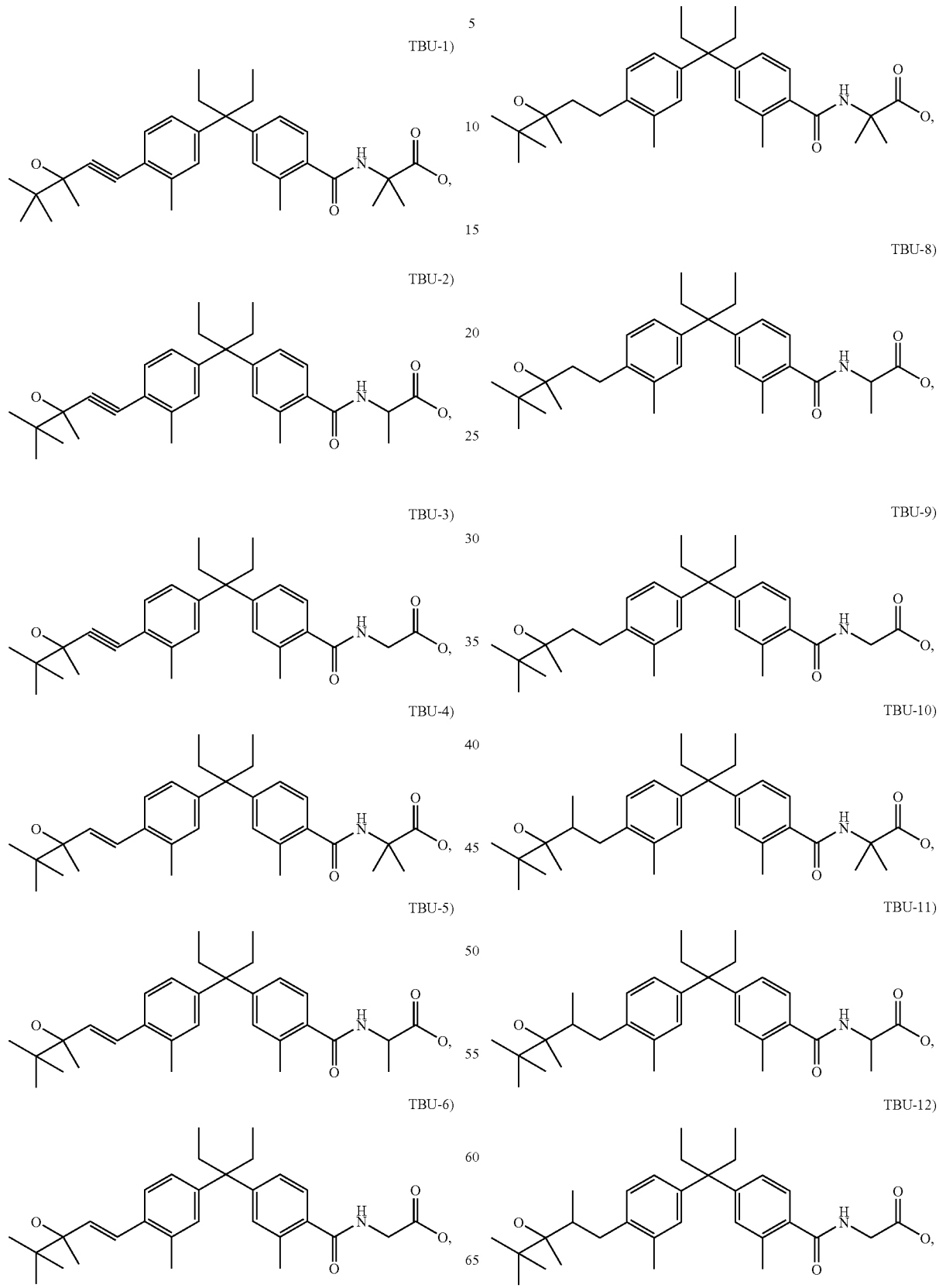

TBU-13)
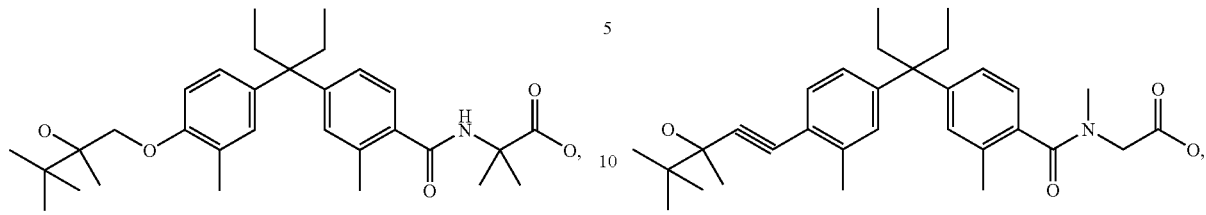
TBU-14)
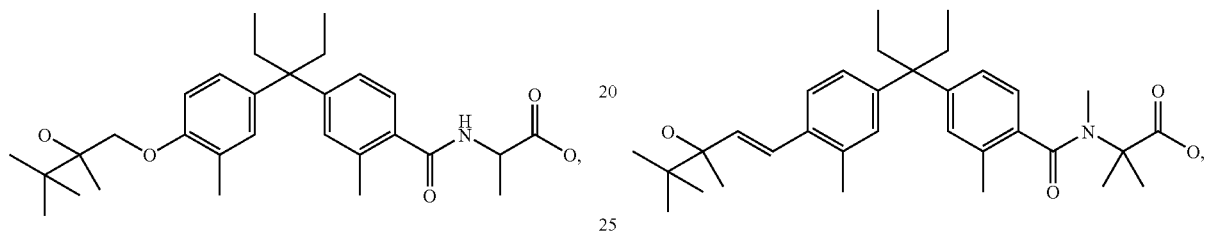
TBU-15)
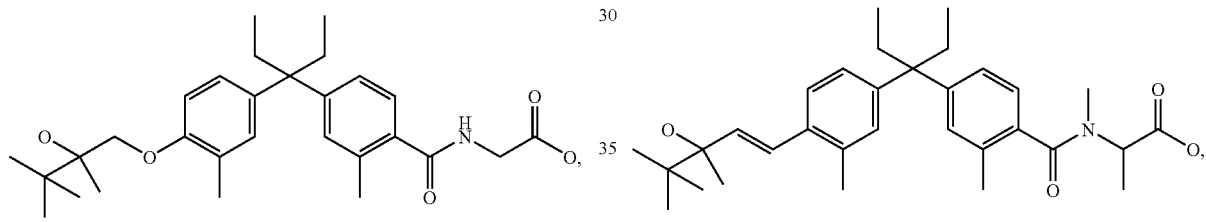
TBU-16)
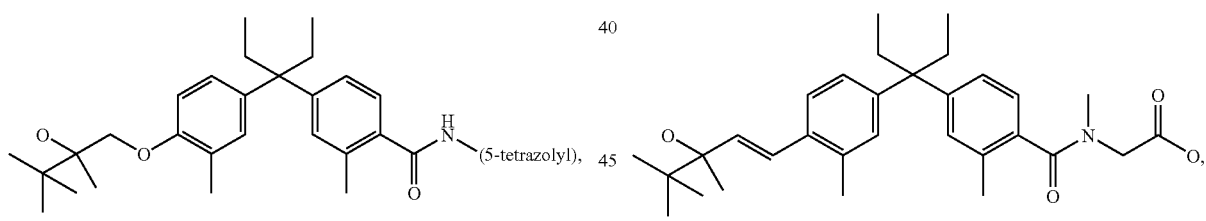
TBU-17)
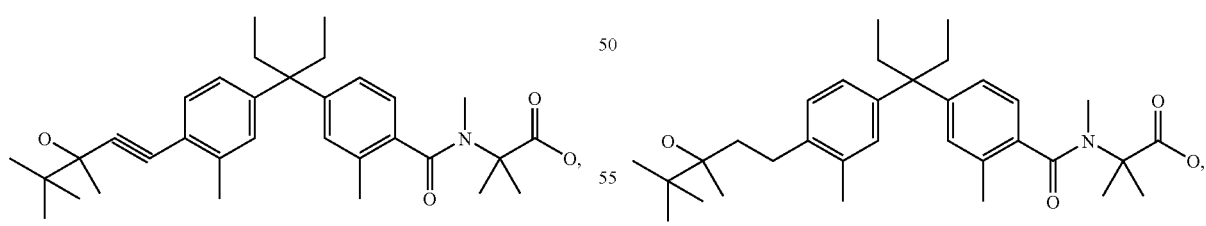
TBU-18)
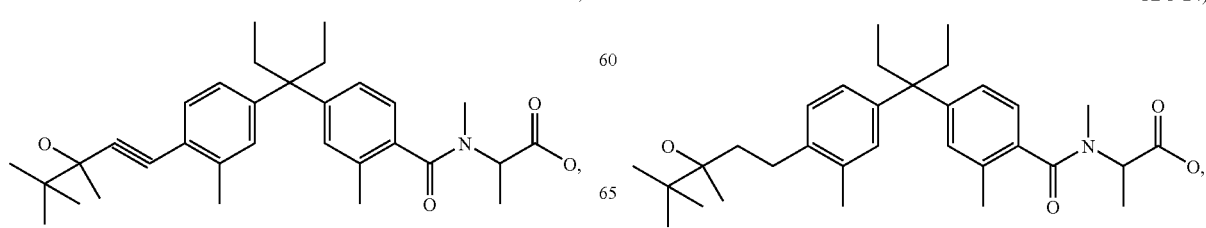
TBU-19)
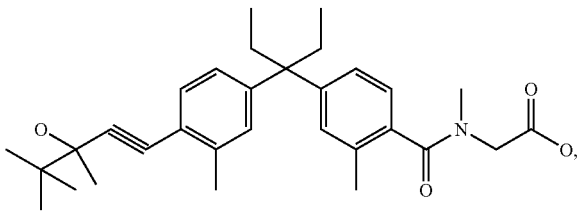
TBU-20)
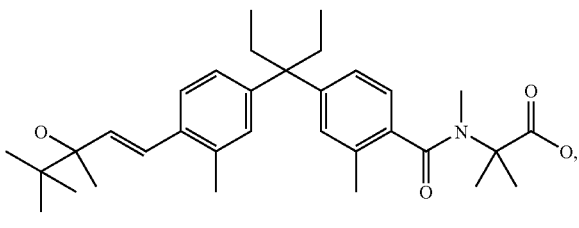
TBU-21)
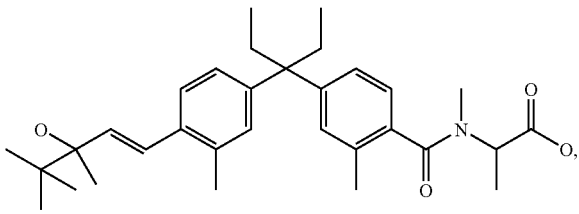
TBU-22)
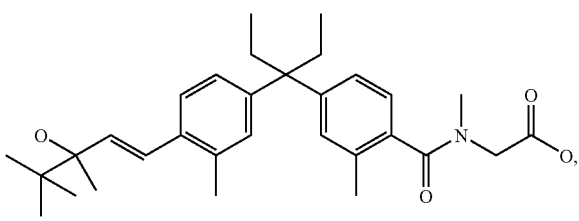
TBU-23)
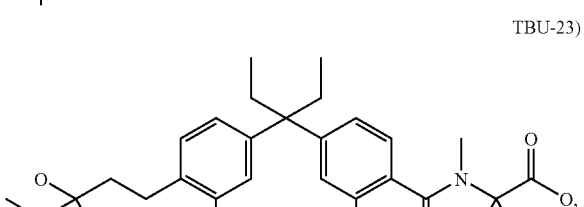
TBU-24)
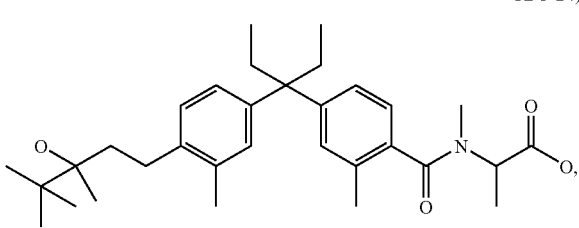

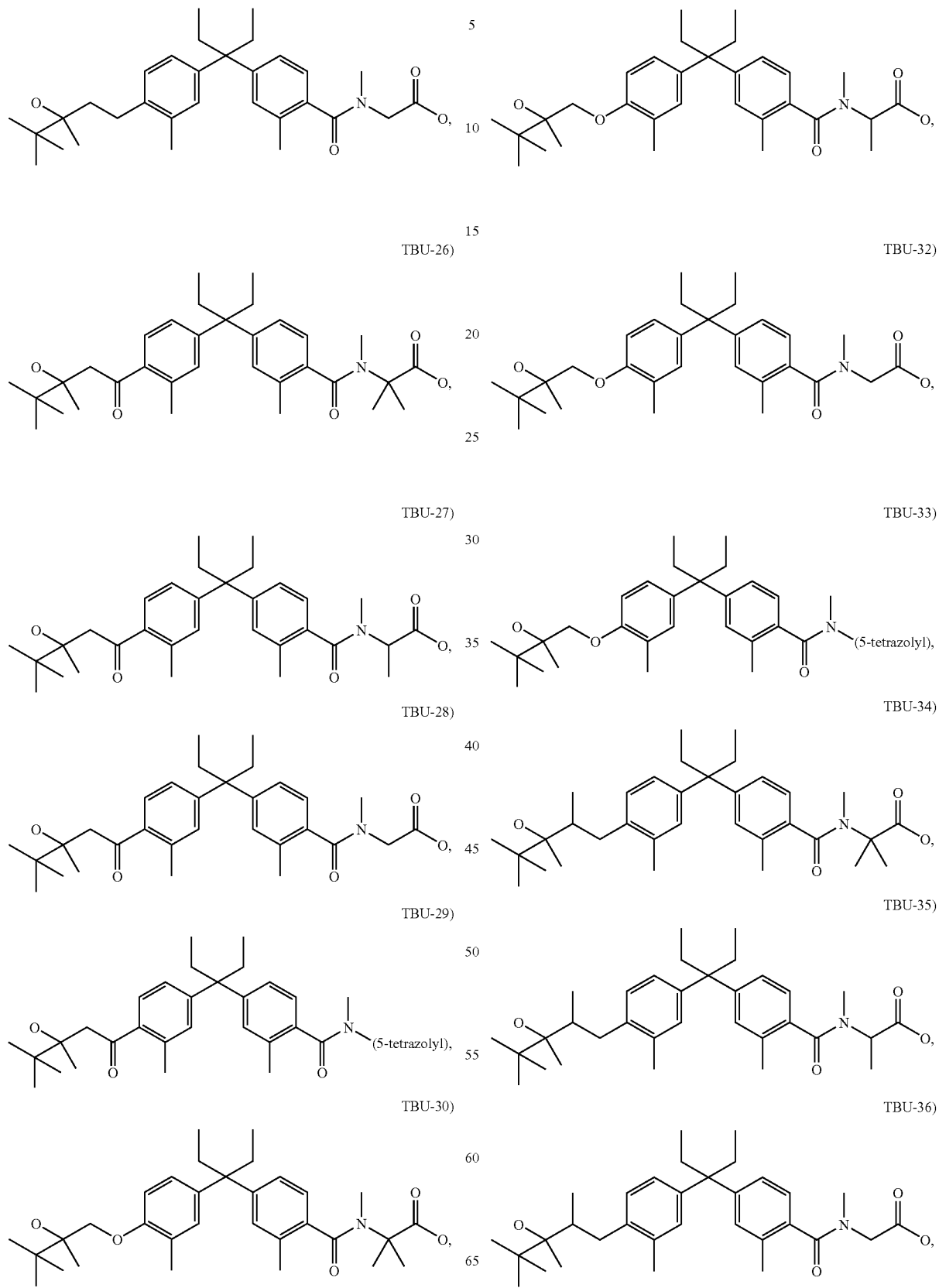

-continued
TBU-37)
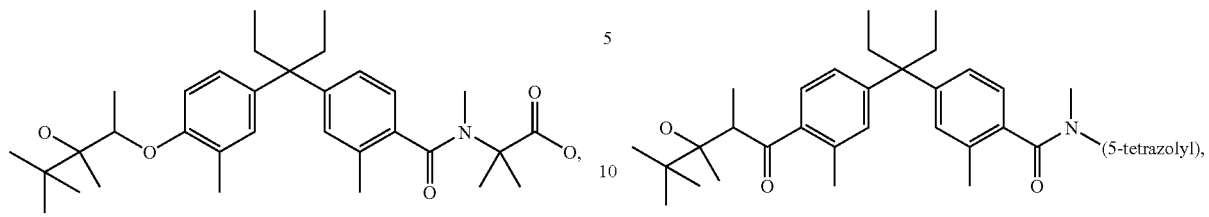
TBU-38
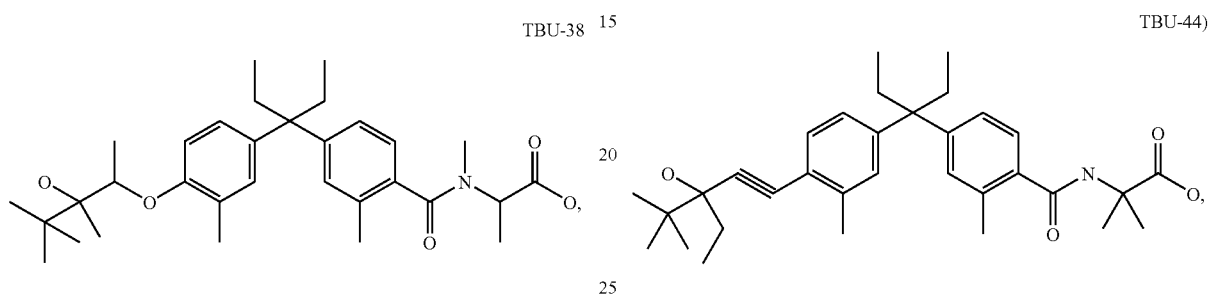
TBU-39)
TBU-40)
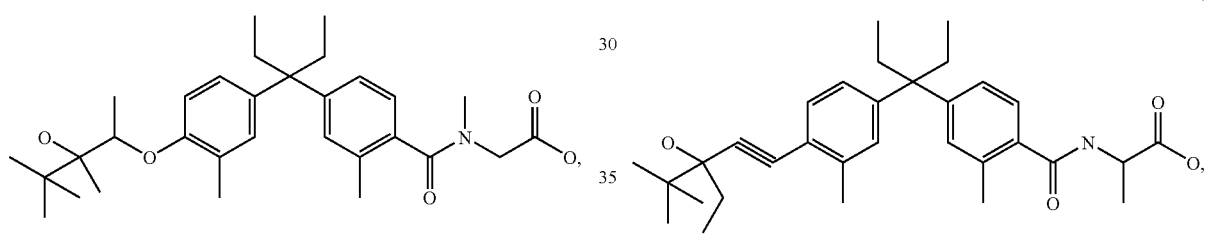
TBU-41)
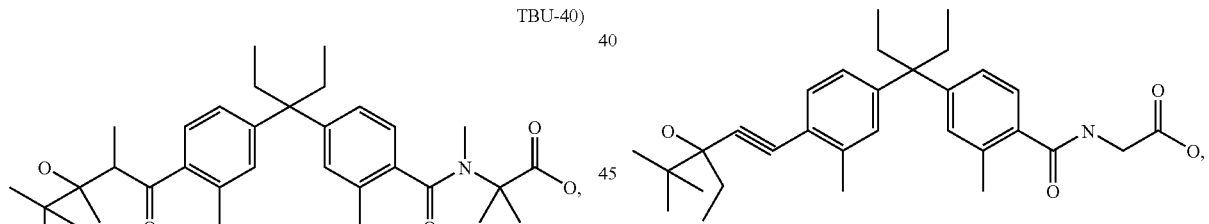
TBU-42)
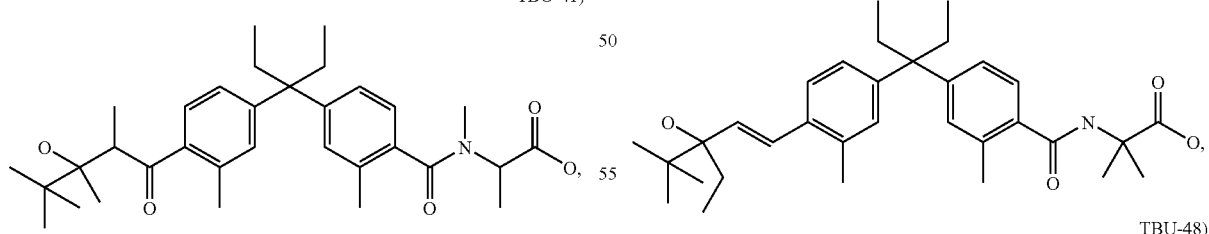
-continued
TBU-43)
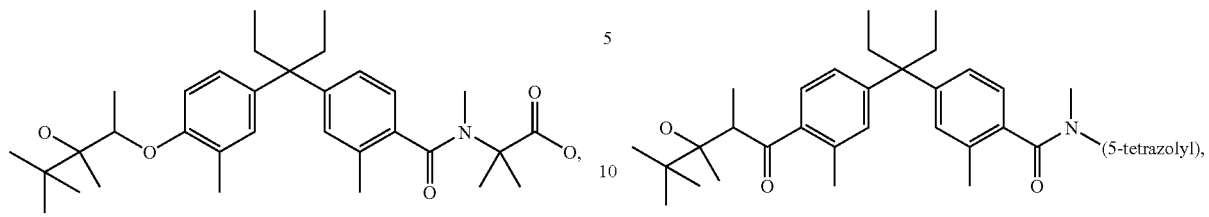
TBU-44)
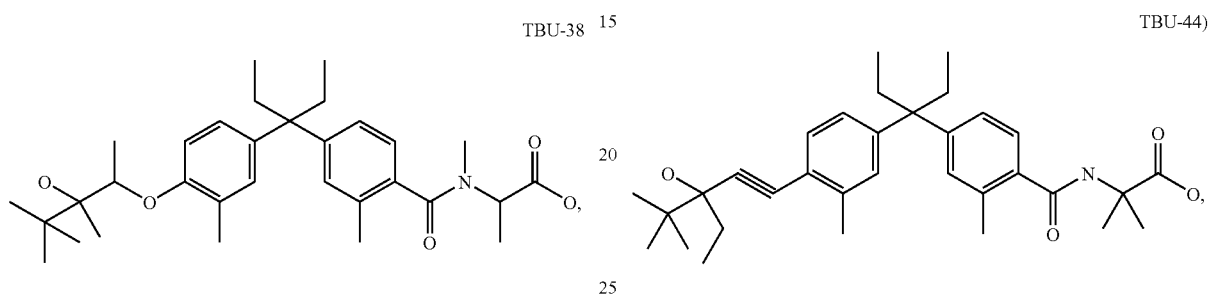
TBU-45)
TBU-46)
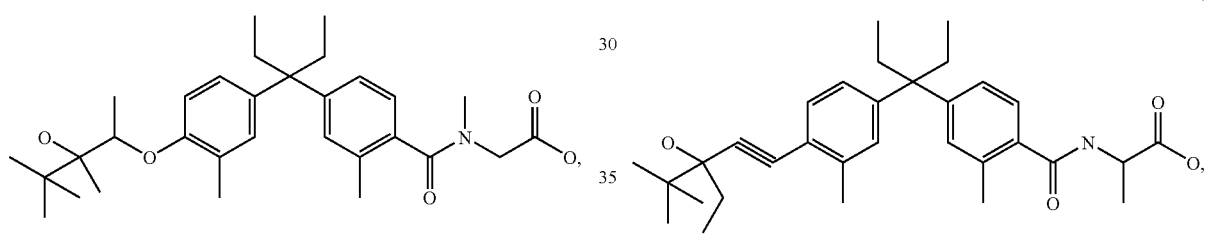
TBU-47)
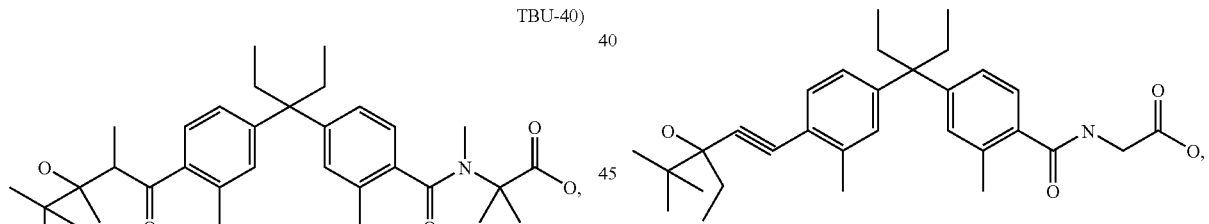
TBU-48)
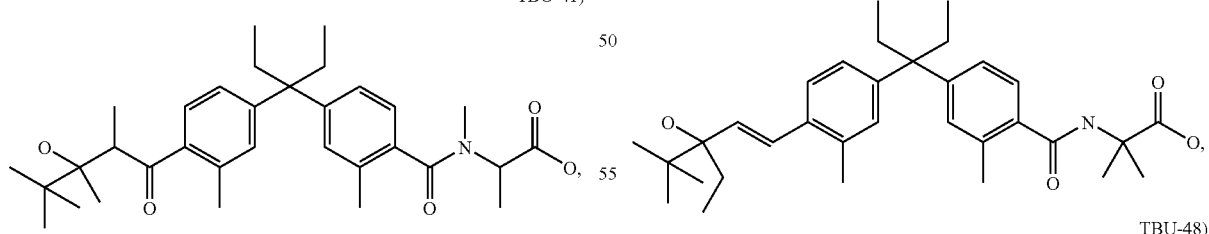

-continued

TBU-49)
TBU-50)
TBU-51)
TBU-52)
TBU-53)
TBU-54)

-continued

TBU-55)
TBU-56)
TBU-57)
TBU-58)
TBU-59) (5-tetrazolyl),
TBU-60)

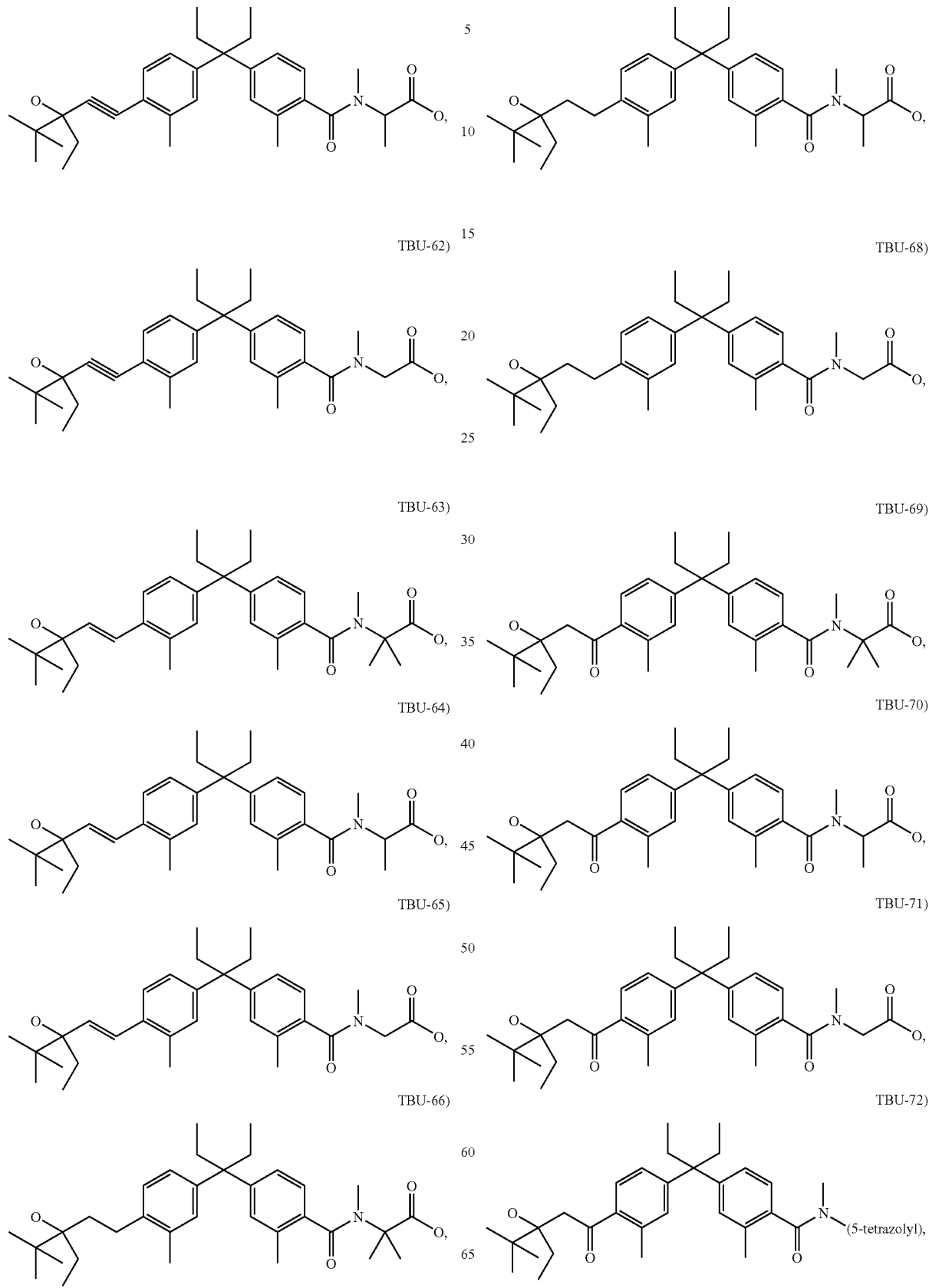

TBU-73)
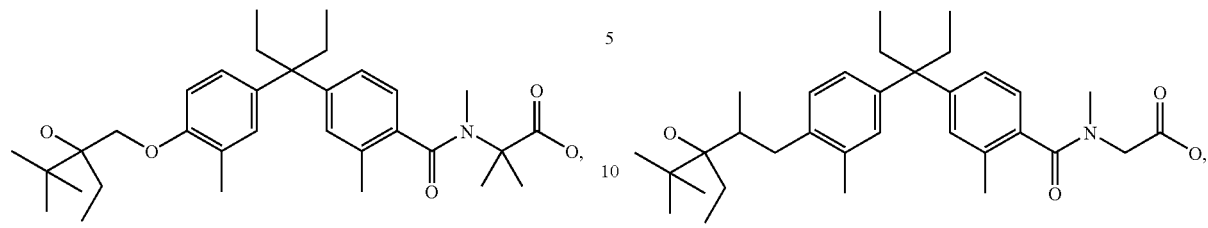
TBU-74)
TBU-75)
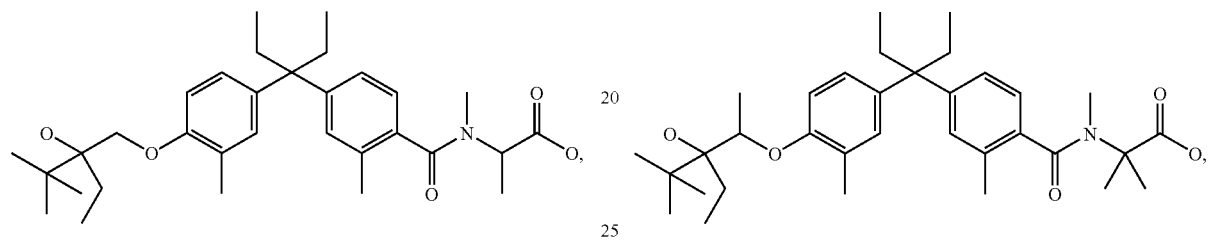
TBU-76)
TBU-77)
TBU-78)
TBU-79)
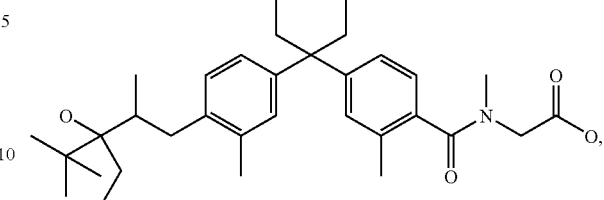
TBU-80)
TBU-81)
TBU-82)
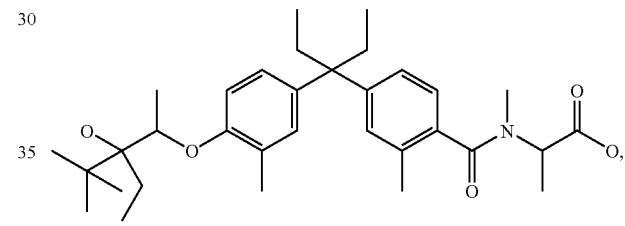
TBU-83)
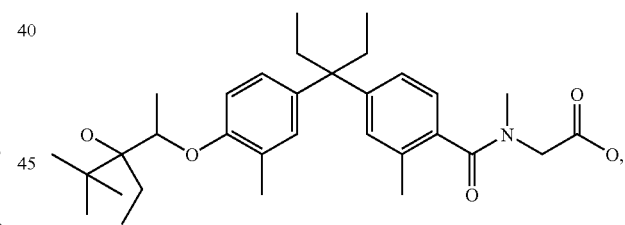
TBU-84)
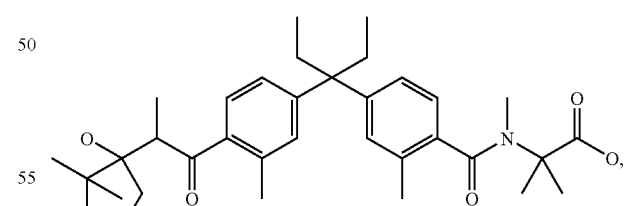
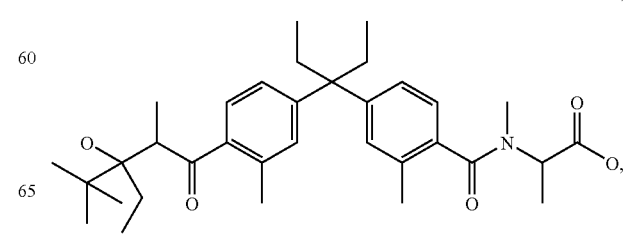

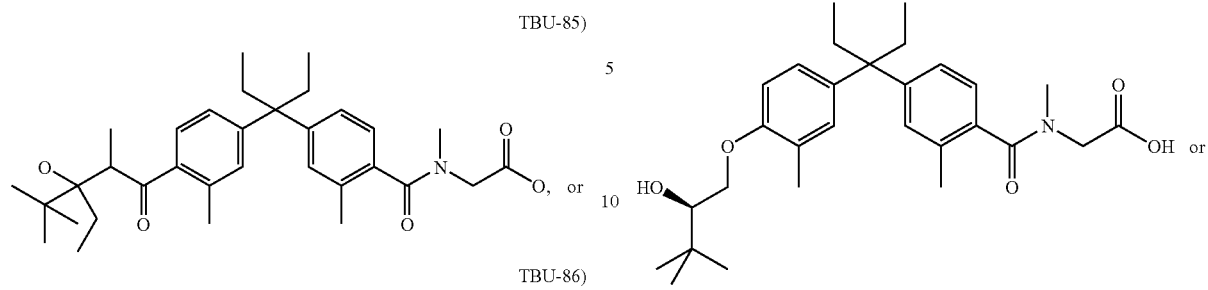

TBU-85)

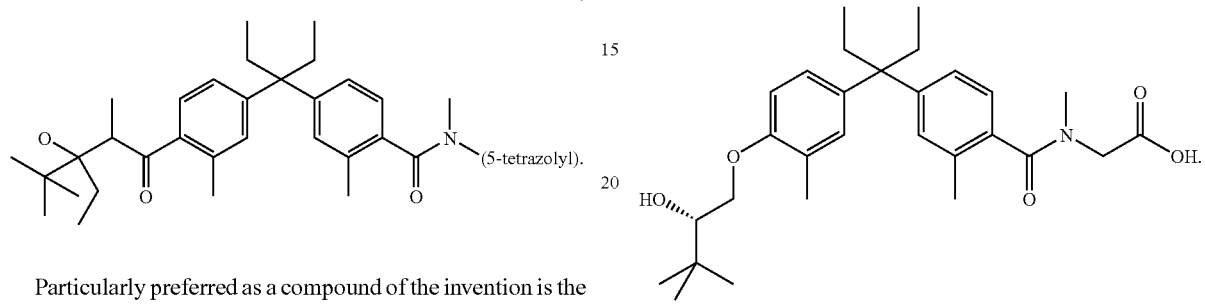

TBU-86)

Particularly preferred as a compound of the invention is the compound or a pharmaceutically acceptable salt or ester prodrug derivative of the compound represented by the formula:

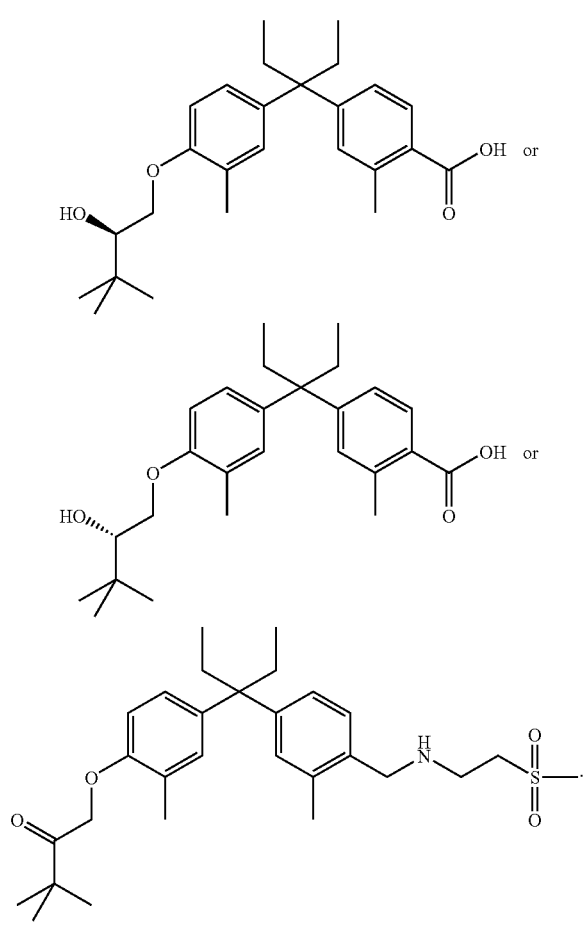

Particularly preferred as a compound of the invention is the compound or a pharmaceutically acceptable salt or ester prodrug derivative of the compound represented by the formula:

For all of the above compounds of the invention defined by Formula (I) the preferred prodrug derivative is a methyl ester, ethyl ester N,N-diethylglycolamido ester or morpholinyl-ethyl ester. In addition, for all of the above compounds of the invention the preferred salt is sodium or potassium.

Other specific compounds that are preferred embodiments of this invention and are preferred for practicing the method of treatment of the invention are set out in the following Tables. All numbers in the Tables cells reciting chemical species are to be understood as subscripts in chemical formulae, for example, in the first row of Table 1, Compound No. 1, the symbol, "CO2Me" is to be understood as the conventional chemical nomenclature, —$CO_2H$—. Each row of the Tables 1 and 2 represents a single compound having an identifying defining the specific substituents in the structural formula displayed above each Tables, as follows:

Among other preferred compounds of the invention are those represented by the formula:

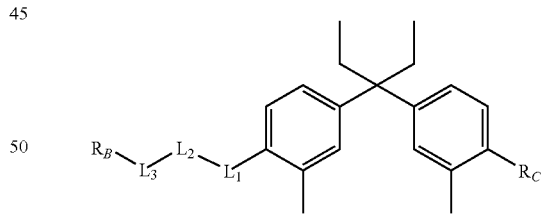

and pharmaceutically acceptable salts thereof; wherein;

said compound is selected from a compound code numbered 1 thru 468, with each compound having the specific selection of substituents $R_B$, $R_C$, $L_1$, $L_2$, and $L_3$ shown in the row following the compound code number, as set out in the following Table 1:

TABLE 1

| No. | $R_B$ | $L_3$ | $L_2$ | $L_1$ | $R_C$ |
|---|---|---|---|---|---|
| 1 | tBu | C(O) | CH2 | O | C(O)CH(Me)CH2CO2H |
| 2 | tBu | CHOH | CH2 | O | C(O)CH(Me)CH2CO2H |
| 3 | tBu | C(Me)OH | CH2 | O | C(O)CH(Me)CH2CO2H |

TABLE 1-continued

| No. | $R_B$ | $L_3$ | $L_2$ | $L_1$ | $R_C$ |
|---|---|---|---|---|---|
| 4 | tBu | C(O) | CH(Me) | O | C(O)CH(Me)CH2CO2H |
| 5 | tBu | CHOH | CH(Me) | O | C(O)CH(Me)CH2CO2H |
| 6 | tBu | C(Me)OH | CH(Me) | O | C(O)CH(Me)CH2CO2H |
| 7 | tBu | C(O) | CH2 | O | CO2H |
| 8 | tBu | CHOH | CH2 | O | CO2H |
| 9 | tBu | C(Me)OH | CH2 | O | CO2H |
| 10 | tBu | C(O) | CH(Me) | O | CO2H |
| 11 | tBu | CHOH | CH(Me) | O | CO2H |
| 12 | tBu | C(Me)OH | CH(Me) | O | CO2H |
| 13 | tBu | C(O) | CH2 | O | C(O)NH2 |
| 14 | tBu | CHOH | CH2 | O | C(O)NH2 |
| 15 | tBu | C(Me)OH | CH2 | O | C(O)NH2 |
| 16 | tBu | C(O) | CH(Me) | O | C(O)NH2 |
| 17 | tBu | CHOH | CH(Me) | O | C(O)NH2 |
| 18 | tBu | C(Me)OH | CH(Me) | O | C(O)NH2 |
| 19 | tBu | C(O) | CH2 | O | C(O)NMe2 |
| 20 | tBu | CHOH | CH2 | O | C(O)NMe2 |
| 21 | tBu | C(Me)OH | CH2 | O | C(O)NMe2 |
| 22 | tBu | C(O) | CH(Me) | O | C(O)NMe2 |
| 23 | tBu | CHOH | CH(Me) | O | C(O)NMe2 |
| 24 | tBu | C(Me)OH | CH(Me) | O | C(O)NMe2 |
| 25 | tBu | C(O) | CH2 | O | 5-tetrazolyl |
| 26 | tBu | CHOH | CH2 | O | 5-tetrazolyl |
| 27 | tBu | C(Me)OH | CH2 | O | 5-tetrazolyl |
| 28 | tBu | C(O) | CH(Me) | O | 5-tetrazolyl |
| 29 | tBu | CHOH | CH(Me) | O | 5-tetrazolyl |
| 30 | tBu | C(Me)OH | CH(Me) | O | 5-tetrazolyl |
| 31 | tBu | C(O) | CH2 | O | C(O)—NH-5-tetrazolyl |
| 32 | tBu | CHOH | CH2 | O | C(O)—NH-5-tetrazolyl |
| 33 | tBu | C(Me)OH | CH2 | O | C(O)—NH-5-tetrazolyl |
| 34 | tBu | C(O) | CH(Me) | O | C(O)—NH-5-tetrazolyl |
| 35 | tBu | CHOH | CH(Me) | O | C(O)—NH-5-tetrazolyl |
| 36 | tBu | C(Me)OH | CH(Me) | O | C(O)—NH-5-tetrazolyl |
| 37 | tBu | C(O) | CH2 | O | C(O)NHCH2SO2Me |
| 38 | tBu | CHOH | CH2 | O | C(O)NHCH2SO2Me |
| 39 | tBu | C(Me)OH | CH2 | O | C(O)NHCH2SO2Me |
| 40 | tBu | C(O) | CH(Me) | O | C(O)NHCH2SO2Me |
| 41 | tBu | CHOH | CH(Me) | O | C(O)NHCH2SO2Me |
| 42 | tBu | C(Me)OH | CH(Me) | O | C(O)NHCH2SO2Me |
| 43 | tBu | C(O) | CH2 | O | C(O)NHCH2S(O)Me |
| 44 | tBu | CHOH | CH2 | O | C(O)NHCH2S(O)Me |
| 45 | tBu | C(Me)OH | CH2 | O | C(O)NHCH2S(O)Me |
| 46 | tBu | C(O) | CH(Me) | O | C(O)NHCH2S(O)Me |
| 47 | tBu | CHOH | CH(Me) | O | C(O)NHCH2S(O)Me |
| 48 | tBu | C(Me)OH | CH(Me) | O | C(O)NHCH2S(O)Me |
| 49 | tBu | C(O) | CH2 | O | C(O)NHCH2CH2SO2Me |
| 50 | tBu | CHOH | CH2 | O | C(O)NHCH2CH2SO2Me |
| 51 | tBu | C(Me)OH | CH2 | O | C(O)NHCH2CH2SO2Me |
| 52 | tBu | C(O) | CH(Me) | O | C(O)NHCH2CH2SO2Me |
| 53 | tBu | CHOH | CH(Me) | O | C(O)NHCH2CH2SO2Me |
| 54 | tBu | C(Me)OH | CH(Me) | O | C(O)NHCH2CH2SO2Me |
| 55 | tBu | C(O) | CH2 | O | C(O)NHCH2CH2S(O)Me |
| 56 | tBu | CHOH | CH2 | O | C(O)NHCH2CH2S(O)Me |
| 57 | tBu | C(Me)OH | CH2 | O | C(O)NHCH2CH2S(O)Me |
| 58 | tBu | C(O) | CH(Me) | O | C(O)NHCH2CH2S(O)Me |
| 59 | tBu | CHOH | CH(Me) | O | C(O)NHCH2CH2S(O)Me |
| 60 | tBu | C(Me)OH | CH(Me) | O | C(O)NHCH2CH2S(O)Me |
| 61 | tBu | C(O) | CH2 | O | C(O)NHSO2Me |
| 62 | tBu | CHOH | CH2 | O | C(O)NHSO2Me |
| 63 | tBu | C(Me)OH | CH2 | O | C(O)NHSO2Me |
| 64 | tBu | C(O) | CH(Me) | O | C(O)NHSO2Me |
| 65 | tBu | CHOH | CH(Me) | O | C(O)NHSO2Me |
| 66 | tBu | C(Me)OH | CH(Me) | O | C(O)NHSO2Me |
| 67 | tBu | C(O) | CH2 | O | C(O)NHS(O)Me |
| 68 | tBu | CHOH | CH2 | O | C(O)NHS(O)Me |
| 69 | tBu | C(Me)OH | CH2 | O | C(O)NHS(O)Me |
| 70 | tBu | C(O) | CH(Me) | O | C(O)NHS(O)Me |
| 71 | tBu | CHOH | CH(Me) | O | C(O)NHS(O)Me |
| 72 | tBu | C(Me)OH | CH(Me) | O | C(O)NHS(O)Me |
| 73 | tBu | C(O) | CH2 | O | C(O)NHSO2Et |
| 74 | tBu | CHOH | CH2 | O | C(O)NHSO2Et |
| 75 | tBu | C(Me)OH | CH2 | O | C(O)NHSO2Et |
| 76 | tBu | C(O) | CH(Me) | O | C(O)NHSO2Et |
| 77 | tBu | CHOH | CH(Me) | O | C(O)NHSO2Et |
| 78 | tBu | C(Me)OH | CH(Me) | O | C(O)NHSO2Et |
| 79 | tBu | C(O) | CH2 | O | C(O)NHS(O)Et |
| 80 | tBu | CHOH | CH2 | O | C(O)NHS(O)Et |
| 81 | tBu | C(Me)OH | CH2 | O | C(O)NHS(O)Et |
| 82 | tBu | C(O) | CH(Me) | O | C(O)NHS(O)Et |
| 83 | tBu | CHOH | CH(Me) | O | C(O)NHS(O)Et |
| 84 | tBu | C(Me)OH | CH(Me) | O | C(O)NHS(O)Et |
| 85 | tBu | C(O) | CH2 | O | C(O)NHSO2iPr |
| 86 | tBu | CHOH | CH2 | O | C(O)NHSO2iPr |
| 87 | tBu | C(Me)OH | CH2 | O | C(O)NHSO2iPr |
| 88 | tBu | C(O) | CH(Me) | O | C(O)NHSO2iPr |
| 89 | tBu | CHOH | CH(Me) | O | C(O)NHSO2iPr |
| 90 | tBu | C(Me)OH | CH(Me) | O | C(O)NHSO2iPr |
| 91 | tBu | C(O) | CH2 | O | C(O)NHS(O)iPr |
| 92 | tBu | CHOH | CH2 | O | C(O)NHS(O)iPr |
| 93 | tBu | C(Me)OH | CH2 | O | C(O)NHS(O)iPr |
| 94 | tBu | C(O) | CH(Me) | O | C(O)NHS(O)iPr |
| 95 | tBu | CHOH | CH(Me) | O | C(O)NHS(O)iPr |
| 96 | tBu | C(Me)OH | CH(Me) | O | C(O)NHS(O)iPr |
| 97 | tBu | C(O) | CH2 | O | C(O)NHSO2tBu |
| 98 | tBu | CHOH | CH2 | O | C(O)NHSO2tBu |
| 99 | tBu | C(Me)OH | CH2 | O | C(O)NHSO2tBu |
| 100 | tBu | C(O) | CH(Me) | O | C(O)NHSO2tBu |
| 101 | tBu | CHOH | CH(Me) | O | C(O)NHSO2tBu |
| 102 | tBu | C(Me)OH | CH(Me) | O | C(O)NHSO2tBu |
| 103 | tBu | C(O) | CH2 | O | C(O)NHS(O)tBu |
| 104 | tBu | CHOH | CH2 | O | C(O)NHS(O)tBu |
| 105 | tBu | C(Me)OH | CH2 | O | C(O)NHS(O)tBu |
| 106 | tBu | C(O) | CH(Me) | O | C(O)NHS(O)tBu |
| 107 | tBu | CHOH | CH(Me) | O | C(O)NHS(O)tBu |
| 108 | tBu | C(Me)OH | CH(Me) | O | C(O)NHS(O)tBu |
| 109 | tBu | C(O) | CH2 | O | CH2NHSO2Me |
| 110 | tBu | CHOH | CH2 | O | CH2NHSO2Me |
| 111 | tBu | C(Me)OH | CH2 | O | CH2NHSO2Me |
| 112 | tBu | C(O) | CH(Me) | O | CH2NHSO2Me |
| 113 | tBu | CHOH | CH(Me) | O | CH2NHSO2Me |
| 114 | tBu | C(Me)OH | CH(Me) | O | CH2NHSO2Me |
| 115 | tBu | C(O) | CH2 | O | CH2NHS(O)Me |
| 116 | tBu | CHOH | CH2 | O | CH2NHS(O)Me |
| 117 | tBu | C(Me)OH | CH2 | O | CH2NHS(O)Me |
| 118 | tBu | C(O) | CH(Me) | O | CH2NHS(O)Me |
| 119 | tBu | CHOH | CH(Me) | O | CH2NHS(O)Me |
| 120 | tBu | C(Me)OH | CH(Me) | O | CH2NHS(O)Me |
| 121 | tBu | C(O) | CH2 | O | CH2NHSO2Et |
| 122 | tBu | CHOH | CH2 | O | CH2NHSO2Et |
| 123 | tBu | C(Me)OH | CH2 | O | CH2NHSO2Et |
| 124 | tBu | C(O) | CH(Me) | O | CH2NHSO2Et |
| 125 | tBu | CHOH | CH(Me) | O | CH2NHSO2Et |
| 126 | tBu | C(Me)OH | CH(Me) | O | CH2NHSO2Et |
| 127 | tBu | C(O) | CH2 | O | CH2NHS(O)Et |
| 128 | tBu | CHOH | CH2 | O | CH2NHS(O)Et |
| 129 | tBu | C(Me)OH | CH2 | O | CH2NHS(O)Et |
| 130 | tBu | C(O) | CH(Me) | O | CH2NHS(O)Et |
| 131 | tBu | CHOH | CH(Me) | O | CH2NHS(O)Et |
| 132 | tBu | C(Me)OH | CH(Me) | O | CH2NHS(O)Et |
| 133 | tBu | C(O) | CH2 | O | CH2NHSO2iPr |
| 134 | tBu | CHOH | CH2 | O | CH2NHSO2iPr |
| 135 | tBu | C(Me)OH | CH2 | O | CH2NHSO2iPr |
| 136 | tBu | C(O) | CH(Me) | O | CH2NHSO2iPr |
| 137 | tBu | CHOH | CH(Me) | O | CH2NHSO2iPr |
| 138 | tBu | C(Me)OH | CH(Me) | O | CH2NHSO2iPr |
| 139 | tBu | C(O) | CH2 | O | CH2NHS(O)iPr |
| 140 | tBu | CHOH | CH2 | O | CH2NHS(O)iPr |
| 141 | tBu | C(Me)OH | CH2 | O | CH2NHS(O)iPr |
| 142 | tBu | C(O) | CH(Me) | O | CH2NHS(O)iPr |
| 143 | tBu | CHOH | CH(Me) | O | CH2NHS(O)iPr |
| 144 | tBu | C(Me)OH | CH(Me) | O | CH2NHS(O)iPr |
| 145 | tBu | C(O) | CH2 | O | CH2NHSO2tBu |
| 146 | tBu | CHOH | CH2 | O | CH2NHSO2tBu |
| 147 | tBu | C(Me)OH | CH2 | O | CH2NHSO2tBu |
| 148 | tBu | C(O) | CH(Me) | O | CH2NHSO2tBu |
| 149 | tBu | CHOH | CH(Me) | O | CH2NHSO2tBu |
| 150 | tBu | C(Me)OH | CH(Me) | O | CH2NHSO2tBu |
| 151 | tBu | C(O) | CH2 | O | CH2NHS(O)tBu |
| 152 | tBu | CHOH | CH2 | O | CH2NHS(O)tBu |
| 153 | tBu | C(Me)OH | CH2 | O | CH2NHS(O)tBu |
| 154 | tBu | C(O) | CH(Me) | O | CH2NHS(O)tBu |
| 155 | tBu | CHOH | CH(Me) | O | CH2NHS(O)tBu |
| 156 | tBu | C(Me)OH | CH(Me) | O | CH2NHS(O)tBu |
| 157 | tBu | C(O) | CH2 | O | CH2—N-pyrrolidin-2-one |
| 158 | tBu | CHOH | CH2 | O | CH2—N-pyrrolidin-2-one |
| 159 | tBu | C(Me)OH | CH2 | O | CH2—N-pyrrolidin-2-one |

TABLE 1-continued

| No. | $R_B$ | $L_3$ | $L_2$ | $L_1$ | $R_C$ |
|---|---|---|---|---|---|
| 160 | tBu | C(O) | CH(Me) | O | CH2—N-pyrrolidin-2-one |
| 161 | tBu | CHOH | CH(Me) | O | CH2—N-pyrrolidin-2-one |
| 162 | tBu | C(Me)OH | CH(Me) | O | CH2—N-pyrrolidin-2-one |
| 163 | tBu | C(O) | CH2 | O | CH2-(1-methylpyrrolidin-2-one-3-yl) |
| 164 | tBu | CHOH | CH2 | O | CH2-(1-methylpyrrolidin-2-one-3-yl) |
| 165 | tBu | C(Me)OH | CH2 | O | CH2-(1-methylpyrrolidin-2-one-3-yl) |
| 166 | tBu | C(O) | CH(Me) | O | CH2-(1-methylpyrrolidin-2-one-3-yl) |
| 167 | tBu | CHOH | CH(Me) | O | CH2-(1-methylpyrrolidin-2-one-3-yl) |
| 168 | tBu | C(Me)OH | CH(Me) | O | CH2-(1-methylpyrrolidin-2-one-3-yl) |
| 169 | tBu | C(O) | CH2 | O | CH2CO2Me |
| 170 | tBu | CHOH | CH2 | O | CH2CO2Me |
| 171 | tBu | C(Me)OH | CH2 | O | CH2CO2Me |
| 172 | tBu | C(O) | CH(Me) | O | CH2CO2Me |
| 173 | tBu | CHOH | CH(Me) | O | CH2CO2Me |
| 174 | tBu | C(Me)OH | CH(Me) | O | CH2CO2Me |
| 175 | tBu | C(O) | CH2 | O | CH2CO2H |
| 176 | tBu | CHOH | CH2 | O | CH2CO2H |
| 177 | tBu | C(Me)OH | CH2 | O | CH2CO2H |
| 178 | tBu | C(O) | CH(Me) | O | CH2CO2H |
| 179 | tBu | CHOH | CH(Me) | O | CH2CO2H |
| 180 | tBu | C(Me)OH | CH(Me) | O | CH2CO2H |
| 181 | tBu | C(O) | CH2 | O | CH2C(O)NH2 |
| 182 | tBu | CHOH | CH2 | O | CH2C(O)NH2 |
| 183 | tBu | C(Me)OH | CH2 | O | CH2C(O)NH2 |
| 184 | tBu | C(O) | CH(Me) | O | CH2C(O)NH2 |
| 185 | tBu | CHOH | CH(Me) | O | CH2C(O)NH2 |
| 186 | tBu | C(Me)OH | CH(Me) | O | CH2C(O)NH2 |
| 187 | tBu | C(O) | CH2 | O | CH2C(O)NMe2 |
| 188 | tBu | CHOH | CH2 | O | CH2C(O)NMe2 |
| 189 | tBu | C(Me)OH | CH2 | O | CH2C(O)NMe2 |
| 190 | tBu | C(O) | CH(Me) | O | CH2C(O)NMe2 |
| 191 | tBu | CHOH | CH(Me) | O | CH2C(O)NMe2 |
| 192 | tBu | C(Me)OH | CH(Me) | O | CH2C(O)NMe2 |
| 193 | tBu | C(O) | CH2 | O | CH2C(O)—N-pyrrolidine |
| 194 | tBu | CHOH | CH2 | O | CH2C(O)—N-pyrrolidine |
| 195 | tBu | C(Me)OH | CH2 | O | CH2C(O)—N-pyrrolidine |
| 196 | tBu | C(O) | CH(Me) | O | CH2C(O)—N-pyrrolidine |
| 197 | tBu | CHOH | CH(Me) | O | CH2C(O)—N-pyrrolidine |
| 198 | tBu | C(Me)OH | CH(Me) | O | CH2C(O)—N-pyrrolidine |
| 199 | tBu | C(O) | CH2 | O | CH2-5-tetrazolyl |
| 200 | tBu | CHOH | CH2 | O | CH2-5-tetrazolyl |
| 201 | tBu | C(Me)OH | CH2 | O | CH2-5-tetrazolyl |
| 202 | tBu | C(O) | CH(Me) | O | CH2-5-tetrazolyl |
| 203 | tBu | CHOH | CH(Me) | O | CH2-5-tetrazolyl |
| 204 | tBu | C(Me)OH | CH(Me) | O | CH2-5-tetrazolyl |
| 205 | tBu | C(O) | CH2 | O | C(O)C(O)OH |
| 206 | tBu | CHOH | CH2 | O | C(O)C(O)OH |
| 207 | tBu | C(Me)OH | CH2 | O | C(O)C(O)OH |
| 208 | tBu | C(O) | CH(Me) | O | C(O)C(O)OH |
| 209 | tBu | CHOH | CH(Me) | O | C(O)C(O)OH |
| 210 | tBu | C(Me)OH | CH(Me) | O | C(O)C(O)OH |
| 211 | tBu | C(O) | CH2 | O | CH(OH)C(O)OH |
| 212 | tBu | CHOH | CH2 | O | CH(OH)C(O)OH |
| 213 | tBu | C(Me)OH | CH2 | O | CH(OH)C(O)OH |
| 214 | tBu | C(O) | CH(Me) | O | CH(OH)C(O)OH |
| 215 | tBu | CHOH | CH(Me) | O | CH(OH)C(O)OH |
| 216 | tBu | C(Me)OH | CH(Me) | O | CH(OH)C(O)OH |
| 217 | tBu | C(O) | CH2 | O | C(O)C(O)NH2 |
| 218 | tBu | CHOH | CH2 | O | C(O)C(O)NH2 |
| 219 | tBu | C(Me)OH | CH2 | O | C(O)C(O)NH2 |
| 220 | tBu | C(O) | CH(Me) | O | C(O)C(O)NH2 |
| 221 | tBu | CHOH | CH(Me) | O | C(O)C(O)NH2 |
| 222 | tBu | C(Me)OH | CH(Me) | O | C(O)C(O)NH2 |
| 223 | tBu | C(O) | CH2 | O | CH(OH)C(O)NH2 |
| 224 | tBu | CHOH | CH2 | O | CH(OH)C(O)NH2 |
| 225 | tBu | C(Me)OH | CH2 | O | CH(OH)C(O)NH2 |
| 226 | tBu | C(O) | CH(Me) | O | CH(OH)C(O)NH2 |
| 227 | tBu | CHOH | CH(Me) | O | CH(OH)C(O)NH2 |
| 228 | tBu | C(Me)OH | CH(Me) | O | CH(OH)C(O)NH2 |
| 229 | tBu | C(O) | CH2 | O | C(O)C(O)NMe2 |
| 230 | tBu | CHOH | CH2 | O | C(O)C(O)NMe2 |
| 231 | tBu | C(Me)OH | CH2 | O | C(O)C(O)NMe2 |
| 232 | tBu | C(O) | CH(Me) | O | C(O)C(O)NMe2 |
| 233 | tBu | CHOH | CH(Me) | O | C(O)C(O)NMe2 |
| 234 | tBu | C(Me)OH | CH(Me) | O | C(O)C(O)NMe2 |
| 235 | tBu | C(O) | CH2 | O | CH(OH)C(O)NMe2 |
| 236 | tBu | CHOH | CH2 | O | CH(OH)C(O)NMe2 |
| 237 | tBu | C(Me)OH | CH2 | O | CH(OH)C(O)NMe2 |
| 238 | tBu | C(O) | CH(Me) | O | CH(OH)C(O)NMe2 |
| 239 | tBu | CHOH | CH(Me) | O | CH(OH)C(O)NMe2 |
| 240 | tBu | C(Me)OH | CH(Me) | O | CH(OH)C(O)NMe2 |
| 241 | tBu | C(O) | CH2 | O | CH2CH2CO2H |
| 242 | tBu | CHOH | CH2 | O | CH2CH2CO2H |
| 243 | tBu | C(Me)OH | CH2 | O | CH2CH2CO2H |
| 244 | tBu | C(O) | CH(Me) | O | CH2CH2CO2H |
| 245 | tBu | CHOH | CH(Me) | O | CH2CH2CO2H |
| 246 | tBu | C(Me)OH | CH(Me) | O | CH2CH2CO2H |
| 247 | tBu | C(O) | CH2 | O | CH2CH2C(O)NH2 |
| 248 | tBu | CHOH | CH2 | O | CH2CH2C(O)NH2 |
| 249 | tBu | C(Me)OH | CH2 | O | CH2CH2C(O)NH2 |
| 250 | tBu | C(O) | CH(Me) | O | CH2CH2C(O)NH2 |
| 251 | tBu | CHOH | CH(Me) | O | CH2CH2C(O)NH2 |
| 252 | tBu | C(Me)OH | CH(Me) | O | CH2CH2C(O)NH2 |
| 253 | tBu | C(O) | CH2 | O | CH2CH2C(O)NMe2 |
| 254 | tBu | CHOH | CH2 | O | CH2CH2C(O)NMe2 |
| 255 | tBu | C(Me)OH | CH2 | O | CH2CH2C(O)NMe2 |
| 256 | tBu | C(O) | CH(Me) | O | CH2CH2C(O)NMe2 |
| 257 | tBu | CHOH | CH(Me) | O | CH2CH2C(O)NMe2 |
| 258 | tBu | C(Me)OH | CH(Me) | O | CH2CH2C(O)NMe2 |
| 259 | tBu | C(O) | CH2 | O | CH2CH2-5-tetrazolyl |
| 260 | tBu | CHOH | CH2 | O | CH2CH2-5-tetrazolyl |
| 261 | tBu | C(Me)OH | CH2 | O | CH2CH2-5-tetrazolyl |
| 262 | tBu | C(O) | CH(Me) | O | CH2CH2-5-tetrazolyl |
| 263 | tBu | CHOH | CH(Me) | O | CH2CH2-5-tetrazolyl |
| 264 | tBu | C(Me)OH | CH(Me) | O | CH2CH2-5-tetrazolyl |
| 265 | tBu | C(O) | CH2 | O | CH2S(O)2Me |
| 266 | tBu | CHOH | CH2 | O | CH2S(O)2Me |
| 267 | tBu | C(Me)OH | CH2 | O | CH2S(O)2Me |
| 268 | tBu | C(O) | CH(Me) | O | CH2S(O)2Me |
| 269 | tBu | CHOH | CH(Me) | O | CH2S(O)2Me |
| 270 | tBu | C(Me)OH | CH(Me) | O | CH2S(O)2Me |
| 271 | tBu | C(O) | CH2 | O | CH2S(O)Me |
| 272 | tBu | CHOH | CH2 | O | CH2S(O2Me |
| 273 | tBu | C(Me)OH | CH2 | O | CH2S(O)Me |
| 274 | tBu | C(O) | CH(Me) | O | CH2S(O)Me |
| 275 | tBu | CHOH | CH(Me) | O | CH2S(O)Me |
| 276 | tBu | C(Me)OH | CH(Me) | O | CH2S(O)Me |
| 277 | tBu | C(O) | CH2 | O | CH2CH2S(O)2Me |
| 278 | tBu | CHOH | CH2 | O | CH2CH2S(O)2Me |
| 279 | tBu | C(Me)OH | CH2 | O | CH2CH2S(O)2Me |
| 280 | tBu | C(O) | CH(Me) | O | CH2CH2S(O)2Me |
| 281 | tBu | CHOH | CH(Me) | O | CH2CH2S(O)2Me |
| 282 | tBu | C(Me)OH | CH(Me) | O | CH2CH2S(O)2Me |
| 283 | tBu | C(O) | CH2 | O | CH2CH2S(O)Me |
| 284 | tBu | CHOH | CH2 | O | CH2CH2S(O)Me |
| 285 | tBu | C(Me)OH | CH2 | O | CH2CH2S(O)Me |
| 286 | tBu | C(O) | CH(Me) | O | CH2CH2S(O)Me |
| 287 | tBu | CHOH | CH(Me) | O | CH2CH2S(O)Me |
| 288 | tBu | C(Me)OH | CH(Me) | O | CH2CH2S(O)Me |
| 289 | tBu | C(O) | CH2 | O | CH2CH2CH2S(O)2Me |
| 290 | tBu | CHOH | CH2 | O | CH2CH2CH2S(O)2Me |
| 291 | tBu | C(Me)OH | CH2 | O | CH2CH2CH2S(O)2Me |
| 292 | tBu | C(O) | CH(Me) | O | CH2CH2CH2S(O)2Me |
| 293 | tBu | CHOH | CH(Me) | O | CH2CH2CH2S(O)2Me |
| 294 | tBu | C(Me)OH | CH(Me) | O | CH2CH2CH2S(O)2Me |
| 295 | tBu | C(O) | CH2 | O | CH2CH2CH2S(O)Me |
| 296 | tBu | CHOH | CH2 | O | CH2CH2CH2S(O)Me |
| 297 | tBu | C(Me)OH | CH2 | O | CH2CH2CH2S(O)Me |
| 298 | tBu | C(O) | CH(Me) | O | CH2CH2CH2S(O)Me |
| 299 | tBu | CHOH | CH(Me) | O | CH2CH2CH2S(O)Me |
| 300 | tBu | C(Me)OH | CH(Me) | O | CH2CH2CH2S(O)Me |
| 301 | tBu | C(O) | CH2 | O | CH2S(O)2Et |
| 302 | tBu | CHOH | CH2 | O | CH2S(O)2Et |
| 303 | tBu | C(Me)OH | CH2 | O | CH2S(O)2Et |
| 304 | tBu | C(O) | CH(Me) | O | CH2S(O)2Et |
| 305 | tBu | CHOH | CH(Me) | O | CH2S(O)2Et |
| 306 | tBu | C(Me)OH | CH(Me) | O | CH2S(O)2Et |
| 307 | tBu | C(O) | CH2 | O | CH2S(O)Et |
| 308 | tBu | CHOH | CH2 | O | CH2S(O)Et |
| 309 | tBu | C(Me)OH | CH2 | O | CH2S(O)Et |

TABLE 1-continued

| No. | $R_B$ | $L_3$ | $L_2$ | $L_1$ | $R_C$ |
|---|---|---|---|---|---|
| 310 | tBu | C(O) | CH(Me) | O | CH2S(O)Et |
| 311 | tBu | CHOH | CH(Me) | O | CH2S(O)Et |
| 312 | tBu | C(Me)OH | CH(Me) | O | CH2S(O)Et |
| 313 | tBu | C(O) | CH2 | O | CH2CH2S(O)2Et |
| 314 | tBu | CHOH | CH2 | O | CH2CH2S(O)2Et |
| 315 | tBu | C(Me)OH | CH2 | O | CH2CH2S(O)2Et |
| 316 | tBu | C(O) | CH(Me) | O | CH2CH2S(O)2Et |
| 317 | tBu | CHOH | CH(Me) | O | CH2CH2S(O)2Et |
| 318 | tBu | C(Me)OH | CH(Me) | O | CH2CH2S(O)2Et |
| 319 | tBu | C(O) | CH2 | O | CH2CH2S(O)Et |
| 320 | tBu | CHOH | CH2 | O | CH2CH2S(O)Et |
| 321 | tBu | C(Me)OH | CH2 | O | CH2CH2S(O)Et |
| 322 | tBu | C(O) | CH(Me) | O | CH2CH2S(O)Et |
| 323 | tBu | CHOH | CH(Me) | O | CH2CH2S(O)Et |
| 324 | tBu | C(Me)OH | CH(Me) | O | CH2CH2S(O)Et |
| 325 | tBu | C(O) | CH2 | O | CH2CH2CH2S(O)2Et |
| 326 | tBu | CHOH | CH2 | O | CH2CH2CH2S(O)2Et |
| 327 | tBu | C(Me)OH | CH2 | O | CH2CH2CH2S(O)2Et |
| 328 | tBu | C(O) | CH(Me) | O | CH2CH2CH2S(O)2Et |
| 329 | tBu | CHOH | CH(Me) | O | CH2CH2CH2S(O)2Et |
| 330 | tBu | C(Me)OH | CH(Me) | O | CH2CH2CH2S(O)2Et |
| 331 | tBu | C(O) | CH2 | O | CH2CH2CH2S(O)Et |
| 332 | tBu | CHOH | CH2 | O | CH2CH2CH2S(O)Et |
| 333 | tBu | C(Me)OH | CH2 | O | CH2CH2CH2S(O)Et |
| 334 | tBu | C(O) | CH(Me) | O | CH2CH2CH2S(O)Et |
| 335 | tBu | CHOH | CH(Me) | O | CH2CH2CH2S(O)Et |
| 336 | tBu | C(Me)OH | CH(Me) | O | CH2CH2CH2S(O)Et |
| 337 | tBu | C(O) | CH2 | O | CH2S(O)2iPr |
| 338 | tBu | CHOH | CH2 | O | CH2S(O)2iPr |
| 339 | tBu | C(Me)OH | CH2 | O | CH2S(O)2iPr |
| 340 | tBu | C(O) | CH(Me) | O | CH2S(O)2iPr |
| 341 | tBu | CHOH | CH(Me) | O | CH2S(O)2iPr |
| 342 | tBu | C(Me)OH | CH(Me) | O | CH2S(O)2iPr |
| 343 | tBu | C(O) | CH2 | O | CH2S(O)iPr |
| 344 | tBu | CHOH | CH2 | O | CH2S(O)iPr |
| 345 | tBu | C(Me)OH | CH2 | O | CH2S(O)iPr |
| 346 | tBu | C(O) | CH(Me) | O | CH2S(O)iPr |
| 347 | tBu | CHOH | CH(Me) | O | CH2S(O)iPr |
| 348 | tBu | C(Me)OH | CH(Me) | O | CH2S(O)iPr |
| 349 | tBu | C(O) | CH2 | O | CH2CH2S(O)2iPr |
| 350 | tBu | CHOH | CH2 | O | CH2CH2S(O)2iPr |
| 351 | tBu | C(Me)OH | CH2 | O | CH2CH2S(O)2iPr |
| 352 | tBu | C(O) | CH(Me) | O | CH2CH2S(O)2iPr |
| 353 | tBu | CHOH | CH(Me) | O | CH2CH2S(O)2iPr |
| 354 | tBu | C(Me)OH | CH(Me) | O | CH2CH2S(O)2iPr |
| 355 | tBu | C(O) | CH2 | O | CH2CH2S(O)iPr |
| 356 | tBu | CHOH | CH2 | O | CH2CH2S(O)iPr |
| 357 | tBu | C(Me)OH | CH2 | O | CH2CH2S(O)iPr |
| 358 | tBu | C(O) | CH(Me) | O | CH2CH2S(O)iPr |
| 359 | tBu | CHOH | CH(Me) | O | CH2CH2S(O)iPr |
| 360 | tBu | C(Me)OH | CH(Me) | O | CH2CH2S(O)iPr |
| 361 | tBu | C(O) | CH2 | O | CH2S(O)2tBu |
| 362 | tBu | CHOH | CH2 | O | CH2S(O)2tBu |
| 363 | tBu | C(Me)OH | CH2 | O | CH2S(O)2tBu |
| 364 | tBu | C(O) | CH(Me) | O | CH2S(O)2tBu |
| 365 | tBu | CHOH | CH(Me) | O | CH2S(O)2tBu |
| 366 | tBu | C(Me)OH | CH(Me) | O | CH2S(O)2tBu |
| 367 | tBu | C(O) | CH2 | O | CH2S(O)tBu |
| 368 | tBu | CHOH | CH2 | O | CH2S(O)tBu |
| 369 | tBu | C(Me)OH | CH2 | O | CH2S(O)tBu |
| 370 | tBu | C(O) | CH(Me) | O | CH2S(O)tBu |
| 371 | tBu | CHOH | CH(Me) | O | CH2S(O)tBu |
| 372 | tBu | C(Me)OH | CH(Me) | O | CH2S(O)tBu |
| 373 | tBu | C(O) | CH2 | O | CH2CH2S(O)2tBu |
| 374 | tBu | CHOH | CH2 | O | CH2CH2S(O)2tBu |
| 375 | tBu | C(Me)OH | CH2 | O | CH2CH2S(O)2tBu |
| 376 | tBu | C(O) | CH(Me) | O | CH2CH2S(O)2tBu |
| 377 | tBu | CHOH | CH(Me) | O | CH2CH2S(O)2tBu |
| 378 | tBu | C(Me)OH | CH(Me) | O | CH2CH2S(O)2tBu |
| 379 | tBu | C(O) | CH2 | O | CH2CH2S(O)tBu |
| 380 | tBu | CHOH | CH2 | O | CH2CH2S(O)tBu |
| 381 | tBu | C(Me)OH | CH2 | O | CH2CH2S(O)tBu |
| 382 | tBu | C(O) | CH(Me) | O | CH2CH2S(O)tBu |
| 383 | tBu | CHOH | CH(Me) | O | CH2CH2S(O)tBu |
| 384 | tBu | C(Me)OH | CH(Me) | O | CH2CH2S(O)tBu |
| 385 | tBu | C(O) | CH2 | O | CH2CH2S(O)2NH2 |
| 386 | tBu | CHOH | CH2 | O | CH2CH2S(O)2NH2 |
| 387 | tBu | C(Me)OH | CH2 | O | CH2CH2S(O)2NH2 |
| 388 | tBu | C(O) | CH(Me) | O | CH2CH2S(O)2NH2 |
| 389 | tBu | CHOH | CH(Me) | O | CH2CH2S(O)2NH2 |
| 390 | tBu | C(Me)OH | CH(Me) | O | CH2CH2S(O)2NH2 |
| 391 | tBu | C(O) | CH2 | O | CH2CH2S(O)NH2 |
| 392 | tBu | CHOH | CH2 | O | CH2CH2S(O)NH2 |
| 393 | tBu | C(Me)OH | CH2 | O | CH2CH2S(O)NH2 |
| 394 | tBu | C(O) | CH(Me) | O | CH2CH2S(O)NH2 |
| 395 | tBu | CHOH | CH(Me) | O | CH2CH2S(O)NH2 |
| 396 | tBu | C(Me)OH | CH(Me) | O | CH2CH2S(O)NH2 |
| 397 | tBu | C(O) | CH2 | O | CH2CH2S(O)2NMe2 |
| 398 | tBu | CHOH | CH2 | O | CH2CH2S(O)2NMe2 |
| 399 | tBu | C(Me)OH | CH2 | O | CH2CH2S(O)2NMe2 |
| 400 | tBu | C(O) | CH(Me) | O | CH2CH2S(O)2NMe2 |
| 401 | tBu | CHOH | CH(Me) | O | CH2CH2S(O)2NMe2 |
| 402 | tBu | C(Me)OH | CH(Me) | O | CH2CH2S(O)2NMe2 |
| 403 | tBu | C(O) | CH2 | O | CH2CH2S(O)NMe2 |
| 404 | tBu | CHOH | CH2 | O | CH2CH2S(O)NMe2 |
| 405 | tBu | C(Me)OH | CH2 | O | CH2CH2S(O)NMe2 |
| 406 | tBu | C(O) | CH(Me) | O | CH2CH2S(O)NMe2 |
| 407 | tBu | CHOH | CH(Me) | O | CH2CH2S(O)NMe2 |
| 408 | tBu | C(Me)OH | CH(Me) | O | CH2CH2S(O)NMe2 |
| 409 | tBu | C(O) | CH2 | O | C(O)CH2S(O)2Me |
| 410 | tBu | CHOH | CH2 | O | C(O)CH2S(O)2Me |
| 411 | tBu | C(Me)OH | CH2 | O | C(O)CH2S(O)2Me |
| 412 | tBu | C(O) | CH(Me) | O | C(O)CH2S(O)2Me |
| 413 | tBu | CHOH | CH(Me) | O | C(O)CH2S(O)2Me |
| 414 | tBu | C(Me)OH | CH(Me) | O | C(O)CH2S(O)2Me |
| 415 | tBu | C(O) | CH2 | O | C(O)CH2S(O)Me |
| 416 | tBu | CHOH | CH2 | O | C(O)CH2S(O)Me |
| 417 | tBu | C(Me)OH | CH2 | O | C(O)CH2S(O)Me |
| 418 | tBu | C(O) | CH(Me) | O | C(O)CH2S(O)Me |
| 419 | tBu | CHOH | CH(Me) | O | C(O)CH2S(O)Me |
| 420 | tBu | C(Me)OH | CH(Me) | O | C(O)CH2S(O)Me |
| 421 | tBu | C(O) | CH2 | O | C(O)CH2CH2S(O)2Me |
| 422 | tBu | CHOH | CH2 | O | C(O)CH2CH2S(O)2Me |
| 423 | tBu | C(Me)OH | CH2 | O | C(O)CH2CH2S(O)2Me |
| 424 | tBu | C(O) | CH(Me) | O | C(O)CH2CH2S(O)2Me |
| 425 | tBu | CHOH | CH(Me) | O | C(O)CH2CH2S(O)2Me |
| 426 | tBu | C(Me)OH | CH(Me) | O | C(O)CH2CH2S(O)2Me |
| 427 | tBu | C(O) | CH2 | O | C(O)CH2CH2S(O)Me |
| 428 | tBu | CHOH | CH2 | O | C(O)CH2CH2S(O)Me |
| 429 | tBu | C(Me)OH | CH2 | O | C(O)CH2CH2S(O)Me |
| 430 | tBu | C(O) | CH(Me) | O | C(O)CH2CH2S(O)Me |
| 431 | tBu | CHOH | CH(Me) | O | C(O)CH2CH2S(O)Me |
| 432 | tBu | C(Me)OH | CH(Me) | O | C(O)CH2CH2S(O)Me |
| 433 | tBu | C(O) | CH2 | O | CH2CH2CH2S(O)2NH2 |
| 434 | tBu | CHOH | CH2 | O | CH2CH2CH2S(O)2NH2 |
| 435 | tBu | C(Me)OH | CH2 | O | CH2CH2CH2S(O)2NH2 |
| 436 | tBu | C(O) | CH(Me) | O | CH2CH2CH2S(O)2NH2 |
| 437 | tBu | CHOH | CH(Me) | O | CH2CH2CH2S(O)2NH2 |
| 438 | tBu | C(Me)OH | CH(Me) | O | CH2CH2CH2S(O)2NH2 |
| 439 | tBu | C(O) | CH2 | O | CH2CH2CH2S(O)NH2 |
| 440 | tBu | CHOH | CH2 | O | CH2CH2CH2S(O)NH2 |
| 441 | tBu | C(Me)OH | CH2 | O | CH2CH2CH2S(O)NH2 |
| 442 | tBu | C(O) | CH(Me) | O | CH2CH2CH2S(O)NH2 |
| 443 | tBu | CHOH | CH(Me) | O | CH2CH2CH2S(O)NH2 |
| 444 | tBu | C(Me)OH | CH(Me) | O | CH2CH2CH2S(O)NH2 |
| 445 | tBu | C(O) | CH2 | CH2 | 1,3,4-oxadiazolin-2-one-5-yl |
| 446 | tBu | CHOH | CH2 | CH2 | 1,3,4-oxadiazolin-2-one-5-yl |
| 447 | tBu | C(Me)OH | CH2 | CH2 | 1,3,4-oxadiazolin-2-one-5-yl |
| 448 | tBu | C(O) | CH(Me) | CH2 | 1,3,4-oxadiazolin-2-one-5-yl |
| 449 | tBu | CHOH | CH(Me) | CH2 | 1,3,4-oxadiazolin-2-one-5-yl |
| 450 | tBu | C(Me)OH | CH(Me) | CH2 | 1,3,4-oxadiazolin-2-one-5-yl |
| 451 | tBu | C(O) | CH2 | CH2 | 1,3,4-oxadiazolin-2-thione-5-yl |
| 452 | tBu | CHOH | CH2 | CH2 | 1,3,4-oxadiazolin-2-thione-5-yl |
| 453 | tBu | C(Me)OH | CH2 | CH2 | 1,3,4-oxadiazolin-2-thione-5-yl |
| 454 | tBu | C(O) | CH(Me) | CH2 | 1,3,4-oxadiazolin-2-thione-5-yl |
| 455 | tBu | CHOH | CH(Me) | CH2 | 1,3,4-oxadiazolin-2-thione-5-yl |
| 456 | tBu | C(Me)OH | CH(Me) | CH2 | 1,3,4-oxadiazolin-2-thione-5-yl |
| 457 | tBu | C(O) | CH2 | CH2 | imidazolidine-2,4-dione-5-yl |
| 458 | tBu | CHOH | CH2 | CH2 | imidazolidine-2,4-dione-5-yl |
| 459 | tBu | C(Me)OH | CH2 | CH2 | imidazolidine-2,4-dione-5-yl |

TABLE 1-continued

| No. | $R_B$ | $L_3$ | $L_2$ | $L_1$ | $R_C$ |
|---|---|---|---|---|---|
| 460 | tBu | C(O) | CH(Me) | CH2 | imidazolidine-2,4-dione-5-yl |
| 461 | tBu | CHOH | CH(Me) | CH2 | imidazolidine-2,4-dione-5-yl |
| 462 | tBu | C(Me)OH | CH(Me) | CH2 | imidazolidine-2,4-dione-5-yl |
| 463 | tBu | C(O) | CH2 | CH2 | isoxazol-3-ol-5-yl |
| 464 | tBu | CHOH | CH2 | CH2 | isoxazol-3-ol-5-yl |
| 465 | tBu | C(Me)OH | CH2 | CH2 | isoxazol-3-ol-5-yl |
| 466 | tBu | C(O) | CH(Me) | CH2 | isoxazol-3-ol-5-yl |
| 467 | tBu | CHOH | CH(Me) | CH2 | isoxazol-3-ol-5-yl |
| 468 | tBu | C(Me)OH | CH(Me) | CH2 | isoxazol-3-ol-5-yl |

Among other preferred compounds of the invention are also those represented by the formula:

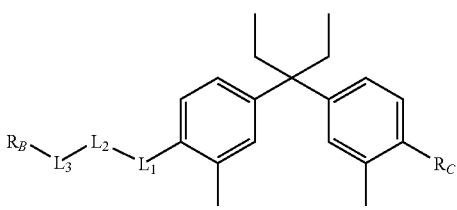

and pharmaceutically acceptable salts thereof; wherein;

said compound is selected from a compound code numbered 1A thru 468A, with each compound having the specific selection of substituents $R_B$, $R_C$, $L_1$, $L_2$, and $L_3$ shown in the row following the compound code number, as set out in the following Table 2:

TABLE 2

| | $R_B$ | $L_3$ | $L_2$ | $L_1$ | $R_C$ |
|---|---|---|---|---|---|
| 1A | tBu | C(O) | CH2 | CH2 | C(O)CH(Me)CH2CO2H |
| 2A | tBu | CHOH | CH2 | CH2 | C(O)CH(Me)CH2CO2H |
| 3A | tBu | C(Me)OH | CH2 | CH2 | C(O)CH(Me)CH2CO2H |
| 4A | tBu | C(O) | CH(Me) | CH2 | C(O)CH(Me)CH2CO2H |
| 5A | tBu | CHOH | CH(Me) | CH2 | C(O)CH(Me)CH2CO2H |
| 6A | tBu | C(Me)OH | CH(Me) | CH2 | C(O)CH(Me)CH2CO2H |
| 7A | tBu | C(O) | CH2 | CH2 | CO2H |
| 8A | tBu | CHOH | CH2 | CH2 | CO2H |
| 9A | tBu | C(Me)OH | CH2 | CH2 | CO2H |
| 10A | tBu | C(O) | CH(Me) | CH2 | CO2H |
| 11A | tBu | CHOH | CH(Me) | CH2 | CO2H |
| 12A | tBu | C(Me)OH | CH(Me) | CH2 | CO2H |
| 13A | tBu | C(O) | CH2 | CH2 | C(O)NH2 |
| 14A | tBu | CHOH | CH2 | CH2 | C(O)NH2 |
| 15A | tBu | C(Me)OH | CH2 | CH2 | C(O)NH2 |
| 16A | tBu | C(O) | CH(Me) | CH2 | C(O)NH2 |
| 17A | tBu | CHOH | CH(Me) | CH2 | C(O)NH2 |
| 18A | tBu | C(Me)OH | CH(Me) | CH2 | C(O)NH2 |
| 19A | tBu | C(O) | CH2 | CH2 | C(O)NMe2 |
| 20A | tBu | CHOH | CH2 | CH2 | C(O)NMe2 |
| 21A | tBu | C(Me)OH | CH2 | CH2 | C(O)NMe2 |
| 22A | tBu | C(O) | CH(Me) | CH2 | C(O)NMe2 |
| 23A | tBu | CHOH | CH(Me) | CH2 | C(O)NMe2 |
| 24A | tBu | C(Me)OH | CH(Me) | CH2 | C(O)NMe2 |
| 25A | tBu | C(O) | CH2 | CH2 | 5-tetrazolyl |
| 26A | tBu | CHOH | CH2 | CH2 | 5-tetrazolyl |
| 27A | tBu | C(Me)OH | CH2 | CH2 | 5-tetrazolyl |
| 28A | tBu | C(O) | CH(Me) | CH2 | 5-tetrazolyl |
| 29A | tBu | CHOH | CH(Me) | CH2 | 5-tetrazolyl |
| 30A | tBu | C(Me)OH | CH(Me) | CH2 | 5-tetrazolyl |
| 31A | tBu | C(O) | CH2 | CH2 | C(O)—NH-5-tetrazolyl |
| 32A | tBu | CHOH | CH2 | CH2 | C(O)—NH-5-tetrazolyl |
| 33A | tBu | C(Me)OH | CH2 | CH2 | C(O)—NH-5-tetrazolyl |
| 34A | tBu | C(O) | CH(Me) | CH2 | C(O)—NH-5-tetrazolyl |
| 35A | tBu | CHOH | CH(Me) | CH2 | C(O)—NH-5-tetrazolyl |
| 36A | tBu | C(Me)OH | CH(Me) | CH2 | C(O)—NH-5-tetrazolyl |
| 37A | tBu | C(O) | CH2 | CH2 | C(O)NHCH2SO2Me |
| 38A | tBu | CHOH | CH2 | CH2 | C(O)NHCH2SO2Me |
| 39A | tBu | C(Me)OH | CH2 | CH2 | C(O)NHCH2SO2Me |
| 40A | tBu | C(O) | CH(Me) | CH2 | C(O)NHCH2SO2Me |
| 41A | tBu | CHOH | CH(Me) | CH2 | C(O)NHCH2SO2Me |
| 42A | tBu | C(Me)OH | CH(Me) | CH2 | C(O)NHCH2SO2Me |
| 43A | tBu | C(O) | CH2 | CH2 | C(O)NHCH2S(O)Me |
| 44A | tBu | CHOH | CH2 | CH2 | C(O)NHCH2S(O)Me |
| 45A | tBu | C(Me)OH | CH2 | CH2 | C(O)NHCH2S(O)Me |
| 46A | tBu | C(O) | CH(Me) | CH2 | C(O)NHCH2S(O)Me |
| 47A | tBu | CHOH | CH(Me) | CH2 | C(O)NHCH2S(O)Me |
| 48A | tBu | C(Me)OH | CH(Me) | CH2 | C(O)NHCH2S(O)Me |
| 49A | tBu | C(O) | CH2 | CH2 | C(O)NHCH2CH2SO2Me |
| 50A | tBu | CHOH | CH2 | CH2 | C(O)NHCH2CH2SO2Me |
| 51A | tBu | C(Me)OH | CH2 | CH2 | C(O)NHCH2CH2SO2Me |
| 52A | tBu | C(O) | CH(Me) | CH2 | C(O)NHCH2CH2SO2Me |
| 53A | tBu | CHOH | CH(Me) | CH2 | C(O)NHCH2CH2SO2Me |
| 54A | tBu | C(Me)OH | CH(Me) | CH2 | C(O)NHCH2CH2SO2Me |
| 55A | tBu | C(O) | CH2 | CH2 | C(O)NHCH2CH2S(O)Me |
| 56A | tBu | CHOH | CH2 | CH2 | C(O)NHCH2CH2S(O)Me |
| 57A | tBu | C(Me)OH | CH2 | CH2 | C(O)NHCH2CH2S(O)Me |
| 58A | tBu | C(O) | CH(Me) | CH2 | C(O)NHCH2CH2S(O)Me |
| 59A | tBu | CHOH | CH(Me) | CH2 | C(O)NHCH2CH2S(O)Me |
| 60A | tBu | C(Me)OH | CH(Me) | CH2 | C(O)NHCH2CH2S(O)Me |
| 61A | tBu | C(O) | CH2 | CH2 | C(O)NHSO2Me |
| 62A | tBu | CHOH | CH2 | CH2 | C(O)NHSO2Me |
| 63A | tBu | C(Me)OH | CH2 | CH2 | C(O)NHSO2Me |
| 64A | tBu | C(O) | CH(Me) | CH2 | C(O)NHSO2Me |
| 65A | tBu | CHOH | CH(Me) | CH2 | C(O)NHSO2Me |
| 66A | tBu | C(Me)OH | CH(Me) | CH2 | C(O)NHSO2Me |
| 67A | tBu | C(O) | CH2 | CH2 | C(O)NHS(O)Me |
| 68A | tBu | CHOH | CH2 | CH2 | C(O)NHS(O)Me |
| 69A | tBu | C(Me)OH | CH2 | CH2 | C(O)NHS(O)Me |
| 70A | tBu | C(O) | CH(Me) | CH2 | C(O)NHS(O)Me |
| 71A | tBu | CHOH | CH(Me) | CH2 | C(O)NHS(O)Me |
| 72A | tBu | C(Me)OH | CH(Me) | CH2 | C(O)NHS(O)Me |
| 73A | tBu | C(O) | CH2 | CH2 | C(O)NHSO2Et |
| 74A | tBu | CHOH | CH2 | CH2 | C(O)NHSO2Et |
| 75A | tBu | C(Me)OH | CH2 | CH2 | C(O)NHSO2Et |
| 76A | tBu | C(O) | CH(Me) | CH2 | C(O)NHSO2Et |
| 77A | tBu | CHOH | CH(Me) | CH2 | C(O)NHSO2Et |
| 78A | tBu | C(Me)OH | CH(Me) | CH2 | C(O)NHSO2Et |
| 79A | tBu | C(O) | CH2 | CH2 | C(O)NHS(O)Et |
| 80A | tBu | CHOH | CH2 | CH2 | C(O)NHS(O)Et |
| 81A | tBu | C(Me)OH | CH2 | CH2 | C(O)NHS(O)Et |
| 82A | tBu | C(O) | CH(Me) | CH2 | C(O)NHS(O)Et |
| 83A | tBu | CHOH | CH(Me) | CH2 | C(O)NHS(O)Et |
| 84A | tBu | C(Me)OH | CH(Me) | CH2 | C(O)NHS(O)Et |
| 85A | tBu | C(O) | CH2 | CH2 | C(O)NHSO2iPr |
| 86A | tBu | CHOH | CH2 | CH2 | C(O)NHSO2iPr |
| 87A | tBu | C(Me)OH | CH2 | CH2 | C(O)NHSO2iPr |
| 88A | tBu | C(O) | CH(Me) | CH2 | C(O)NHSO2iPr |
| 89A | tBu | CHOH | CH(Me) | CH2 | C(O)NHSO2iPr |
| 90A | tBu | C(Me)OH | CH(Me) | CH2 | C(O)NHSO2iPr |
| 91A | tBu | C(O) | CH2 | CH2 | C(O)NHS(O)iPr |
| 92A | tBu | CHOH | CH2 | CH2 | C(O)NHS(O)iPr |
| 93A | tBu | C(Me)OH | CH2 | CH2 | C(O)NHS(O)iPr |
| 94A | tBu | C(O) | CH(Me) | CH2 | C(O)NHS(O)iPr |
| 95A | tBu | CHOH | CH(Me) | CH2 | C(O)NHS(O)iPr |
| 96A | tBu | C(Me)OH | CH(Me) | CH2 | C(O)NHS(O)iPr |
| 97A | tBu | C(O) | CH2 | CH2 | C(O)NHSO2tBu |
| 98A | tBu | CHOH | CH2 | CH2 | C(O)NHSO2tBu |
| 99A | tBu | C(Me)OH | CH2 | CH2 | C(O)NHSO2tBu |
| 100A | tBu | C(O) | CH(Me) | CH2 | C(O)NHSO2tBu |
| 101A | tBu | CHOH | CH(Me) | CH2 | C(O)NHSO2tBu |
| 102A | tBu | C(Me)OH | CH(Me) | CH2 | C(O)NHSO2tBu |
| 103A | tBu | C(O) | CH2 | CH2 | C(O)NHS(O)tBu |
| 104A | tBu | CHOH | CH2 | CH2 | C(O)NHS(O)tBu |
| 105A | tBu | C(Me)OH | CH2 | CH2 | C(O)NHS(O)tBu |
| 106A | tBu | C(O) | CH(Me) | CH2 | C(O)NHS(O)tBu |
| 107A | tBu | CHOH | CH(Me) | CH2 | C(O)NHS(O)tBu |
| 108A | tBu | C(Me)OH | CH(Me) | CH2 | C(O)NHS(O)tBu |
| 109A | tBu | C(O) | CH2 | CH2 | CH2NHSO2Me |
| 110A | tBu | CHOH | CH2 | CH2 | CH2NHSO2Me |
| 111A | tBu | C(Me)OH | CH2 | CH2 | CH2NHSO2Me |
| 112A | tBu | C(O) | CH(Me) | CH2 | CH2NHSO2Me |
| 113A | tBu | CHOH | CH(Me) | CH2 | CH2NHSO2Me |
| 114A | tBu | C(Me)OH | CH(Me) | CH2 | CH2NHSO2Me |

TABLE 2-continued

| $R_B$ | $L_3$ | $L_2$ | $L_1$ | $R_C$ |
|---|---|---|---|---|
| 115A tBu | C(O) | CH2 | CH2 | CH2NHS(O)Me |
| 116A tBu | CHOH | CH2 | CH2 | CH2NHS(O)Me |
| 117A tBu | C(Me)OH | CH2 | CH2 | CH2NHS(O)Me |
| 118A tBu | C(O) | CH(Me) | CH2 | CH2NHS(O)Me |
| 119A tBu | CHOH | CH(Me) | CH2 | CH2NHS(O)Me |
| 120A tBu | C(Me)OH | CH(Me) | CH2 | CH2NHS(O)Me |
| 121A tBu | C(O) | CH2 | CH2 | CH2NHSO2Et |
| 122A tBu | CHOH | CH2 | CH2 | CH2NHSO2Et |
| 123A tBu | C(Me)OH | CH2 | CH2 | CH2NHSO2Et |
| 124A tBu | C(O) | CH(Me) | CH2 | CH2NHSO2Et |
| 125A tBu | CHOH | CH(Me) | CH2 | CH2NHSO2Et |
| 126A tBu | C(Me)OH | CH(Me) | CH2 | CH2NHSO2Et |
| 127A tBu | C(O) | CH2 | CH2 | CH2NHS(O)Et |
| 128A tBu | CHOH | CH2 | CH2 | CH2NHS(O)Et |
| 129A tBu | C(Me)OH | CH2 | CH2 | CH2NHS(O)Et |
| 130A tBu | C(O) | CH(Me) | CH2 | CH2NHS(O)Et |
| 131A tBu | CHOH | CH(Me) | CH2 | CH2NHS(O)Et |
| 132A tBu | C(Me)OH | CH(Me) | CH2 | CH2NHS(O)Et |
| 133A tBu | C(O) | CH2 | CH2 | CH2NHSO2iPr |
| 134A tBu | CHOH | CH2 | CH2 | CH2NHSO2iPr |
| 135A tBu | C(Me)OH | CH2 | CH2 | CH2NHSO2iPr |
| 136A tBu | C(O) | CH(Me) | CH2 | CH2NHSO2iPr |
| 137A tBu | CHOH | CH(Me) | CH2 | CH2NHSO2iPr |
| 138A tBu | C(Me)OH | CH(Me) | CH2 | CH2NHSO2iPr |
| 139A tBu | C(O) | CH2 | CH2 | CH2NHS(O)iPr |
| 140A tBu | CHOH | CH2 | CH2 | CH2NHS(O)iPr |
| 141A tBu | C(Me)OH | CH2 | CH2 | CH2NHS(O)iPr |
| 142A tBu | C(O) | CH(Me) | CH2 | CH2NHS(O)iPr |
| 143A tBu | CHOH | CH(Me) | CH2 | CH2NHS(O)iPr |
| 144A tBu | C(Me)OH | CH(Me) | CH2 | CH2NHS(O)iPr |
| 145A tBu | C(O) | CH2 | CH2 | CH2NHSO2tBu |
| 146A tBu | CHOH | CH2 | CH2 | CH2NHSO2tBu |
| 147A tBu | C(Me)OH | CH2 | CH2 | CH2NHSO2tBu |
| 148A tBu | C(O) | CH(Me) | CH2 | CH2NHSO2tBu |
| 149A tBu | CHOH | CH(Me) | CH2 | CH2NHSO2tBu |
| 150A tBu | C(Me)OH | CH(Me) | CH2 | CH2NHSO2tBu |
| 151A tBu | C(O) | CH2 | CH2 | CH2NHS(O)tBu |
| 152A tBu | CHOH | CH2 | CH2 | CH2NHS(O)tBu |
| 153A tBu | C(Me)OH | CH2 | CH2 | CH2NHS(O)tBu |
| 154A tBu | C(O) | CH(Me) | CH2 | CH2NHS(O)tBu |
| 155A tBu | CHOH | CH(Me) | CH2 | CH2NHS(O)tBu |
| 156A tBu | C(Me)OH | CH(Me) | CH2 | CH2NHS(O)tBu |
| 157A tBu | C(O) | CH2 | CH2 | CH2—N-pyrrolidin-2-one |
| 158A tBu | CHOH | CH2 | CH2 | CH2—N-pyrrolidin-2-one |
| 159A tBu | C(Me)OH | CH2 | CH2 | CH2—N-pyrrolidin-2-one |
| 160A tBu | C(O) | CH(Me) | CH2 | CH2—N-pyrrolidin-2-one |
| 161A tBu | CHOH | CH(Me) | CH2 | CH2—N-pyrrolidin-2-one |
| 162A tBu | C(Me)OH | CH(Me) | CH2 | CH2—N-pyrrolidin-2-one |
| 163A tBu | C(O) | CH2 | CH2 | CH2-(1-methylpyrrolidin-2-one-3-yl) |
| 164A tBu | CHOH | CH2 | CH2 | CH2-(1-methylpyrrolidin-2-one-3-yl) |
| 165A tBu | C(Me)OH | CH2 | CH2 | CH2-(1-methylpyrrolidin-2-one-3-yl) |
| 166A tBu | C(O) | CH(Me) | CH2 | CH2-(1-methylpyrrolidin-2-one-3-yl) |
| 167A tBu | CHOH | CH(Me) | CH2 | CH2-(1-methylpyrrolidin-2-one-3-yl) |
| 168A tBu | C(Me)OH | CH(Me) | CH2 | CH2-(1-methylpyrrolidin-2-one-3-yl) |
| 169A tBu | C(O) | CH2 | CH2 | CH2CO2Me |
| 170A tBu | CHOH | CH2 | CH2 | CH2CO2Me |
| 171A tBu | C(Me)OH | CH2 | CH2 | CH2CO2Me |
| 172A tBu | C(O) | CH(Me) | CH2 | CH2CO2Me |
| 173A tBu | CHOH | CH(Me) | CH2 | CH2CO2Me |
| 174A tBu | C(Me)OH | CH(Me) | CH2 | CH2CO2Me |
| 175A tBu | C(O) | CH2 | CH2 | CH2CO2H |
| 176A tBu | CHOH | CH2 | CH2 | CH2CO2H |
| 177A tBu | C(Me)OH | CH2 | CH2 | CH2CO2H |
| 178A tBu | C(O) | CH(Me) | CH2 | CH2CO2H |
| 179A tBu | CHOH | CH(Me) | CH2 | CH2CO2H |
| 180A tBu | C(Me)OH | CH(Me) | CH2 | CH2CO2H |
| 181A tBu | C(O) | CH2 | CH2 | CH2C(O)NH2 |
| 182A tBu | CHOH | CH2 | CH2 | CH2C(O)NH2 |
| 183A tBu | C(Me)OH | CH2 | CH2 | CH2C(O)NH2 |
| 184A tBu | C(O) | CH(Me) | CH2 | CH2C(O)NH2 |
| 185A tBu | CHOH | CH(Me) | CH2 | CH2C(O)NH2 |
| 186A tBu | C(Me)OH | CH(Me) | CH2 | CH2C(O)NH2 |
| 187A tBu | C(O) | CH2 | CH2 | CH2C(O)NMe2 |
| 188A tBu | CHOH | CH2 | CH2 | CH2C(O)NMe2 |
| 189A tBu | C(Me)OH | CH2 | CH2 | CH2C(O)NMe2 |
| 190A tBu | C(O) | CH(Me) | CH2 | CH2C(O)NMe2 |
| 191A tBu | CHOH | CH(Me) | CH2 | CH2C(O)NMe2 |
| 192A tBu | C(Me)OH | CH(Me) | CH2 | CH2C(O)NMe2 |
| 193A tBu | C(O) | CH2 | CH2 | CH2C(O)—N-pyrrolidine |
| 194A tBu | CHOH | CH2 | CH2 | CH2C(O)—N-pyrrolidine |
| 195A tBu | C(Me)OH | CH2 | CH2 | CH2C(O)—N-pyrrolidine |
| 196A tBu | C(O) | CH(Me) | CH2 | CH2C(O)—N-pyrrolidine |
| 197A tBu | CHOH | CH(Me) | CH2 | CH2C(O)—N-pyrrolidine |
| 198A tBu | C(Me)OH | CH(Me) | CH2 | CH2C(O)—N-pyrrolidine |
| 199A tBu | C(O) | CH2 | CH2 | CH2-5-tetrazolyl |
| 200A tBu | CHOH | CH2 | CH2 | CH2-5-tetrazolyl |
| 201A tBu | C(Me)OH | CH2 | CH2 | CH2-5-tetrazolyl |
| 202A tBu | C(O) | CH(Me) | CH2 | CH2-5-tetrazolyl |
| 203A tBu | CHOH | CH(Me) | CH2 | CH2-5-tetrazolyl |
| 204A tBu | C(Me)OH | CH(Me) | CH2 | CH2-5-tetrazolyl |
| 205A tBu | C(O) | CH2 | CH2 | C(O)C(O)OH |
| 206A tBu | CHOH | CH2 | CH2 | C(O)C(O)OH |
| 207A tBu | C(Me)OH | CH2 | CH2 | C(O)C(O)OH |
| 208A tBu | C(O) | CH(Me) | CH2 | C(O)C(O)OH |
| 209A tBu | CHOH | CH(Me) | CH2 | C(O)C(O)OH |
| 210A tBu | C(Me)OH | CH(Me) | CH2 | C(O)C(O)OH |
| 211A tBu | C(O) | CH2 | CH2 | CH(OH)C(O)OH |
| 212A tBu | CHOH | CH2 | CH2 | CH(OH)C(O)OH |
| 213A tBu | C(Me)OH | CH2 | CH2 | CH(OH)C(O)OH |
| 214A tBu | C(O) | CH(Me) | CH2 | CH(OH)C(O)OH |
| 215A tBu | CHOH | CH(Me) | CH2 | CH(OH)C(O)OH |
| 216A tBu | C(Me)OH | CH(Me) | CH2 | CH(OH)C(O)OH |
| 217A tBu | C(O) | CH2 | CH2 | C(O)C(O)NH2 |
| 218A tBu | CHOH | CH2 | CH2 | C(O)C(O)NH2 |
| 219A tBu | C(Me)OH | CH2 | CH2 | C(O)C(O)NH2 |
| 220A tBu | C(O) | CH(Me) | CH2 | C(O)C(O)NH2 |
| 221A tBu | CHOH | CH(Me) | CH2 | C(O)C(O)NH2 |
| 222A tBu | C(Me)OH | CH(Me) | CH2 | C(O)C(O)NH2 |
| 223A tBu | C(O) | CH2 | CH2 | CH(OH)C(O)NH2 |
| 224A tBu | CHOH | CH2 | CH2 | CH(OH)C(O)NH2 |
| 225A tBu | C(Me)OH | CH2 | CH2 | CH(OH)C(O)NH2 |
| 226A tBu | C(O) | CH(Me) | CH2 | CH(OH)C(O)NH2 |
| 227A tBu | CHOH | CH(Me) | CH2 | CH(OH)C(O)NH2 |
| 228A tBu | C(Me)OH | CH(Me) | CH2 | CH(OH)C(O)NH2 |
| 229A tBu | C(O) | CH2 | CH2 | C(O)C(O)NMe2 |
| 230A tBu | CHOH | CH2 | CH2 | C(O)C(O)NMe2 |
| 231A tBu | C(Me)OH | CH2 | CH2 | C(O)C(O)NMe2 |
| 232A tBu | C(O) | CH(Me) | CH2 | C(O)C(O)NMe2 |
| 233A tBu | CHOH | CH(Me) | CH2 | C(O)C(O)NMe2 |
| 234A tBu | C(Me)OH | CH(Me) | CH2 | C(O)C(O)NMe2 |
| 235A tBu | C(O) | CH2 | CH2 | CH(OH)C(O)NMe2 |
| 236A tBu | CHOH | CH2 | CH2 | CH(OH)C(O)NMe2 |
| 237A tBu | C(Me)OH | CH2 | CH2 | CH(OH)C(O)NMe2 |
| 238A tBu | C(O) | CH(Me) | CH2 | CH(OH)C(O)NMe2 |
| 239A tBu | CHOH | CH(Me) | CH2 | CH(OH)C(O)NMe2 |
| 240A tBu | C(Me)OH | CH(Me) | CH2 | CH(OH)C(O)NMe2 |
| 241A tBu | C(O) | CH2 | CH2 | CH2CH2CO2H |
| 242A tBu | CHOH | CH2 | CH2 | CH2CH2CO2H |
| 243A tBu | C(Me)OH | CH2 | CH2 | CH2CH2CO2H |
| 244A tBu | C(O) | CH(Me) | CH2 | CH2CH2CO2H |
| 245A tBu | CHOH | CH(Me) | CH2 | CH2CH2CO2H |
| 246A tBu | C(Me)OH | CH(Me) | CH2 | CH2CH2CO2H |
| 247A tBu | C(O) | CH2 | CH2 | CH2CH2C(O)NH2 |
| 248A tBu | CHOH | CH2 | CH2 | CH2CH2C(O)NH2 |
| 249A tBu | C(Me)OH | CH2 | CH2 | CH2CH2C(O)NH2 |
| 250A tBu | C(O) | CH(Me) | CH2 | CH2CH2C(O)NH2 |
| 251A tBu | CHOH | CH(Me) | CH2 | CH2CH2C(O)NH2 |
| 252A tBu | C(Me)OH | CH(Me) | CH2 | CH2CH2C(O)NH2 |
| 253A tBu | C(O) | CH2 | CH2 | CH2CH2C(O)NMe2 |
| 254A tBu | CHOH | CH2 | CH2 | CH2CH2C(O)NMe2 |
| 255A tBu | C(Me)OH | CH2 | CH2 | CH2CH2C(O)NMe2 |
| 256A tBu | C(O) | CH(Me) | CH2 | CH2CH2C(O)NMe2 |
| 257A tBu | CHOH | CH(Me) | CH2 | CH2CH2C(O)NMe2 |
| 258A tBu | C(Me)OH | CH(Me) | CH2 | CH2CH2C(O)NMe2 |
| 259A tBu | C(O) | CH2 | CH2 | CH2CH2-5-tetrazolyl |
| 260A tBu | CHOH | CH2 | CH2 | CH2CH2-5-tetrazolyl |
| 261A tBu | C(Me)OH | CH2 | CH2 | CH2CH2-5-tetrazolyl |
| 262A tBu | C(O) | CH(Me) | CH2 | CH2CH2-5-tetrazolyl |

TABLE 2-continued

| $R_B$ | $L_3$ | $L_2$ | $L_1$ | $R_C$ |
|---|---|---|---|---|
| 263A tBu | CHOH | CH(Me) | CH2 | CH2CH2-5-tetrazolyl |
| 264A tBu | C(Me)OH | CH(Me) | CH2 | CH2CH2-5-tetrazolyl |
| 265A tBu | C(O) | CH2 | CH2 | CH2S(O)2Me |
| 266A tBu | CHOH | CH2 | CH2 | CH2S(O)2Me |
| 267A tBu | C(Me)OH | CH2 | CH2 | CH2S(O)2Me |
| 268A tBu | C(O) | CH(Me) | CH2 | CH2S(O)2Me |
| 269A tBu | CHOH | CH(Me) | CH2 | CH2S(O)2Me |
| 270A tBu | C(Me)OH | CH(Me) | CH2 | CH2S(O)2Me |
| 271A tBu | C(O) | CH2 | CH2 | CH2S(O)Me |
| 272A tBu | CHOH | CH2 | CH2 | CH2S(O2)Me |
| 273A tBu | C(Me)OH | CH2 | CH2 | CH2S(O)Me |
| 274A tBu | C(O) | CH(Me) | CH2 | CH2S(O)Me |
| 275A tBu | CHOH | CH(Me) | CH2 | CH2S(O)Me |
| 276A tBu | C(Me)OH | CH(Me) | CH2 | CH2S(O)Me |
| 277A tBu | C(O) | CH2 | CH2 | CH2CH2S(O)2Me |
| 278A tBu | CHOH | CH2 | CH2 | CH2CH2S(O)2Me |
| 279A tBu | C(Me)OH | CH2 | CH2 | CH2CH2S(O)2Me |
| 280A tBu | C(O) | CH(Me) | CH2 | CH2CH2S(O)2Me |
| 281A tBu | CHOH | CH(Me) | CH2 | CH2CH2S(O)2Me |
| 282A tBu | C(Me)OH | CH(Me) | CH2 | CH2CH2S(O)2Me |
| 283A tBu | C(O) | CH2 | CH2 | CH2CH2S(O)Me |
| 284A tBu | CHOH | CH2 | CH2 | CH2CH2S(O)Me |
| 285A tBu | C(Me)OH | CH2 | CH2 | CH2CH2S(O)Me |
| 286A tBu | C(O) | CH(Me) | CH2 | CH2CH2S(O)Me |
| 287A tBu | CHOH | CH(Me) | CH2 | CH2CH2S(O)Me |
| 288A tBu | C(Me)OH | CH(Me) | CH2 | CH2CH2S(O)Me |
| 289A tBu | C(O) | CH2 | CH2 | CH2CH2CH2S(O)2Me |
| 290A tBu | CHOH | CH2 | CH2 | CH2CH2CH2S(O)2Me |
| 291A tBu | C(Me)OH | CH2 | CH2 | CH2CH2CH2S(O)2Me |
| 292A tBu | C(O) | CH(Me) | CH2 | CH2CH2CH2S(O)2Me |
| 293A tBu | CHOH | CH(Me) | CH2 | CH2CH2CH2S(O)2Me |
| 294A tBu | C(Me)OH | CH(Me) | CH2 | CH2CH2CH2S(O)2Me |
| 295A tBu | C(O) | CH2 | CH2 | CH2CH2CH2S(O)Me |
| 296A tBu | CHOH | CH2 | CH2 | CH2CH2CH2S(O)Me |
| 297A tBu | C(Me)OH | CH2 | CH2 | CH2CH2CH2S(O)Me |
| 298A tBu | C(O) | CH(Me) | CH2 | CH2CH2CH2S(O)Me |
| 299A tBu | CHOH | CH(Me) | CH2 | CH2CH2CH2S(O)Me |
| 300A tBu | C(Me)OH | CH(Me) | CH2 | CH2CH2CH2S(O)Me |
| 301A tBu | C(O) | CH2 | CH2 | CH2S(O)2Et |
| 302A tBu | CHOH | CH2 | CH2 | CH2S(O)2Et |
| 303A tBu | C(Me)OH | CH2 | CH2 | CH2S(O)2Et |
| 304A tBu | C(O) | CH(Me) | CH2 | CH2S(O)2Et |
| 305A tBu | CHOH | CH(Me) | CH2 | CH2S(O)2Et |
| 306A tBu | C(Me)OH | CH(Me) | CH2 | CH2S(O)2Et |
| 307A tBu | C(O) | CH2 | CH2 | CH2S(O)Et |
| 308A tBu | CHOH | CH2 | CH2 | CH2S(O)Et |
| 309A tBu | C(Me)OH | CH2 | CH2 | CH2S(O)Et |
| 310A tBu | C(O) | CH(Me) | CH2 | CH2S(O)Et |
| 311A tBu | CHOH | CH(Me) | CH2 | CH2S(O)Et |
| 312A tBu | C(Me)OH | CH(Me) | CH2 | CH2S(O)Et |
| 313A tBu | C(O) | CH2 | CH2 | CH2CH2S(O)2Et |
| 314A tBu | CHOH | CH2 | CH2 | CH2CH2S(O)2Et |
| 315A tBu | C(Me)OH | CH2 | CH2 | CH2CH2S(O)2Et |
| 316A tBu | C(O) | CH(Me) | CH2 | CH2CH2S(O)2Et |
| 317A tBu | CHOH | CH(Me) | CH2 | CH2CH2S(O)2Et |
| 318A tBu | C(Me)OH | CH(Me) | CH2 | CH2CH2S(O)2Et |
| 319A tBu | C(O) | CH2 | CH2 | CH2CH2S(O)Et |
| 320A tBu | CHOH | CH2 | CH2 | CH2CH2S(O)Et |
| 321A tBu | C(Me)OH | CH2 | CH2 | CH2CH2S(O)Et |
| 322A tBu | C(O) | CH(Me) | CH2 | CH2CH2S(O)Et |
| 323A tBu | CHOH | CH(Me) | CH2 | CH2CH2S(O)Et |
| 324A tBu | C(Me)OH | CH(Me) | CH2 | CH2CH2S(O)Et |
| 325A tBu | C(O) | CH2 | CH2 | CH2CH2CH2S(O)2Et |
| 326A tBu | CHOH | CH2 | CH2 | CH2CH2CH2S(O)2Et |
| 327A tBu | C(Me)OH | CH2 | CH2 | CH2CH2CH2S(O)2Et |
| 328A tBu | C(O) | CH(Me) | CH2 | CH2CH2CH2S(O)2Et |
| 329A tBu | CHOH | CH(Me) | CH2 | CH2CH2CH2S(O)2Et |
| 330A tBu | C(Me)OH | CH(Me) | CH2 | CH2CH2CH2S(O)2Et |
| 331A tBu | C(O) | CH2 | CH2 | CH2CH2CH2S(O)Et |
| 332A tBu | CHOH | CH2 | CH2 | CH2CH2CH2S(O)Et |
| 333A tBu | C(Me)OH | CH2 | CH2 | CH2CH2CH2S(O)Et |
| 334A tBu | C(O) | CH(Me) | CH2 | CH2CH2CH2S(O)Et |
| 335A tBu | CHOH | CH(Me) | CH2 | CH2CH2CH2S(O)Et |
| 336A tBu | C(Me)OH | CH(Me) | CH2 | CH2CH2CH2S(O)Et |
| 337A tBu | C(O) | CH2 | CH2 | CH2S(O)2iPr |
| 338A tBu | CHOH | CH2 | CH2 | CH2S(O)2iPr |
| 339A tBu | C(Me)OH | CH2 | CH2 | CH2S(O)2iPr |
| 340A tBu | C(O) | CH(Me) | CH2 | CH2S(O)2iPr |
| 341A tBu | CHOH | CH(Me) | CH2 | CH2S(O)2iPr |
| 342A tBu | C(Me)OH | CH(Me) | CH2 | CH2S(O)2iPr |
| 343A tBu | C(O) | CH2 | CH2 | CH2S(O)iPr |
| 344A tBu | CHOH | CH2 | CH2 | CH2S(O)iPr |
| 345A tBu | C(Me)OH | CH2 | CH2 | CH2S(O)iPr |
| 346A tBu | C(O) | CH(Me) | CH2 | CH2S(O)iPr |
| 347A tBu | CHOH | CH(Me) | CH2 | CH2S(O)iPr |
| 348A tBu | C(Me)OH | CH(Me) | CH2 | CH2S(O)iPr |
| 349A tBu | C(O) | CH2 | CH2 | CH2CH2S(O)2iPr |
| 350A tBu | CHOH | CH2 | CH2 | CH2CH2S(O)2iPr |
| 351A tBu | C(Me)OH | CH2 | CH2 | CH2CH2S(O)2iPr |
| 352A tBu | C(O) | CH(Me) | CH2 | CH2CH2S(O)2iPr |
| 353A tBu | CHOH | CH(Me) | CH2 | CH2CH2S(O)2iPr |
| 354A tBu | C(Me)OH | CH(Me) | CH2 | CH2CH2S(O)2iPr |
| 355A tBu | C(O) | CH2 | CH2 | CH2CH2S(O)iPr |
| 356A tBu | CHOH | CH2 | CH2 | CH2CH2S(O)iPr |
| 357A tBu | C(Me)OH | CH2 | CH2 | CH2CH2S(O)iPr |
| 358A tBu | C(O) | CH(Me) | CH2 | CH2CH2S(O)iPr |
| 359A tBu | CHOH | CH(Me) | CH2 | CH2CH2S(O)iPr |
| 360A tBu | C(Me)OH | CH(Me) | CH2 | CH2CH2S(O)iPr |
| 361A tBu | C(O) | CH2 | CH2 | CH2S(O)2tBu |
| 362A tBu | CHOH | CH2 | CH2 | CH2S(O)2tBu |
| 363A tBu | C(Me)OH | CH2 | CH2 | CH2S(O)2tBu |
| 364A tBu | C(O) | CH(Me) | CH2 | CH2S(O)2tBu |
| 365A tBu | CHOH | CH(Me) | CH2 | CH2S(O)2tBu |
| 366A tBu | C(Me)OH | CH(Me) | CH2 | CH2S(O)2tBu |
| 367A tBu | C(O) | CH2 | CH2 | CH2S(O)tBu |
| 368A tBu | CHOH | CH2 | CH2 | CH2S(O)tBu |
| 369A tBu | C(Me)OH | CH2 | CH2 | CH2S(O)tBu |
| 370A tBu | C(O) | CH(Me) | CH2 | CH2S(O)tBu |
| 371A tBu | CHOH | CH(Me) | CH2 | CH2S(O)tBu |
| 372A tBu | C(Me)OH | CH(Me) | CH2 | CH2S(O)tBu |
| 373A tBu | C(O) | CH2 | CH2 | CH2CH2S(O)2tBu |
| 374A tBu | CHOH | CH2 | CH2 | CH2CH2S(O)2tBu |
| 375A tBu | C(Me)OH | CH2 | CH2 | CH2CH2S(O)2tBu |
| 376A tBu | C(O) | CH(Me) | CH2 | CH2CH2S(O)2tBu |
| 377A tBu | CHOH | CH(Me) | CH2 | CH2CH2S(O)2tBu |
| 378A tBu | C(Me)OH | CH(Me) | CH2 | CH2CH2S(O)2tBu |
| 379A tBu | C(O) | CH2 | CH2 | CH2CH2S(O)tBu |
| 380A tBu | CHOH | CH2 | CH2 | CH2CH2S(O)tBu |
| 381A tBu | C(Me)OH | CH2 | CH2 | CH2CH2S(O)tBu |
| 382A tBu | C(O) | CH(Me) | CH2 | CH2CH2S(O)tBu |
| 383A tBu | CHOH | CH(Me) | CH2 | CH2CH2S(O)tBu |
| 384A tBu | C(Me)OH | CH(Me) | CH2 | CH2CH2S(O)tBu |
| 385A tBu | C(O) | CH2 | CH2 | CH2CH2S(O)2NH2 |
| 386A tBu | CHOH | CH2 | CH2 | CH2CH2S(O)2NH2 |
| 387A tBu | C(Me)OH | CH2 | CH2 | CH2CH2S(O)2NH2 |
| 388A tBu | C(O) | CH(Me) | CH2 | CH2CH2S(O)2NH2 |
| 389A tBu | CHOH | CH(Me) | CH2 | CH2CH2S(O)2NH2 |
| 390A tBu | C(Me)OH | CH(Me) | CH2 | CH2CH2S(O)2NH2 |
| 391A tBu | C(O) | CH2 | CH2 | CH2CH2S(O)NH2 |
| 392A tBu | CHOH | CH2 | CH2 | CH2CH2S(O)NH2 |
| 393A tBu | C(Me)OH | CH2 | CH2 | CH2CH2S(O)NH2 |
| 394A tBu | C(O) | CH(Me) | CH2 | CH2CH2S(O)NH2 |
| 395A tBu | CHOH | CH(Me) | CH2 | CH2CH2S(O)NH2 |
| 396A tBu | C(Me)OH | CH(Me) | CH2 | CH2CH2S(O)NH2 |
| 397A tBu | C(O) | CH2 | CH2 | CH2CH2S(O)2NMe2 |
| 398A tBu | CHOH | CH2 | CH2 | CH2CH2S(O)2NMe2 |
| 399A tBu | C(Me)OH | CH2 | CH2 | CH2CH2S(O)2NMe2 |
| 400A tBu | C(O) | CH(Me) | CH2 | CH2CH2S(O)2NMe2 |
| 401A tBu | CHOH | CH(Me) | CH2 | CH2CH2S(O)2NMe2 |
| 402A tBu | C(Me)OH | CH(Me) | CH2 | CH2CH2S(O)2NMe2 |
| 403A tBu | C(O) | CH2 | CH2 | CH2CH2S(O)NMe2 |
| 404A tBu | CHOH | CH2 | CH2 | CH2CH2S(O)NMe2 |
| 405A tBu | C(Me)OH | CH2 | CH2 | CH2CH2S(O)NMe2 |
| 406A tBu | C(O) | CH(Me) | CH2 | CH2CH2S(O)NMe2 |
| 407A tBu | CHOH | CH(Me) | CH2 | CH2CH2S(O)NMe2 |
| 408A tBu | C(Me)OH | CH(Me) | CH2 | CH2CH2S(O)NMe2 |
| 409A tBu | C(O) | CH2 | CH2 | C(O)CH2S(O)2Me |
| 410A tBu | CHOH | CH2 | CH2 | C(O)CH2S(O)2Me |
| 411A tBu | C(Me)OH | CH2 | CH2 | C(O)CH2S(O)2Me |
| 412A tBu | C(O) | CH(Me) | CH2 | C(O)CH2S(O)2Me |
| 413A tBu | CHOH | CH(Me) | CH2 | C(O)CH2S(O)2Me |
| 414A tBu | C(Me)OH | CH(Me) | CH2 | C(O)CH2S(O)2Me |
| 415A tBu | C(O) | CH2 | CH2 | C(O)CH2S(O)Me |
| 416A tBu | CHOH | CH2 | CH2 | C(O)CH2S(O)Me |

TABLE 2-continued

| $R_B$ | $L_3$ | $L_2$ | $L_1$ | $R_C$ |
|---|---|---|---|---|
| 417A | tBu | C(Me)OH | CH2 | CH2 | C(O)CH2S(O)Me |
| 418A | tBu | C(O) | CH(Me) | CH2 | C(O)CH2S(O)Me |
| 419A | tBu | CHOH | CH(Me) | CH2 | C(O)CH2S(O)Me |
| 420A | tBu | C(Me)OH | CH(Me) | CH2 | C(O)CH2S(O)Me |
| 421A | tBu | C(O) | CH2 | CH2 | C(O)CH2CH2S(O)2Me |
| 422A | tBu | CHOH | CH2 | CH2 | C(O)CH2CH2S(O)2Me |
| 423A | tBu | C(Me)OH | CH2 | CH2 | C(O)CH2CH2S(O)2Me |
| 424A | tBu | C(O) | CH(Me) | CH2 | C(O)CH2CH2S(O)2Me |
| 425A | tBu | CHOH | CH(Me) | CH2 | C(O)CH2CH2S(O)2Me |
| 426A | tBu | C(Me)OH | CH(Me) | CH2 | C(O)CH2CH2S(O)2Me |
| 427A | tBu | C(O) | CH2 | CH2 | C(O)CH2CH2S(O)Me |
| 428A | tBu | CHOH | CH2 | CH2 | C(O)CH2CH2S(O)Me |
| 429A | tBu | C(Me)OH | CH2 | CH2 | C(O)CH2CH2S(O)Me |
| 430A | tBu | C(O) | CH(Me) | CH2 | C(O)CH2CH2S(O)Me |
| 431A | tBu | CHOH | CH(Me) | CH2 | C(O)CH2CH2S(O)Me |
| 432A | tBu | C(Me)OH | CH(Me) | CH2 | C(O)CH2CH2S(O)Me |
| 433A | tBu | C(O) | CH2 | CH2 | CH2CH2CH2S(O)2NH2 |
| 434A | tBu | CHOH | CH2 | CH2 | CH2CH2CH2S(O)2NH2 |
| 435A | tBu | C(Me)OH | CH2 | CH2 | CH2CH2CH2S(O)2NH2 |
| 436A | tBu | C(O) | CH(Me) | CH2 | CH2CH2CH2S(O)2NH2 |
| 437A | tBu | CHOH | CH(Me) | CH2 | CH2CH2CH2S(O)2NH2 |
| 438A | tBu | C(Me)OH | CH(Me) | CH2 | CH2CH2CH2S(O)2NH2 |
| 439A | tBu | C(O) | CH2 | CH2 | CH2CH2CH2S(O)NH2 |
| 440A | tBu | CHOH | CH2 | CH2 | CH2CH2CH2S(O)NH2 |
| 441A | tBu | C(Me)OH | CH2 | CH2 | CH2CH2CH2S(O)NH2 |
| 442A | tBu | C(O) | CH(Me) | CH2 | CH2CH2CH2S(O)NH2 |
| 443A | tBu | CHOH | CH(Me) | CH2 | CH2CH2CH2S(O)NH2 |
| 444A | tBu | C(Me)OH | CH(Me) | CH2 | CH2CH2CH2S(O)NH2 |
| 445A | tBu | C(O) | CH2 | CH2 | 1,3,4-oxadiazolin-2-one-5-yl |
| 446A | tBu | CHOH | CH2 | CH2 | 1,3,4-oxadiazolin-2-one-5-yl |
| 447A | tBu | C(Me)OH | CH2 | CH2 | 1,3,4-oxadiazolin-2-one-5-yl |
| 448A | tBu | C(O) | CH(Me) | CH2 | 1,3,4-oxadiazolin-2-one-5-yl |
| 449A | tBu | CHOH | CH(Me) | CH2 | 1,3,4-oxadiazolin-2-one-5-yl |
| 450A | tBu | C(Me)OH | CH(Me) | CH2 | 1,3,4-oxadiazolin-2-one-5-yl |
| 451A | tBu | C(O) | CH2 | CH2 | 1,3,4-oxadiazolin-2-thione-5-yl |
| 452A | tBu | CHOH | CH2 | CH2 | 1,3,4-oxadiazolin-2-thione-5-yl |
| 453A | tBu | C(Me)OH | CH2 | CH2 | 1,3,4-oxadiazolin-2-thione-5-yl |
| 454A | tBu | C(O) | CH(Me) | CH2 | 1,3,4-oxadiazolin-2-thione-5-yl |
| 455A | tBu | CHOH | CH(Me) | CH2 | 1,3,4-oxadiazolin-2-thione-5-yl |
| 456A | tBu | C(Me)OH | CH(Me) | CH2 | 1,3,4-oxadiazolin-2-thione-5-yl |
| 457A | tBu | C(O) | CH2 | CH2 | imidazolidine-2,4-dione-5-yl |
| 458A | tBu | CHOH | CH2 | CH2 | imidazolidine-2,4-dione-5-yl |
| 459A | tBu | C(Me)OH | CH2 | CH2 | imidazolidine-2,4-dione-5-yl |
| 460A | tBu | C(O) | CH(Me) | CH2 | imidazolidine-2,4-dione-5-yl |
| 461A | tBu | CHOH | CH(Me) | CH2 | imidazolidine-2,4-dione-5-yl |
| 462A | tBu | C(Me)OH | CH(Me) | CH2 | imidazolidine-2,4-dione-5-yl |
| 463A | tBu | C(O) | CH2 | CH2 | isoxazol-3-ol-5-yl |
| 464A | tBu | CHOH | CH2 | CH2 | isoxazol-3-ol-5-yl |
| 465A | tBu | C(Me)OH | CH2 | CH2 | isoxazol-3-ol-5-yl |
| 466A | tBu | C(O) | CH(Me) | CH2 | isoxazol-3-ol-5-yl |
| 467A | tBu | CHOH | CH(Me) | CH2 | isoxazol-3-ol-5-yl |
| 468A | tBu | C(Me)OH | CH(Me) | CH2 | isoxazol-3-ol-5-yl |

Among other preferred compounds of the invention are also those represented by the formula:

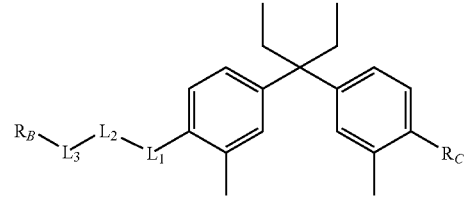

and pharmaceutically acceptable salts thereof;

wherein;

said compound is selected from a compound code numbered 1B thru 81B, with each compound having the specific selection of substituents $R_B$, $R_C$, $L_1$, $L_2$, and $L_3$ shown in the row following the compound code number, as set out in the following Table 3:

TABLE 3

| $R_B$ | $L_3$ | $L_2$ | $L_1$ | $R_C$ |
|---|---|---|---|---|
| 1B | tBu | C(O) | CH2 | O | —C(O)NH—CH2—C(O)OH |
| 2B | tBu | CHOH | CH2 | O | —C(O)NH—CH2—C(O)OH |
| 3B | tBu | C(Me)OH | CH2 | O | —C(O)NH—CH2—C(O)OH |
| 4B | tBu | C(O) | CH(Me) | O | —C(O)NH—CH2—C(O)OH |
| 5B | tBu | CHOH | CH(Me) | O | —C(O)NH—CH2—C(O)OH |
| 6B | tBu | C(Me)OH | CH(Me) | O | —C(O)NH—CH2—C(O)OH |
| 7B | tBu | C(O) | CH2 | O | —C(O)NH—CH(Me)—C(O)OH |
| 8B | tBu | CHOH | CH2 | O | —C(O)NH—CH(Me)—C(O)OH |
| 9B | tBu | C(Me)OH | CH2 | O | —C(O)NH—CH(Me)—C(O)OH |
| 10B | tBu | C(O) | CH(Me) | O | —C(O)NH—CH(Me)—C(O)OH |
| 11B | tBu | CHOH | CH(Me) | O | —C(O)NH—CH(Me)—C(O)OH |
| 12B | tBu | C(Me)OH | CH(Me) | O | —C(O)NH—CH(Me)—C(O)OH |
| 13B | tBu | C(O) | CH2 | O | —C(O)NH—CH(Et)—C(O)OH |
| 14B | tBu | CHOH | CH2 | O | —C(O)NH—CH(Et)—C(O)OH |

TABLE 3-continued

| $R_B$ | $L_3$ | $L_2$ | $L_1$ | $R_C$ |
|---|---|---|---|---|
| 15B tBu | C(Me)OH | CH2 | O | —C(O)NH—CH(Et)—C(O)OH |
| 16B tBu | C(O) | CH(Me) | O | —C(O)NH—CH(Et)—C(O)OH |
| 17B tBu | CHOH | CH(Me) | O | —C(O)NH—CH(Et)—C(O)OH |
| 18B tBu | C(Me)OH | CH(Me) | O | —C(O)NH—CH(Et)—C(O)OH |
| 19B tBu | C(O) | CH2 | O | —C(O)NH—C(Me)$_2$—C(O)OH |
| 20B tBu | CHOH | CH2 | O | —C(O)NH—C(Me)$_2$—C(O)OH |
| 21B tBu | C(Me)OH | CH2 | O | —C(O)NH—C(Me)$_2$—C(O)OH |
| 22B tBu | C(O) | CH(Me) | O | —C(O)NH—C(Me)$_2$—C(O)OH |
| 23B tBu | CHOH | CH(Me) | O | —C(O)NH—C(Me)$_2$—C(O)OH |
| 24B tBu | C(Me)OH | CH(Me) | O | —C(O)NH—C(Me)$_2$—C(O)OH |
| 25B tBu | C(O) | CH2 | O | —C(O)NH—CMe(Et)—C(O)OH |
| 26B tBu | CHOH | CH2 | O | —C(O)NH—CMe(Et)—C(O)OH |
| 27B tBu | C(Me)OH | CH2 | O | —C(O)NH—CMe(Et)—C(O)OH |
| 28B tBu | C(O) | CH(Me) | O | —C(O)NH—CMe(Et)—C(O)OH |
| 29B tBu | CHOH | CH(Me) | O | —C(O)NH—CMe(Et)—C(O)OH |
| 30B tBu | C(Me)OH | CH(Me) | O | —C(O)NH—CMe(Et)—C(O)OH |
| 31B tBu | C(O) | CH2 | O | —C(O)NH—CH(F)—C(O)OH |
| 32B tBu | CHOH | CH2 | O | —C(O)NH—CH(F)—C(O)OH |
| 33B tBu | C(Me)OH | CH2 | O | —C(O)NH—CH(F)—C(O)OH |
| 34B tBu | C(O) | CH(Me) | O | —C(O)NH—CH(F)—C(O)OH |
| 35B tBu | CHOH | CH(Me) | O | —C(O)NH—CH(F)—C(O)OH |
| 36B tBu | C(Me)OH | CH(Me) | O | —C(O)NH—CH(F)—C(O)OH |
| 37B tBu | C(O) | CH2 | O | —C(O)NH—CH(CF$_3$)—C(O)OH |
| 38B tBu | CHOH | CH2 | O | —C(O)NH—CH(CF$_3$)—C(O)OH |
| 39B tBu | C(Me)OH | CH2 | O | —C(O)NH—CH(CF$_3$)—C(O)OH |
| 40B tBu | C(O) | CH(Me) | O | —C(O)NH—CH(CF$_3$)—C(O)OH |
| 41B tBu | CHOH | CH(Me) | O | —C(O)NH—CH(CF$_3$)—C(O)OH |
| 42B tBu | C(Me)OH | CH(Me) | O | —C(O)NH—CH(CF$_3$)—C(O)OH |
| 43B tBu | C(O) | CH2 | O | —C(O)NH—CH(OH)—C(O)OH |
| 44B tBu | CHOH | CH2 | O | —C(O)NH—CH(OH)—C(O)OH |
| 45B tBu | C(Me)OH | CH2 | O | —C(O)NH—CH(OH)—C(O)OH |
| 46B tBu | C(O) | CH(Me) | O | —C(O)NH—CH(OH)—C(O)OH |
| 47B tBu | CHOH | CH(Me) | O | —C(O)NH—CH(OH)—C(O)OH |
| 48B tBu | C(Me)OH | CH(Me) | O | —C(O)NH—CH(OH)—C(O)OH |
| 49B tBu | C(O) | CH2 | O | —C(O)NH—CH(cyclopropyl)-C(O)OH |
| 50B tBu | CHOH | CH2 | O | —C(O)NH—CH(cyclopropyl)-C(O)OH |
| 51B tBu | C(Me)OH | CH2 | O | —C(O)NH—CH(cyclopropyl)-C(O)OH |
| 52B tBu | C(O) | CH(Me) | O | —C(O)NH—CH(cyclopropyl)-C(O)OH |
| 53B tBu | CHOH | CH(Me) | O | —C(O)NH—CH(cyclopropyl)-C(O)OH |
| 54B tBu | C(Me)OH | CH(Me) | O | —C(O)NH—CH(cyclopropyl)-C(O)OH |
| 55B tBu | C(O) | CH2 | O | —C(O)NH—CH(Me)—C(O)OH |
| 56B tBu | CHOH | CH2 | O | —C(O)NH—CH(Me)—C(O)OH |
| 57B tBu | C(Me)OH | CH2 | O | —C(O)NH—CH(Me)—C(O)OH |
| 58B tBu | C(O) | CH(Me) | O | —C(O)NH—CH(Me)—C(O)OH |
| 59B tBu | CHOH | CH(Me) | O | —C(O)NH—CH(Me)—C(O)OH |
| 60B tBu | C(Me)OH | CH(Me) | O | —C(O)NH—CH(Me)—C(O)OH |
| 61B tBu | C(O) | CH2 | O | —C(O)NH—C(Me)$_2$—C(O)OH |
| 62B tBu | CHOH | CH2 | O | —C(O)NH—C(Me)$_2$—C(O)OH |
| 63B tBu | C(Me)OH | CH2 | O | —C(O)NH—C(Me)$_2$—C(O)OH |
| 64B tBu | C(O) | CH(Me) | O | —C(O)NH—C(Me)$_2$—C(O)OH |
| 65B tBu | CHOH | CH(Me) | O | —C(O)NH—C(Me)$_2$—C(O)OH |
| 66B tBu | C(Me)OH | CH(Me) | O | —C(O)NH—C(Me)$_2$—C(O)OH |
| 67B tBu | C(O) | CH2 | O | —C(O)NH—CF(Me)—C(O)OH |
| 68B tBu | CHOH | CH2 | O | —C(O)NH—CF(Me)—C(O)OH |
| 69B tBu | C(Me)OH | CH2 | O | —C(O)NH—CF(Me)—C(O)OH |
| 70B tBu | C(O) | CH(Me) | O | —C(O)NH—CF(Me)—C(O)OH |
| 71B tBu | CHOH | CH(Me) | O | —C(O)NH—CF(Me)—C(O)OH |
| 72B tBu | C(Me)OH | CH(Me) | O | —C(O)NH—CF(Me)—C(O)OH |
| 73B tBu | C(O) | CH2 | O | —C(O)NH—C(Me)(CF$_3$)—C(O)OH |
| 74B tBu | CHOH | CH2 | O | —C(O)NH—C(Me)(CF$_3$)—C(O)OH |
| 75B tBu | C(Me)OH | CH2 | O | —C(O)NH—C(Me)(CF$_3$)—C(O)OH |
| 76B tBu | C(O) | CH(Me) | O | —C(O)NH—C(Me)(CF$_3$)—C(O)OH |
| 77B tBu | CHOH | CH(Me) | O | —C(O)NH—C(Me)(CF$_3$)—C(O)OH |
| 78B tBu | C(Me)OH | CH(Me) | O | —C(O)NH—C(Me)(CF$_3$)—C(O)OH |
| 79B tBu | C(O) | CH2 | O | —C(O)NH—C(Me)(OH)—C(O)OH |
| 80B tBu | CHOH | CH2 | O | —C(O)NH—C(Me)(OH)—C(O)OH |
| 81B tBu | C(Me)OH | CH2 | O | —C(O)NH—C(Me)(OH)—C(O)OH |
| 82B tBu | C(O) | CH(Me) | O | —C(O)NH—C(Me)(OH)—C(O)OH |
| 83B tBu | CHOH | CH(Me) | O | —C(O)NH—C(Me)(OH)—C(O)OH |
| 84B tBu | C(Me)OH | CH(Me) | O | —C(O)NH—C(Me)(OH)—C(O)OH |
| 85B tBu | C(O) | CH2 | O | —C(O)NH—C(Me)(cyclopropyl)CO$_2$H |
| 86B tBu | CHOH | CH2 | O | —C(O)NH—C(Me)(cyclopropyl)CO$_2$H |
| 87B tBu | C(Me)OH | CH2 | O | —C(O)NH—C(Me)(cyclopropyl)CO$_2$H |
| 88B tBu | C(O) | CH(Me) | O | —C(O)NH—C(Me)(cyclopropyl)CO$_2$H |
| 89B tBu | CHOH | CH(Me) | O | —C(O)NH—C(Me)(cyclopropyl)CO$_2$H |
| 90B tBu | C(Me)OH | CH(Me) | O | —C(O)NH—C(Me)(cyclopropyl)CO$_2$H |
| 91B tBu | C(O) | CH2 | O | —C(O)NMe—CH$_2$—C(O)OH |

TABLE 3-continued

| | $R_B$ | $L_3$ | $L_2$ | $L_1$ | $R_C$ |
|---|---|---|---|---|---|
| 92B | tBu | CHOH | CH2 | O | —C(O)NMe—CH$_2$—C(O)OH |
| 93B | tBu | C(Me)OH | CH2 | O | —C(O)NMe—CH$_2$—C(O)OH |
| 94B | tBu | C(O) | CH(Me) | O | —C(O)NMe—CH$_2$—C(O)OH |
| 95B | tBu | CHOH | CH(Me) | O | —C(O)NMe—CH$_2$—C(O)OH |
| 96B | tBu | C(Me)OH | CH(Me) | O | —C(O)NMe—CH$_2$—C(O)OH |
| 97B | tBu | C(O) | CH2 | O | —C(O)NMe—CH(Me)—C(O)OH |
| 98B | tBu | CHOH | CH2 | O | —C(O)NMe—CH(Me)—C(O)OH |
| 99B | tBu | C(Me)OH | CH2 | O | —C(O)NMe—CH(Me)—C(O)OH |
| 100B | tBu | C(O) | CH(Me) | O | —C(O)NMe—CH(Me)—C(O)OH |
| 101B | tBu | CHOH | CH(Me) | O | —C(O)NMe—CH(Me)—C(O)OH |
| 102B | tBu | C(Me)OH | CH(Me) | O | —C(O)NMe—CH(Me)—C(O)OH |
| 103B | tBu | C(O) | CH2 | O | —C(O)NMe—CH(F)—C(O)OH |
| 104B | tBu | CHOH | CH2 | O | —C(O)NMe—CH(F)—C(O)OH |
| 105B | tBu | C(Me)OH | CH2 | O | —C(O)NMe—CH(F)—C(O)OH |
| 106B | tBu | C(O) | CH(Me) | O | —C(O)NMe—CH(F)—C(O)OH |
| 107B | tBu | CHOH | CH(Me) | O | —C(O)NMe—CH(F)—C(O)OH |
| 108B | tBu | C(Me)OH | CH(Me) | O | —C(O)NMe—CH(F)—C(O)OH |
| 109B | tBu | C(O) | CH2 | O | —C(O)NMe—CH(CF$_3$)—C(O)OH |
| 110B | tBu | CHOH | CH2 | O | —C(O)NMe—CH(CF$_3$)—C(O)OH |
| 111B | tBu | C(Me)OH | CH2 | O | —C(O)NMe—CH(CF$_3$)—C(O)OH |
| 112B | tBu | C(O) | CH(Me) | O | —C(O)NMe—CH(CF$_3$)—C(O)OH |
| 113B | tBu | CHOH | CH(Me) | O | —C(O)NMe—CH(CF$_3$)—C(O)OH |
| 114B | tBu | C(Me)OH | CH(Me) | O | —C(O)NMe—CH(CF$_3$)—C(O)OH |
| 115B | tBu | C(O) | CH2 | O | —C(O)NMe—CH(OH)—C(O)OH |
| 116B | tBu | CHOH | CH2 | O | —C(O)NMe—CH(OH)—C(O)OH |
| 117B | tBu | C(Me)OH | CH2 | O | —C(O)NMe—CH(OH)—C(O)OH |
| 118B | tBu | C(O) | CH(Me) | O | —C(O)NMe—CH(OH)—C(O)OH |
| 119B | tBu | CHOH | CH(Me) | O | —C(O)NMe—CH(OH)—C(O)OH |
| 120B | tBu | C(Me)OH | CH(Me) | O | —C(O)NMe—CH(OH)—C(O)OH |
| 121B | tBu | C(O) | CH2 | O | —C(O)NMe—CH(cyclopropyl)-C(O)OH |
| 122B | tBu | CHOH | CH2 | O | —C(O)NMe—CH(cyclopropyl)-C(O)OH |
| 123B | tBu | C(Me)OH | CH2 | O | —C(O)NMe—CH(cyclopropyl)-C(O)OH |
| 124B | tBu | C(O) | CH(Me) | O | —C(O)NMe—CH(cyclopropyl)-C(O)OH |
| 125B | tBu | CHOH | CH(Me) | O | —C(O)NMe—CH(cyclopropyl)-C(O)OH |
| 126B | tBu | C(Me)OH | CH(Me) | O | —C(O)NMe—CH(cyclopropyl)-C(O)OH |
| 127B | tBu | C(O) | CH2 | O | —C(O)NMe—C(Me)$_2$—C(O)OH |
| 128B | tBu | CHOH | CH2 | O | —C(O)NMe—C(Me)$_2$—C(O)OH |
| 129B | tBu | C(Me)OH | CH2 | O | —C(O)NMe—C(Me)$_2$—C(O)OH |
| 130B | tBu | C(O) | CH(Me) | O | —C(O)NMe—C(Me)$_2$—C(O)OH |
| 131B | tBu | CHOH | CH(Me) | O | —C(O)NMe—C(Me)$_2$—C(O)OH |
| 132B | tBu | C(Me)OH | CH(Me) | O | —C(O)NMe—C(Me)$_2$—C(O)OH |
| 133B | tBu | C(O) | CH2 | O | —C(O)NMe—CF(Me)—C(O)OH |
| 134B | tBu | CHOH | CH2 | O | —C(O)NMe—CF(Me)—C(O)OH |
| 135B | tBu | C(Me)OH | CH2 | O | —C(O)NMe—CF(Me)—C(O)OH |
| 136B | tBu | C(O) | CH(Me) | O | —C(O)NMe—CF(Me)—C(O)OH |
| 137B | tBu | CHOH | CH(Me) | O | —C(O)NMe—CF(Me)—C(O)OH |
| 138B | tBu | C(Me)OH | CH(Me) | O | —C(O)NMe—CF(Me)—C(O)OH |
| 139B | tBu | C(O) | CH2 | O | —C(O)NMe—C(Me)(CF$_3$)—C(O)OH |
| 140B | tBu | CHOH | CH2 | O | —C(O)NMe—C(Me)(CF$_3$)—C(O)OH |
| 141B | tBu | C(Me)OH | CH2 | O | —C(O)NMe—C(Me)(CF$_3$)—C(O)OH |
| 142B | tBu | C(O) | CH(Me) | O | —C(O)NMe—C(Me)(CF$_3$)—C(O)OH |
| 143B | tBu | CHOH | CH(Me) | O | —C(O)NMe—C(Me)(CF$_3$)—C(O)OH |
| 144B | tBu | C(Me)OH | CH(Me) | O | —C(O)NMe—C(Me)(CF$_3$)—C(O)OH |
| 145B | tBu | C(O) | CH2 | O | —C(O)NMe—C(Me)(OH)—C(O)OH |
| 146B | tBu | CHOH | CH2 | O | —C(O)NMe—C(Me)(OH)—C(O)OH |
| 147B | tBu | C(Me)OH | CH2 | O | —C(O)NMe—C(Me)(OH)—C(O)OH |
| 148B | tBu | C(O) | CH(Me) | O | —C(O)NMe—C(Me)(OH)—C(O)OH |
| 149B | tBu | CHOH | CH(Me) | O | —C(O)NMe—C(Me)(OH)—C(O)OH |
| 150B | tBu | C(Me)OH | CH(Me) | O | —C(O)NMe—C(Me)(OH)—C(O)OH |
| 151B | tBu | C(O) | CH2 | O | —C(O)NMe—C(Me)(cyclopropyl)-C(O)OH |
| 152B | tBu | CHOH | CH2 | O | —C(O)NMe—C(Me)(cyclopropyl)-C(O)OH |
| 153B | tBu | C(Me)OH | CH2 | O | —C(O)NMe—C(Me)(cyclopropyl)-C(O)OH |
| 154B | tBu | C(O) | CH(Me) | O | —C(O)NMe—C(Me)(cyclopropyl)-C(O)OH |
| 155B | tBu | CHOH | CH(Me) | O | —C(O)NMe—C(Me)(cyclopropyl)-C(O)OH |
| 156B | tBu | C(Me)OH | CH(Me) | O | —C(O)NMe—C(Me)(cyclopropyl)-C(O)OH |
| 157B | tBu | C(O) | CH2 | O | —C(O)—N(Me)-5-tetrazolyl |
| 158B | tBu | CHOH | CH2 | O | —C(O)—N(Me)-5-tetrazolyl |
| 159B | tBu | C(Me)OH | CH2 | O | —C(O)—N(Me)-5-tetrazolyl |
| 160B | tBu | C(O) | CH(Me) | O | —C(O)—N(Me)-5-tetrazolyl |
| 161B | tBu | CHOH | CH(Me) | O | —C(O)—N(Me)-5-tetrazolyl |
| 162B | tBu | C(Me)OH | CH(Me) | O | —C(O)—N(Me)-5-tetrazolyl |

Among other preferred compounds of the invention are also those represented by the formula:

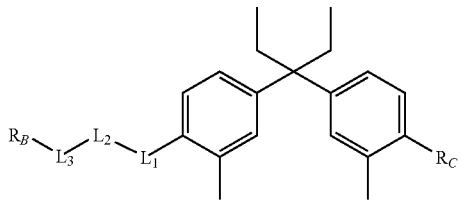

and pharmaceutically acceptable salts thereof;

wherein;

said compound is selected from a compound code numbered 1C thru 162C, with each compound having the specific selection of substituents $R_B$, $R_C$, $L_1$, $L_2$, and $L_3$ shown in the row following the compound code number, as set out in the following Table 4:

TABLE 4

|  | $R_B$ | $L_3$ | $L_2$ | $L_1$ | $R_C$ |
|---|---|---|---|---|---|
| 1C | tBu | C(O) | CH2 | CH2 | —C(O)NH—CH$_2$—C(O)OH |
| 2C | tBu | CHOH | CH2 | CH2 | —C(O)NH—CH$_2$—C(O)OH |
| 3C | tBu | C(Me)OH | CH2 | CH2 | —C(O)NH—CH$_2$—C(O)OH |
| 4C | tBu | C(O) | CH(Me) | CH2 | —C(O)NH—CH$_2$—C(O)OH |
| 5C | tBu | CHOH | CH(Me) | CH2 | —C(O)NH—CH$_2$—C(O)OH |
| 6C | tBu | C(Me)OH | CH(Me) | CH2 | —C(O)NH—CH$_2$—C(O)OH |
| 7C | tBu | C(O) | CH2 | CH2 | —C(O)NH—CH(Me)—C(O)OH |
| 8C | tBu | CHOH | CH2 | CH2 | —C(O)NH—CH(Me)—C(O)OH |
| 9C | tBu | C(Me)OH | CH2 | CH2 | —C(O)NH—CH(Me)—C(O)OH |
| 10C | tBu | C(O) | CH(Me) | CH2 | —C(O)NH—CH(Me)—C(O)OH |
| 11C | tBu | CHOH | CH(Me) | CH2 | —C(O)NH—CH(Me)—C(O)OH |
| 12C | tBu | C(Me)OH | CH(Me) | CH2 | —C(O)NH—CH(Me)—C(O)OH |
| 13C | tBu | C(O) | CH2 | CH2 | —C(O)NH—CH(Et)—C(O)OH |
| 14C | tBu | CHOH | CH2 | CH2 | —C(O)NH—CH(Et)—C(O)OH |
| 15C | tBu | C(Me)OH | CH2 | CH2 | —C(O)NH—CH(Et)—C(O)OH |
| 16C | tBu | C(O) | CH(Me) | CH2 | —C(O)NH—CH(Et)—C(O)OH |
| 17C | tBu | CHOH | CH(Me) | CH2 | —C(O)NH—CH(Et)—C(O)OH |
| 18C | tBu | C(Me)OH | CH(Me) | CH2 | —C(O)NH—CH(Et)—C(O)OH |
| 19C | tBu | C(O) | CH2 | CH2 | —C(O)NH—C(Me)$_2$—C(O)OH |
| 20C | tBu | CHOH | CH2 | CH2 | —C(O)NH—C(Me)$_2$—C(O)OH |
| 21C | tBu | C(Me)OH | CH2 | CH2 | —C(O)NH—C(Me)$_2$—C(O)OH |
| 22C | tBu | C(O) | CH(Me) | CH2 | —C(O)NH—C(Me)$_2$—C(O)OH |
| 23C | tBu | CHOH | CH(Me) | CH2 | —C(O)NH—C(Me)$_2$—C(O)OH |
| 24C | tBu | C(Me)OH | CH(Me) | CH2 | —C(O)NH—C(Me)$_2$—C(O)OH |
| 25C | tBu | C(O) | CH2 | CH2 | —C(O)NH—CMe(Et)—C(O)OH |
| 26C | tBu | CHOH | CH2 | CH2 | —C(O)NH—CMe(Et)—C(O)OH |
| 27C | tBu | C(Me)OH | CH2 | CH2 | —C(O)NH—CMe(Et)—C(O)OH |
| 28C | tBu | C(O) | CH(Me) | CH2 | —C(O)NH—CMe(Et)—C(O)OH |
| 29C | tBu | CHOH | CH(Me) | CH2 | —C(O)NH—CMe(Et)—C(O)OH |
| 30C | tBu | C(Me)OH | CH(Me) | CH2 | —C(O)NH—CMe(Et)—C(O)OH |
| 31C | tBu | C(O) | CH2 | CH2 | —C(O)NH—CH(F)—C(O)OH |
| 32C | tBu | CHOH | CH2 | CH2 | —C(O)NH—CH(F)—C(O)OH |
| 33C | tBu | C(Me)OH | CH2 | CH2 | —C(O)NH—CH(F)—C(O)OH |
| 34C | tBu | C(O) | CH(Me) | CH2 | —C(O)NH—CH(F)—C(O)OH |
| 35C | tBu | CHOH | CH(Me) | CH2 | —C(O)NH—CH(F)—C(O)OH |
| 36C | tBu | C(Me)OH | CH(Me) | CH2 | —C(O)NH—CH(F)—C(O)OH |
| 37C | tBu | C(O) | CH2 | CH2 | —C(O)NH—CH(CF$_3$)—C(O)OH |
| 38C | tBu | CHOH | CH2 | CH2 | —C(O)NH—CH(CF$_3$)—C(O)OH |
| 39C | tBu | C(Me)OH | CH2 | CH2 | —C(O)NH—CH(CF$_3$)—C(O)OH |
| 40C | tBu | C(O) | CH(Me) | CH2 | —C(O)NH—CH(CF$_3$)—C(O)OH |
| 41C | tBu | CHOH | CH(Me) | CH2 | —C(O)NH—CH(CF$_3$)—C(O)OH |
| 42C | tBu | C(Me)OH | CH(Me) | CH2 | —C(O)NH—CH(CF$_3$)—C(O)OH |
| 43C | tBu | C(O) | CH2 | CH2 | —C(O)NH—CH(OH)—C(O)OH |
| 44C | tBu | CHOH | CH2 | CH2 | —C(O)NH—CH(OH)—C(O)OH |
| 45C | tBu | C(Me)OH | CH2 | CH2 | —C(O)NH—CH(OH)—C(O)OH |
| 46C | tBu | C(O) | CH(Me) | CH2 | —C(O)NH—CH(OH)—C(O)OH |
| 47C | tBu | CHOH | CH(Me) | CH2 | —C(O)NH—CH(OH)—C(O)OH |
| 48C | tBu | C(Me)OH | CH(Me) | CH2 | —C(O)NH—CH(OH)—C(O)OH |
| 49C | tBu | C(O) | CH2 | CH2 | —C(O)NH—CH(cyclopropyl)-C(O)OH |
| 50C | tBu | CHOH | CH2 | CH2 | —C(O)NH—CH(cyclopropyl)-C(O)OH |
| 51C | tBu | C(Me)OH | CH2 | CH2 | —C(O)NH—CH(cyclopropyl)-C(O)OH |
| 52C | tBu | C(O) | CH(Me) | CH2 | —C(O)NH—CH(cyclopropyl)-C(O)OH |
| 53C | tBu | CHOH | CH(Me) | CH2 | —C(O)NH—CH(cyclopropyl)-C(O)OH |
| 54C | tBu | C(Me)OH | CH(Me) | CH2 | —C(O)NH—CH(cyclopropyl)-C(O)OH |
| 55C | tBu | C(O) | CH2 | CH2 | —C(O)NH—CH(Me)—C(O)OH |
| 56C | tBu | CHOH | CH2 | CH2 | —C(O)NH—CH(Me)—C(O)OH |
| 57C | tBu | C(Me)OH | CH2 | CH2 | —C(O)NH—CH(Me)—C(O)OH |
| 58C | tBu | C(O) | CH(Me) | CH2 | —C(O)NH—CH(Me)—C(O)OH |
| 59C | tBu | CHOH | CH(Me) | CH2 | —C(O)NH—CH(Me)—C(O)OH |

TABLE 4-continued

|  | $R_B$ | $L_3$ | $L_2$ | $L_1$ | $R_C$ |
|---|---|---|---|---|---|
| 60C | tBu | C(Me)OH | CH(Me) | CH2 | —C(O)NH—CH(Me)—C(O)OH |
| 61C | tBu | C(O) | CH2 | CH2 | —C(O)NH—C(Me)$_2$—C(O)OH |
| 62C | tBu | CHOH | CH2 | CH2 | —C(O)NH—C(Me)$_2$—C(O)OH |
| 63C | tBu | C(Me)OH | CH2 | CH2 | —C(O)NH—C(Me)$_2$—C(O)OH |
| 64C | tBu | C(O) | CH(Me) | CH2 | —C(O)NH—C(Me)$_2$—C(O)OH |
| 65C | tBu | CHOH | CH(Me) | CH2 | —C(O)NH—C(Me)$_2$—C(O)OH |
| 66C | tBu | C(Me)OH | CH(Me) | CH2 | —C(O)NH—C(Me)$_2$—C(O)OH |
| 67C | tBu | C(O) | CH2 | CH2 | —C(O)NH—CF(Me)—C(O)OH |
| 68C | tBu | CHOH | CH2 | CH2 | —C(O)NH—CF(Me)—C(O)OH |
| 69C | tBu | C(Me)OH | CH2 | CH2 | —C(O)NH—CF(Me)—C(O)OH |
| 70C | tBu | C(O) | CH(Me) | CH2 | —C(O)NH—CF(Me)—C(O)OH |
| 71C | tBu | CHOH | CH(Me) | CH2 | —C(O)NH—CF(Me)—C(O)OH |
| 72C | tBu | C(Me)OH | CH(Me) | CH2 | —C(O)NH—CF(Me)—C(O)OH |
| 73C | tBu | C(O) | CH2 | CH2 | —C(O)NH—C(Me)(CF$_3$)—C(O)OH |
| 74C | tBu | CHOH | CH2 | CH2 | —C(O)NH—C(Me)(CF$_3$)—C(O)OH |
| 75C | tBu | C(Me)OH | CH2 | CH2 | —C(O)NH—C(Me)(CF$_3$)—C(O)OH |
| 76C | tBu | C(O) | CH(Me) | CH2 | —C(O)NH—C(Me)(CF$_3$)—C(O)OH |
| 77C | tBu | CHOH | CH(Me) | CH2 | —C(O)NH—C(Me)(CF$_3$)—C(O)OH |
| 78C | tBu | C(Me)OH | CH(Me) | CH2 | —C(O)NH—C(Me)(CF$_3$)—C(O)OH |
| 79C | tBu | C(O) | CH2 | CH2 | —C(O)NH—C(Me)(OH)—C(O)OH |
| 80C | tBu | CHOH | CH2 | CH2 | —C(O)NH—C(Me)(OH)—C(O)OH |
| 81C | tBu | C(Me)OH | CH2 | CH2 | —C(O)NH—C(Me)(OH)—C(O)OH |
| 82C | tBu | C(O) | CH(Me) | CH2 | —C(O)NH—C(Me)(OH)—C(O)OH |
| 83C | tBu | CHOH | CH(Me) | CH2 | —C(O)NH—C(Me)(OH)—C(O)OH |
| 84C | tBu | C(Me)OH | CH(Me) | CH2 | —C(O)NH—C(Me)(OH)—C(O)OH |
| 85C | tBu | C(O) | CH2 | CH2 | —C(O)NH—C(Me)(cyclopropyl)CO$_2$H |
| 86C | tBu | CHOH | CH2 | CH2 | —C(O)NH—C(Me)(cyclopropyl)CO$_2$H |
| 87C | tBu | C(Me)OH | CH2 | CH2 | —C(O)NH—C(Me)(cyclopropyl)CO$_2$H |
| 88C | tBu | C(O) | CH(Me) | CH2 | —C(O)NH—C(Me)(cyclopropyl)CO$_2$H |
| 89C | tBu | CHOH | CH(Me) | CH2 | —C(O)NH—C(Me)(cyclopropyl)CO$_2$H |
| 90C | tBu | C(Me)OH | CH(Me) | CH2 | —C(O)NH—C(Me)(cyclopropyl)CO$_2$H |
| 91C | tBu | C(O) | CH2 | CH2 | —C(O)NMe—CH$_2$—C(O)OH |
| 92C | tBu | CHOH | CH2 | CH2 | —C(O)NMe—CH$_2$—C(O)OH |
| 93C | tBu | C(Me)OH | CH2 | CH2 | —C(O)NMe—CH$_2$—C(O)OH |
| 94C | tBu | C(O) | CH(Me) | CH2 | —C(O)NMe—CH$_2$—C(O)OH |
| 95C | tBu | CHOH | CH(Me) | CH2 | —C(O)NMe—CH$_2$—C(O)OH |
| 96C | tBu | C(Me)OH | CH(Me) | CH2 | —C(O)NMe—CH$_2$—C(O)OH |
| 97C | tBu | C(O) | CH2 | CH2 | —C(O)NMe—CH(Me)—C(O)OH |
| 98C | tBu | CHOH | CH2 | CH2 | —C(O)NMe—CH(Me)—C(O)OH |
| 99C | tBu | C(Me)OH | CH2 | CH2 | —C(O)NMe—CH(Me)—C(O)OH |
| 100C | tBu | C(O) | CH(Me) | CH2 | —C(O)NMe—CH(Me)—C(O)OH |
| 101C | tBu | CHOH | CH(Me) | CH2 | —C(O)NMe—CH(Me)—C(O)OH |
| 102C | tBu | C(Me)OH | CH(Me) | CH2 | —C(O)NMe—CH(Me)—C(O)OH |
| 103C | tBu | C(O) | CH2 | CH2 | —C(O)NMe—CH(F)—C(O)OH |
| 104C | tBu | CHOH | CH2 | CH2 | —C(O)NMe—CH(F)—C(O)OH |
| 105C | tBu | C(Me)OH | CH2 | CH2 | —C(O)NMe—CH(F)—C(O)OH |
| 106C | tBu | C(O) | CH(Me) | CH2 | —C(O)NMe—CH(F)—C(O)OH |
| 107C | tBu | CHOH | CH(Me) | CH2 | —C(O)NMe—CH(F)—C(O)OH |
| 108C | tBu | C(Me)OH | CH(Me) | CH2 | —C(O)NMe—CH(F)—C(O)OH |
| 109C | tBu | C(O) | CH2 | CH2 | —C(O)NMe—CH(CF$_3$)—C(O)OH |
| 110C | tBu | CHOH | CH2 | CH2 | —C(O)NMe—CH(CF$_3$)—C(O)OH |
| 111C | tBu | C(Me)OH | CH2 | CH2 | —C(O)NMe—CH(CF$_3$)—C(O)OH |
| 112C | tBu | C(O) | CH(Me) | CH2 | —C(O)NMe—CH(CF$_3$)—C(O)OH |
| 113C | tBu | CHOH | CH(Me) | CH2 | —C(O)NMe—CH(CF$_3$)—C(O)OH |
| 114C | tBu | C(Me)OH | CH(Me) | CH2 | —C(O)NMe—CH(CF$_3$)—C(O)OH |
| 115C | tBu | C(O) | CH2 | CH2 | —C(O)NMe—CH(OH)—C(O)OH |
| 116C | tBu | CHOH | CH2 | CH2 | —C(O)NMe—CH(OH)—C(O)OH |
| 117C | tBu | C(Me)OH | CH2 | CH2 | —C(O)NMe—CH(OH)—C(O)OH |
| 118C | tBu | C(O) | CH(Me) | CH2 | —C(O)NMe—CH(OH)—C(O)OH |
| 119C | tBu | CHOH | CH(Me) | CH2 | —C(O)NMe—CH(OH)—C(O)OH |
| 120C | tBu | C(Me)OH | CH(Me) | CH2 | —C(O)NMe—CH(OH)—C(O)OH |
| 121C | tBu | C(O) | CH2 | CH2 | —C(O)NMe—CH(cyclopropyl)-C(O)OH |
| 122C | tBu | CHOH | CH2 | CH2 | —C(O)NMe—CH(cyclopropyl)-C(O)OH |
| 123C | tBu | C(Me)OH | CH2 | CH2 | —C(O)NMe—CH(cyclopropyl)-C(O)OH |
| 124C | tBu | C(O) | CH(Me) | CH2 | —C(O)NMe—CH(cyclopropyl)-C(O)OH |
| 125C | tBu | CHOH | CH(Me) | CH2 | —C(O)NMe—CH(cyclopropyl)-C(O)OH |
| 126C | tBu | C(Me)OH | CH(Me) | CH2 | —C(O)NMe—CH(cyclopropyl)-C(O)OH |
| 127C | tBu | C(O) | CH2 | CH2 | —C(O)NMe—C(Me)$_2$—C(O)OH |
| 128C | tBu | CHOH | CH2 | CH2 | —C(O)NMe—C(Me)$_2$—C(O)OH |
| 129C | tBu | C(Me)OH | CH2 | CH2 | —C(O)NMe—C(Me)$_2$—C(O)OH |
| 130C | tBu | C(O) | CH(Me) | CH2 | —C(O)NMe—C(Me)$_2$—C(O)OH |
| 131C | tBu | CHOH | CH(Me) | CH2 | —C(O)NMe—C(Me)$_2$—C(O)OH |
| 132C | tBu | C(Me)OH | CH(Me) | CH2 | —C(O)NMe—C(Me)$_2$—C(O)OH |
| 133C | tBu | C(O) | CH2 | CH2 | —C(O)NMe—CF(Me)—C(O)OH |
| 134C | tBu | CHOH | CH2 | CH2 | —C(O)NMe—CF(Me)—C(O)OH |
| 135C | tBu | C(Me)OH | CH2 | CH2 | —C(O)NMe—CF(Me)—C(O)OH |
| 136C | tBu | C(O) | CH(Me) | CH2 | —C(O)NMe—CF(Me)—C(O)OH |

TABLE 4-continued

| | $R_B$ | $L_3$ | $L_2$ | $L_1$ | $R_C$ |
|---|---|---|---|---|---|
| 137C | tBu | CHOH | CH(Me) | CH2 | —C(O)NMe—CF(Me)—C(O)OH |
| 138C | tBu | C(Me)OH | CH(Me) | CH2 | —C(O)NMe—CF(Me)—C(O)OH |
| 139C | tBu | C(O) | CH2 | CH2 | —C(O)NMe—C(Me)(CF$_3$)—C(O)OH |
| 140C | tBu | CHOH | CH2 | CH2 | —C(O)NMe—C(Me)(CF$_3$)—C(O)OH |
| 141C | tBu | C(Me)OH | CH2 | CH2 | —C(O)NMe—C(Me)(CF$_3$)—C(O)OH |
| 142C | tBu | C(O) | CH(Me) | CH2 | —C(O)NMe—C(Me)(CF$_3$)—C(O)OH |
| 143C | tBu | CHOH | CH(Me) | CH2 | —C(O)NMe—C(Me)(CF$_3$)—C(O)OH |
| 144C | tBu | C(Me)OH | CH(Me) | CH2 | —C(O)NMe—C(Me)(CF$_3$)—C(O)OH |
| 145C | tBu | C(O) | CH2 | CH2 | —C(O)NMe—C(Me)(OH)—C(O)OH |
| 146C | tBu | CHOH | CH2 | CH2 | —C(O)NMe—C(Me)(OH)—C(O)OH |
| 147C | tBu | C(Me)OH | CH2 | CH2 | —C(O)NMe—C(Me)(OH)—C(O)OH |
| 148C | tBu | C(O) | CH(Me) | CH2 | —C(O)NMe—C(Me)(OH)—C(O)OH |
| 149C | tBu | CHOH | CH(Me) | CH2 | —C(O)NMe—C(Me)(OH)—C(O)OH |
| 150C | tBu | C(Me)OH | CH(Me) | CH2 | —C(O)NMe—C(Me)(OH)—C(O)OH |
| 151C | tBu | C(O) | CH2 | CH2 | —C(O)NMe—C(Me)(cyclopropyl)-C(O)OH |
| 152C | tBu | CHOH | CH2 | CH2 | —C(O)NMe—C(Me)(cyclopropyl)-C(O)OH |
| 153C | tBu | C(Me)OH | CH2 | CH2 | —C(O)NMe—C(Me)(cyclopropyl)-C(O)OH |
| 154C | tBu | C(O) | CH(Me) | CH2 | —C(O)NMe—C(Me)(cyclopropyl)-C(O)OH |
| 155C | tBu | CHOH | CH(Me) | CH2 | —C(O)NMe—C(Me)(cyclopropyl)-C(O)OH |
| 156C | tBu | C(Me)OH | CH(Me) | CH2 | —C(O)NMe—C(Me)(cyclopropyl)-C(O)OH |
| 157C | tBu | C(O) | CH2 | CH2 | —C(O)—N(Me)-5-tetrazolyl |
| 158C | tBu | CHOH | CH2 | CH2 | —C(O)—N(Me)-5-tetrazolyl |
| 159C | tBu | C(Me)OH | CH2 | CH2 | —C(O)—N(Me)-5-tetrazolyl |
| 160C | tBu | C(O) | CH(Me) | CH2 | —C(O)—N(Me)-5-tetrazolyl |
| 161C | tBu | CHOH | CH(Me) | CH2 | —C(O)—N(Me)-5-tetrazolyl |
| 162C | tBu | C(Me)OH | CH(Me) | CH2 | —C(O)—N(Me)-5-tetrazolyl |

Method of Making the Compounds of the Invention:

Compounds of the invention represented by formula (I) may be prepared by the methods set out below. It will be understood by one skilled in the chemical arts that the reactants may be varied to analogous molecules to provide desired substitutions in the final reaction product.

Definitions of Symbols Used in the Schemes:
  (PhO)2P(O)N3—diphenyl phosphorus azide
  BBr3—boron tribromide
  BF3-OEt2—boron trifluoride etherate
  BnBr—benzyl bromide
  CH3CN—acetonitrile
  DMAP—4-(dimethylamino)pyridine
  DMF—N,N-dimethylformamide
  DMSO—dimethylsulfoxide
  DPPF—dichloro[1,1'-bis(diphenylphosphino)ferrocene
  DPPB—1,4-bis(diphenylphosphino)butane
  EDCI—3-Ethyl-1-[3-(dimethylamino)propyl]carbodiimide hydrochloride
  Et3N—triethylamine
  EtOH—ethanol
  H2NCH2CO2Me—methyl glycinate
  HN(OMe)Me—N-methyl-O-methyl hydroxylamine
  HNMe2—dimethyl amine
  K2CO3—potassium carbonate
  KOH—potassium hydroxide
  LAH—lithium aluminum hydride
  LiHMDS—lithium hexamethyldisilazide
  mCPBA—meta-chloroperbenzoic acid
  MeI—methyl iodide
  MeOH—methanol
  NaBH4—sodium borohydride
  NaH—sodium hydride
  NaI—sodium iodide
  NMP—N-methylpyrrolidin-2-one
  Na—S—R3—sodium alkylmercaptide
  PBr3—phosphorus tribromide
  Pd(OAc)2— palladium (II) acetate
  Pd—C—palladium on carbon
  pTSA—para-toluenesulfonic acid
  Pyr—pyridine
  R2MgBr—alkyl magnesium bromide
  R3MgBr—alkyl magnesium bromide
  R5MgBr—alkyl magnesium bromide
  R2S(O)2NH2—alkylsulfonamide
  tBuC(O)CH2Br—2-bromopinacolone
  Tf2O—triflic anhydride
  TFA—trifluoroacetic acid
  THF—tetrahydrofuran Description of the Schemes:

Preparation of diphenyl acid and diphenyl acylaminotetrazole (Scheme 1).

A mixture of 3-substituted-4-hydroxy benzoic acid 1a and methanol is treated with HCl (gas) to yield methyl benzoate ester 1. Methyl benzoate ester 1 is reacted with excess alkyl magnesium bromide to produce tertiary alcohol 2. Tertiary alcohol 2 is converted to phenol 4 by reaction with O-benzyl-2-substituted phenol 3a and BF3-Et2O. O-benzyl-2-substituted phenol 3a is derived from the reaction of 2-substituted phenol 3 with benzylbromide and NaH. Phenol 4 is reacted with triflic anhydride/pyridine to give triflate 5 which is subjected to methoxycarbonylation with Pd(OAc)2, DPPF, CO (689-6895 KPa), methanol and triethylamine in either DMF or DMSO at 80-100° C. to yield methyl ester 6. DPPB may be used instead of DPPF for the methoxycarbonylation reaction. Methyl ester 6 is subjected to palladium catalyzed hydrogenolysis and alkylated with NaH/pinacolone bromide to give ketone 7. Ketone 7 is sequentially reacted with sodium borohydride/MeOH and potassium hydroxide/EtOH/H2O/80° C. to produce acid 8. Acid 8 is coupled with EDCI, DMAP and 5-aminotetrazole to give acylamino tetrazole 9. Acid 8 is also coupled with EDCI, DMAP and alkylsulfonamide to give acylsulfonamide 9a.

Preparation of functionalized sidechain analogs (Scheme 2).

Ester 6 is reduced with LAH to give benzyl alcohol 10. Benzyl alcohol 10 is converted to benzylic bromide 11 with PBr3 and alklylated with the enolate of pinacolone to afford ketone 12. Ketone 12 is transformed into keto-ester 14 via Pd—C catalyzed hydrogenolysis, triflate formation with triflic anhydride/pyridine and palladium catalyzed methoxycarbonylation. Keto-ester 14 is subjected to sodium borohydride reduction and potassium hydroxide hydrolysis to produce alcohol-acid 15. Alcohol-acid 15 is coupled with EDCI/Et3N/DMAP/R4NHCH2CO2Me and hydrolyzed with LiOH/EtOH/H2O to afford amide-acid 15a.

Preparation of alkylated pinacolol sidechain (Scheme 3).

Ketone 7 is alkylated with LiHMDS/MeI and reduced with NaBH4/MeOH to give alcohol 16. Alcohol 16 is hydrolyzed with potassium hydroxide to afford alcohol-acid 17. Alcohol-acid 17 is reacted sequentially with 1) EDCI/Et3N/DMAP/R4NHCH2CO2Me; and 2) LiOH/EtOH/H2O to give amide-acid 17a.

Preparation of alkylsulfonylmethyl sidechain analogs (Scheme 4).

Benzylic bromide 11 is reacted with sodium alkylmercaptide and oxidized with mCPBA to give sulfone 18. Sulfone 18 is hydrogenolyzed with Pd—C/H2 and alkylated with pinacolone chloride, potassium carbonate and sodium iodide to produce ketone sulfone 19. Ketone sulfone 19 is reduced with sodium borohydride to afford alcohol sulfone 20.

Preparation of unsymmetrical central link diphenyl scaffold (Scheme 5).

3-Substituted-4-hydroxybenzoic acid is coupled with EDCI/N-methyl-N-methoxyamine/DMAP and alkylated with benzyl bromide to give amide 21. Amide 21 is sequentially reacted with R2MgBr and R3MgBr Grignard reagents to afford tertiary alcohol 23. Alcohol 23 is reacted with 2-substituted phenol 3 and BF3-OEt2 to produce diphenylalkane 24. Diphenylalkane 24 is reacted with triflic anhydride/pyridine and methoxycarbonylated with Pd(OAc)2, (DPPF or DPPB), carbon monoxide, MeOH, and Et3N to give ester 26. Ester 26 is hydrogenolyzed with Pd—C/H2 and alkylated with pinacolone bromide to yield ketone ester 27. Ketone ester 27 is reduced with sodium borohydride and hydrolyzed with potassium hydroxide to afford alcohol-acid 28. Alcohol-acid 28 is coupled with EDCI/Et3N/DMAP/R4NHCH2CO2Me and hydrolyzed with LiOH/EtOH/H2O to afford amide-acid 28a.

Preparation of tertiary alcohol sidechain analog (Scheme 6).

Phenol 4 is alkylated with pinacolone bromide and reacted with MeMgBr or EtMgBr to give alcohol 29. Alcohol 29 is hydrogenolyzed with Pd—C/H2, reacted with triflic anhydride/pyridine and methoxycarbonylated to afford ester 30. Ester 30 is hydrolyzed with potassium hydroxide, coupled with EDCI/Et3N/DMAP/R4NHCH2CO2Me, and hydrolyzed to produce tertiary alcohol amide-acid 31.

Preparation of direct linked tetrazole (Scheme 7).

Acid 8 is reacted with formamide and sodium methoxide to give primary amide 32. Primary amide 32 is treated with trifluoroacetic acid and methylene chloride followed by 2-chloro-1,3-dimethyl-2-imidazolinium hexafluorophosphate to give nitrile 33. Nitrile 33 is reacted with sodium azide and triethylammonium hydrochloride in N-methylpyrrolidin-2-one to afford tetrazole 34.

Preparation of amide (Scheme 8).

Acid 8 is reacted with diphenyl phosphorus azide and triethylamine followed by treatment with dimethylamine and 4-(dimethylamino)pyridine to yield amide 35.

Preparation of esters (Scheme 9).

Acid 8 is treated with sodium iodide and N,N-dimethyl-2-chloroacetamide to give ester 36. Acid 8 is treated with sodium iodide and N-morpholinocarbonylmethyl chloride to give ester 37.

Alternative Synthesis of Diphenylalkyl Scaffold (Scheme 10).

Phenol 2 is heated with pTSA to give olefin 38. Olefin 38 is alkylated with 2-chloropinacolone and reacted with a 2-substituted phenol/BF3-OEt2 to yield phenol 40. Phenol 40 is converted to the corresponding phenolic triflate and reduced to alcohol 41. Alcohol 41 is methoxycarbonylated to afford ester 42. Ester 42 is hydrolyzed to produce acid 8.

Synthesis of Pentynol Phenyl alkyl Phenyl Acids (Scheme 11).

Ester 26 is hydrogenolyzed with Pd—C/H2 and reacted with Tf2O/pyridine to give triflate 43. Triflate 43 is sequentially reacted with 1) TMS-acetylene, PdCl2(PPh3)2, Et3N, and DMF and 2) CsF and water to afford acetylene 44. Acetylene 44 is treated with Zn(OTf)2/t-butyl aldehyde/chiral auxiliary (with or without) to give alcohol 46. Alternatively, acetylene 44 is reacted with LiHMDS/ketone 45 to give alcohol 46. Alcohol 46 is hydrolyzed with KOH/EtOH/H2O to afford acid 47. Acid 47 is sequentially reacted with 1) EDCI/Et3N/DMAP/R4NHCH2CO2Me and 2) LiOH/EtOH/H2O to give amide-acid 48.

Synthesis of Cis-Pentenol Phenyl alkyl Phenyl Acids (Scheme 12).

Amide-acid 48 is hydrogenated with Lindlar catalyst to afford cis-pentenol amide-acid 49.

Synthesis of trans-Pentenol Phenyl Alkyl Phenyl Acids (Scheme 13).

Triflate 25 is sequentially reacted with 1) TMS-acetylene, PdCl2(PPh3)2, Et3N, and DMF and 2) CsF and water to afford acetylene 50. Acetylene 50 is treated with Zn(OTf)2/t-butyl aldehyde/chiral auxiliary (with or without) to give alcohol 51. Alternatively, acetylene 50 is reacted with LiHMDS/ketone 45 to give alcohol 51. Alcohol 51 is reduced with LAH or DiBAH to afford trans-pentenol 52. Trans-pentenol 52 is sequentially reacted with 1) Pd—C/H2; 2) Tf2O/pyridine; 3) Pd(OAc)2, DPPF, CO, MeOH, Et3N, DMF; 4) KOH/EtOH/H2O; 5) EDCI/Et3N/DMAP/R4NHCH2CO2Me; and 6) LiOH/EtOH/H2O to give trans-pentenol amide-acid 53. For reaction step 3, DPPB and DMSO.

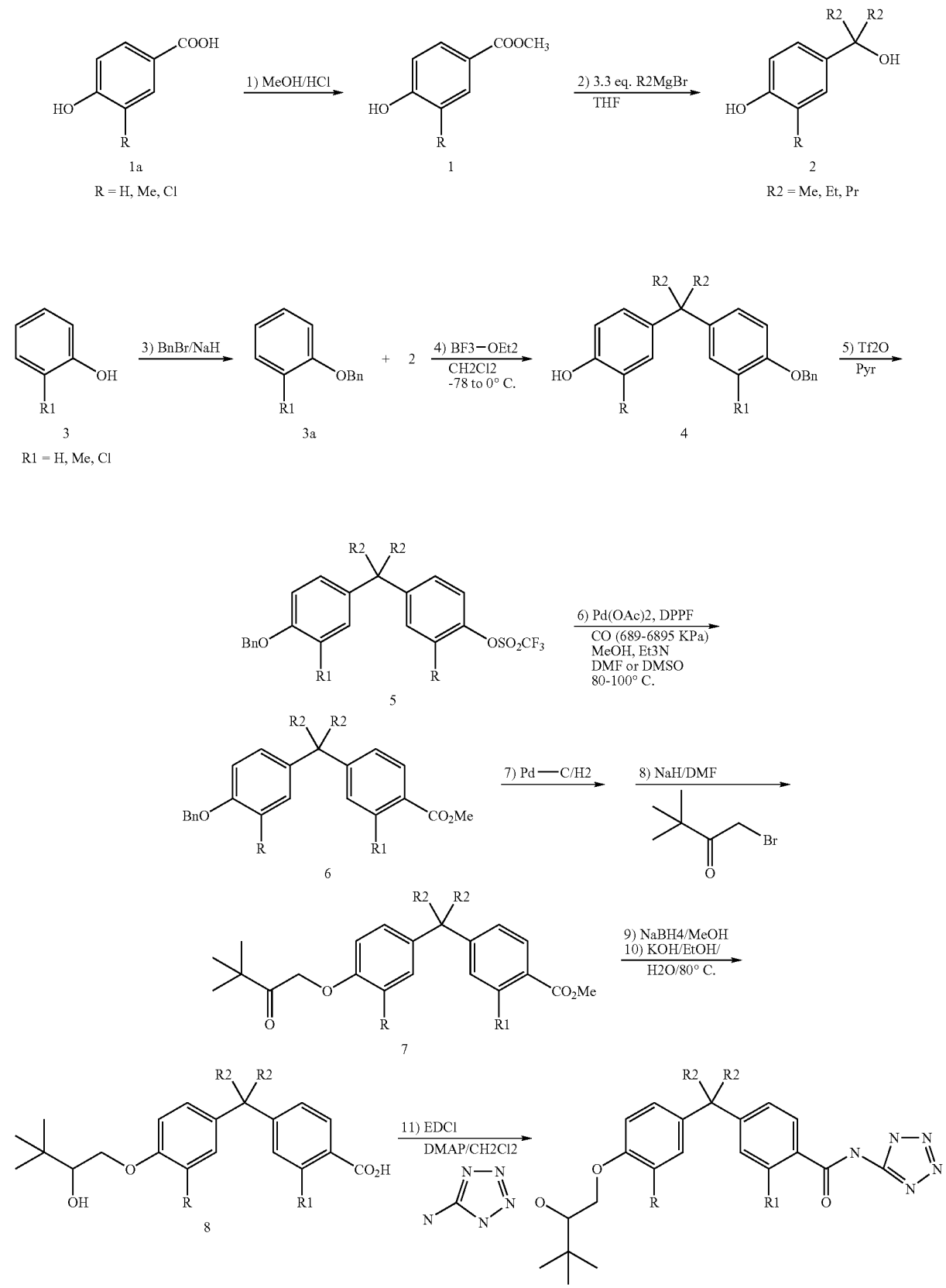

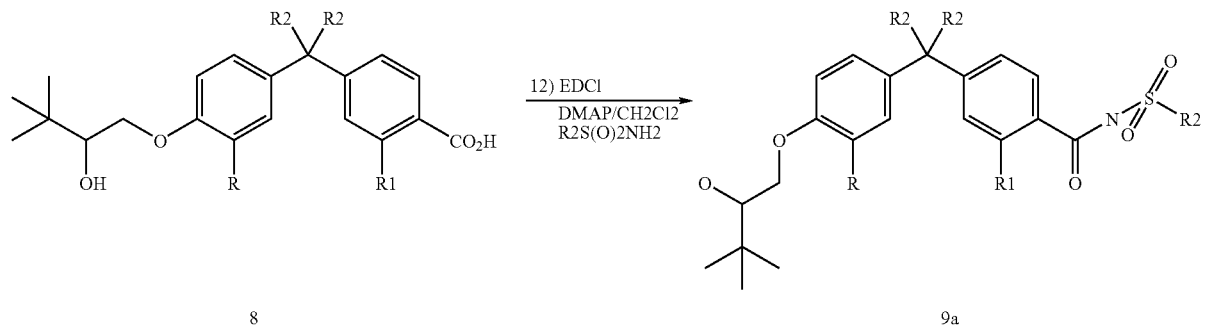
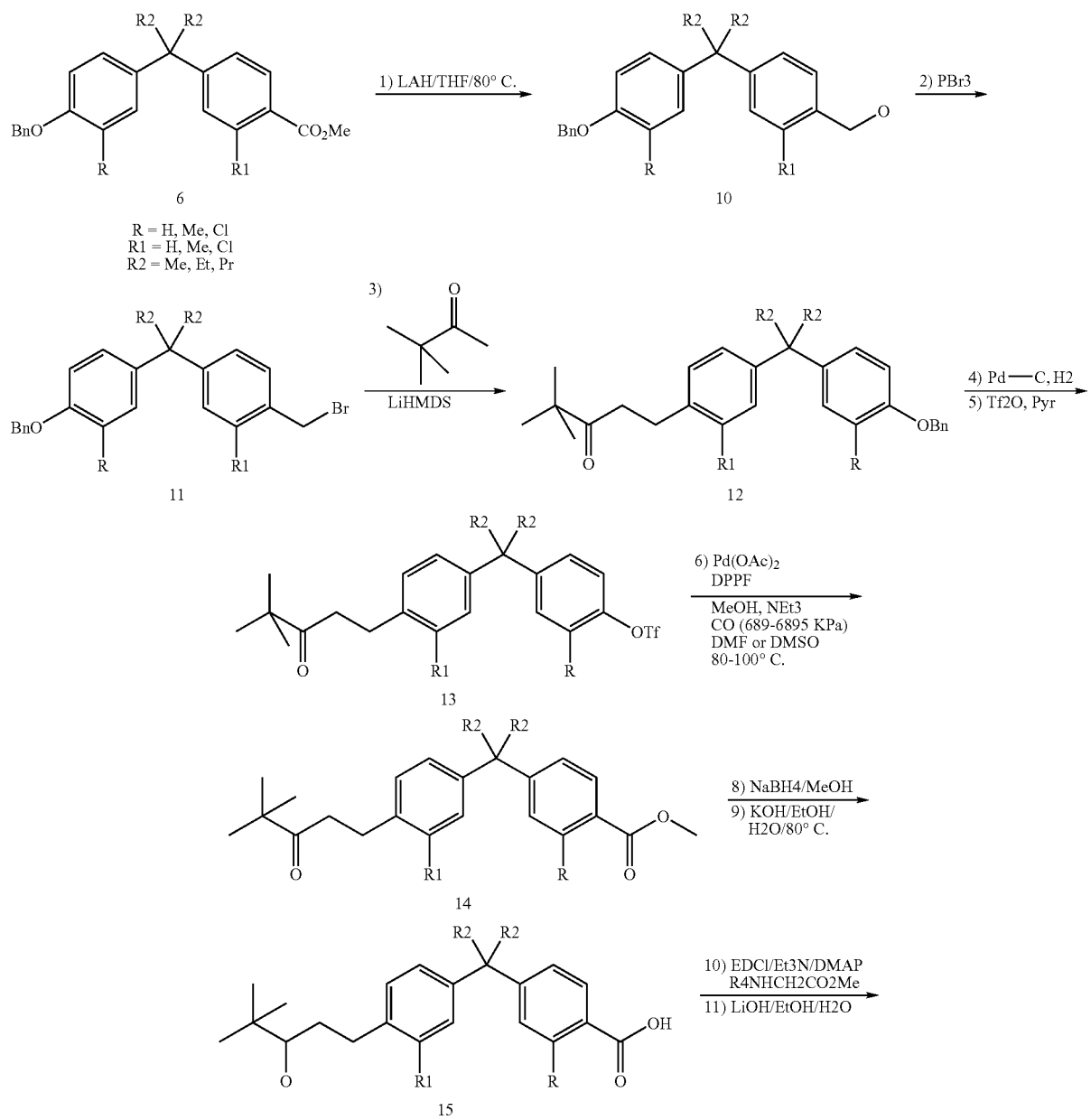
Scheme 2: Synthesis of Functionalized of Sidechain Analogs
R = H, Me, Cl
R1 = H, Me, Cl
R2 = Me, Et, Pr

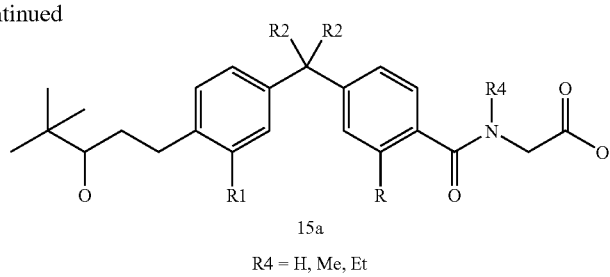
15a
R4 = H, Me, Et
Scheme 3: Synthesis of Alkyl Pinacolol Sidechain
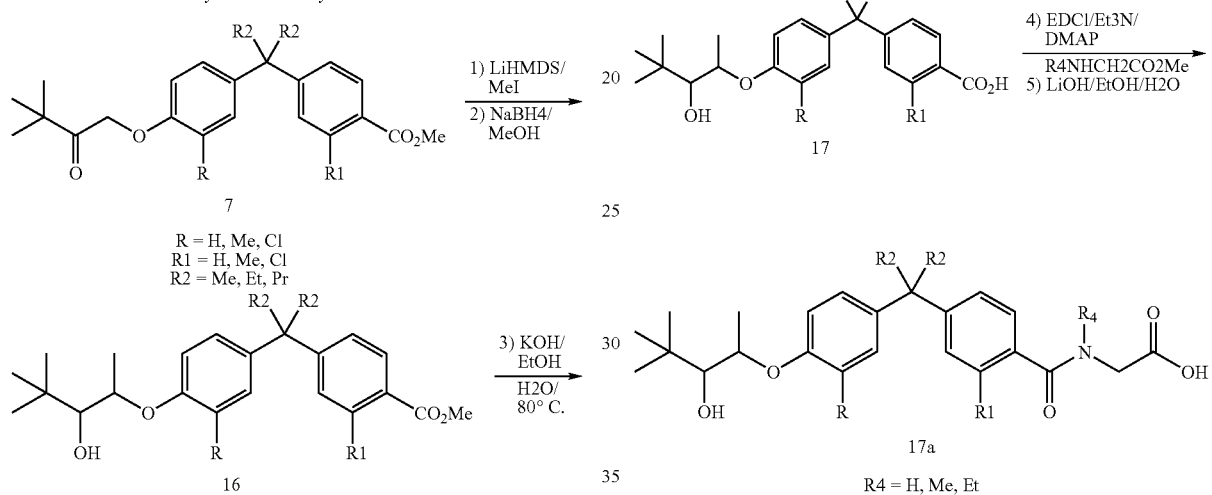
R = H, Me, Cl
R1 = H, Me, Cl
R2 = Me, Et, Pr
17a
R4 = H, Me, Et
Scheme 4: Synthesis of Alkylsulfonylmethyl Sidechain Analogs
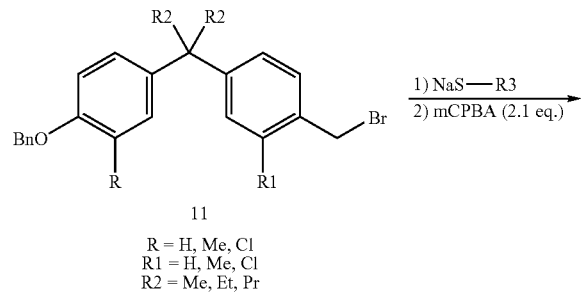
R = H, Me, Cl
R1 = H, Me, Cl
R2 = Me, Et, Pr
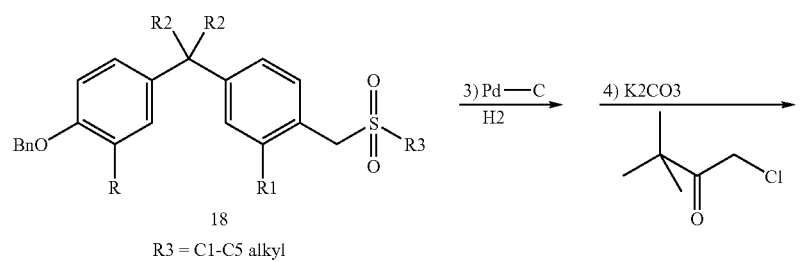
R3 = C1-C5 alkyl

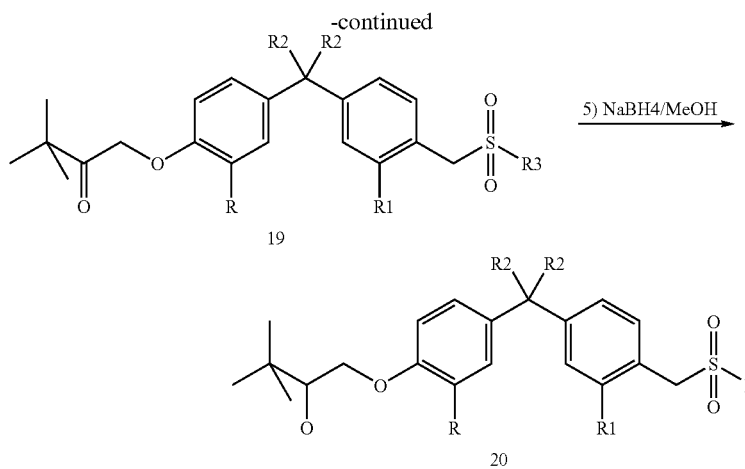
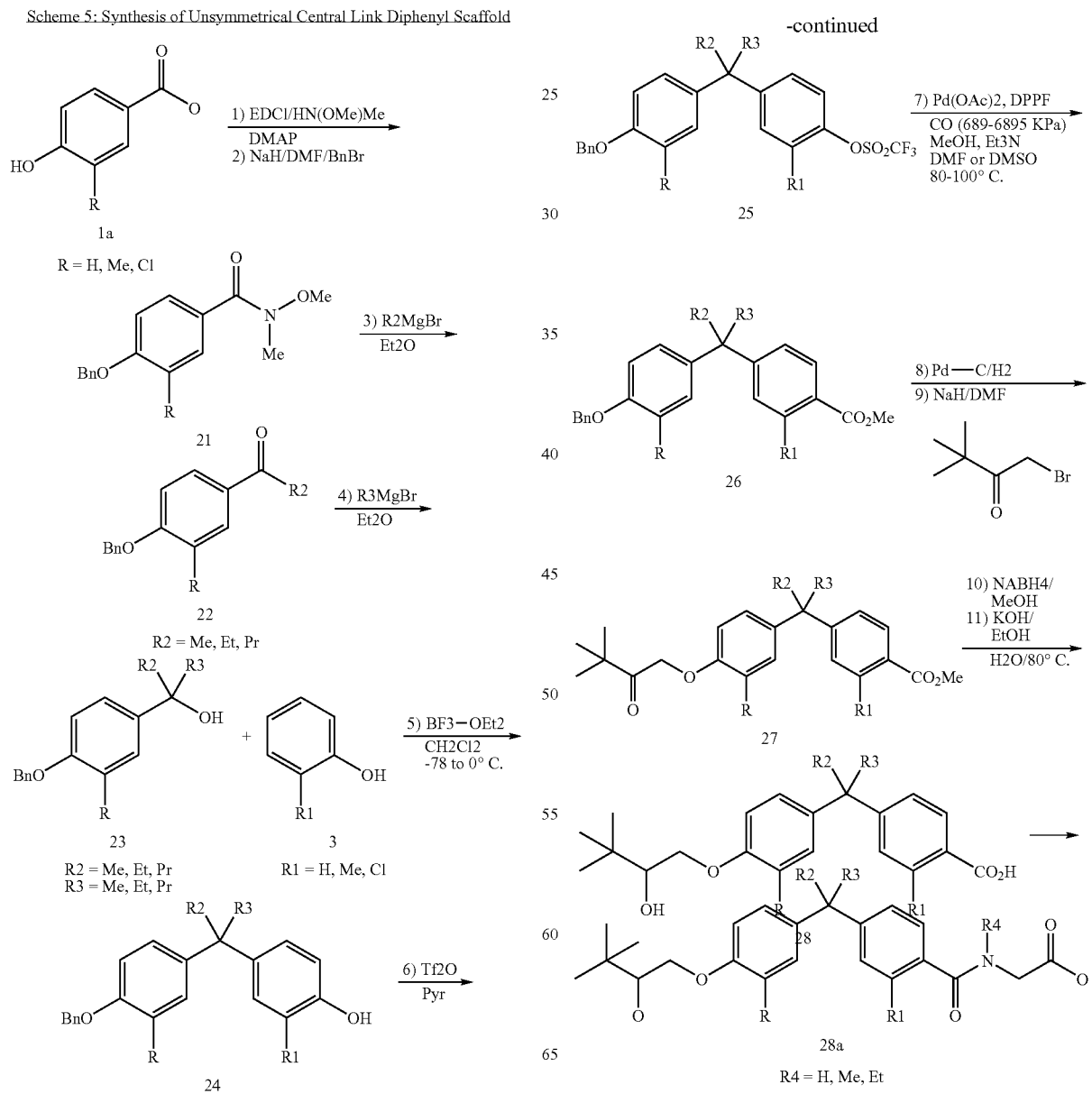
Scheme 5: Synthesis of Unsymmetrical Central Link Diphenyl Scaffold
R4 = H, Me, Et Scheme 6: Synthesis of Tertiary Alcohol Sidechain
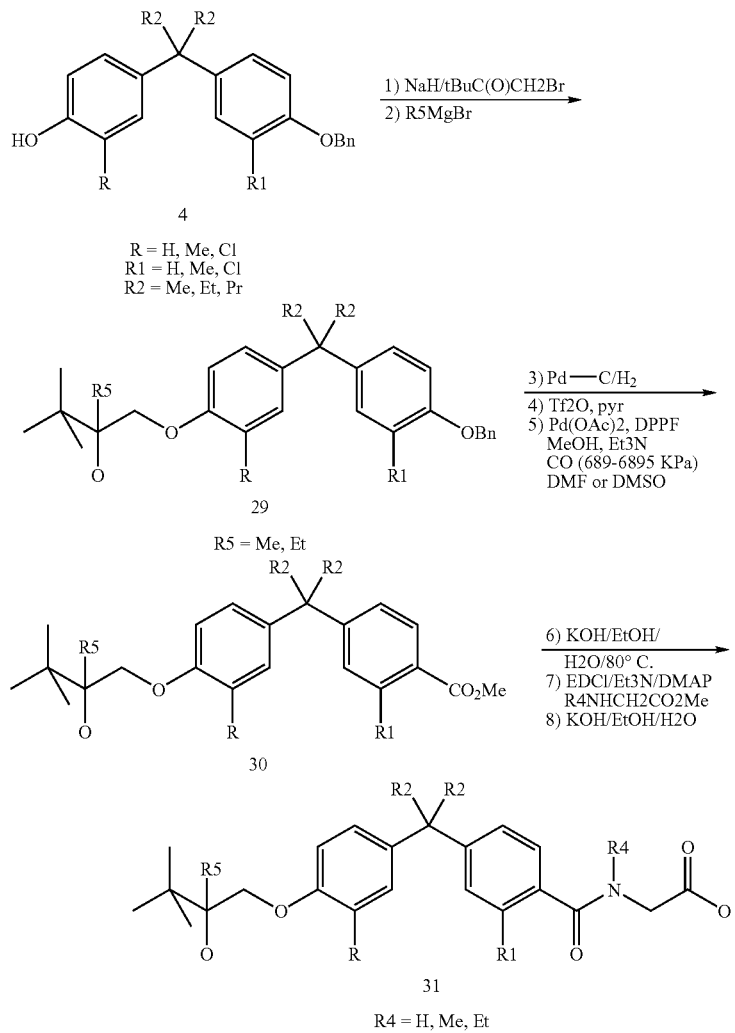
Scheme 7: Synthesis of Direct Linked Tetrazole
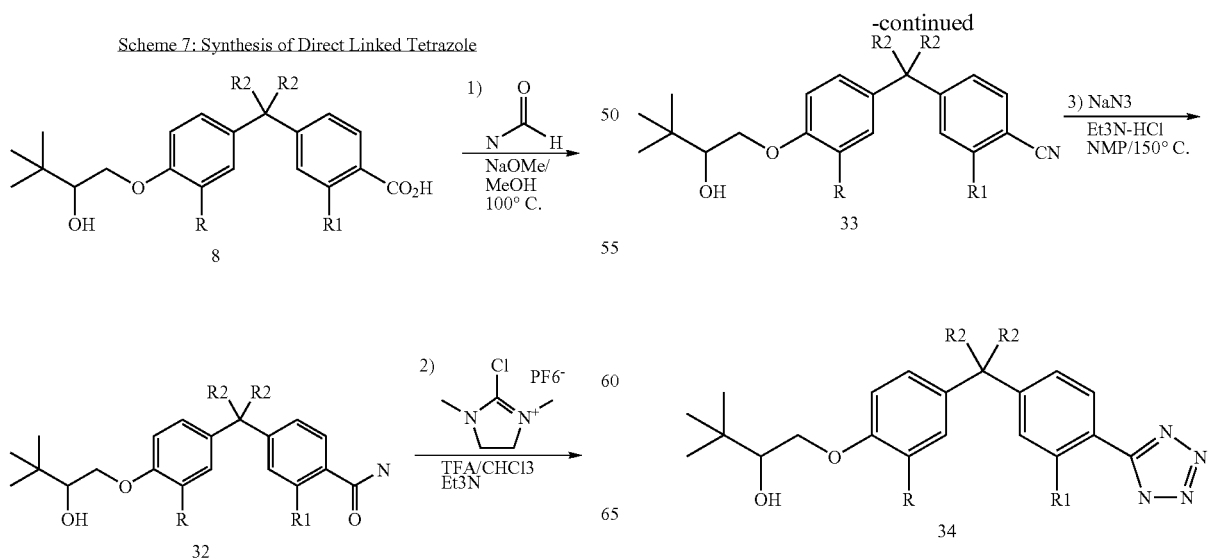

Scheme 8: Synthesis of Amide
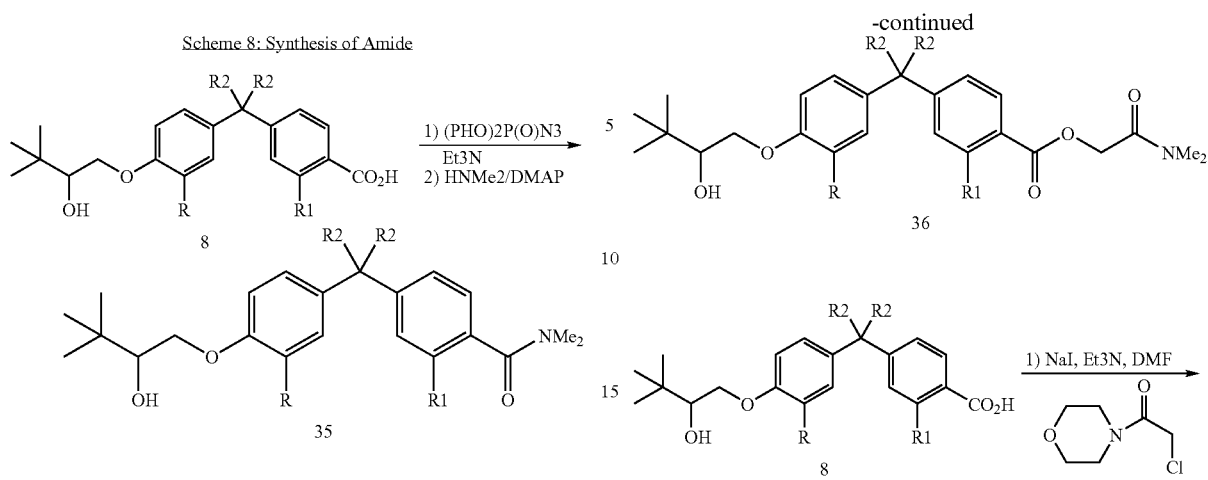
Scheme 9: Synthesis of Ester Prodrugs
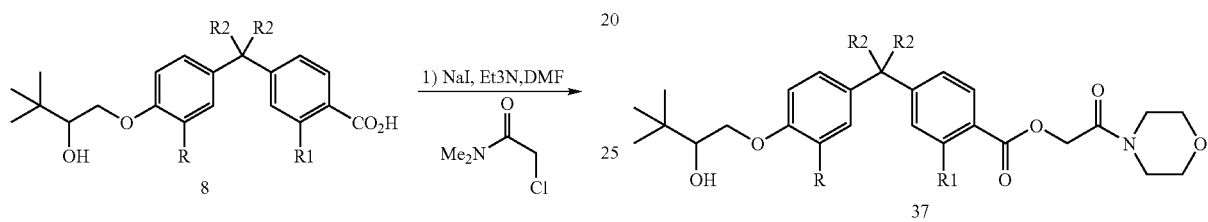
Scheme 10: Alternative Synthesis of Diphenyl Alkyl Scaffold
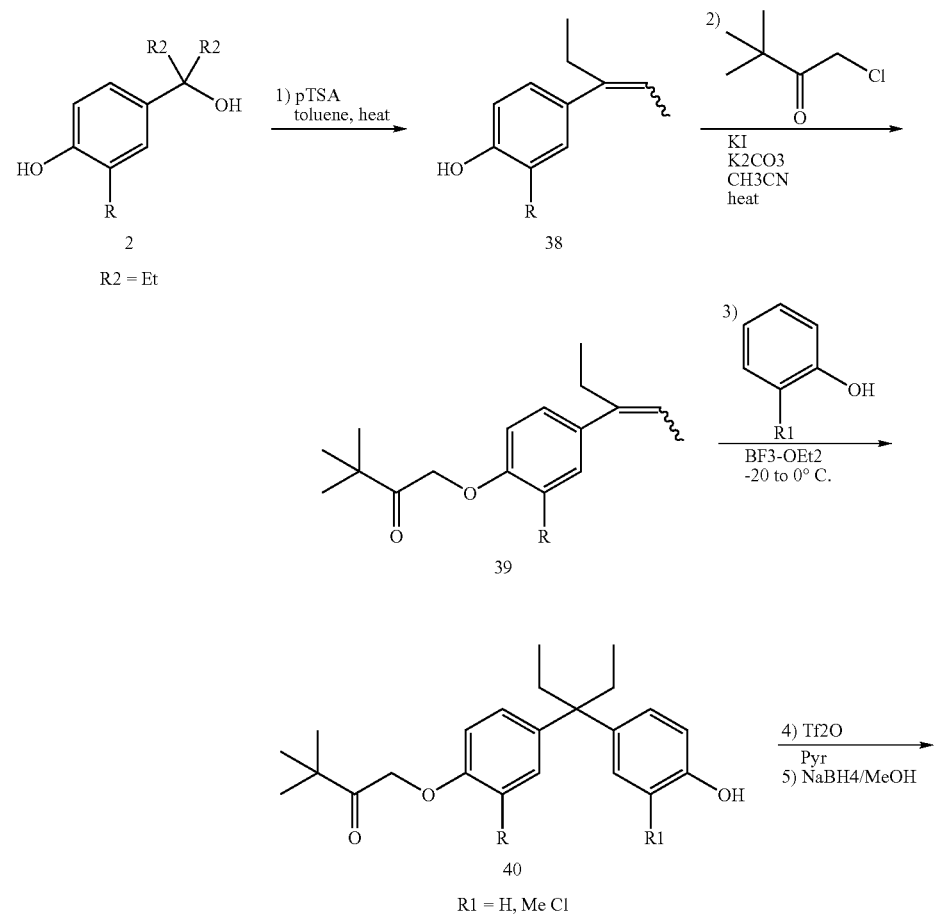
R1 = H, Me Cl

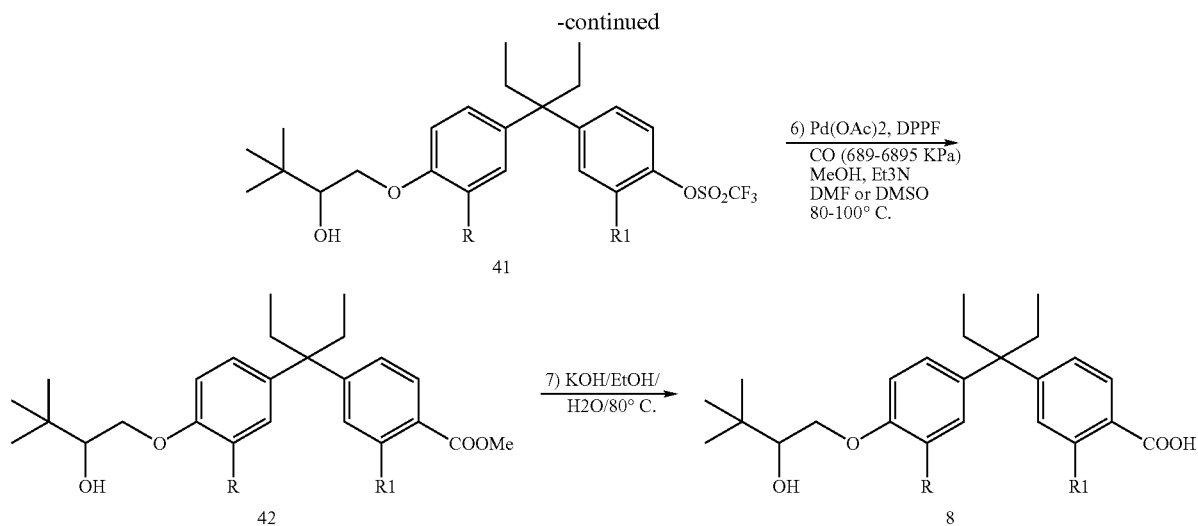
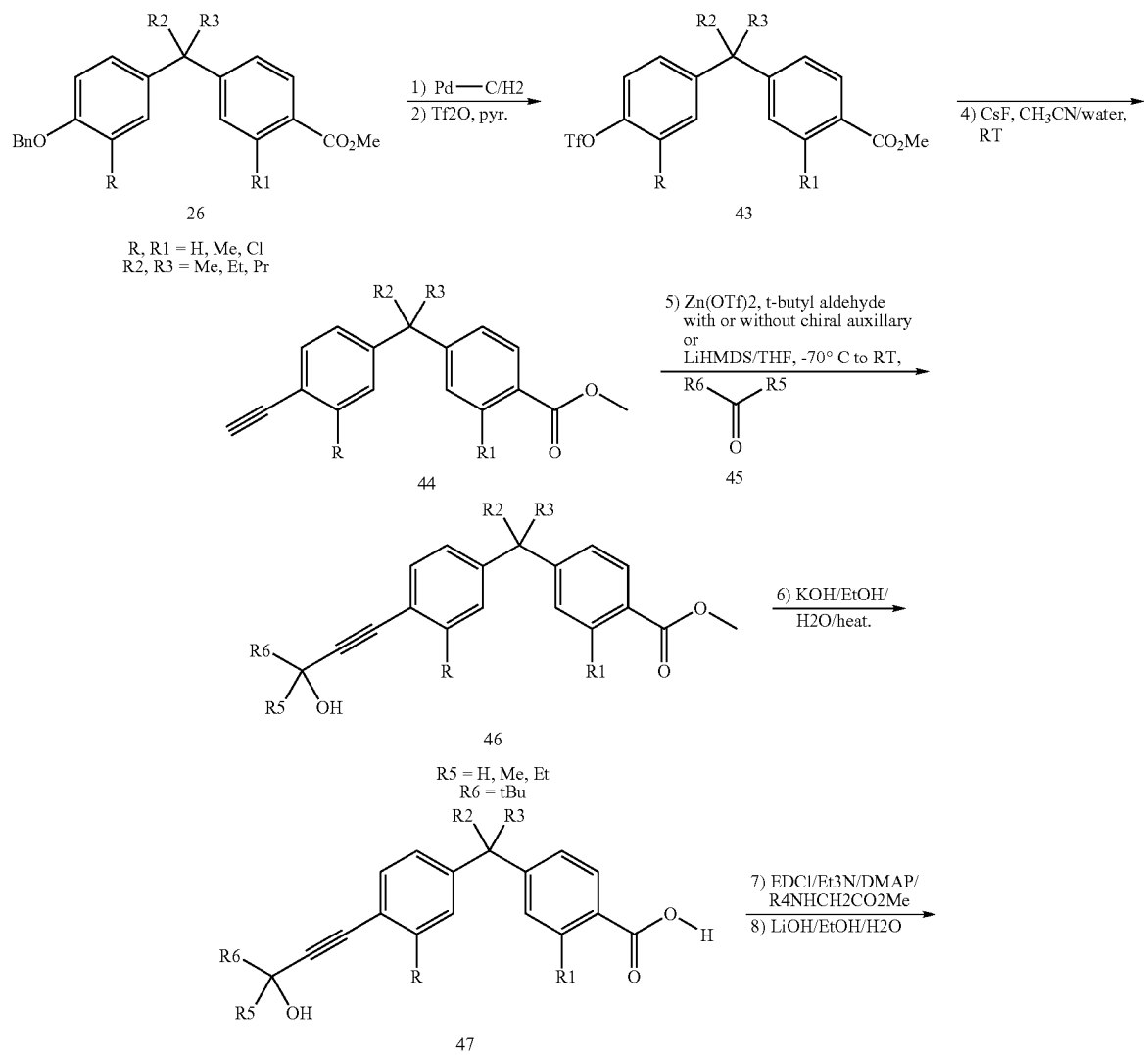
Scheme 11: Synthesis of Pentynol Phenyl Alkyl Phenyl Acids -continued
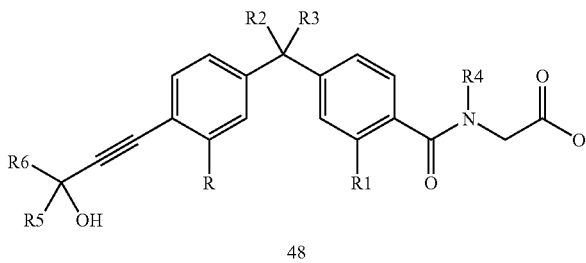
48
R, R1 = H, Me, Cl
R2, R3 = Me, Et, Pr
R4 = H, Me, Et
R5 = H, Me, Et
R6 = tBu
Scheme 12: Synthesis of Cis-Pentenol Phenyl Alkyl Phenyl Amide-Acids
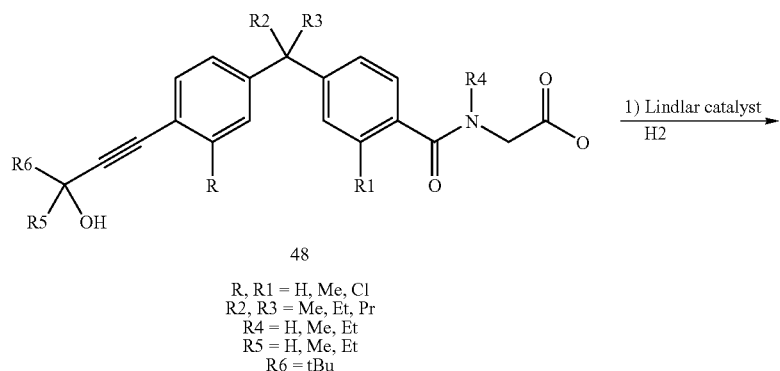
48
R, R1 = H, Me, Cl
R2, R3 = Me, Et, Pr
R4 = H, Me, Et
R5 = H, Me, Et
R6 = tBu
1) Lindlar catalyst
H2 →
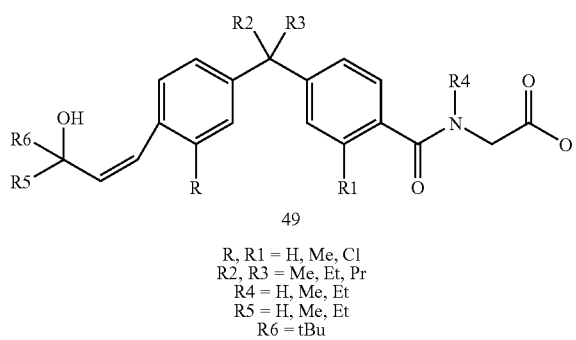
49
R, R1 = H, Me, Cl
R2, R3 = Me, Et, Pr
R4 = H, Me, Et
R5 = H, Me, Et
R6 = tBu Scheme 13: Synthesis of Trans-Pentenol Phenyl Alkyl Phenyl Amide-Acids

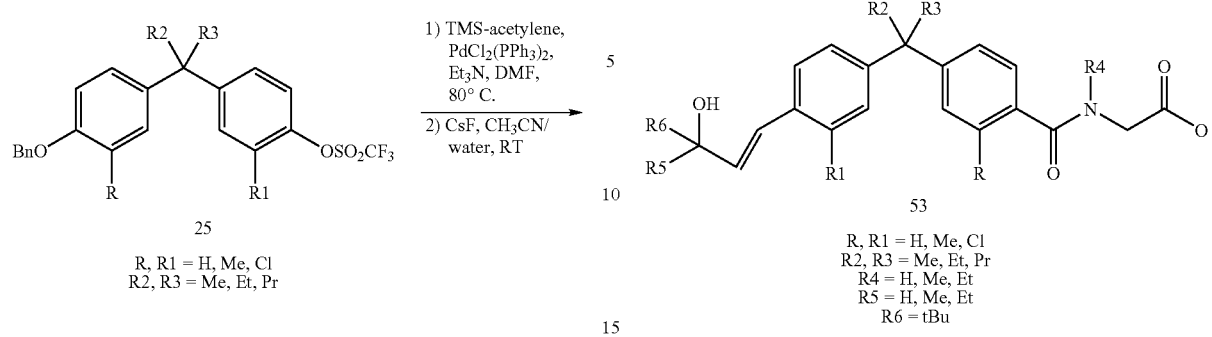

25

R, R1 = H, Me, Cl
R2, R3 = Me, Et, Pr

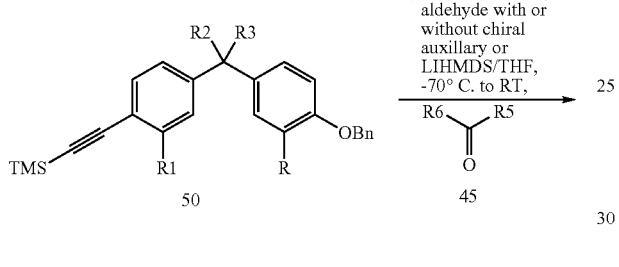

50

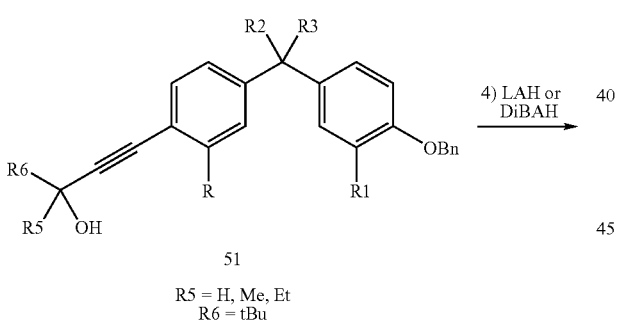

51

R5 = H, Me, Et
R6 = tBu

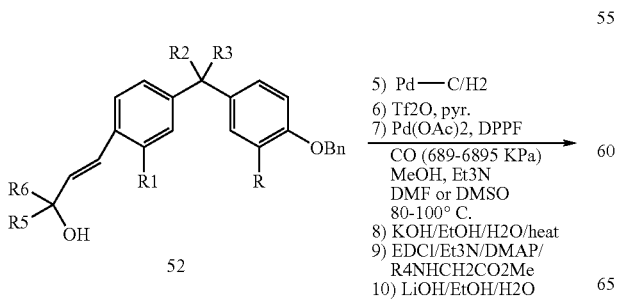

52

53

R, R1 = H, Me, Cl
R2, R3 = Me, Et, Pr
R4 = H, Me, Et
R5 = H, Me, Et
R6 = tBu

EXAMPLES

Abbreviations:
The following examples use several standard abbreviations, for example;
"RT" is room temperature, "Rt" or $t_{ret}$ are symbols for retention time, and "Hex" refers to hexanes
Concentration is performed by evaporation from RT to about 70° C. under vacuum (1-10 mm)

Example 1

Preparation of racemic 3'-[4-(2-hydroxy-3,3-dimethylbutoxy)-3-methylphenyl]-3'-[4-methoxycarbonyl-3-methylphenyl]pentane

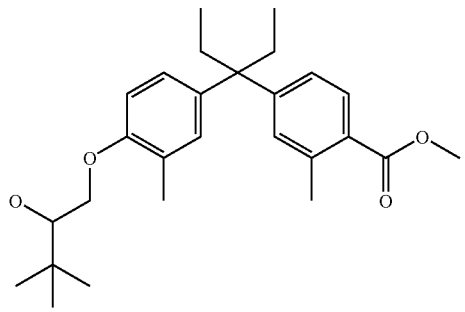

A. 3',3'-Bis[4-hydroxy-3-methylphenyl]pentane

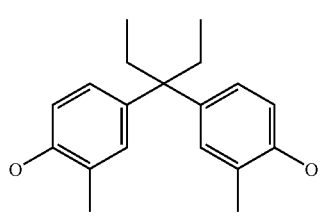

To a mixture of o-cresol (196 g, 1.81 mol) and 3-pentanone (60 ml, 0.57 mol) is added methanesulfonic acid (45 ml, 0.69 mol) and stirred for 3 days. The reaction is basified to pH 8 with satd Na₂CO₃ and extracted with EtOAc. The organic layer is washed with water (6×500 ml), Na₂SO₄ dried, concentrated, chromatographed (2 kg SiO2, Hex to 80% EtOAc/Hex), and triturated with Hex to give the title compound as a white solid (100 g, 61%).

NMR 400 mHz (DMSO): δ 0.49 (t, J=7.3 Hz, 6H), 1.91 (q, J=7.3 Hz, 4H), 2.02 (s, 6H), 6.61 (d, J=8.3 Hz, 2H), 6.73 (d, J=8.3 Hz, 2H), 6.76 (s, 2H), 8.94 (s, 2H).

High Res. EI-MS: 284.1794; calc. for $C_{19}H_{24}O_2$: 284.1776

B. 3'-[4-(2-Oxo-3,3-dimethylbutoxy)-3-methylphenyl)]-3'-[4-hydroxy-3-methylphenyl]pentane

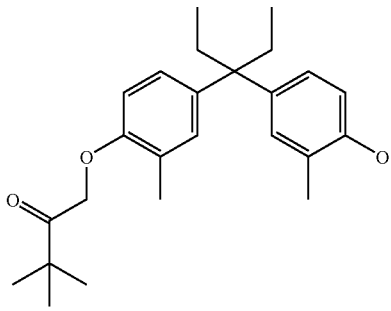

To a mixture of 60% NaH disp (8.0 g, 200 mmol) and DMF (600 ml) is added 3,3-bis[4-hydroxy-3-methylphenyl]pentane (56.88 g, 200 mmol) and stirred for 2 h. To the reaction is added 3,3-dimethyl-1-bromo-2-butanone (26.93 ml, 200 mmol) dropwise and stirred overnight. The solvent is removed in-vacuo. To the resulting residue is added EtOAc/water (800 ml/200 ml), acidified to pH 3 with 5N HCl, and partitioned. The organic layer is washed with water (2×), brine, Na₂SO₄ dried, concentrated, and chromatographed (3 kg SiO₂, hex to 15% EtOAc/hex) to give the title compound as a white solid (35 g, 46%).

NMR (300 mHz, DMSO): δ 0.52 (t, J=7.3 Hz, 6H), 1.16 (s, 9H), 1.95 (q, J=7.3 Hz, 4H), 2.04 (s, 3H), 2.12 (s, 3H), 5.05 (s, 2H), 6.57 (d, J=9.1 Hz, 1H), 6.63 (d, J=8.1 Hz, 1H), 6.81 (m, 2H), 8.97 (s, 1H).

ES-MS: 400 (M+NH4).

C. 3'-[4-(2-Oxo-3,3-dimethylbutoxy)-3-methylphenyl]-3'-[4-trifluoromethylsulfonyloxy-3-methylphenyl]pentane

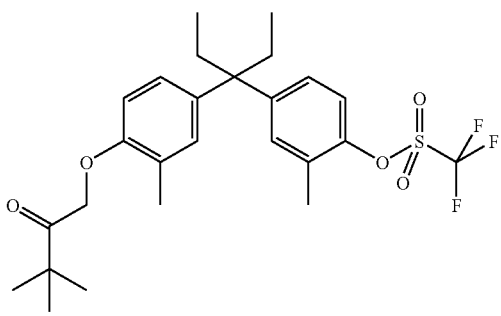

To a 0° C. solution of 3'-[4-(2-oxo-3,3-dimethylbutoxy)-3-methylphenyl)]-3'-[4-hydroxy-3-methylphenyl]pentane (20 g, 52 mmol), pyridine (30 ml) is added Tf₂O (9.7 ml, 57 mmol). The mixture is warmed to RT and stirred 14 h. The reaction is concentrated. The residue is partitioned between Et₂O/1N HCl. The organic layer is washed with water, brine, Na₂SO₄ dried, concentrated, and chromatographed (hex to 10% EtOAc/hex) to give the title compound as an oil (26.3 g, 98%).

NMR (300 mHz, DMSO): δ 0.53 (t, J=7.3 Hz, 6H), 1.16 (s, 9H), 2.04 (q, J=7.3 Hz, 4H), 2.14 (s, 3H), 2.28 (s, 3H), 5.07 (s, 2H), 6.61 (d, J=8.8 Hz, 1H), 6.86 (dd, J=2.2, 8.8 Hz, 1H), 6.91 (d, J=1.8 Hz, 1H), 7.10 (dd, J=2.2, 8.8 Hz, 1H), 7.25 (m, 2H).

ES-MS: 532.5 (M+NH4).

D. 3'-[4-(2-Hydroxy-3,3-dimethylbutoxy)-3-methylphenyl]-3'-[4-trifluoromethylsulfonyloxy-3-methylphenyl]pentane

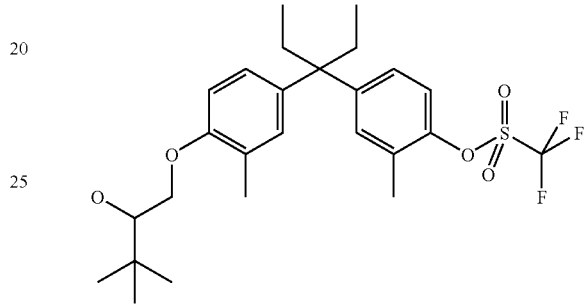

To a 0° C. mixture of 3'-[4-(2-oxo-3,3-dimethylbutoxy)-3-methylphenyl]-3'-[4-trifluoromethylsulfonyloxy-3-methylphenyl]pentane (25.5 g, 49.5 mmol) and MeOH (200 ml) is added NaBH₄ (2.63 g, 59.4 mol) in portions. After stirring for 15 m, the reaction is allowed to warm to RT and stirred for 16 h. The reaction is concentrated and partitioned between Et₂O/1N HCl. The organic layer is washed with water, Na₂SO₄ dried, and concentrated to give the title compound as an oil (26.0 g, quant).

NMR (300 mHz, DMSO): δ 0.55 (t, J=7.3 Hz, 6H), 0.92 (s, 9H), 2.04 (q, J=7.3 Hz, 4H), 2.11 (s, 3H), 2.28 (s, 3H), 3.46 (m, 1H), 3.76 (m, 1H), 4.03 (m, 1H), 4.78 (d, J=5.5 Hz, 1H), 6.89 (m, 3H), 7.10 (dd, J=1.8, 8.8 Hz, 1H), 7.23 (m, 2H).

High Res. EI-MS, m/e: 516.2171; calc. for $C_{26}H_{35}F_3O_5S$: 516.2157.

E. 3'-[4-(2-hydroxy-3,3-dimethylbutoxy)-3-methylphenyl]-3'-[4-methoxycarbonyl-3-methylphenyl]pentane A mixture of 3'-[4-(2-hydroxy-3,3-dimethylbutoxy)-3-methylphenyl]-3'-[4-trifluoromethylsulfonyloxy-3-methylphenyl]pentane (27 g, 52.2 mmol), Pd(OAc)₂ (1.2 g, 5.22 mmol), Dppf (5.8 g, 10.4 mmol), MeOH (21 ml, 522 mmol), Et₃N (22 ml, 157 mmol), and DMF (100 ml) is pressurized with carbon monoxide (1000 psi) and heated to 110° C. for 48 h. After cooling, the reaction is filtered through diatomaceous earth with EtOAc wash. The filtrate is diluted with 1:1 Et₂O:EtOAc, washed with 1N HCl, and filtered through diatomaceous earth, Na₂SO₄ dried, concentrated, and chromatographed (hex to 10% EtOAc/hex) to give the title compound (14 g, 63%).

NMR 300 MHz(DMSO): δ 0.54 (t, J=7.3 Hz, 6H), 0.92 (s, 9H), 2.04 (q, J=7.3 Hz, 4H), 2.09 (s, 3H), 2.46 (s, 3H), 3.45 (m, 1H), 3.76 (m, 4H), 4.02 (m, 1H), 4.78 (d, J=5.5 Hz, 1H), 6.83 (m, 2H), 6.92 (dd, J=2.2, 8.4 Hz, 1H), 7.07 (m, 2H), 7.74 (d, J=8.1 Hz, 1H).

High Res. FAB-MS: 426.2750; calc. for $C_{27}H_{38}O_4$: 426.2770.

Example 2

Preparation of racemic 3'-[4-(2-hydroxy-3,3-dimethylbutoxy)-3-methylphenyl]-3'-[4-carboxyl-3-methylphenyl]pentane

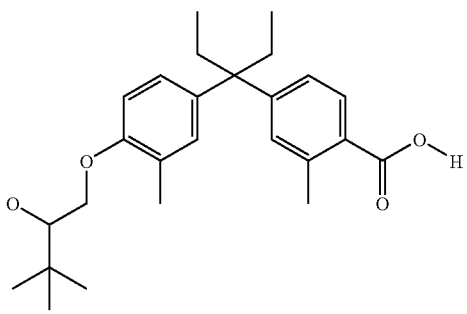

A mixture of 3'-[4-(2-hydroxy-3,3-dimethylbutoxy)-3-methylphenyl]-3'-[4-methoxycarbonyl-3-methylphenyl]pentane (8.3 g, 19.4 mmol), EtOH (100 ml), water (100 ml) is added KOH (10.8 g, 97 mmol) and heated to 75° C. for 8 h. The reaction is concentrated with a stream of nitrogen and the residue is partitioned between 1:1 $Et_2O:EtOAc$ and 1N HCl. The organic layer is washed with water, $Na_2SO_4$ dried, concentrated, and chromatographed (gradient 20% EtOAc/$MeCl_2$ to 30% EtOAc/$CHCl_3$) to give the title compound as a white foam (7.85 g, 95%).

NMR mHz(DMSO): δ 0.54 (t, J=7.3 Hz, 6H), 0.92 (s, 9H), 2.05 (q, J=7.3 Hz, 4H), 2.10 (s, 3H), 2.47 (s, 3H), 3.45 (m, 1H), 3.76 (m, 1H), 4.02 (dd, J=3.3, 9.9 Hz, 1H), 4.78 (d, J=5.1 Hz, 1H), 6.83 (m, 2H), 6.92 (dd, J=1.8, 8.4 Hz, 1H), 7.05 (m, 2H), 7.72 (d, J=8.1 Hz, 1H), 12.60 (br s, 1H).

High Res. ES-MS: 435.2498; calc. for $C_{26}H_{36}O_4$+Na: 435.2511

Example 3A and Example 3B

Preparation of enantiomers of 3'-[4-(2-hydroxy-3,3-dimethylbutoxy)-3-methylphenyl]-3'-[4-carboxyl-3-methylphenyl)]pentane

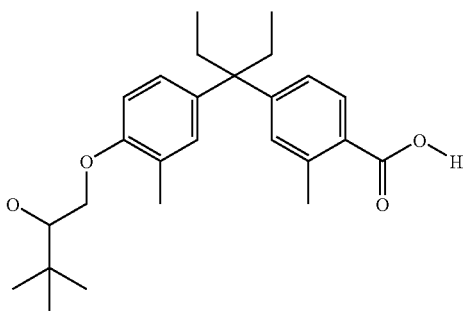

A mixture of racemic 3'-[4-(2-hydroxy-3,3-dimethylbutoxy)-3-methylphenyl]-3'-[4-carboxyl-3-methylphenyl)]pentane, Example 3, is chromatographed with a ChiralPak AD column to give enantiomer 1, Example 3A (110 mg, 37%) and enantiomer 2, Example 3B (110 mg, 37%).

Enantiomer 1, Example 3A
HPLC: ChiralPak AD (4.6×250 mm); 0.1% TFA/20% IPA/80% heptane; 1 ml/m (flow rate); Rt=6.2 m
NMR eq. To Example 2.
High Res. ES-MS: 411.2521; calc. for $C_{26}H_{36}O_4$—H: 411.2535

Enantiomer 2, Example 3B
HPLC: ChiralPak AD (4.6×250 mm); 0.1% TFA/20% IPA/80% heptane; 1 ml/m (flow rate); Rt=7.3 m
NMR eq. To Example 2.
High Res. ES-MS: 413.2728; calc. for $C_{26}H_{36}O_4$+H, 413.2692

Example 3A Alternate Method

Preparation of enantiomer 1 of 3'-[4-(2-hydroxy-3,3-dimethylbutoxy)-3-methylphenyl]-3'-[4-carboxyl-3-methylphenyl]pentane from enantiomer 1 of 3'-[4-(2-hydroxy-3,3-dimethylbutoxy)-3-methylphenyl]-3'-[4-methoxycarbonyl-3-methylphenyl]pentane Using a procedure analogous to Example 2, enantiomer 1 of 3'-[4-(2-hydroxy-3,3-dimethylbutoxy)-3-methylphenyl]-3'-[4-methoxycarbonyl-3-methylphenyl]pentane, Example 4A, gave the title compound as a glassy solid (1.3 g, quant).

Enantiomer 1, Example 3A
HPLC: ChiralPak AD (4.6×250 mm); 0.1% TFA/20% IPA/80% heptane; 1 ml/m (flow rate); Rt=7.0 m
NMR eq. To Example 2.
High Res. ES-MS: 435.2533; calc. for $C_{26}H_{36}O_4$+Na: 435.2511
High Res. ES-MS: 430.2943; calc. for $C_{26}H_{36}O_4$+$NH_4$: 430.2943
HPLC correlation of Example 3A (derived from chiral HPLC of 2) and 3A (derived from the hydrolysis of 4A):
A mixture of Example 3A (1 mg) (derived from chiral HPLC of 2) and 3A (1 mg) (derived from the hydrolysis of 4A) is dissolved in TFA/20% IPA/80% and analyzed by HPLC; ChiralPak AD (4.6×250 mm); 0.1% TFA/20% IPA/80% heptane; 1 ml/m (flow rate); to give a single peak with Rt=7.0 m.

Example 3B Alternate Method

Preparation of enantiomer 2 of 3'-[4-(2-hydroxy-3,3-dimethylbutoxy)-3-methylphenyl]-3'-[4-carboxyl-3-methylphenyl]pentane from enantiomer 2 of 3'-[4-(2-hydroxy-3,3-dimethylbutoxy)-3-methylphenyl]-3'-[4-methoxycarbonyl-3-methylphenyl]pentane Using a procedure analogous to Example 2, enantiomer 2 of 3'-[4-(2-hydroxy-3,3-dimethylbutoxy)-3-methylphenyl]-3'-[4-methoxycarbonyl-3-methylphenyl]pentane, Example 4B, gave the title compound as a glassy solid (1.3 g, quant).

Enantiomer 2, Example 3B
HPLC: ChiralPak AD (4.6×250 mm); 0.1% TFA/20% IPA/80% heptane; 1 ml/m (flow rate); Rt=8.0 m
NMR eq. To Example 2.
High Res. ES-MS: 435.2536; calc. for $C_{26}H_{36}O_4$+Na: 435.2511
HPLC correlation of Example 3B (derived from chiral HPLC of 2) and 3B (derived from the hydrolysis of 4B): A mixture of Example 3B (1 mg) (derived from chiral HPLC of 2) and 3B (1 mg) (derived from the hydrolysis of 4B) is dissolved in TFA/20% IPA/80% and analyzed by HPLC;

ChiralPak AD (4.6×250 mm); 0.1% TFA/20% IPA/80% heptane; 1 ml/m (flow rate); to give a single peak with Rt=8.16 m.

Example 4A and 4B

Preparation of enantiomers of 3'-[4-(2-hydroxy-3,3-dimethylbutoxy)-3-methylphenyl]-3'-[4-methoxycarbonyl-3-methylphenyl]pentane

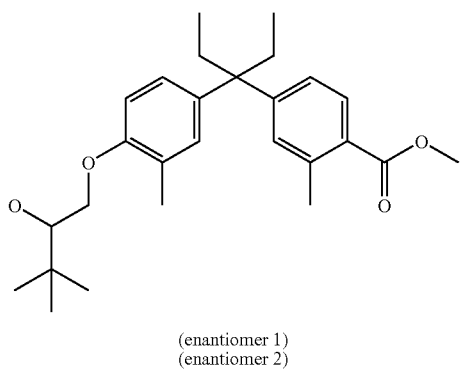

(enantiomer 1)
(enantiomer 2)

A mixture of racemic 3'-[4-(2-hydroxy-3,3-dimethylbutoxy)-3-methylphenyl]-3'-[4-methoxycarbonyl-3-methylphenyl]pentane, Example 1, is chromatographed with a ChiralPak AD column to give enantiomer 1, Example 4A (1.72 g, 49%) and enantiomer 2, Example 4B (1.72 g, 49%).

Enantiomer 1, Example 4A
  HPLC: ChiralPak AD (4.6×250 mm); 15% IPA/80% heptane; 1 ml/m (flow rate); Rt=5.4 m
  NMR eq. To Example 1.
  High Res. ES-MS: 444.3130; calc. for $C_{27}H_{38}O_4+NH_4$: 444.3114

Enantiomer 2, Example 4B
  HPLC: ChiralPak AD (4.6×250 mm); 15% IPA/80% heptane; 1 ml/m (flow rate); Rt=8.0 m
  NMR eq. To Example 1.
  High Res. ES-MS: 444.3134; calc. for $C_{27}H_{38}O_4+NH_4$: 444.3114

Example 5

Preparation of 3'-[4-(2-hydroxy-3,3-dimethylbutoxy)-3-methylphenyl]-3'-[4-methylsulfonylaminocarbonyl-3-methylphenyl)]pentane

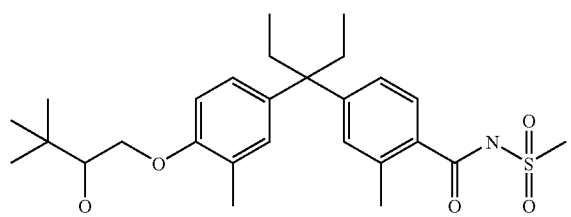

To a mixture of methane sulfonamide (92 mg, 0.97 mmol), EDCI (186 mg, 0.97 mmol), DMAP (118 mg, 0.97 mmol) and $CH_2Cl_2$ (7 ml) is added 3'-[4-(2-hydroxy-3,3-dimethylbutoxy)-3-methylphenyl]-3'-[4-carboxyl-3-methylphenyl]pentane, Example 1, (400 mg, 0.97 mmol) and stirred overnight. The reaction is diluted with $CH_2Cl_2$, washed with 1N HCl (4×20 ml), $Na_2SO_4$ dried, concentrated, and chromatographed (gradient $CHCl_3$ to 10% $CH_3CN/CHCl_3$) to give the title compound as a solid (240 mg, 51%).

NMR mHz(DMSO): δ 0.60 (t, J=7.3 Hz, 6H), 1.01 (s, 9H), 2.06 (q, J=7.3 Hz, 4H), 2.17 (s, 3H), 2.42 (d, J=2.9 Hz, 1H), 2.49 (s, 3H), 3.43 (s, 3H), 3.70 (d, J=8.8 Hz, 1H), 3.86 (t, J=8.8 Hz, 1H), 4.09 (dd, J=2.4, 9.3 Hz, 1H), 6.71 (d, 8.8 Hz, 1H), 6.82 (d, J=2.0 Hz, 1H), 6.91 (dd, J=2.4, 8.8 Hz, 1H), 7.09 (m, 2H), 7.37 (d, J=7.8 Hz, 1H), 12.30 (s, 1H).

High Res. ES-MS: 490.2633; calc. for $C_{27}H_{39}NO_5S+H$, 490.2627

Example 6

Preparation of 3'-[4-(2-oxo-3,3-dimethylbutoxy)-3-methylphenyl]-3'-[4-(2-carboxylethyl)-3-methylphenyl]pentane

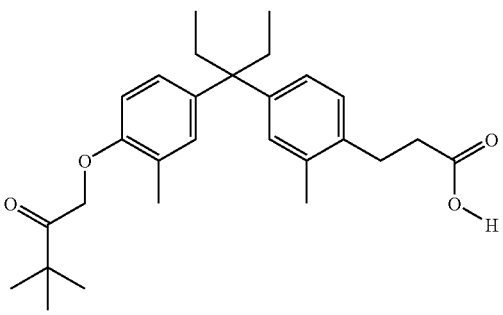

A. 3'-[4-Benzyloxy-3-methylphenyl]-3'-[4-hydroxy-3-methylphenyl]pentane

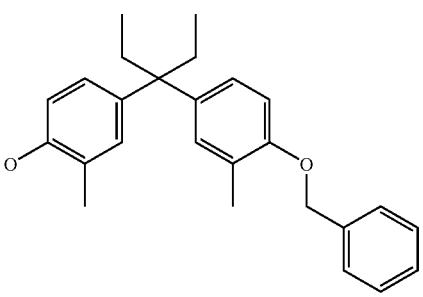

To a solution of 3,3-bis[4-hydroxy-3-methylphenyl]pentane (10 g, 35.2 mmol) and DMF (180 ml) is added 60% NaH disp (1.4 g, 35.2 mmol). After stirring for 30 m, to the reaction is added benzyl bromide (4.2 ml, 35.2 mmol). The mixture is stirred for 14 h and concentrated in vacuo. The residue is partitioned between $Et_2O$/water. The organic layer is washed with 1N HCl, water, brine, $Na_2SO_4$ dried, concentrated, and chromatographed ($MeCl_2$) to give the title compound as an oil (6.5 g, 49%).

NMR 300 MHz(DMSO): δ 0.52 (t, J=7.3 Hz, 6H), 1.96 (q, J=7.3 Hz, 4H), 2.04 (s, 3H), 2.12 (s, 3H), 5.05 (s, 2H), 6.63 (d, J=8.1 Hz, 1H), 6.75 (dd, J=2.2, 8.1 Hz, 1H), 6.79 (s, 1H), 6.89 (m, 3H), 7.44 (m, 5H), 8.96 (s, 1H).

High Res. FAB-MS: 374.2237; calc. for $C_{26}H_{30}O_2$: 374.2246

B. 3'-[4-Benzyloxy-3-methylphenyl]-3'-[4-trifluoromethylsulfonyloxy-3-methylphenyl]pentane

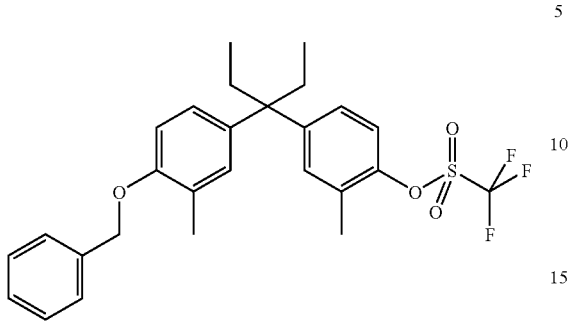

Using a procedure analogous to Example 1C, 3'-[4-benzyloxy-3-methylphenyl]-3'-[4-hydroxy-3-methylphenyl]pentane gives the title compound as an oil (21.5 g, 91%).

NMR 300 MHz(DMSO): δ 0.54 (t, J=7.3 Hz, 6H), 2.05 (q, J=7.3 Hz, 4H), 2.14 (s, 3H), 2.28 (s, 3H), 5.06 (s, 2H), 7.10 (dd, J=2.2, 8.8 Hz, 1H), 7.26 (m, 2H), 7.34 (d, J=7.0 Hz, 1H), 7.39 (m, 4H).

High Res. FAB-MS: 506.1743; calc. for $C_{27}H_{29}F_3O_4S$: 506.1739

C. 3'-[4-Benzyloxy-3-methylphenyl]-3'-[4-(2-ethoxycarbonylethyl)-3-methylphenyl]pentane

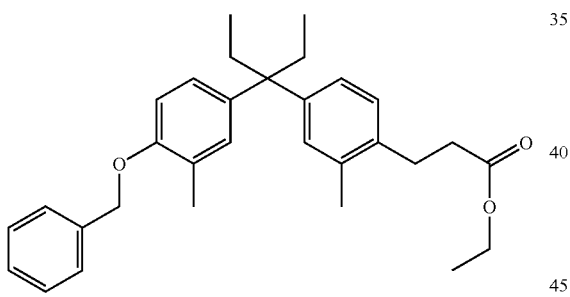

To a mixture of 3'-[4-benzyloxy-3-methylphenyl]-3'-[4-trifluoromethylsulfonyloxy-3-methylphenyl]pentane (5.3 g, 10.5 mmol) and THF (5 ml) is sequentially added Pd(dppf)Cl$_2$ (860 mg, 1.05 mmol), LiCl (1.78 g, 42 mmol), and 0.5 M BrZnCH$_2$CH$_2$CO$_2$Et in THF (63 ml, 31.4 mmol). The mixture is heated to 60° C. for 18 h. After cooling to RT, the mixture is concentrated in-vacuo, partitioned between Et$_2$O/EtOAc/1N HCl. The organic layer is washed with 1N HCl, water, Na$_2$SO$_4$ dried, concentrated, and chromatographed (hex to 10% EtOAc/hex) to give the title compound (2.5 g, 52%).

NMR 400 MHz(DMSO): δ 0.51 (t, J=7.3 Hz, 6H), 1.14 (t, J=7.1 Hz, 3H), 2.00 (q, J=7.3 Hz, 4H), 2.10 (s, 3H), 2.18 (s, 3H), 2.52 (t, J=8.1 Hz, 2H), 2.75 (t, J=8.1 Hz, 2H), 4.01 (q, J=7.1 Hz, 2H), 5.03 (s, 2H), 6.87 (m, 5H), 6.98 (d, J=7.8 Hz, 1H), 7.31 (d, J=7.3 Hz, 1H), 7.37 (m, 2H), 7.43 (d, J=7.1 Hz, 2H).

High Res. ES-MS: 476.3178; calc. for $C_{31}H_{38}O_3+NH_4$: 476.3165

D. 3'-[4-Hydroxy-3-methylphenyl]-3'-[4-(2-ethoxycarbonylethyl)-3-methylphenyl]pentane

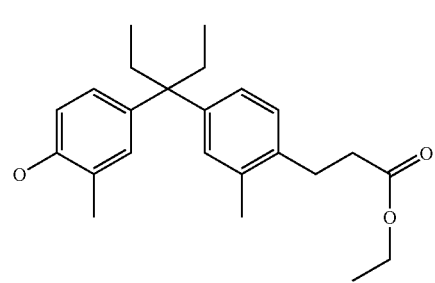

A mixture of 3'-[4-benzyloxy-3-methylphenyl]-3'-[4-(2-ethoxycarbonyl ethyl)-3-methylphenyl]pentane (2.4 g, 5.45 mmol), EtOH (20 ml), and 10% Pd/C (250 mg) is hydrogenated at atmospheric pressure for 18 h. The reaction is filtered through diatomaceous earth with EtOAc wash. The filtrate is concentrated to give the title compound (2 g, quant).

NMR 400 MHz(DMSO): δ 0.49 (t, J=7.3 Hz, 6H), 1.12 (t, J=7.1 Hz, 3H), 1.95 (q, J=7.3 Hz, 4H), 2.01 (s, 3H), 2.18 (s, 3H), 2.52 (t, J=7.7 Hz, 2H), 2.75 (t, J=7.7 Hz, 2H), 4.01 (q, J=7.1 Hz, 2H), 6.61 (d, J=8.3 Hz, 1H), 6.73 (d, J=8.3 Hz, 1H), 6.77 (s, 1H), 6.86 (m, 2H), 6.97 (d, J=7.8 Hz, 1H), 8.98 (s, 1H).

High Res. ES-MS: 391.2218; calc. for $C_{24}H_{32}O_3+Na$: 391.2249

E. 3'-[4-(2-Oxo-3,3-dimethylbutoxy)-3-methylphenyl]-3'-[4-(2-ethoxycarbonylethyl)-3-methylphenyl]pentane

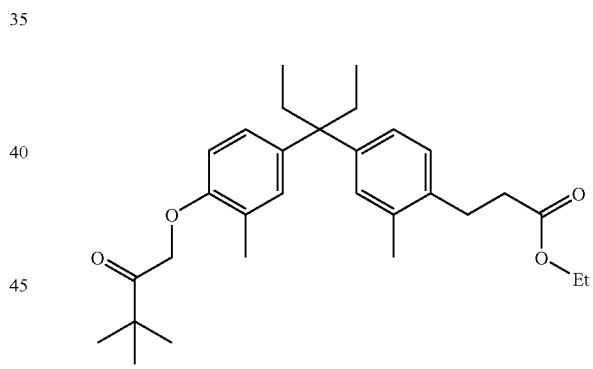

Using a procedure analogous to Example 1B, 3'-[4-hydroxy-3-methylphenyl]-3'-[4-(2-ethoxycarbonylethyl)-3-methylphenyl]pentane and 1-bromo-3,3-dimethyl-2-butanone gave the title compound (2.1 g, 83%).

$^1$H NMR 400 MHz (DMSO-d$_6$): δ 0.50 (t, J=7.3 Hz, 6H), 1.05-1.14 (m, 12H), 1.98 (q, J=7.3 Hz, 4H), 2.10 (s, 3H), 2.18 (s, 3H), 2.52 (t, J=7.7, 2H), 2.75 (t, J=7.7, 2H), 4.02 (q, J=7.2 Hz, 2H), 5.04 (s, 2H), 6.55 (d, J=8.3 Hz, 1H), 6.82-6.89 (m, 4H), 6.98 (d, J=8.1, 1H).

High Res. ES-MS: 489.2990; calc. for $C_{30}H_{42}O_4+Na$: 489.2981

F. 3'-[4-(2-oxo-3,3-dimethylbutoxy)-3-methylphenyl]-3'-[4-carboxylethyl-3-methylphenyl]pentane Using a procedure analogous to Example 2,3'-[4-(2-oxo-3,3-dimethylbutoxy)-3-methylphenyl]-3'-[4-(2-ethoxycarbonylethyl)-3-methylphenyl]pentane gives the title compound (1.8 g, 95%).

$^1$H NMR 300 MHz (DMSO-d$_6$): δ 0.52 (t, J=7.3 Hz, 6H), 1.16 (s, 9H), 2.01 (q, J=7.32 Hz, 4H), 2.13 (s, 3H), 2.20 (s, 3H), 2.46 (t, J=7.3 Hz, 2H), 2.74 (t, J=7.3 Hz, 2H), 5.06 (s, 2H), 6.58 (d, J=8.4 Hz, 1H), 6.89 (m, 4H), 7.01 (d, J=7.7 Hz, 1H).

High Res. ES-MS: 461.2669; calc. for C$_{28}$H$_{38}$O$_4$+Na: 461.2668

Example 7

Preparation of 3'-[4-(2-oxo-3,3-dimethylbutoxy)-3-methylphenyl]-3'-[4-(2-dimethylcarbamoylethyl)-3-methylphenyl]pentane

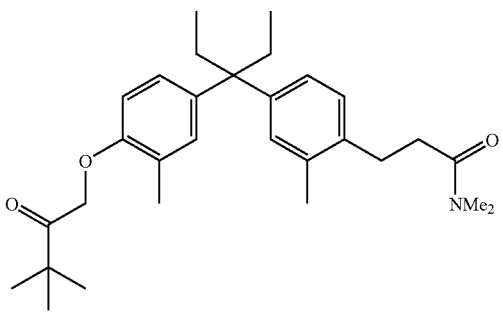

To a 0° C. mixture of 3'-[4-(2-oxo-3,3-dimethylbutoxy)-3-methylphenyl]-3'-[4-(2-carboxylethyl)-3-methylphenyl]pentane (500 mg, 1.14 mmol), pyridine (101 ul, 1.25 mmol), DMF (4.4 ul, 0.057 mmol) and MeCl$_2$ (4 ml) is added oxalyl chloride (104 ul, 1.2 mmol). After stirring for 10 m, to the mixture is added 2M Me$_2$NH/THF (2.3 ml, 4.56 mmol). To the reaction is added MeCl$_2$ (4 ml) and stirred at RT for 2 h. The mixture is concentrated and partitioned between Et$_2$O/1N HCl. The organic layer is washed with water, Na$_2$SO$_4$ dried, concentrated, and chromatographed (hex to CH2Cl2 to 15% EtOAc/MeCl$_2$) to give the title compound as a solid (85 mg, 16%).

$^1$H NMR 400 MHz (DMSO-d$_6$): δ 0.51 (t, J=7.3 Hz, 6H), 1.14 (s, 9H), 1.96 (q, J=7.3 Hz, 4H), 2.11 (s, 3H), 2.19 (s, 3H), 2.48 (t, J=7.2, J=8.8 Hz, 2H, under DMSO peak), 2.69 (t, J=7.2, J=8.8 Hz, 2H), 2.79 (s, 3H), 2.88 (s, 3H), 5.05 (s, 2H), 6.55 (d, J=8.8 Hz, 1H), 6.84-6.87 (m, 4H), 6.99 (d, J=8.3 Hz, 1H).

ES-MS: 466.2 (M+H)

Example 8

Preparation of 3'-[4-(2-hydroxy-3,3-dimethylbutoxy)-3-methylphenyl]-3'-[4-(2-dimethylcarbamoylethyl)-3-methylphenyl]pentane

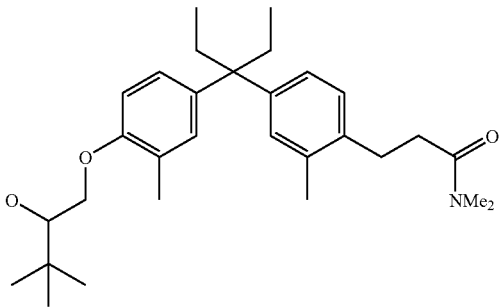

Using a procedure analogous to Example 1D, 3'-[4-(2-oxo-3,3-dimethylbutoxy)-3-methylphenyl]-3'-[4-(2-dimethylcarbamoylethyl)-3-methylphenyl]pentane gives the title compound as a white glassy solid (65 mg, quant).

$^1$H NMR 300 MHz (DMSO-d$_6$): δ 0.53 (t, J=7.0 Hz, 6H), 0.92 (s, 9H), 6.96 (q, J=6.96 Hz, 4H), 2.10 (s, 3H), 2.20 (s, 3H), 2.50 (t, J=6.9, J=8.4 Hz, 2H, under DMSO peak), 2.71 (t, J=6.9, J=8.4 Hz, 2H), 2.80 (s, 3H), 2.90 (s, 3H), 3.45 (m, 1H), 3.75 (m, 1H), 4.01 (dd, J=2.9, J=6.9 Hz, 1H), 6.80 (d, J=8.4, 1H), 6.89 (m, 4H), 7.01 (d, J=8.0 Hz, 1H).

High Res. ES-MS: 490.3301; calc. for C$_{30}$H$_{45}$NO$_3$+Na: 490.3297

Example 9

Preparation of 3'-[4-(2-hydroxy-3,3-dimethylbutoxy)-3-methylphenyl]-3'-[4-(2-dimethylcarbamoyl-t-ethylidene)-3-methylphenyl]pentane

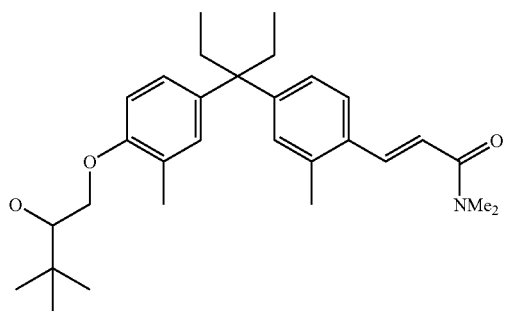

To a mixture of 3'-[4-(2-hydroxy-3,3-dimethylbutoxy)-3-methylphenyl]-3'-[4-trifluoromethylsulfonyloxy-3-methylphenyl]pentane (640 mg, 1.24 mmol), Pd(OAc)$_2$ (14 mg, 0.062), DPPP (51 mg, 0.124 mmol), and DMF (2.5 ml) is added Et$_3$N (0.69 ml, 4.96 mmol). The mixture is purged with N$_2$ and N,N-dimethylacrylamide (0.39 ml, 3.71 mmol) is added. The reaction is heated to 80° C. for 14 h and then cooled. The mixture is partitioned between EtOAc/water. The organic layer is washed with 1N HCl, water, brine, Na$_2$SO$_4$ dried, concentrated, and chromatographed (MeCl$_2$ to 60% EtOAc/MeCl$_2$) to give the title compound as a white foam (90 mg, 16%).

$^1$H NMR 300 MHz (DMSO-d$_6$): δ 0.55 (t, J=7.0 Hz, 6H), 0.92 (s, 9H), 2.04 (q, J=7.0 Hz, 4H), 2.10 (s, 3H), 2.31 (s, 3H), 2.92 (s, 3H), 3.13 (s, 3H), 3.45 (m, 1H), 3.75 (dd, J=7.4, 9.9 Hz, 1H), 4.02 (dd, J=3.3, 9.9 Hz, 1H), 4.78 (d, J=5.1 Hz, 1H), 6.81 (d, J=8.8 Hz, 1H), 6.87 (s, 1H), 6.96 (m, 3H), 7.01 (s, 1H), 7.62 (m, 2H).

High Res. ES-MS: 466.3328; calc. for C$_{30}$H$_{44}$NO$_3$+H, 466.3321

Preparation of enantiomers of 3'-[4-(2-hydroxy-1,3,3-trimethylbutoxy)-3-methylphenyl]-3'-[4-methoxycarbonyl-3-methylphenyl]pentane

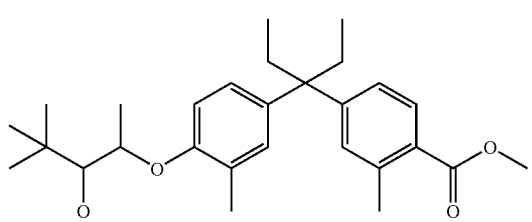

(enantiomer 1) Example 10Da
JB5-A03275-45-1
(enantiomer 2) Example 10Db

A. 3'-[4-(2-oxo-3,3-dimethylbutoxy)-3-methylphenyl]-3'-[4-methoxycarbonyl-3-methylphenyl]pentane

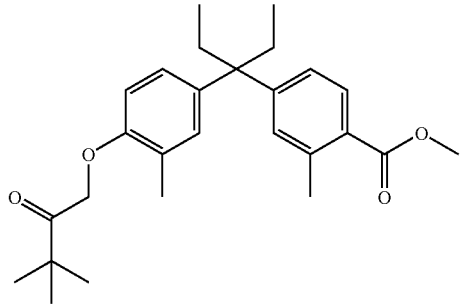

Using a procedure analogous to Example 1B, 3'-[4-hydroxy)-3-methylphenyl]-3'-[4-methoxycarbonyl-3-methylphenyl]pentane gave the title compound as a white solid (19.5 g, 88%).

NMR 300 mHz(DMSO): δ 0.54 (t, J=7.3 Hz, 6H), 1.16 (s, 9H), 2.05 (q, J=7.3 Hz, 4H), 2.13 (s, 3H), 2.47 (s, 3H), 3.79 (s, 3H), 5.07 (s, 2H), 6.59 (d, J=9.1 Hz, 1H), 6.86 (m, 2H), 7.06 (d, J=8.1 Hz, 1H), 7.11 (s, 1H), 7.72 (d, J=8.1 Hz, 1H).

High Res. ES-MS: 442.2953; calc. for $C_{27}H_{36}O_4+NH_4$: 442.2957.

B. 3'-[4-(2-oxo-1,3,3-trimethylbutoxy)-3-methylphenyl]-3'-[4-methoxycarbonyl-3-methylphenyl]pentane

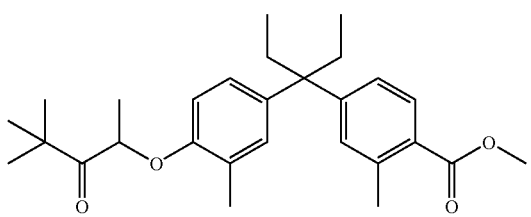

To a −78° C. mixture of 3'-[4-(2-oxo-3,3-dimethylbutoxy)-3-methylphenyl]-3'-[4-(2-methoxycarbonyl-3-methylphenyl)]pentane (2.0 g, 4.7 mmol) in THF (10 ml) is added 1M LiHMDS/THF (5.2 ml, 5.2 mmol). The reaction is warmed to −45° C., stirred for 1.25 h, added MeI (351 ul, 5.6 mmol). After warming to RT and stirred overnight, the reaction is diluted with Et2O, washed with 1N HCl, water, and Na2SO4 dried. The organic solution is concentrated and chromatographed (50% CHCl3/hex) to give the title compound (1.75 g, 85%).

NMR 300 mHz(DMSO): δ 0.53 (t, J=7.3 Hz, 6H), 1.10 (s, 9H), 1.34 (d, J=6.6 Hz, 3H), 2.04 (q, J=7.3 Hz, 4H), 2.10 (s, 3H), 2.46 (s, 3H), 3.79 (s, 3H), 5.32 (q, J=6.6 Hz, 1H), 6.88 (m, 3H), 7.05 (d, J=8.4 Hz, 1H), 7.10 (s, 1H), 7.71 (d, J=8.1 Hz, 1H).

High Res. ES-MS: 456.3107; calc. for $C_{28}H_{38}O_4+NH_4$: 456.3114

C. 3'-[4-(2-hydroxy-1,3,3-trimethylbutoxy)-3-methylphenyl]-3'-[4-methoxycarbonyl-3-methylphenyl]pentane

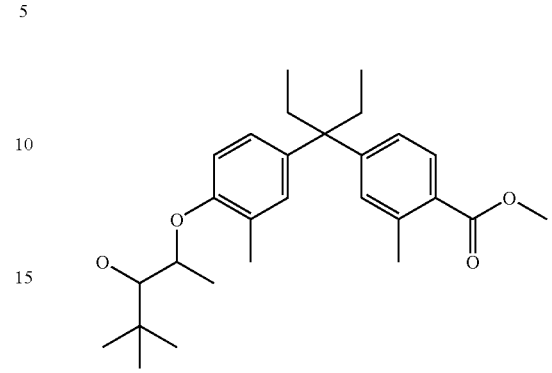

Using a procedure analogous to Example 1D, 3'-[4-(2-oxo-1,3,3-trimethylbutoxy)-3-methylphenyl]-3'-[4-methoxycarbonyl-3-methylphenyl]pentane gives the title compound (1.6 g, 100%).

NMR 300 mHz(DMSO): δ 0.54 (t, J=7.3 Hz, 6H), 0.91 (s, 9H), 1.19 (d, J=5.9 Hz, 3H), 2.07 (m, 7H), 2.48 (s, 3H), 3.08 (dd, J=1.1, 7.7 Hz, 1H), 3.79 (s, 3H), 4.35 (d, J=7.7 Hz, 1H), 4.57 (br q, J=5.9 Hz, 1H), 6.84 (m, 3H), 7.06 (br d, J=8.4 Hz, 1H), 7.14 (s, 1H), 7.72 (d, J=8.4 Hz, 1H).

High Res. ES-MS: 456.3107; calc. for $C_{28}H_{38}O_4+NH_4$: 456.3114.

D. Enantiomers of 3'-[4-(2-hydroxy-1,3,3-trimethylbutoxy)-3-methylphenyl]-3'-[4-methoxycarbonyl-3-methylphenyl]pentane Using a procedure analogous to Example 1D, 3'-[4-(2-oxo-1,3,3-trimethylbutoxy)-3-methylphenyl]-3'-[4-methoxycarbonyl-3-methylphenyl]pentane gave a racemic mixture of the title compound. The mixture is chromatographed (Chiralpak AD) to give enantiomer 1 (543 mg, 36%, Rt=) and enantiomer 2 (822 mg, 55%, Rt=).

Enantiomer 1 Example 10Da

NMR 300 mHz (DMSO): δ 0.54 (t, J=7.3 Hz, 6H), 0.91 (s, 9H), 1.20 (d, J=6.2 Hz, 3H), 2.07 (m, 7H), 2.48 (s, 3H), 3.08 (dd, J=1.5, 7.7 Hz, 1H), 3.79 (s, 3H), 4.35 (d, J=7.7 Hz, 1H), 4.57 (m, 1H), 6.84 (m, 3H), 7.06 (dd, J=1.1, 8.4 Hz, 1H), 7.14 (s, 1H), 7.72 (d, J=8.4 Hz, 1H).

High Res. ES-MS: 458.3257; calc. for $C_{28}H_{40}O_4+NH_4$: 458.3270.

Enantiomer 2 Example 10Db

NMR 300 mHz (DMSO): eq. to enantiomer 1.

MS: 440.29 (M+).

High Res. ES-MS: calc. for $C_{27}H_{39}NO_5S+H$:

Example 11

Preparation of enantiomer 1 of 3'-[4-(2-hydroxy-1,3,3-trimethylbutoxy)-3-methylphenyl]-3'-[4-carboxyl-3-methylphenyl]pentane

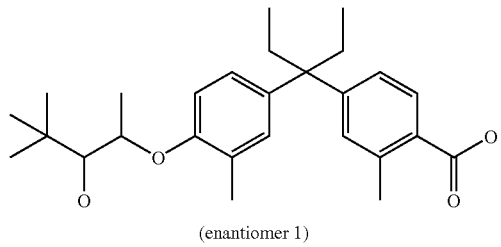

(enantiomer 1)

Using a procedure analogous to Example 2, enantiomer 1 of 3'-[4-(1-methyl-2-hydroxy-3,3-dimethylbutoxy)-3-methylphenyl]-3'-[4-methoxycarbonyl-3-methylphenyl]pentane, Example 10Da, gave the title compound (420 mg, 96%).

HPLC: ChiralPak AD (4.6×250 mm); 0.1% TFA/20% IPA/80% heptane; 1 ml/m (flow rate); Rt=m NMR 300 mHz (DMSO): δ 0.54 (t, J=7.3 Hz, 6H), 0.91 (s, 9H), d, J=5.9 Hz, 3H), 2.07 (m, 7H), 2.48 (s, 3H), 3.08 (dd, J=1.1, 7.7 Hz, 1H), 4.35 (d, J=7.7 Hz, 1H), 4.57 (m, 1H), 6.84 (m, 3H), 7.04 (d, J=8.1 Hz, 1H), 7.10 (s, 1H), 7.72 (d, J=8.1 Hz, 1H), 12.60 (br s, 1H).

High Res. ES-MS: 875.5439; calc. for $[C_{27}H_{38}O_4+Na]+$ $C_{27}H_{38}O_4$: 875.5438.

Example 12

Preparation of enantiomer 2 of 3'-[4-(2-hydroxy-3,3-trimethylbutoxy)-3-methylphenyl]-3'-[4-carboxyl-3-methylphenyl)]pentane

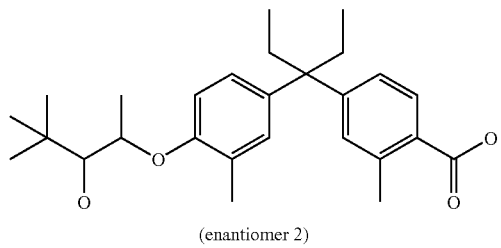

(enantiomer 2)

Using a procedure analogous to Example 2, enantiomer 2 of 3'-[4-(2-hydroxy-1,3,3-trimethylbutoxy)-3-methylphenyl]-3'-[4-methoxycarbonyl-3-methylphenyl]pentane, Example 10Db, gave the title compound (680 mg, 94%).

HPLC: ChiralPak AD (4.6×250 mm); 0.1% TFA/20% IPA/80% heptane; 1 ml/m (flow rate); Rt=m NMR 300 mHz (DMSO): eq. to enantiomer 1.

High Res. ES-MS: 449.2657; calc. for $C_{27}H_{38}O_4+Na$: 449.2668.

Example 12a

Preparation enantiomer 1 of 3'-[4-(2-hydroxy-3,3-dimethylbutoxy)-3-methylphenyl]-3'-[4-(tetrazol-5-ylaminocarbonyl)-3-methylphenyl]pentane

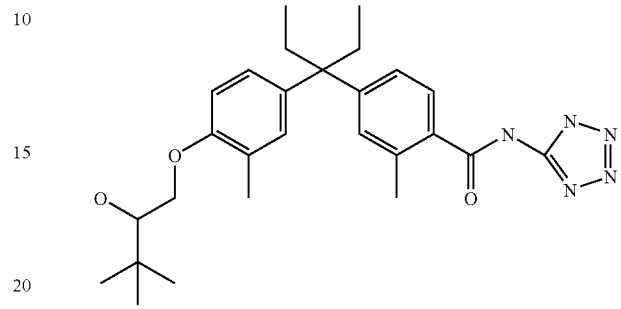

Using a procedure analogous to Example 5, enantiomer 1 of 3'-[4-(2-hydroxy-3,3-dimethylbutoxy)-3-methylphenyl]-3'-[4-carboxyl-3-methylphenyl]pentane, Example 3A, and 5-aminotetrazole give the title compound (440 mg, 95%).

NMR 300 mHz (DMSO): 0.57 (t, J=7.3 Hz, 6H), 0.92 (s, 9H), 2.09 (m, 7H), 2.40 (s, 3H), 3.46 (m, 1H), 3.76 (dd, J=7.3, 10.2 Hz, 1H), 4.03 (dd, J=3.3, 10.2 Hz, 1H), 4.79 (d, J=5.5 Hz, 1H), 6.83 (d, J=8.4 Hz, 1H), 6.89 (s, 1H), 6.95 (d, J=8.4 Hz, 1H), 7.08 (d, J=8.1 Hz, 1H), 7.12 (s, 1H), 7.52 (d, J=8.1 Hz, 1H), 12.23 (s, 1H), 16.00 (br s, 1H).

High Res. ES-MS: 480.2983; calc. for $C_{27}H_{37}N_5O_3+H$, 480.2975.

Example 12b

Preparation enantiomer 2 of 3'-[4-(2-hydroxy-3,3-dimethylbutoxy)-3-methylphenyl]-3'-[4-(tetrazol-5-ylaminocarbonyl)-3-methylphenyl]pentane

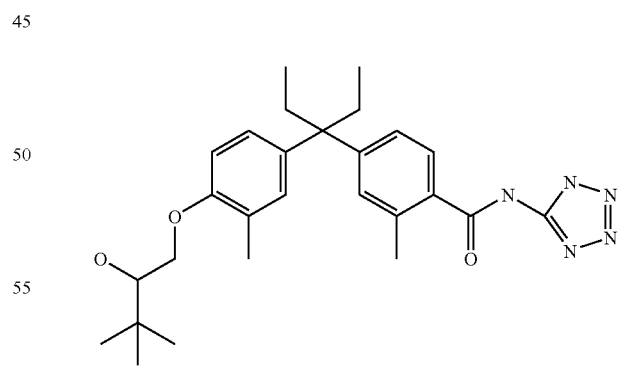

Using a procedure analogous to Example 5, enantiomer 2 of 3'-[4-(2-hydroxy-3,3-dimethylbutoxy)-3-methylphenyl]-3'-[4-carboxyl-3-methylphenyl]pentane, Example 3B, and 5-aminotetrazole gives the title compound (385 mg, 83%).

NMR 300 mHz (DMSO): eq. to enantiomer of 1.

High Res. ES-MS: 480.2968; calc. for $C_{27}H_{37}N_5O_3+H$, 480.2975.

Example 13

Preparation of 1-[4-(1-ethyl-1-{4-[(2-methanesulfonyl-ethylamino)-methyl]-3-methyl-phenyl}-propyl)-2-methyl-phenoxy]-3,3-dimethyl-butan-2-one

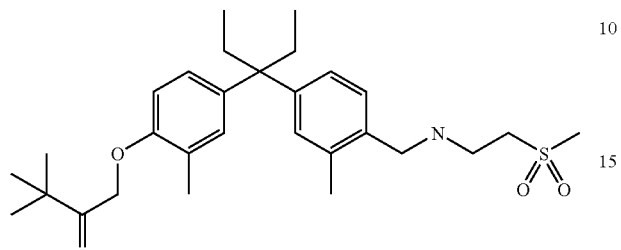

A. Methyl 4-(1-{4-[2-(tert-Butyldimethylsilanyloxy)-3,3-dimethyl-butoxy]-3-methylphenyl}-1-ethylpropyl)-2-methyl-benzoate

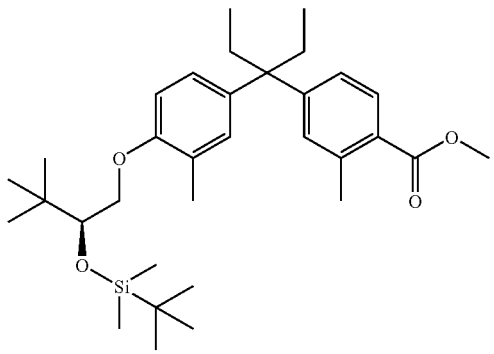

To a solution of the methyl 4-(1-{4-[2-(hydroxy)-3,3-dimethyl-butoxy]-3-methylphenyl}-1-ethylpropyl)-2-methyl-benzoate (4.79 g, 11.24 mmol), Example 1, in DMF (40 mL) is added imidazole (1.14 g, 16.87 mmol) followed by the addition of TBSCl (1.78 g, 11.80 mmol). The mixture is stirred at RT overnight and concentrated. The mixture is partitioned between 0.1 M HCl (100 mL) and EtOAc (100 mL). The aqueous layer is extracted with EtOAC. The combined organic layers is MgSO$_4$ dried, concentrated, and chromatographed (10% EtOAc/Hex) to give the title compound (4.37 g, 72%).

$^1$H NMR (CDCl$_3$): δ 0.04 (s, 3H), 0.10 (s, 3H), 0.60 (t, J=7.0 Hz, 6H), 0.89 (s, 9H), 0.96 (s, 9H), 2.04-2.09 (m, 4H), 2.16 (s, 3H), 2.55 (s, 3H), 3.66 (dd, J=5.6, 3.6 Hz, 1H), 3.82-3.86 (m, 4H), 3.97 (dd, J=10.0, 3.2 Hz, 1H), 6.65 (d, J=8.4 Hz, 1H), 6.83-7.06 (m, 4H), 7.79 (d, J=7.6 Hz, 1H). ES-MS (m/z): calcd for C$_{33}$H$_{52}$O$_4$Si (M$^+$): 540.9; found: 541.2.

B. [4-(1-{4-[2-(tert-Butyldimethylsilanyloxy)-3,3-dimethylbutoxy]-3-methylphenyl}-1-ethylpropyl)-2-methylphenyl]-methanol

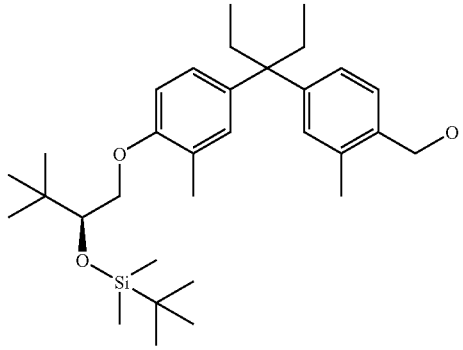

To a 0° C. solution of the methyl 4-(1-{4-[2-(t-butyldimethylsilanyloxy)-3,3-dimethyl-butoxy]-3-methylphenyl}-1-ethylpropyl)-2-methyl-benzoate (4.37 g, 8.09 mmol) in THF (50 mL) is added LiAlH$_4$ (0.31 g, 8.09 mmol). The reaction is stirred for 10 m and allowed to warm to RT overnight. The mixture is cooled to 0° C. and quenched successively with H$_2$O (0.3 mL), 15% NaOH (0.3 mL) and H$_2$O (0.9 mL). The mixture is stirred for 10 m, warmed to RT, stirred for 20 m, filtered through celite with EtOAc (100 mL) wash, and concentrated to give the title compound (4.14 g, 8.08 mmol, 99%).

$^1$H NMR (CDCl$_3$): δ 0.04 (s, 3H), 0.10 (s, 3H), 0.59 (t, J=7.1 Hz, 6H), 0.89 (s, 9H), 0.94 (s, 9H), 2.05 (q, J=7.1 Hz, 4H), 2.17 (s, 3H), 2.31 (s, 3H), 3.66 (dd, J=6.0, 3.6 Hz, 1H), 3.70 (t, J=5.6 Hz, 1H), 3.84 (dd, J=9.8, 5.2 Hz, 1H), 3.97 (dd, J=9.8, 3.6 Hz, 1H), 4.67 (s, 2H), 6.65 (d, J=8.4 Hz, 1H), 6.88-7.02 (m, 4H), 7.21 (d, J=8.0 Hz, 1H). ES-MS (m/z): calcd for C$_{32}$H$_{56}$NO$_3$Si (M+NH$_4$)$^+$: 530.9; found: 530.2.

C. 4-(1-{4-[2-(t-Butyldimethylsilanyloxy)-3,3-dimethylbutoxy]-3-methylphenyl}-1-ethylpropyl)-2-methylbenzaldehyde

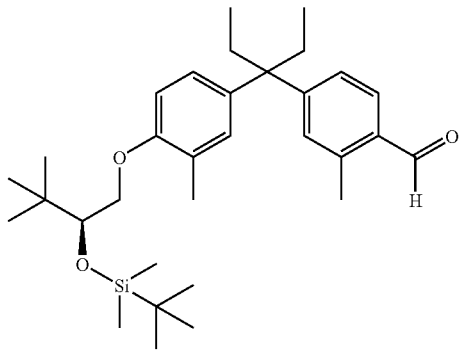

To a solution of [4-(1-{4-[2-(t-butyldimethylsilanyloxy)-3,3-dimethylbutoxy]-3-methylphenyl}-1-ethylpropyl)-2-methylphenyl]methanol (0.25 g, 0.48 mmol) in CH$_2$Cl$_2$ (4 mL) is added powdered 4 Å molecular sieves (250 mg) followed by the addition of NMO (84 mg, 0.72 mmol), and TPAP (8.4 mg, 0.02 mmol). The resulting mixture is stirred at RT for 5 m, filtered through silica gel, washed with EtOAc, and the combined filtrate is concentrated to give the title compound (0.20 g, 83%).

$^1$H NMR (CDCl$_3$): δ 0.04 (s, 3H), 0.10 (s, 3H), 0.61 (t, J=7.2 Hz, 6H), 0.89 (s, 9H), 0.96 (s, 9H), 2.09 (q, J=7.2 Hz, 4H), 2.17 (s, 3H), 2.62 (s, 3H), 3.67 (dd, J=5.4, 3.4 Hz, 1H), 3.85 (dd, J=9.8, 5.4 Hz, 1H), 3.97 (dd, J=9.8, 3.4 Hz, 1H), 6.67 (d, J=8.4 Hz, 1H), 6.84-6.92 (m, 2H), 7.08 (s, 1H), 7.17 (d, J=8.0 Hz, 1H), 7.67 (d, J=8.4 Hz, 1H), 10.21 (s, 1H). ES-MS (m/z): calcd for C$_{32}$H$_{51}$O$_3$Si (M+H)$^+$: 511.8; found: 511.2.

D. [4-(1-{4-[2-(t-Butyldimethylsilanyloxy)-3,3-dimethylbutoxy]-3-methylphenyl}-1-ethylpropyl)-2-methylbenzyl]-(2-methanesulfonylethyl)amine

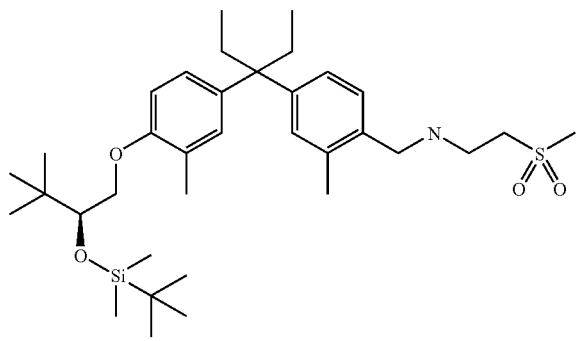

To a mixture of 4-(1-{4-[2-(t-butyldimethylsilanyloxy)-3,3-dimethylbutoxy]-3-methylphenyl}-1-ethylpropyl)-2-methylbenzaldehyde (2.40 g, 4.71 mmol), Et$_3$N (0.9 ml, 6.12 mmol), and 2-aminoethylmethylsulfone hydrochloride (0.78 g, 5.18 mmol) is treated with Ti(OiPr)$_4$ (1.8 ml, 6.12 mmol). The mixture is stirred for 1 h, diluted with CH$_3$OH (20 mL), then NaBCNH$_3$ (0.33 g, 5.18 mmol) is added. The mixture is stirred overnight, quenched with H$_2$O (3 mL), stirred for 1 h., and filtered through SiO$_2$ with EtOAc (100 mL) wash. The filtrate is concentrated and chromatographed (75-80% EtOAc) to give the title compound (1.47 g, 2.38 mmol, 51%).

$^1$H NMR (CDCl$_3$), δ 0.05 (s, 3H), 0.12 (s, 3H), 0.61 (t, J=7.4 Hz, 6H), 0.91 (s, 9H), 0.97 (s, 9H), 2.05 (q, J=7.4 Hz, 4H), 2.19 (s, 3H), 2.33 (s, 3H), 2.99 (s, 3H), 3.21-3.27 (m, 3.5 H), 3.66-3.72 (m, 1.5H), 3.83 (s, 2H), 3.86 (t, J=5.9 Hz, 1H), 3.98 (dd, J=9.8, 3.4 Hz, 1H), 6.65 (d, J=8.3 Hz, 1H), 6.86-6.88 (m, 1H), 6.92 (dd, J=8.3, 2.4 Hz, 1H), 6.99 (s, 1H), 7.00 (bs, 1H), 7.14 (d, J=8.2 Hz, 1H). ES-MS (m/z): calcd for C$_{35}$H$_{60}$O$_4$SSi (M+H)$^+$: 619.0; found: 619.6.

E. 1-[4-(1-Ethyl-1-{4-[(2-methanesulfonylethylamino)methyl]-3-methylphenyl}propyl)-2-methylphenoxy]-3,3-dimethylbutan-2-ol

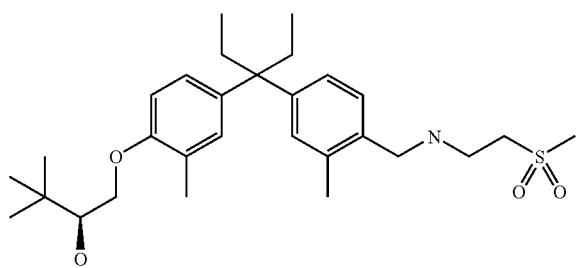

To a mixture of [4-(1-{4-[2-(t-butyldimethylsilanyloxy)-3,3-dimethylbutoxy]-3-methylphenyl}-1-ethylpropyl)-2-methylbenzyl]-(2-methanesulfonylethyl)amine (1.47 g, 2.43 mmol) in THF (30 mL) is added 1M TBAF (2.7 mL, 2.7 mmol), and refluxed for 2 h. After cooling to RT, the mixture is diluted with H$_2$O (20 mL) and extracted with EtOAc (3×30 mL). The combined organic layers are MgSO$_4$ dried, concentrated, and chromatographed (80% EtOAc/Hex) to give the title compound (0.97 g, 1.93 mmol, 79%).

$^1$H NMR (CDCl$_3$), δ 0.60 (t, J=7.4 Hz, 6H), 1.02 (s, 9H), 2.05 (q, J=7.4 Hz, 4H), 2.18 (s, 3H), 2.34 (s, 3H), 3.01 (s, 3H), 3.32 (bs, 4H), 3.71 (dd, J=8.8, 2.4 Hz, 1H), 3.86 (t, J=9.3 Hz, 1H), 3.88 (s, 2H), 4.09 (dd, J=9.3, 2.4 Hz, 1H), 6.70 (d, J=8.3 Hz, 1H), 6.89 (bs, 1H), 6.90-6.96 (m, 1H), 6.98 (s, 1H), 7.00 (s, 1H), 7.13 (d, J=7.5 Hz, 1H). ES-MS (m/z): calcd for C$_{29}$H$_{46}$O$_4$S (M+H)$^+$: 504.8; found: 504.4.

F. t-Butyl (4-{1-ethyl-1-[4-(2-hydroxy-3,3-dimethylbutoxy)-3-methylphenyl]-propyl}-2-methylbenzyl)-(2-methanesulfonylethyl)carbamate

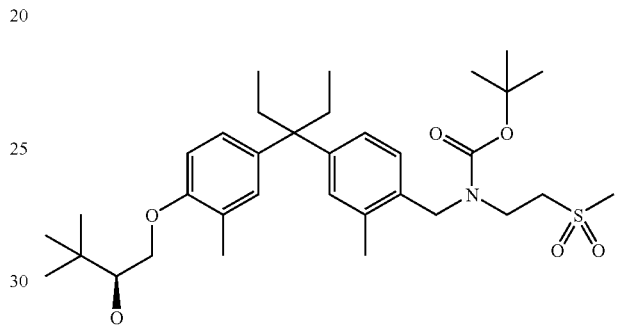

To a mixture of 1-[4-(1-ethyl-1-{4-[(2-methanesulfonyl-ethyl-amino)methyl]-3-methylphenyl}propyl)-2-methylphenoxy]-3,3-dimethylbutan-2-ol (0.97 g, 1.92 mmol), NaHCO$_3$ (0.32 g, 3.84 mmol), H$_2$O (10 mL), and THF (5 mL), is added (Boc)$_2$O (0.46 g, 2.11 mmol). The reaction is stirred overnight, diluted with H$_2$O (10 mL), and extracted with EtOAc (2×20 mL). The combined organic layers are washed with 0.1 M HCl (15 mL), brine (10 mL); MgSO$_4$ dried, and chromatographed (40% EtOAc/Hex) to give the title compound (0.86 g, 1.43 mmol, 74%).

$^1$H NMR (CDCl$_3$), δ 0.61 (t, J=7.3 Hz, 6H), 1.02 (s, 9H), 1.45 (bs, 9H), 2.05 (q, J=7.3 Hz, 4H), 2.19 (s, 3H), 2.24 (s, 3H), 2.44 (bs, 1H), 2.70-3.20 (b, 5H), 3.58 (bs, 2H), 3.71 (dd, J=8.8, 2.9 Hz, 1H), 3.86 (t, J=8.8 Hz, 1H), 4.10 (dd, J=8.8, 2.9 Hz, 1H), 4.47 (s, 2H), 6.71 (d, J=8.4 Hz, 1H), 6.80-7.01 (m, 5H). ES-MS (m/z): calcd for C$_{34}$H$_{57}$N$_2$O$_6$S (M+NH$_4$)$^+$: 621.9; found: 621.3.

G. t-Butyl (4-{1-[4-(3,3-dimethyl-2-oxobutoxy)-3-methylphenyl]-1-ethylpropyl}-2-methylbenzyl)-(2-methanesulfonylethyl)carbamate

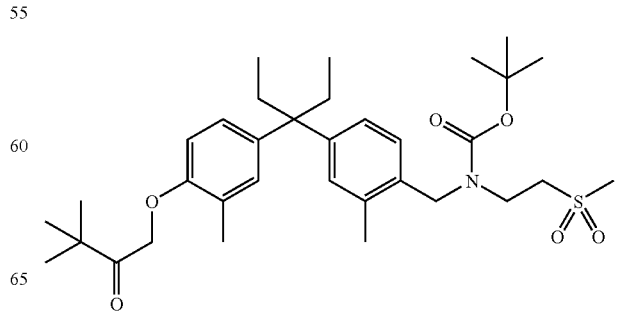

Using a procedure analogous to Example 13C, from t-butyl (4-{1-ethyl-1-[4-(2-hydroxy-3,3-dimethylbutoxy)-3-methylphenyl]-propyl}-2-methylbenzyl)-(2-methanesulfonylethyl)carbamate (0.26 g, 0.43 mmol) to give the title compound (0.25 g, 0.42 mmol, 95%).

$^1$H NMR (CDCl$_3$), δ 0.60 (t, J=7.5 Hz, 6H), 1.26 (s, 9H), 1.48 (bs, 9H), 2.05 (q, J=7.5 Hz, 4H), 2.23 (s, 3H), 2.25 (s, 3H), 2.60-3.20 (m, 5H), 3.57 (bs, 2H), 4.46 (s, 2H), 4.84 (s, 2H), 6.50 (d, J=8.1 Hz, 1H), 6.80-7.01 (m, 5H). ES-MS (m/z): calcd for C$_{34}$H$_{51}$O$_6$S: 601.9; found: 602.2.

H. 1-[4-(1-Ethyl-1-{4-[(2-methanesulfonylethylamino)-methyl]-3-methylphenyl}propyl)-2-methylphenoxy]-3,3-dimethylbutan-2-one

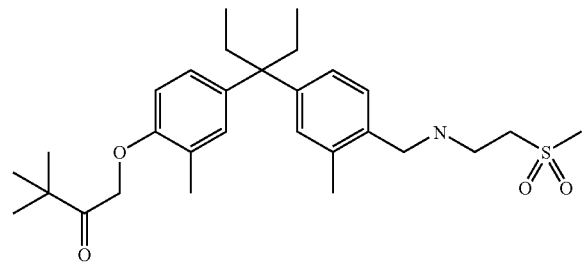

To a mixture of t-butyl (4-{1-[4-(3,3-dimethyl-2-oxobutoxy)-3-methylphenyl]-1-ethylpropyl}-2-methylbenzyl)-(2-methanesulfonylethyl)carbamate (0.25, g, 0.41 mmol) and CH$_2$Cl$_2$ (5 mL) is added TFA (5 mL,), stirred for 10 m, and concentrated. The residue is diluted with EtOAc (100 mL), washed with sat.d NaHCO$_3$ (2×30 mL); MgSO$_4$ dried, and chromatographed (90% EtOAc) to give the title compound (0.19 g, 0.39 mmol, 95%).

$^1$H NMR (CDCl$_3$), δ 0.61 (t, J=7.2 Hz, 6H), 1.27 (s, 9H), 2.05 (q, J=7.2 Hz, 4H), 2.25 (s, 3H), 2.32 (s, 3H), 2.99 (s, 3H), 3.25 (s, 4H), 3.81 (s, 2H), 4.84 (s, 2H), 6.49 (d, J=8.3 Hz, 1H), 6.85-7.00 (m, 4H), 7.13 (d, J=7.7 Hz, 1H). ES-MS (m/z): calcd for C$_{29}$H$_{44}$NO$_4$S (M+H)$^+$: 502.7; found: 502.2.

Example 14

Preparation of 4-{1-ethyl-1-[4-(2-hydroxy-3,3-dimethylbutoxy)-3-methylphenyl]propyl}-N-(2-methanesulfonylethyl)-2-methylbenzamide

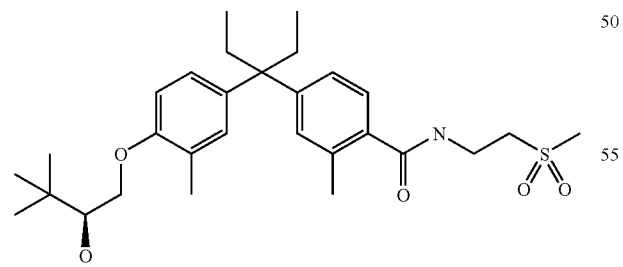

To a mixture of 4-(1-{4-[2-(hydroxy)-3,3-dimethyl-butoxy]-3-methylphenyl}-1-ethylpropyl)-2-methylbenzoic acid, Example 1, (0.53 g, 1.29 mmol), 2-aminoethylmethylsulfone hydrochloride (0.21 g, 1.29 mmol), HOBt (0.19 g, 1.43 mmol), Et$_3$N (0.72 mL, 5.19 mmol) and CH$_2$Cl$_2$ (10 mL) is added EDCI (0.249 g, 1.29 mmol) and stirred overnight. The reaction is diluted with CH$_2$Cl$_2$ (50 mL), washed with 1M HCl (2×30 mL), H$_2$O (20 mL), satd NaHCO$_3$ (2×20 mL), and brine (20 mL). The organic layer is MgSO$_4$ dried, concentrated, and chromatographed (75% EtOAc/Hex) to give the title compound (0.51 g, 76%).

$^1$H NMR (CDCl$_3$), δ 0.59 (t, J=7.8 Hz, 6H), 1.01 (s, 9H), 2.00-2.28 (m, 4H), 2.17 (s, 3H), 2.41 (s, 3H), 3.00 (s, 3H), 3.35 (t, J=5.6 Hz, 1H), 3.70 (bd, J=8.6 Hz, 1H), 3.85 (t, J=9.1 Hz, 1H), 3.97 (dd, J=12.3, 5.6 Hz, 2H), 4.09 (dd, J=9.1, 3.0 Hz, 1H), 6.53 (t, J=5.9 Hz, 1H), 6.69 (d, J=7.8 Hz, 1H), 6.85 (s, 1H), 6.91-7.01 (m, 2H), 7.25-7.29 (m, 2H). ES-MS (m/z): calcd for C$_{29}$H$_{44}$NO$_5$S (M+H)$^+$: 518.7; found: 518.3.

Example 15A & 15B

Preparation of enantiomer 1 and 2 of 4-{1-ethyl-1-[4-(2-hydroxy-3,3-dimethylbutoxy)-3-methylphenyl]propyl}-N-(2-methanesulfonylethyl)-2-methylbenzamide

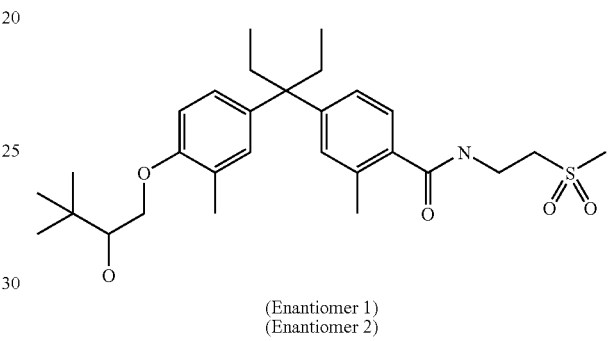

(Enantiomer 1)
(Enantiomer 2)

A racemic mixture of 4-{1-ethyl-1-[4-(2-hydroxy-3,3-dimethylbutoxy)-3-methylphenyl]propyl}-N-(2-methanesulfonylethyl)-2-methylbenzamide (0.34 g), Example 14, is chromatographed (HPLC: ChiralPak AD, 60% EtOH/Hept) to give enantiomer 1 (0.10 g, 29%, rt=4.9 m) and enantiomer 2 (0.125 g, 37%, rt=6.3 m).

Example 15A, 2071445 (enantiomer 1):
HPLC: ChiralPak AD (4.6×250 mm); 60% EtOH/Hept; 1.0 mL/m (flow rate); rt=4.9 m; @ 240 nm.
NMR & LC/MS: equivalent to the racemate, Example 14.

Example 15B, 2071447 (enantiomer 2):
HPLC: ChiralPak AD (4.6×250 mm); 60% EtOH/Hept; 1.0 mL/m (flow rate); rt=6.3 m; @ 240 nm.
NMR & LC/MS: equivalent to the racemate, Example 14.

Example 16

Preparation of 4-{1-[4-(3,3-dimethyl-2-oxobutoxy)-3-methylphenyl]-1-ethylpropyl}-N-(2-methanesulfonylethyl)-2-methylbenzamide

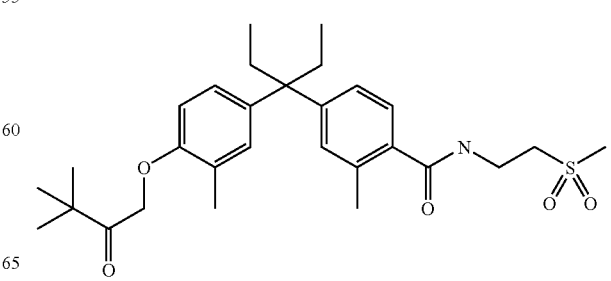

Using a procedure analogous to Example 13C, from 4-{1-ethyl-1-[4-(2-hydroxy-3,3-dimethylbutoxy)-3-methylphenyl]propyl}-N-(2-methanesulfonylethyl)-2-methylbenzamide, Example 14, (0.08 g, 0.16 mmol), NMO (27 mg, 0.24 mmol), and TPAP (2.8 mg, 0.08 mmol) are reacted for 1 h to give the title compound (0.06 g, 76%).

$^1$H NMR (CDCl$_3$): δ 0.60 (t, J=7.4 Hz, 6H), 1.27 (s, 9H), 2.05 (q, J=7.4 Hz, 4H), 2.24 (s, 3H), 2.42 (s, 3H), 3.01 (s, 3H), 3.36 (t, J=6.0 Hz, 2H), 3.94-4.02, (m, 2H), 4.82 (s, 2H), 6.46-6.57 (m, 2H), 6.82-7.23 (m, 5H). ES-MS (m/z): calcd for C$_{29}$H$_{42}$NO$_5$S (M+H)$^+$: 516.7; found: 516.4.

Example 17

Preparation of 4-{1-[4-(3,3-dimethyl-2-oxobutoxy)-3-methylphenyl]-1-ethylpropyl}-2-methylbenzoic acid

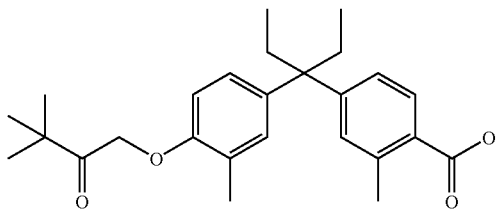

To a mixture of 4-{1-[4-(3,3-dimethyl-2-hydroxybutoxy)-3-methylphenyl]-1-ethylpropyl}-2-methylbenzoic acid, Example 1, (0.50 g, 1.22 mmol) in CH$_2$Cl$_2$ (10 mL) is added a solution of the Dess-Martin reagent (0.57 g, 1.34 mmol) in CH$_2$CL$_2$ (10 mL) dropwise and stirred for 2 h. The reaction is diluted with EtOAc (100 mL), washed with 10% Na$_2$SO$_3$ (2×20 ml), 0.1 M HCl (20 ml), and H$_2$O (20 ml). The organic layer is MgSO$_4$ dried, and concentrated to give the title compound (0.48 g, 1.17 mmol, 95%).

$^1$H NMR (CDCl$_3$), δ 0.62 (t, J=7.2 Hz, 6H), 1.27 (s, 9H), 2.09 (q, J=7.2 Hz, 4H), 2.25 (s, 3H), 2.61 (s, 3H), 4.85 (s, 2H), 6.51 (d, J=8.8 Hz, 1H), 6.85-6.91 (m, 2H), 7.05-7.10 (m, 2H), 7.93 (d, J=9.0 Hz, 1H). ES-MS (m/z): calcd for C$_{26}$H$_{38}$NO$_4$ (M+NH$_4$)$^+$: 428.6; found: 428.3.

Example 18

Preparation of enantiomer 1 of [(4-{1-ethyl-1-[4-(2-hydroxy-3,3-dimethyl-butoxy)-3-methyl-phenyl]-propyl}-2-methyl-benzoyl)-methyl-amino]-acetic acid

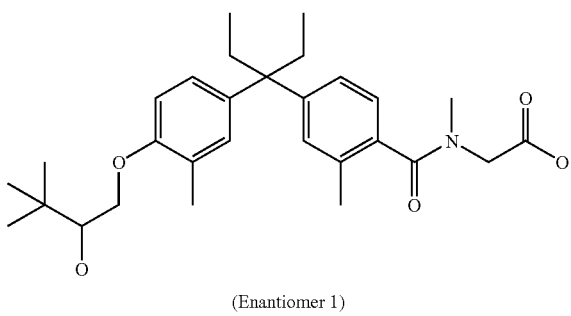
(Enantiomer 1)

A. Enantiomer 1 of [(4-{1-Ethyl-1-[4-(2-hydroxy-3,3-dimethyl-butoxy)-3-methyl-phenyl]-propyl}-2-methyl-benzoyl)-methyl-amino]-acetic acid methyl ester

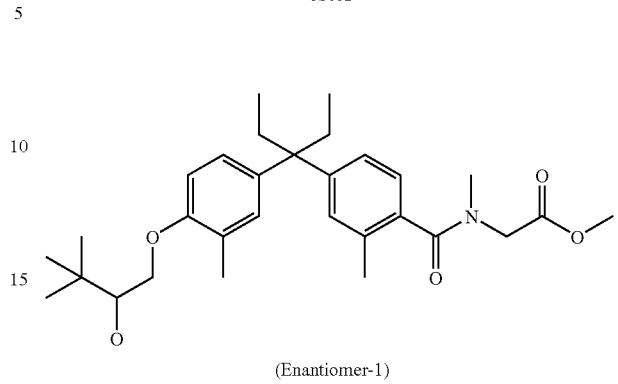
(Enantiomer-1)

Using a procedure analogous to Example 5, from enantiomer 1 of 4-(1-{4-[2-(hydroxy)-3,3-dimethyl-butoxy]-3-methylphenyl}-1-ethylpropyl)-2-methylbenzoic acid, Example 3A, (1.28 g, 3.17 mmol) and N-methyl glycine methyl ester hydrochloride (0.48 g, 3.41 mmol) to give the title compound (1.43 g, 2.88 mmol, 93%). $^1$H NMR (CDCl$_3$), δ 0.57-0.65 (m, 6H), 1.02 (s, 9H), 2.00-2.11 (m, 4H), 2.18 (s, 3H), 2.25 (s, 0.80H), 2.32 (s, 2.20H), 2.89 (s, 2.20H), 3.15 (s, 0.80H), 3.70 (s, 0.8H), 3.72 (d, J=2.6 Hz, 1H), 3.79 (s, 2.2H), 3.86 (t, J=8.8 Hz, 1H), 3.91 (s, 0.52H), 4.09 (dd, J=7.0, 2.6 Hz, 1H), 4.32 (bs, 1.48H), 6.70 (d, J=8.3 Hz, 1H), 6.85-7.11 (m, 5H). ES-MS (m/z): calcd for C$_{30}$H$_{44}$NO$_5$ (M+H)$^+$: 498.7; found: 498.3.

B. Enantiomer 1 of [(4-{1-ethyl-1-[4-(2-hydroxy-3,3-dimethyl-butoxy)-3-methyl-phenyl]-propyl}-2-methyl-benzoyl)-methyl-amino]-acetic acid

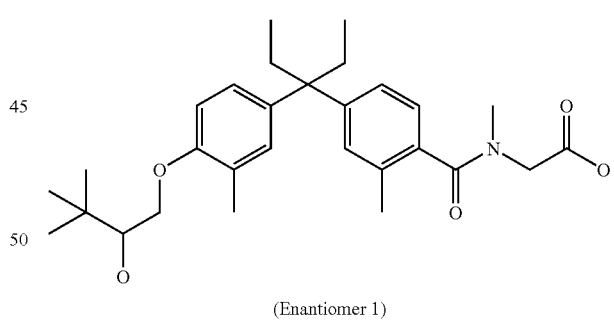
(Enantiomer 1)

Using a procedure analogous to Example 2, from enantiomer 1 of [(4-{1-ethyl-1-[4-(2-hydroxy-3,3-dimethyl-butoxy)-3-methyl-phenyl]-propyl}-2-methyl-benzoyl)-methyl-amino]-acetic acid methyl ester (1.43 g, 2.88 mmol) to give the title compound (1.24 g, 2.57 mmol, 90%). $^1$H NMR (CDCl$_3$), δ 0.56-0.63 (m, 6H), 1.02 (s, 9H), 2.01-2.09 (m, 4H), 2.11 (s, 0.7H), 2.18 (s, 2.3H), 2.23 (s, 0.70H), 2.29 (s, 2.30H), 2.91 (s, 2.30H), 3.14 (s, 0.70H), 3.71 (dd, J=8.8, 2.6 Hz, 1H), 3.86 (t, J=8.8 Hz, 1H), 3.92 (s, 0.47H), 4.09 (dd, J=8.8, 2.6 Hz, 1H), 4.33 (bs, 1.53H), 6.69 (d, J=8.8 Hz, 0.23H), 6.70 (d, J=8.3 Hz, 0.77H), 6.85-7.11 (m, 5H). ES-MS (m/z): calcd for C$_{29}$H$_{40}$NO$_5$ (M−H)$^-$: 482.7; found: 482.3.

Example 19

Enantiomer 2 of [(4-{1-Ethyl-1-[4-(2-hydroxy-3,3-dimethyl-butoxy)-3-methyl-phenyl]-propyl}-2-methyl-benzoyl)-methyl-amino]-acetic acid

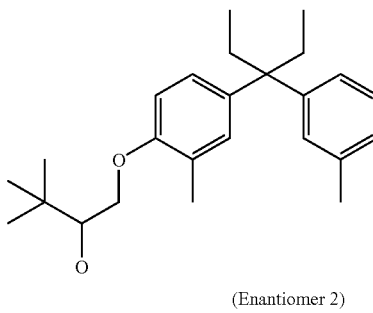

(Enantiomer 2)

A. Enantiomer 2 of [(4-{1-Ethyl-1-[4-(2-hydroxy-3,3-dimethyl-butoxy)-3-methyl-phenyl]-propyl}-2-methyl-benzoyl)-methyl-amino]-acetic acid methyl ester

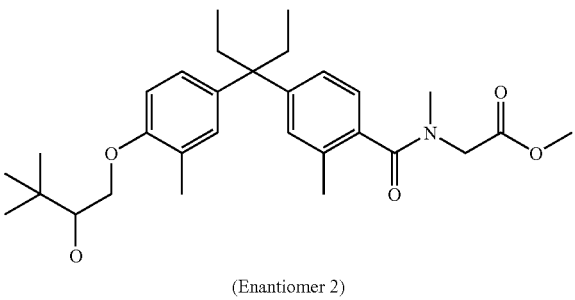

(Enantiomer 2)

Using a procedure analogous to Example 5, from enantiomer 2 of 4-(1-{4-[2-(hydroxy)-3,3-dimethyl-butoxy]-3-methylphenyl}-1-ethylpropyl)-2-methylbenzoic acid, Example 3B, (1.08 g, 2.62 mmol) to give the title compound (1.16 g, 2.33 mmol, 89%).

$^1$H NMR & LC/MS: equivalent to Example 18A.

B. Enantiomer 2 of [(4-{1-Ethyl-1-[4-(2-hydroxy-3,3-dimethyl-butoxy)-3-methyl-phenyl]-propyl}-2-methyl-benzoyl)-methyl-amino]-acetic acid Using a procedure analogous to Example 2, from enantiomer 2 of [(4-{1-ethyl-1-[4-(2-hydroxy-3,3-dimethyl-butoxy)-3-methyl-phenyl]-propyl}-2-methyl-benzoyl)-methyl-amino]-acetic acid methyl ester (0.58 g, 1.16 mmol) gives the title compound (0.53 g, 1.10 mmol, 95%). $^1$H NMR & LC/MS: equivalent to Example 18B.

Example 20

A. 2-(4-{1-Ethyl-1-[4-(2-hydroxy-3,3-dimethyl-butoxy)-3-methyl-phenyl]-propyl}-2-methyl-benzoylamino)-2-methyl-propionic acid methyl ester

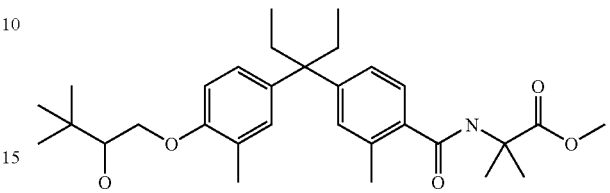

Using the procedure analogous to Example 5, from enantiomer 1 of 4-{1-ethyl-1-[4-(2-hydroxy-3,3-dimethyl-butoxy)-3-methyl-phenyl]-propyl}-2-methyl-benzoic acid, Example 3A, (0.40 g, 0.97 mmol) and 2-aminoisobutyric acid methyl ester hydrochloride (0.15 g, 1.07 mmol) to furnish the title compound (0.36 g, 0.70 mmol, 72%). $^1$H NMR (CDCl$_3$), δ 0.60 (t, J=7.6 Hz, 6H), 1.01 (s, 9H), 1.64 (s, 6H), 2.01-2.09 (m, 4H), 2.17 (s, 3H), 2.40 (s, 3H), 2.70 (d, J=9.0 Hz, 1H), 3.77 (s, 3H), 3.85 (t, J=9.1 Hz, 1H), 4.09 (d, J=9.6 Hz, 1H), 6.28 (s, 1H), 6.70 (dd, J=8.9, 2.6 Hz, 1H), 6.85 (s, 1H), 6.93 (d, J=8.6 Hz, 1H), 6.95-7.02 (m, 2H), 7.27 (dd, J=7.9, 2.6 Hz, 1H). ES-MS (m/z): calcd. for C$_{31}$H$_{46}$NO$_5$ (M+H)$^+$: 512.3; found: 512.3.

B. 2-(4-{1-Ethyl-1-[4-(2-hydroxy-3,3-dimethyl-butoxy)-3-methyl-phenyl]-propyl}-2-methyl-benzoylamino)-2-methyl-propionic acid

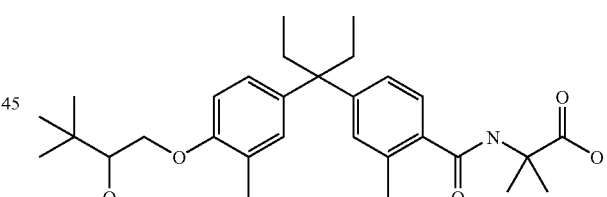

Enantiomer 1

Using a procedure analogous to Example 2, from enantiomer 1 of 2-(4-{1-ethyl-1-[4-(2-hydroxy-3,3-dimethyl-butoxy)-3-methyl-phenyl]-propyl}-2-methyl-benzoylamino)-2-methyl-propionic acid methyl ester (0.36 g, 0.70 mmol) to furnish the titled compound (0.35 g, 0.70 mmol, 92%). $^1$H NMR (CDCl$_3$), δ 0.59 (t, J=7.3 Hz, 6H), 1.01 (s, 9H), 1.67 (s, 6H), 2.05 (q, J=7.3 Hz, 4H), 2.17 (s, 3H), 2.40 (s, 3H), 3.70 (dd, J=8.7, 2.7 Hz, 1H), 3.86 (t, J=8.9 Hz, 1H), 4.09 (dd, J=9.1, 2.7 Hz, 1H), 6.28 (s, 1H), 6.70 (d, J=8.5 Hz, 1H), 6.85 (d, J=2.3 Hz, 1H), 6.93 (dd, J=8.5, 2.3 Hz, 1H), 6.98-7.03 (m, 2H), 7.26 (d, J=7.9 Hz, 1H). ES-MS (m/z): calcd. for C$_{30}$H$_{44}$NO$_5$ (M+H)$^+$: 498.3; found: 498.3.

Example 21

Preparation of 4-{1-[4-(3,3-Dimethyl-2-oxo-butoxy)-3-methyl-phenyl]-1-ethyl-propyl}-benzoic acid

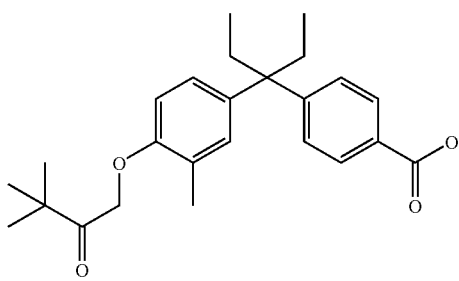

A. 4-(Z/E-2-Penten-3-yl)-O-trifluoromethylsulfonyl-phenol

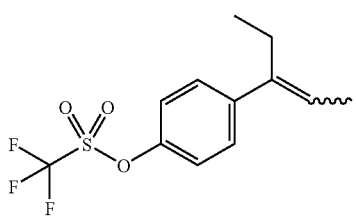

To a mixture of 4-(Z/E-2-penten-3-yl)phenol (7.45 g, 45.9 mmol), CH$_2$Cl$_2$ (150 mL), and Tf$_2$O (13.4 g, 47.5 mmol) is added DIPEA (6.13 g, 47.5 mol) drop wise. After stirring overnight, the reaction is poured into ice water (100 mL) and separated. The organic layer is washed with cold water (2×50 mL), Na$_2$SO$_4$ dried, filtered and concentrated to give the title compound as an oil (10.5 g, 78%) which is used as is.

B. 4-[(1-Ethyl-1-(3-methyl-4-hydroxyphenyl)propyl]-O-trifluoromethylsulfonylphenol

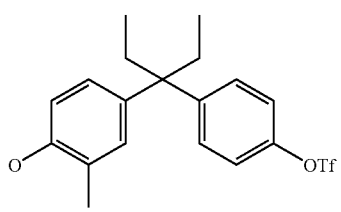

To 4-(Z/E-2-penten-3-yl)-O-trifluoromethylsulfonyl-phenol (5.25 g, 17.8 mmol) and O-cresol (7.7 g, 71.4 mmol) in CH$_2$Cl$_2$ (20 mL) at −20° C. is added BF$_3$·Et$_2$O (240 μL, 1.9 mmol), and the mixture is allowed to come to RT and stirred 16 h. To the reaction is added ethylene glycol (5 mL), and the CH$_2$Cl$_2$ is evaporated under vacuum. The residue is vacuum distilled up to 70° C. at 0.116 mm to remove the excess phenol and ethylene glycol. The residue is partitioned between Et$_2$O (50 mL) and water (50 mL). The organic layer is washed with water (3×50 mL), saturated brine, Na$_2$SO$_4$ dried, filtered and concentrated. The residue is chromatographed to give the title compound (3.9 g, 54%).

$^1$H-NMR ppm in CDCl$_3$: 7.24 (2H, d, J=9.0 Hz); 7.14 (2H, d, J=9.2 Hz); 6.84 (1H, s); 6.83 (1H, d, J=8.0 Hz); 6.66 (1H, d, J=8.0 Hz); 4.70 (1H, s); 2.20 (3H, s); 2.05 (4H, q, J=7.2 Hz); 0.61 (6H, t, J=7.2 Hz). LC-MS: 401.1 (M−1).

C. 4-[(1-Ethyl-1-(3-methyl-4-hydroxyphenyl)propyl]-benzoic acid, methyl ester

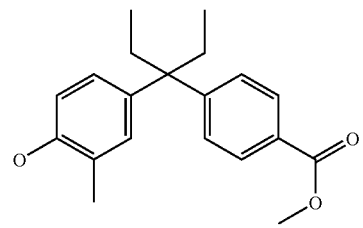

Using a procedure analogous to Example 1E, from 4-[(1-ethyl-1-(3-methyl-4-hydroxyphenyl)propyl]-O-trifluoromethylsulfonylphenol (2.5 g, 6.2 mmol) gives the title compound (1.08 g, 56%).

$^1$H-NMR ppm in CDCl$_3$: 7.89 (2H, d, J=8.0 Hz); 7.23 (2H, d, J=8.0 Hz); 6.84 (1H, s); 6.83 (1H, d, J=8.2 Hz); 6.65 (1H, d, J=8.2 Hz); 4.58 (1H, s); 3.89 (3H, s); 2.18 (3H, s); 2.08 (4H, q, J=7.2 Hz); 0.61 (6H, t, J=7.2 Hz). LC/MS: 313.1 (M+1), 311.1 (M−1).

D. 4-{1-[4-(3,3-Dimethyl-2-oxo-butoxy)-3-methyl-phenyl]-1-ethyl-propyl}-benzoic acid methyl ester

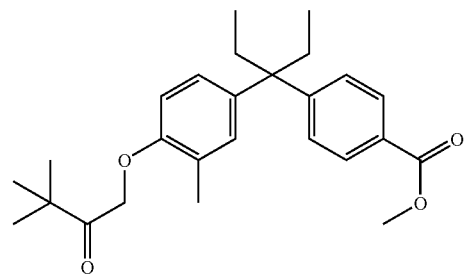

Using a procedure analogous to Example 1B, from 4-[(1-ethyl-1-(3-methyl-4-hydroxyphenyl)propyl]-benzoic acid, methyl ester (0.88 g, 2.81 mmol) gives the title compound (0.95 g, 2.32 mmol, 95%). $^1$H NMR (CDCL$_3$), δ 0.61 (t, J=7.4 Hz, 6H), 1.26 (s, 9H), 2.09 (q, J=7.4 Hz, 4H), 2.24 (s, 3H), 3.89 (s, 3H), 4.84 (s, 2H), 6.49 (d, J=8.8 Hz, 1H), 6.85-6.89 (m, 2H), 7.24 (d, J=8.4 Hz, 2H), 7.91 (d, J=9.4 Hz, 2H). ES-MS (m/z): calcd for C$_{26}$H$_{38}$NO$_4$ (M+NH$_4$)$^+$: 428.6; found: 428.3.

E. 4-{1-Ethyl-1-[4-(2-hydroxy-3,3-dimethyl-butoxy)-3-methyl-phenyl]-propyl}-benzoic acid methyl ester

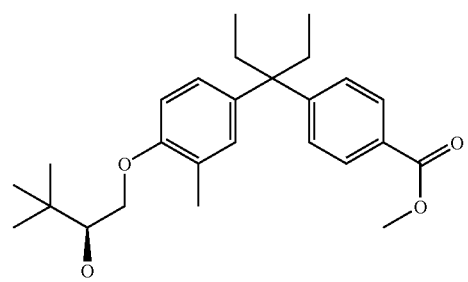

Using a procedure analogous to Example 1D, from 4-{1-[4-(3,3-dimethyl-2-oxo-butoxy)-3-methyl-phenyl]-1-ethyl-propyl}-benzoic acid methyl ester (0.94 g, 2.29 mmol) to give the title compound (0.93 g, 2.26 mmol, 99%). $^1$H NMR (CDCl$_3$), δ 0.62 (t, J=7.6 Hz, 6H), 1.02 (s, 9H), 2.10 (q, J=7.6 Hz, 4H), 2.17 (s, 3H), 3.71 (dd, J=8.8, 2.9 Hz, 1H), 3.86 (t, J=8.6 Hz, 1H), 3.90 (s, 3H), 4.09 (dd, J=9.3, 2.9 Hz, 1H), 6.71 (d, J=8.3 Hz, 1H), 6.86 (d, J=2.1 Hz, 1H), 6.92 (d, J=2.4 Hz, 1H), 6.94 (d, J=2.6 Hz, 1H), 7.25 (d, J=8.3 Hz, 1H), 7.91 (d, J=8.6 Hz, 2H). ES-MS (m/z): calcd for C$_{26}$H$_{37}$O$_4$ (M+H)$^+$: 413.6; found: 413.3.

F. 4-{1-Ethyl-1-[4-(2-hydroxy-3,3-dimethylbutoxy)-3-methylphenyl]-propyl}benzoic acid

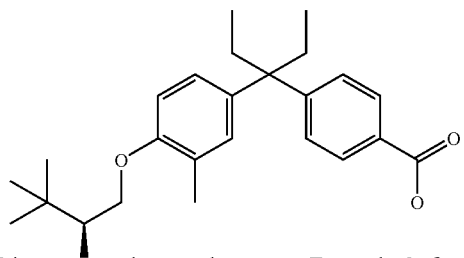

Using a procedure analogous to Example 2, from 4-{1-ethyl-1-[4-(2-hydroxy-3,3-dimethyl-butoxy)-3-methyl-phenyl]-propyl}-benzoic acid methyl ester (0.93 g, 2.25 mmol) gives the title compound (0.81 mmol, 2.02 mmol, 90%). $^1$H NMR (CDCl$_3$), δ 0.63 (t, J=7.2 Hz, 6H), 1.02 (s, 9H), 2.12 (q, J=7.2 Hz, 4H), 2.18 (s, 3H), 3.71 (dd, J=8.7, 2.4 Hz, 1H), 3.86 (t, J=9.3 Hz, 1H), 4.09 (dd, J=9.3, 2.4 Hz, 1H), 6.71 (d, J=8.3 Hz, 1H), 6.87 (d, J=1.9 Hz, 1H), 6.93 (d, J=2.4 Hz, 1H), 6.95 (d, J=2.0 Hz, 1H), 7.28 (d, J=8.4 Hz, 1H), 7.97 (d, J=8.8 Hz, 2H). ES-MS (m/z): calcd for C$_{25}$H$_{33}$O$_4$ (M−H)$^-$: 397.6; found: 397.2.

G. 4-{1-[4-(3,3-Dimethyl-2-oxo-butoxy)-3-methylphenyl]-1-ethyl-propyl}-benzoic acid Using a procedure analogous to Example 17, from 4-{1-ethyl-1-[4-(2-hydroxy-3,3-dimethylbutoxy)-3-methylphenyl]-propyl}benzoic acid (0.31 g, 0.79 mmol) and Dess-Martin reagent (366 mg, 0.86 mmol) gives the title compound (0.27 g, 0.69 mmol, 88%). %). $^1$H NMR (CDCl$_3$), δ 0.62 (t, J=7.0 Hz, 6H), 1.27 (s, 9H), 2.10 (q, J=7.0 Hz, 4H), 2.24 (s, 3H), 4.85 (s, 2H), 6.50 (d, J=9.1 Hz, 1H), 6.85-6.90 (m, 2H), 7.28 (d, J=8.1 Hz, 2H), 7.96 (d, J=8.2 Hz, 2H). ES-MS (m/z): calcd for C$_{25}$H$_{31}$O$_4$ (M−H)$^-$: 395.6; found: 395.2.

Example 22 and 23

Preparation of enantiomer 1 and 2 of 4-{1-Ethyl-1-[4-(2-hydroxy-3,3-dimethylbutoxy)-3-methylphenyl]-propyl}benzoic acid

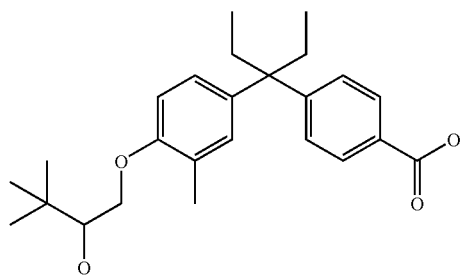

(Enantiomer-1)
(Enantiomer-2)

A racemic mixture of 4-{1-ethyl-1-[4-(2-hydroxy-3,3-dimethylbutoxy)-3-methylphenyl]-propyl}benzoic acid (500 mg) is chromatographed (CHIRALPAK AD column, Heptane, 90%; EtOH, 9.5%, CH$_3$OH, 0.5%, TFA, 0.1%) to give enantiomer 1 (rt=7.4 m), Example 22 (231 mg, 46%) and enantiomer 2 (rt=9.4 m), Example 23 (230 mg, 46%).

Example 22(Enantiomer 1)

rt=7.4m

NMR & LC/MS: Identical to the racemic material, Example 21F.

Example 23(Enantiomer 2)

rt=9.4m

NMR & LC/MS: Identical to the racemic material, Example 21F.

Example 24

Preparation of (4-{1-ethyl-1-[4-(2-hydroxy-3,3-dimethylbutoxy)-3-methylphenyl]-propyl}-2-methylbenzoylamino)acetic acid

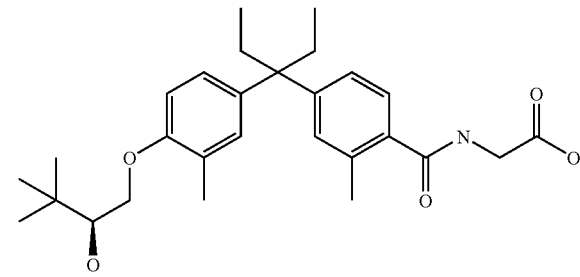

A. Methyl (4-{1-ethyl-1-[4-(2-hydroxy-3,3-dimethylbutoxy)-3-methylphenyl]propyl}-2-methylbenzoylamino)acetate

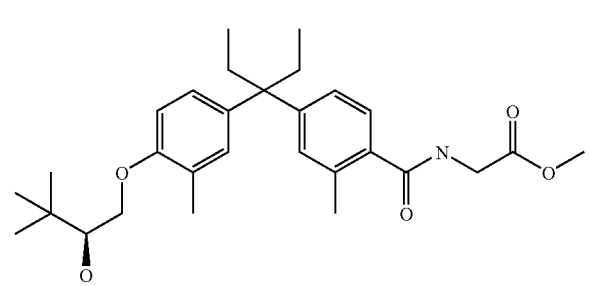

Using a procedure analogous to Example 5, from 4-(1-{4-[2-(hydroxy)-3,3-dimethyl-butoxy]-3-methylphenyl}-1-ethylpropyl)-2-methylbenzoic acid (0.50 g, 1.22 mmol) and glycine methyl ester hydrochloride (0.15 g, 1.22 mmol) give the title compound (0.587 g, 1.21 mmol, 99%).

$^1$H NMR (CDCl$_3$), δ 0.62 (t, J=7.5 Hz, 6H), 1.03 (s, 9H), 2.07 (q, J=7.5 Hz, 4H), 2.19 (s, 3H), 2.43 (s, 3H), 3.71 (dd, J=8.8, 2.9 Hz, 1H), 3.80 (s, 3H), 3.87 (t, J=8.8 Hz, 1H), 4.08-4.12 (m, 1H), 4.24 (d, J=5.4 Hz, 1H), 6.26 (t, J=5.4 Hz, 1H), 6.71 (d, J=8.8 Hz, 1H), 6.88 (d, J=2.0 Hz, 1H), 6.94 (dd, J=8.5, 2.5 Hz, 1H), 6.99-7.04 (m, 2H), 7.32 (d, J=7.8 Hz, 1H). ES-MS (m/z): calcd for C$_{29}$H$_{42}$NO$_5$ (M+H)$^+$: 484.7; found: 484.2.

B. (4-{1-Ethyl-1-[4-(2-hydroxy-3,3-dimethylbutoxy)-3-methylphenyl]-propyl}-2-methylbenzoylamino)acetic acid A mixture of methyl (4-{1-ethyl-1-[4-(2-hydroxy-3,3-dimethylbutoxy)-3-methylphenyl]propyl}-2-methylbenzoylamino)acetate (0.43 g, 0.89 mmol), CH$_3$OH (10 ml), NaOH (0.18 g, 4.46 mmol), and H$_2$O (1 mL) is refluxed for 2 h. The reaction is concentrated, diluted with H$_2$O (5 ml), acidified (pH 3-4) with 0.1 M HCl and extracted with EtOAc (3×15 mL). The combined organic layers are MgSO$_4$ dried, and concentrated to give the title compound (0.29 g, 71%).

$^1$H NMR (CD$_3$OD), δ 0.66 (t, J=7.2 Hz, 6H), 1.05 (s, 9H), 2.15 (q, J=7.2 Hz, 4H), 2.20 (s, 3H), 2.42 (s, 3H), 3.63-3.68 (m, 1H), 3.91 (dd, J=10.0, 7.8 Hz, 1H), 4.09 (s, 2H), 4.16 (dd, J=10.0, 2.9 Hz, 1H), 6.81 (d, J=9.3 Hz, 1H), 6.86 (d, J=2.1 Hz, 1H), 7.02 (dd, J=8.4, 2.1 Hz, 1H), 7.09 (s, 1H), 7.11 (s, 1H), 7.37 (d, J=8.1 Hz, 1H). ES-MS (m/z): calcd for C$_{28}$H$_{40}$NO$_5$ (M+H)$^+$: 470.6; found: 470.2.

Example 25A and Example 25B

Preparation of enantiomer 1 and 2 of (4-{1-ethyl-1-[4-(2-hydroxy-3,3-dimethylbutoxy)-3-methylphenyl]-propyl}-2-methylbenzoylamino)acetic acid

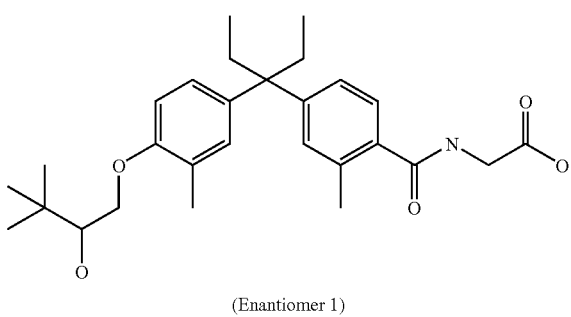

(Enantiomer 1)
(Enantiomer 2)

A racemic mixture of (4-{1-ethyl-1-[4-(2-hydroxy-3,3-dimethylbutoxy)-3-methylphenyl]-propyl}-2-methylbenzoylamino)acetic acid (0.217 g), Example 24, is chromatographed (HPLC: ChiralPak AD, 0.1% TFA in 0.75:14.25:85 CH$_3$OH:EtOH:Hept) to give enantiomer 1 (80.6 mg, 37%, rt=8.0 m) and enantiomer 2 (81.1 mg, 37%, rt=10.1 μm).

(Enantiomer 1) Example 25A

HPLC: ChiralPak AD (4.6×250 mm); 0.1% TFA in 0.75:14.25:85 CH$_3$OH:EtOH:Hept; 1.0 mL/m (flow rate); rt=8.0 m; @ 280 nm; 97.8% ee.

NMR & LC/MS: equivalent to the racemate, Example 24.

(Enantiomer 2) Example 25B

HPLC: ChiralPac AD (4.6×250 mm); 0.1% TFA in 0.75:14.25:85 CH$_3$OH:EtOH:Hept; 1.0 mL/m (flow rate); rt=10.1 m; @ 280 nm; 95.2% ee.

NMR & LC/MS: equivalent to the racemate, Example 24.

Example 26

Preparation enantiomer 1 of 3'-[4-(2-hydroxy-3,3-dimethylbutoxy)-3-methylphenyl]-3'-[4-(tetrazol-5-ylaminocarbonyl)-3-methylphenyl]pentane

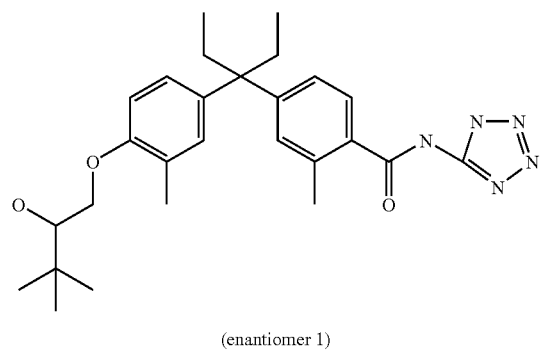

(enantiomer 1)

Using a procedure analogous to Example 5, enantiomer 1 of 3'-[4-(2-hydroxy-3,3-dimethylbutoxy)-3-methylphenyl]-3'-[4-carboxyl-3-methylphenyl]pentane and 5-aminotetrazole give the title compound (440 mg, 95%).

NMR 300 mHz (DMSO): 0.57 (t, J=7.3 Hz, 6H), 0.92 (s, 9H), 2.09 (m, 7H), 2.40 (s, 3H), 3.46 (m, 1H), 3.76 (dd, J=7.3, 10.2 Hz, 1H), 4.03 (dd, J=3.3, 10.2 Hz, 1H), 4.79 (d, J=5.5 Hz, 1H), 6.83 (d, J=8.4 Hz, 1H), 6.89 (s, 1H), 6.95 (d, J=8.4 Hz, 1H), 7.08 (d, J=8.1 Hz, 1H), 7.12 (s, 1H), 7.52 (d, J=8.1 Hz, 1H), 12.23 (s, 1H), 16.00 (br s, 1H).

High Res. ES-MS: 480.2983; calc. for C$_{27}$H$_{37}$N$_5$O$_3$+H, 480.2975.

Example 27

Preparation enantiomer 2 of 3'-[4-(2-hydroxy-3,3-dimethylbutoxy)-3-methylphenyl]-3'-[4-(tetrazol-5-ylaminocarbonyl)-3-methylphenyl]pentane

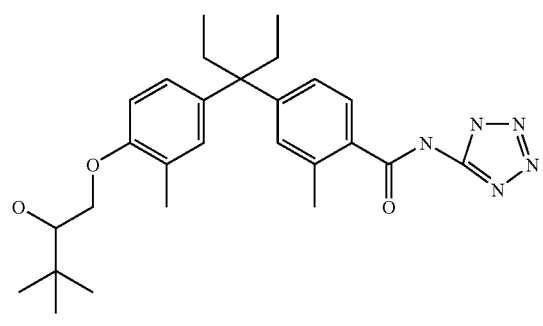

(enantiomer 2)

Using a procedure analogous to Example 5, enantiomer 2 of 3'-[4-(2-hydroxy-3,3-dimethylbutoxy)-3-methylphenyl]-3'-[4-carboxyl-3-methylphenyl]pentane and 5-aminotetrazole gives the title compound (385 mg, 83%).

NMR 300 mHz (DMSO): eq. to enantiomer of 1.
High Res. ES-MS: 480.2968; calc. for $C_{27}H_{37}N_5O_3$+H, 480.2975.

Preparation of 4-{1-Ethyl-1-[4-(2-hydroxy-1,3,3-trimethyl-butoxy)-3-methyl-phenyl]-propyl}-2-methyl-benzoic acid

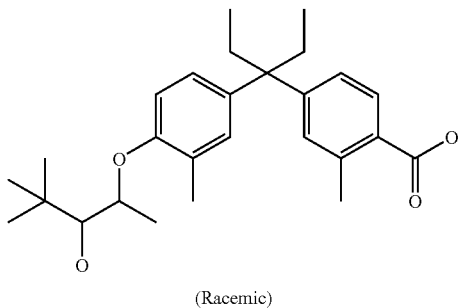

(Racemic)

Using a procedure analogous to Example 2, from racemic 4-{1-ethyl-1-[4-(2-hydroxy-1,3,3-trimethyl-butoxy)-3-methyl-phenyl]-propyl}-2-methyl-benzoic acid methyl ester, Example 10C, (4.70 g, 10.68 mmol) gives the title compound (2.93 g, 6.87 mmol, 64%).

$^1$H NMR and ES-MS: equivalent to the pure enantiomer 1, Example 11.

Example 29

Preparation enantiomer 1 of 3'-[4-(2-hydroxy-1,3,3-trimethylbutoxy)-3-methylphenyl]-3'-[4-(tetrazol-5-ylaminocarbonyl)-3-methylphenyl]pentane

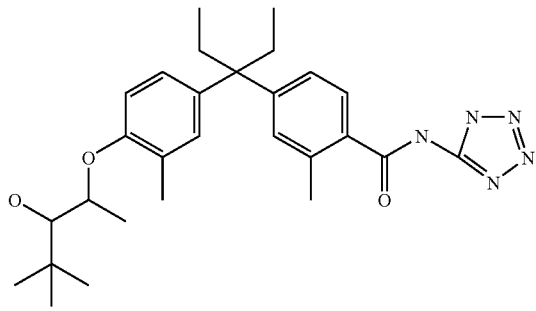

(enantiomer 1)

Using a procedure analogous to Example 5, enantiomer 1 of 3'-[4-(2-hydroxy-1,3,3-trimethylbutoxy)-3-methylphenyl]-3'-[4-carboxyl-3-methylphenyl]pentane, Example 11, and 5-aminotetrazole give the title compound (125 mg, 72%).

$^1$H NMR 400 MHz (DMSO-$d_6$): δ 0.57 (t, J=7.3 Hz, 6H), 0.91 (s, 9H), 1.20 (d, J=6.3 Hz, 3H), 2.07 (m, 7H), 2.41 (s, 3H), 3.07 (br s, 1H), 4.37 (br s, 1H), 4.57 (q, J=5.8, 1H), 6.87 (m, 3H), 7.06 (d, J=7.8 Hz, 1H), 7.15 (s, 1H), 7.50 (d, J=7.8 Hz, 1H), 12.24 (s, 1H), 16.0 (s, 1H).

High Res ES(+)MS m/z: 494.3127; calc. for $C_{28}H_{39}N_5O_3$+H, 494.3131

Example 30

Preparation enantiomer 2 of 3'-[4-(2-hydroxy-1,3,3-trimethylbutoxy)-3-methylphenyl]-3'-[4-(tetrazol-5-ylaminocarbonyl)-3-methylphenyl]pentane

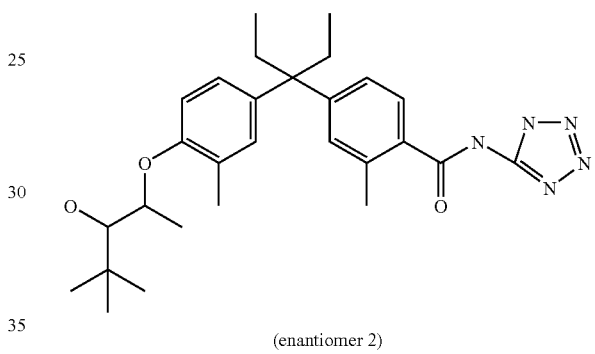

(enantiomer 2)

Using a procedure analogous to Example 5, enantiomer 2 of 3'-[4-(2-hydroxy-1,3,3-trimethylbutoxy)-3-methylphenyl]-3'-[4-carboxyl-3-methylphenyl]pentane, Example 12, and 5-aminotetrazole give the title compound (150 mg, 74%).

High Res ES(+)MS m/z: 494.3144; calc. for $C_{29}H_{39}N_5O_3$+H, 494.3131

Example 31

Preparation enantiomer 1 of 3'-[4-(2-hydroxy-1,3,3-trimethylbutoxy)-3-methylphenyl]-3'-[4-(carboxymethylaminocarbonyl)-3-methylphenyl]pentane

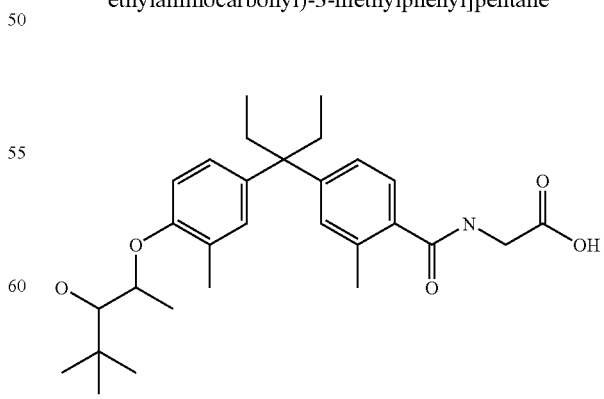

(enantiomer 1)

A. Enantiomer 1 of 3'-[4-(2-hydroxy-1,3,3-trimethylbutoxy)-3-methylphenyl]-3'-[4-(methoxycarbonylmethylaminocarbonyl)-3-methylphenyl]pentane

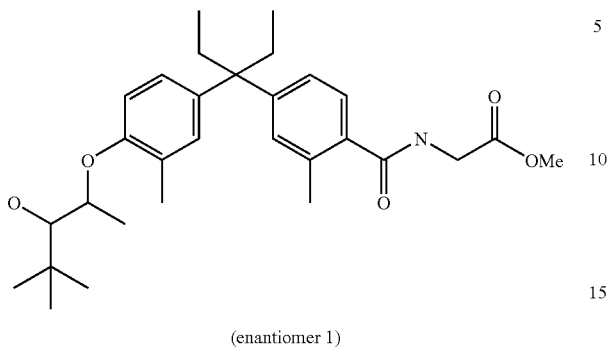

(enantiomer 1)

Using a procedure analogous to Example 5, enantiomer 1 of 3'-[4-(2-hydroxy-1,3,3-trimethylbutoxy)-3-methylphenyl]-3'-[4-carboxyl-3-methylphenyl]pentane, methyl glycinate hydrochloride, and DMAP (2.5 eq) give the title compound (150 mg, 86%).

$^1$H NMR 400 MHz (DMSO-d$_6$): δ 0.55 (t, J=7.3 Hz, 6H), 0.91 (s, 9H), 1.20 (d, J=5.9 Hz, 3H), 1.98-2.07 (m, 7H), 2.32 (s, 3H), 3.07 (s, 1H), 3.65 (s, 3H), 3.93 (d, J=6.3 Hz, 2H), 4.36 (br s, 1H), 4.55 (q, J=7.2 Hz, 1H), 6.80-6.84 (m, 2H), 6.89 (d, J=8.3 Hz, 1H), 7.00 (d, J=7.8 Hz, 1H), 7.05 (s, 1H), 7.24 (d, J=8.3 Hz, 1H), 8.61 (t, J=5.9 Hz, 1H).

High Res ES(+)MS m/z: 498.3224; calc. for C$_{30}$H$_{43}$NO$_5$+H, 498.3219.

B. Enantiomer 1 of 3'-[4-(2-hydroxy-1,3,3-trimethylbutoxy)-3-methylphenyl]-3'-[4-(carboxymethylaminocarbonyl)-3-methylphenyl]pentane Using a procedure analogous to Example 2 but reacted at RT, enantiomer 1 of 3'-[4-(2-hydroxy-1,3,3-trimethylbutoxy)-3-methylphenyl]-3'-[4-(methoxycarbonylmethylaminocarbonyl)-3-methylphenyl]pentane gives the title compound (130 mg, 99%).

$^1$H NMR 400 MHz (DMSO-d$_6$): δ 0.55 (t, J=7.3 Hz, 6H), 0.91 (s, 9H), 1.20 (d, J=5.9 Hz, 3H), 1.98-2.07 (m, 7H), 2.32 (s, 3H), 3.07 (s, 1H), 3.84 (d, J=5.8 Hz, 2H), 4.37 (br s, 1H), 4.56 (q, J=6.3 Hz, 1H), 6.80-6.84 (m, 2H), 6.89 (dd, J=2.4, J=8.3 Hz, 1H), 7.00 (d, J=8.3 Hz, 1H), 7.04 (s, 1H), 7.25 (d, J=7.8 Hz, 1H), 8.48 (t, J=5.9 Hz, 1H)

High Res ES(+)MS m/z: 484.3041; calc. for C$_{29}$H$_{41}$NO$_5$+H, 484.3063

Example 32

Preparation enantiomer 2 of 3'-[4-(2-hydroxy-1,3,3-trimethylbutoxy)-3-methylphenyl]-3'-[4-(carboxymethylaminocarbonyl)-3-methylphenyl]pentane

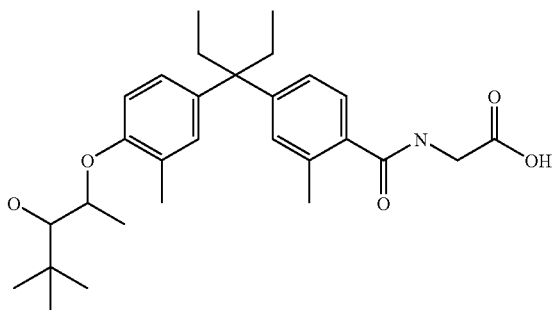

(enantiomer 2)

A. Enantiomer 2 of 3'-[4-(2-hydroxy-1,3,3-trimethylbutoxy)-3-methylphenyl]-3'-[4-(methoxycarbonylmethylaminocarbonyl)-3-methylphenyl]pentane

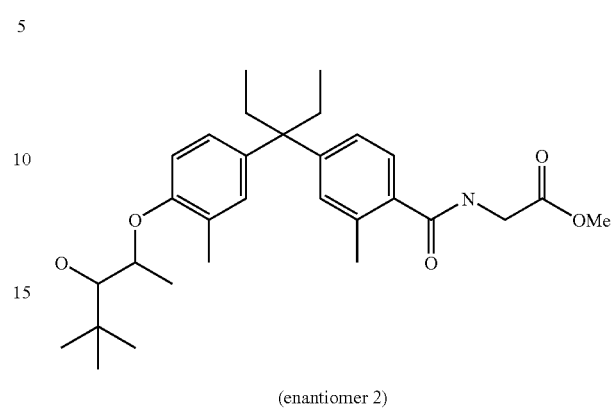

(enantiomer 2)

Using a procedure analogous to Example 5, enantiomer 2 of 3'-[4-(2-hydroxy-1,3,3-trimethylbutoxy)-3-methylphenyl]-3'-[4-carboxyl-3-methylphenyl]pentane, methyl glycinate hydrochloride, and DMAP (2.5 eq) give the title compound (160 mg, 78%).

NMR equivalent to Example 31A.

High Res ES(+)MS m/z: 498.3200; calc. for C$_{30}$H$_{43}$NO$_5$+H, 498.3219

B. Enantiomer 2 of 3'-[4-(2-hydroxy-1,3,3-trimethylbutoxy)-3-methylphenyl]-3'-[4-(carboxymethylaminocarbonyl)-3-methylphenyl]pentane Using a procedure analogous to Example 2 but reacted at RT, enantiomer 2 of 3'-[4-(2-hydroxy-1,3,3-trimethylbutoxy)-3-methylphenyl]-3'-[4-(methoxycarbonylmethylaminocarbonyl)-3-methylphenyl]pentane gives the title compound (145 mg, quant).

NMR equivalent to Example 31B.

High Res ES(+)MS m/z: 484.3080; calc. for C$_{29}$H$_{41}$NO$_5$+H, 484.3063

Example 33

Preparation of enantiomer 1 of (4-{1-ethyl-1-[4-(2-hydroxy-3,3-dimethyl-butoxy)-3-methyl-phenyl]-propyl}-2-methyl-benzyloxy)-acetic acid

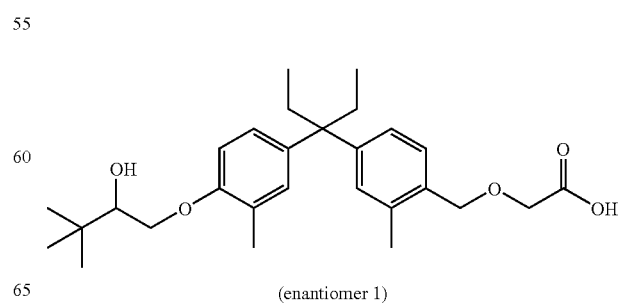

(enantiomer 1)

A. Enantiomer 1 of 4-(1-{4-[2-(tert-butyl-dimethyl-silanyloxy)-3,3-dimethyl-butoxy]-3-methyl-phenyl}-1-ethyl-propyl)-2-methyl-benzoic acid methyl ester

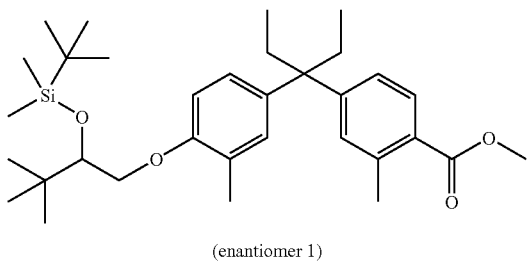

(enantiomer 1)

Using a procedure analogous to Example 13A, from enantiomer 1 of 4-{1-ethyl-1-[4-(2-hydroxy-3,3-dimethyl-butoxy)-3-methyl-phenyl]-propyl}-2-methyl-benzoic acid methyl ester (1.90 g, 4.45 mmol to furnish the title compound (2.40 g, 4.45 mmol, >99%).

$^1$H NMR & ES-MS: equivalent to (Example 13A).

B. Enantiomer 1 of [4-(1-{4-[2-(tert-butyl-dimethyl-silanyloxy)-3,3-dimethyl-butoxy]-3-methyl-phenyl}-1-ethyl-propyl)-2-methyl-phenyl]-methanol

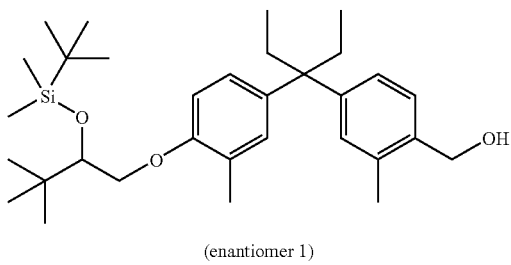

(enantiomer 1)

Using a procedure analogous to 13B, from enantiomer 1 of 4-(1-{4-[2-(tert-butyl-dimethyl-silanyloxy)-3,3-dimethyl-butoxy]-3-methyl-phenyl}-1-ethyl-propyl)-2-methyl-benzoic acid methyl ester (2.40 g, 4.45 mmol) to furnish the title compound (2.10 g, 4.09 mmol, 91%).

$^1$H NMR & ES-MS: equivalent to (Example 13B).

C. [4-(1-{4-[2-(tert-Butyl-dimethyl-silanyloxy)-3,3-dimethyl-butoxy]-3-methyl-phenyl}-1-ethyl-propyl)-2-methyl-benzyloxy]-acetic acid methyl ester

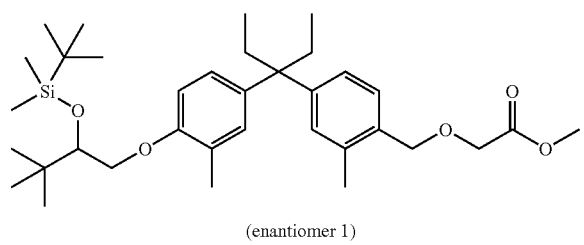

(enantiomer 1)

To a solution of enantiomer 1 of [4-(1-{4-[2-(tert-butyl-dimethyl-silanyloxy)-3,3-dimethyl-butoxy]-3-methyl-phenyl}-1-ethyl-propyl)-2-methyl-phenyl]-methanol, (2.10 g, 4.10 mmol) and PhCH$_3$ (10 mL) is added methyl glycolate (6.5 mL, 81.89 mmol) and MeReO$_3$ (0.02 g, 0.082 mmol). The solution is heated at a reflux for 2 hours with the use of a Dean-Stark trap. The solution is concentrated and chromatographed to give the title compound (0.96 g, 1.64 nmol, 40%).

$^1$H NMR (CDCl$_3$), δ 0.06 (s, 3H), 0.11 (s, 3H), 0.61 (t, J=7.3 Hz, 6H), 0.90 (s, 9H), 0.97 (s, 9H), 2.05 (q, J=7.3 Hz, 4H), 2.18 (s, 3H), 2.33 (s, 3H), 3.67 (dd, J=5.7, 3.2 Hz, 1H), 3.77 (s, 3H), 3.85 (dd, J=9.7, 5.7 Hz, 1H), 3.98 (dd, J=9.7, 3.5 Hz, 1H), 4.12 (s, 2H), 4.60 (s, 2H), 6.65 (d, J=8.4 Hz, 1H), 6.87 (d, J=2.1 Hz, 1H), 6.92 (dd, J=8.4, 2.6 Hz, 1H), 6.97-7.01 (m, 2H), 7.17 (d, J=8.4 Hz, 1H).).

D. Enantiomer 1 of (4-{1-ethyl-1-[4-(2-hydroxy-3,3-dimethyl-butoxy)-3-methyl-phenyl]-propyl}-2-methyl-benzyloxy)-acetic acid To a solution of enantiomer 1 of [4-(1-{4-[2-(tert-butyl-dimethyl-silanyloxy)-3,3-dimethyl-butoxy]-3-methyl-phenyl}-1-ethyl-propyl)-2-methyl-benzyloxy]-acetic acid methyl ester (0.96 g, 1.64 mmol) and THF (10 mL) is added 1M TBAF (3.3 mL, 3.28 mmol). The solution is heated at a reflux overnight and concentrated. The residue is dissolved in MeOH (5 mL) and water (1 mL), NaOH (0.33 g, 8.21 mmol) is added and the solution is heated at reflux for 3 hours. The solution is concentration, dissolved in EtOAc (20 mL), washed with 1M HCl (15 mL), water (15 mL), brine (15 mL), dried over MgSO$_4$, and concentrated. The residue is chromatographed to furnish the title compound (0.45 g, 0.99 mmol, 60%).

$^1$H NMR (CDCl$_3$), δ 0.60 (t, J=7.3 Hz, 6H), 1.02 (s, 9H), 2.05 (q, J=7.3 Hz, 4H), 2.17 (s, 3H), 2.31 (s, 3H), 3.71 (dd, J=8.8, 2.6 Hz, 1H), 3.86 (t, J=8.8 Hz, 1H), 4.09 (dd, J=8.8, 2.6 Hz, 1H), 4.13 (s, 2H), 4.62 (s, 2H), 6.70 (d, J=8.3 Hz, 1H), 6.90-7.02 (m, 4H), 7.16 (d, J=7.5 Hz, 1H).

ES-MS (m/z): calcd. for C$_{28}$H$_{41}$O$_6$ (M−H)$^-$: 455.6; found: 455.2.

Example 34

Preparation of epimer 1 of D-2-(4-{1-ethyl-1-[4-(2-hydroxy-3,3-dimethyl-butoxy)-3-methyl-phenyl]-propyl}-2-methyl-benzoylamino)-propionic acid

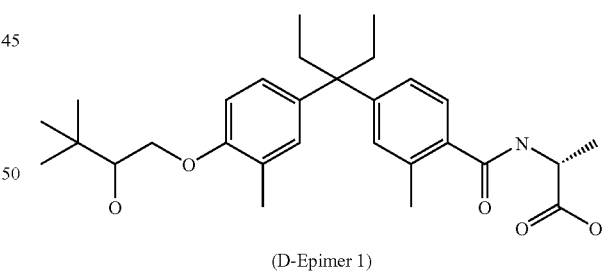

(D-Epimer 1)

A. Epimer 1 of D-2-(4-{1-Ethyl-1-[4-(2-hydroxy-3,3-dimethyl-butoxy)-3-methyl-phenyl]-propyl}-2-methyl-benzoylamino)-propionic acid methyl ester D-Epimer 1

Using a procedure analogous to Example 5, from enantiomer 1 of 4-{1-ethyl-1-[4-(2-hydroxy-3,3-dimethyl-butoxy)-3-methyl-phenyl]-propyl}-2-methyl-benzoic acid (0.40 g, 0.97 mmol) and D-alanine methyl ester hydrochloride (0.15 g, 1.07 mmol) to furnish the title compound (0.36 g, 0.72 mmol, 75%).

¹H NMR (CDCl₃), δ 0.60 (t, J=7.2 Hz, 6H), 1.00 (s, 9H), 1.49 (d, J=7.1 Hz, 3H), 2.05 (q, J=7.2 Hz, 4H), 2.17 (s, 3H), 2.40 (s, 3H), 3.69 (dd, J=8.5, 2.7 Hz, 1H), 3.76 (s, 3H), 3.84 (t, J=9.1 Hz, 1H), 4.07 (dd, J=9.1, 2.5 Hz, 1H), 4.72-4.81 (m, 1H), 6.42 (d, J=7.9 Hz, 1H), 6.68 (d, J=8.4 Hz, 1H), 6.84 (d, J=2.4 Hz, 1H), 6.92 (dd, J=8.4, 2.4 Hz, 1H), 6.96-7.01 (m, 2H), 7.28 (d, J=8.1 Hz, 1H).

ES-MS (m/z): calcd. for $C_{30}H_{44}NO_5$ (M+H)⁺: 498.3; found: 498.3.

B. Epimer 1 of D-2-(4-{1-Ethyl-1-[4-(2-hydroxy-3,3-dimethyl-butoxy)-3-methyl-phenyl]-propyl}-2-methyl-benzoylamino)-propionic acid Using a procedure analogous to Example 2, from epimer 1 of D-2-(4-{1-ethyl-1-[4-(2-hydroxy-3,3-dimethyl-butoxy)-3-methyl-phenyl]-propyl}-2-methyl-benzoylamino)-propionic acid methyl ester (0.36 g, 0.72 mmol) to furnish the titled compound (0.31 g, 0.64 mmol, 89%).

¹H NMR (CDCl₃), δ 0.60 (t, J=7.5 Hz, 6H), 1.01 (s, 9H), 1.50 (d, J=7.3 Hz, 3H), 2.05 (q, J=7.5 Hz, 4H), 2.17 (s, 3H), 2.41 (s, 3H), 3.71 (dd, J=8.4, 2.5 Hz, 1H), 3.85 (t, J=8.9 Hz, 1H), 4.09 (dd, J=9.3, 2.7 Hz, 1H), 4.74-4.83 (m, 1H), 6.33 (d, J=7.8 Hz, 1H), 6.70 (d, J=8.5 Hz, 1H), 6.85 (d, J=2.2 Hz, 1H), 6.93 (dd, J=8.2, 2.2 Hz), 6.98-7.03 (m, 1H), 7.01 (s, 1H), 7.30 (d, J=8.0 Hz, 1H).

ES-MS (m/z): calcd. for $C_{29}H_{42}NO_5$ (M+H)⁺: 484.3; found: 484.3.

Example 35

Preparation of racemic 3'-[3-chloro-4-(2-hydroxy-3,3-dimethylbutoxy)phenyl]-3'-[4-carboxyphenyl]pentane

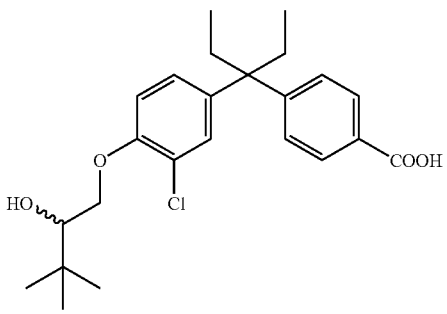

A. 3-(3-Chloro-4-hydroxyphenyl)-3-pentanol

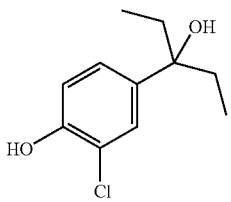

To a solution of methyl 3-chloro-4-hydroxybenzoate (25.0 g, 133 mmol) in THF (250 mL) is added dropwise 1.0 M ethylmagnesium bromide/THF (442 mL, 442 mmol) at a rate maintaining the temperature below 27° C. The brownish grey reaction is stirred for 72 h. The reaction mixture is cooled in an ice bath and quenched with satd ammonium chloride (1 ml portions) until evolution of ethane subsides. Additional satd NH4Cl solution is added (total of 50 mL) and the mixture is concentrated to remove most of the THF. The residue is added to water and ether, filtered through diatomaceous earth, and partitioned. The organic layer is washed with brine (3×), MgSO4 dried, and concentrated to give the title compound (28.6 g, 99%).

H-NMR (300 mHz, CDCl3): δ 7.38 (1H, d, J=1.6 Hz), 7.07 (1H, dd, J=8.4 Hz, J=1.6 Hz), 6.95 (1H, d, J=8.4 Hz), 5.53 (1H, br s), 1.80 (4H, m), 0.76 (6H, t, J=7.6 Hz).

IR (CHCl₃): 3600 cm⁻¹, 3540 cm⁻¹.

EI (+) TOF MS: Observed m/z 214.076; Calc. m/z. 214.0761

B. [E,Z]-3-(3-Chloro-4-hydroxyphenyl)-3-pentene

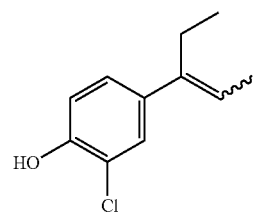

A mixture of 3-(3-chloro-4-hydroxyphenyl)-3-pentanol (10.0 g, 46.5 mmol), pTSA monohydrate (20 mg, catalytic amount), and toluene (300 mL) is heated on a steam bath for 3 h. Analysis by TLC indicates the loss of starting material and formation of a much less polar compound. The toluene solution is cooled to RT, washed with satd sodium carbonate solution (25 mL), MgSO4 dried, and concentrated to give the title compounds as a [E:Z] isomeric mixture of [85:15] (9.2 g, quant).

TLC (CHCl3): Rf~0.7

H-NMR (300 mHz, DMSO-d6): δ 6.85-7.30 (3H, m), 5.65 (0.85H, q, J=6.8 Hz), 5.43 (0.15H, q, J=6.8 Hz), 2.43 ((1.7H, q, J=7.6 Hz), 2.28 (0.3H, q, J=7.6 Hz), 1.72 (2.55H, d, J=7.6 Hz), 1.52 (0.45H, d, J=7.6 Hz), 0.90 (2.55H, t, J=7.6 Hz) 0.85 (0.45H, t, J=7.6 Hz)

C. [E,Z]-3-[3-Chloro-4-(2-oxo-3,3-dimethylbutoxy)phenyl]-3-pentene

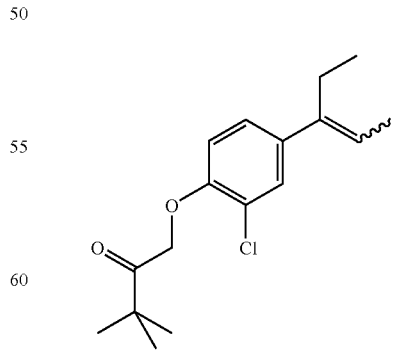

A mixture of [E,Z]-3-(3-chloro-4-hydroxyphenyl)-3-pentene (4.00 g, 20.3 mmol) and 1-chloropinacolone (2.73 g, 20.3 mmol), anhydrous KI (0.17 g, 1.0 mmol), K2CO3 (14.0 g, 102 mmol) and acetonitrile (80 mL) is refluxed for 3 h. The reaction is cooled to RT and concentrated. The residue is partitioned between methylene chloride (50 mL) and ice water (50 mL). The organic layer is $MgSO_4$ dried, concentrated, and chromatographed (40% to 70% chloroform in hexane) to give the title compounds as an 85:15 [E. Z] mixture (5.07 g, 85%).

H-NMR (300 mHz, DMSO-d6): δ 7.37 (0.85H, d, J=2.1 Hz), 7.22 (0.85H, dd, J=2.1, J=8.6 Hz), 7.18 (0.15H, d, J=2.1 Hz), 7.03 (0.15H, dd, J=2.0 Hz, J=8.4 Hz), 6.88 (0.15H, d, J=8.4 Hz), 6.85 (0.85H, d, J=8.6 Hz), 5.71 (0.85H, m), 5.52 (0.15H, m), 5.25 (2H, s), 2.45 (1.70H, q, J=7.6 Hz), 2.30 (0.30H, q, J=7.6 Hz), 1.75 (2.55H, d, J=7.6 Hz), 1.53 (0.45H, d, J=7.6 Hz), 1.17 (9H, s), 0.91 (2.55H, t, J=7.6 Hz), 9.88 (0.45H, t, J=7.6 Hz).

EI (+) TOF MS: Observed m/z 294.139; Calc. m/z 294.1387.

D. 3'-[3-Chloro-4-(2-oxo-3.3-dimethylbutoxy)phenyl]-3'-(4-hydroxyphenyl)pentane

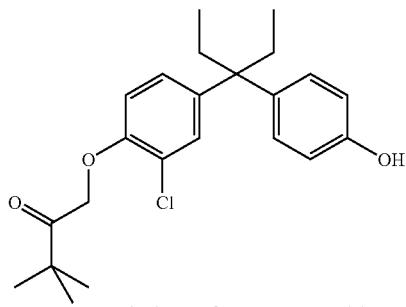

A −20° C. solution of [E,Z]-3-[3-chloro-4-(2-oxo-3,3-dimethylbutoxy)phenyl]-3-pentene (4.5 g, 15.2 mmol), phenol (17.2 g, 183 mmol) and methylene chloride (30 mL) is treated with BF3-etherate (0.863 g, 6.1 mmol) and stirred for 30 m while maintaining the temperature near −20° C. The resulting light reddish brown solution is allowed to warm to 0° C. and kept at that temperature for 16 h. The reaction is distilled at 45° C./0.04 mm to remove most of the excess phenol. The residue is treated with powderized NaHCO3 (600 mg), ethylene glycol (15 ml), and distilled to remove the last of the phenol and almost all of the glycol. The resulting viscous tan oily residue is cooled to RT and distributed between sat NaHCO3 (25 mL) and ethyl acetate (200 mL). The organic layer is separated, washed with water (5×50 mL), Na2SO4 dried, and concentrated to give the title compound as an oil (5.8 g, 98%).

H-NMR (300 mHz, CDCl3): 7.21 (1H, d, J=2.3 Hz), 6.99 (2H, d, J=8.7 Hz), 6.95 (1H, dd, J=2.3 Hz, J=8.6 Hz), 6.75 (2H, d, J=8.7 Hz), 6.62 (1H, d, J=8.6 Hz), 4.91 (2H, s), 4.86 (1H, s), 2.02 (4H, q, J=7.3 Hz), 1.28 (9H, s), 0.62 (6H, t, J=7.3 Hz).

ES(+) MS m/z: 389.3 [M+H]; calc. m/z 389.1883 [M+H].

E. 3'-[3-chloro-4-(2-oxo-3.3-dimethylbutoxy)]-3'-(4-trifluoromethylsulfonyloxyphenyl)pentane

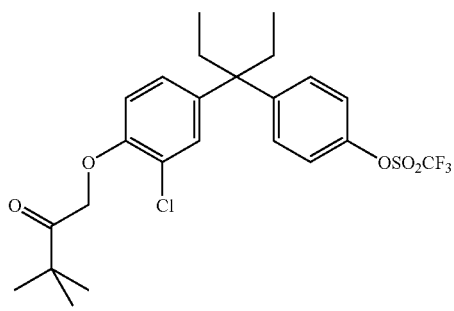

Using a procedure analogous to Example 1C with isopropyldiethylamine as the base, allowing the reaction to warm from 0 to RT overnight, and with potassium phosphate monobasic/sodium hydroxide buffer quench, 3'-[3-chloro-4-(2-oxo-3.3-dimethylbutoxy)phenyl]-3'-(4-hydroxyphenyl) pentane and triflic anhydride give the title compound as a colorless oil (3.7 g, 69%).

H-NMR (300 mHz, DMSO-D6): δ 7.40 (2H, d, J=8.7 Hz), 7.33 (2H, d, J=8.7 Hz), 7.15 (1H, d, J=2.1 Hz), 6.98 (1H, dd, J=2.1 Hz, J=8.6 Hz), 6.78 (2H, d, J=8.6 Hz), 5.22 (2H, s), 2.07 (4H, q, J=7.3 Hz), 1.17 (9H, s), 0.55 (6H, t, J=7.3 Hz).

FAB+MS m/z: 521.0 [M+H]; calc. 521.1376 [M+H].

ES MS: 521.3 [M+1], 538.3 [M+NH4], 543.2 [M+Na].

F. 3'-[4-(2-oxo-3,3-trimethylbutoxy)-3-chloro-phenyl]-3'-4-carbomethoxyphenyl)-pentane

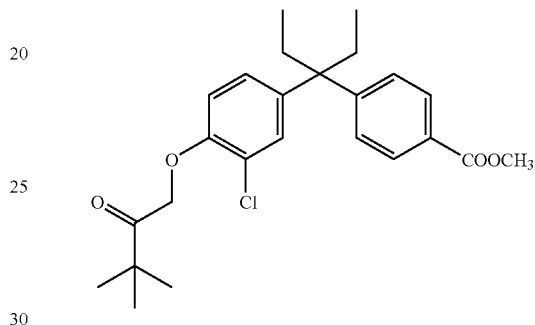

To 3'-[4-(2-oxo-3,3-dimethylbutoxy)-3-chlorophenyl]-3'-(4-trifluoromethyl-sulfonyloxy-phenyl)-pentane (3.7 g 7.1 mmol), palladium acetate (64 mg, 0.28 mmol), dppf (315 mg, 0.28 mmol), and triethylamine (4 mL) are heated in the absence of air under an atmosphere of carbon monoxide (initial 100 psig) in DMF (20 mL) and methanol (2 mL) at 110° C. for 48 h. The reaction mixture is cooled to room temperature, vented, and filtered. The filtrate is partitioned between EtOAc and water. The organic phase is washed 3 times with water, once with sat brine, dried over anhydrous Na2SO4, and concentrated under vacuum. The residue is chromatographed on 10 g silica gel with 8% EtOAc in hexanes to give the title compound (1.12 g, 37%).

H-NMR (400 mHz, CDCl3): δ 7.91 (2H, d, J=8.8 Hz), 7.21 (2H, d, J=8.8 Hz), 7.16 (1H, s), 6.88 (1H, d, J=8.8 Hz), 6.59 (1H, d, J=8.8 Hz), 4.90 (2H, s), 3.89 (3H, s), 2.07 (4H, q, J=7.2 Hz), 1.25 (9H, s), 0.61 (6H, t, J=7.2 Hz).

FAB(+) MS m/z [M]: 431.1; calc. m/z 431.3.

ES (+) MS: m/z 431.3 [M+H], 448.3 [M+NH4].

G. Racemic 3'-[3-chloro-4-(2-hydroxy-3,3-dimethylbutoxy)phenyl]-3'-[4-carbomethoxyphenyl]pentane

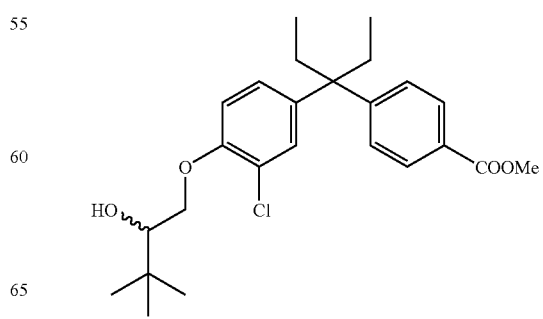

A solution of 3'-[4-(2-oxo-3,3-trimethylbutoxy)-3-chlorophenyl]-3'-(4-methoxycarbonyl-phenyl)-pentane (0.825 g, 1.91 mmol) in MeOH (10 mL) under a N2 atmosphere is cooled to 0° C. Sodium borohydride (0.076 g, 2.01 mmol) is added in one portion and the reaction mixture is stirred for 15 minutes. Acetone (1 mL) followed by potassium phosphate monobasic/sodium hydroxide buffer (3 mL) are added and the resulting mixture is concentrated to remove most of the MeOH. The residue is distributed into water and CH2Cl2 and the organic layer is separated and dried over anhydrous MgSO4. The desired product is obtained as a colorless oil, (0.816 g, 98.5%).

H-NMR (300 mHz, CDCl3): δ 7.92 (2H, d, J=8.8 Hz), 7.22 (2H, m), 7.15 (1H, d, J=2.3), 6.93 (1H, dd, J=2.3 Hz, J=8.8 Hz), 6.84 (1H, d, J=8.8 Hz), 4.17 (1H, dd, J=2.6 Hz, J=9.0 Hz), 3.89 (s, 3H), 3.87 (t, J=8.9 Hz,), 3.62 (1H, dt, J=2.6, J=8.9, J=3.0), 2.60, (1H, d, J=3.0 Hz), 2.09 (4H, q, J=7.3 Hz), 1.01 (9H, s), 0.61 (6H, t, J=7.3 Hz).

FAB(+) MS m/z [M]: 432.2; calc. for C25H33ClO4: m/z 432.2.

IR(CHCl3): 1718 cm$^{-1}$

H. Racemic 3'-[3-chloro-4-(2-hydroxy-3,3-dimethyl-butoxy)phenyl]-3'-[4-carboxyphenyl]pentane, sodium salt

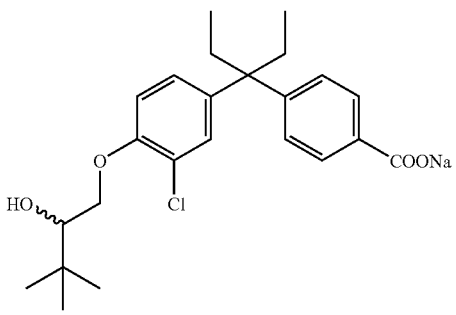

The methyl ester of 3'-[3-chloro-4-(2-hydroxy-3,3-dimethyl-butoxy)phenyl]-3'-[4-(carboxy)phenyl]pentane (0.600 g, 1.38 mmol) and 2N NaOH (3.46 mL, 6.93 mmol) are refluxed in EtOH (15 mL) under a N2 atmosphere for 1 h. TLC (SiO2; CHCl3) shows the loss of the starting material and appearance of a more polar compound spot near the origin. The reaction is allowed to cool to near RT and subsequently it is concentrated under reduced pressure to remove EtOH and provide a white residue. The residue is dissolved in a minimum amount of hot water (approx. 20 mL) and cooled and scratched to provide the desired sodium salt as white crystals (0.582 g, 96%).

H-NMR (300 mHz, DMSO): δ 7.73 (2H, d, J=8.7 Hz), 7.00 to 7.06 (5H, m), 4.88 (1H, d, J=5.1 Hz), 4.10 (1H, dd, J=3.0 Hz, J=10.2 Hz), 3.86 (1H, dd, J=3.1 Hz, J=10.2 Hz), 3.47 (1H, m), 2.04 (4H, q, J=7.3 Hz), 0.92 (9H, s), 0.55 (6H, t, J=7.3 Hz).

ES (+) MS m/z 436.2 [M+NH4], 441.1 [M+Na]
ES (−) MS m/z 417.2 [M−H].
IR(CHCl3): 1601 cm$^{-1}$.

I. Racemic 3'-[3-chloro-4-(2-hydroxy-3,3-dimethyl-butoxy)phenyl]-3'-[4-carboxyphenyl]pentane A portion of the above 3'-[3-chloro-4-(2-hydroxy-3,3-dimethyl-butoxy)phenyl]-3'-[4-(carboxy)phenyl]pentane, sodium salt (0.182 g, 0.413 mmol) is dissolved in 50 ml of hot water. After the solution is allowed to cool to near to RT it is acidified with dropwise addition of 5N HCl. The resulting white precipitate is collected and washed with ice water and subsequently vacuum dried to provide the desired free acid (0.169 g, 98%).

H-NMR (300 mHz, DMSO): δ 7.85 (2H, d, J=8.3 Hz), 7.27 (2H, d, J=8.3) 7.00 to 7.12 (3H, m), 4.85 (1H, d, J=5.1 Hz), 4.11 (1H, dd, J=3.0 Hz, J=10.2 Hz), 3.87 (1H, dd, J=3.1 Hz, J=10.2 Hz), 3.47 (1H, m), 2.08 (4H, q, J=7.3 Hz), 0.94 (9H, s), 0.56 (6H, t, J=7.3 Hz).

ES (+) MS: 436.2 [M+NH4], 441.1 [M+Na]
ES (−) MS: 417.2 [M−1].
IR (CHCl3): 1691 cm$^{-1}$.

Example 36 and 37

Separation of optical isomers of 3'-[3-chloro-4-(2-hydroxy-3,3-dimethylbutoxy)phenyl]-3'-[4-carboxyphenyl]pentane

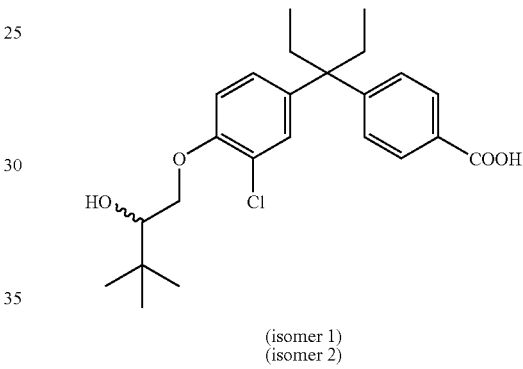

(isomer 1)
(isomer 2)

A racemic mixture of the Na salt of 3'-[3-chloro-4-(2-hydroxy-3,3-dimethylbutoxy)phenyl]-3'-4-carboxyphenyl) pentane (350 mg) is chromatographed with a Chiralpak AD column to give enantiomer 1, Example 36 (120 mg, 36%) and enantiomer 2, Example 37 (117 mg, 35%).

Example 36, Enantiomer 1

HPLC: Chiralpak AD (4.6×150 mm); 100% 3A Alcohol; 0.6 mL/m (flow rate); rt=7.3 m; 240 nm; ee 99.7% by HPLC.

H-NMR (300 mHz, DMSO): δ 7.85 (2H, d, J=8.3 Hz), 7.27 (2H, d, J=8.3) 7.00 to 7.12 (3H, m), 4.85 (1H, d, J=5.1 Hz), 4.11 (1H, dd, J=3.0 Hz, J=10.2 Hz), 3.87 (1H, dd, J=3.1 Hz, J=10.2 Hz), 3.47 (1H, m), 2.08 (4H, q, J=7.3 Hz), 0.94 (9H, s), 0.56 (6H, t, J=7.3 Hz).

ES (+) MS: 436.2 [M+NH4], 441.1 [M+Na]
ES (−) MS: 417.2 [M−1].

Example 37, Enantiomer 2

HPLC: Chiralpak AD (4.6×150 mm); 100% 3A Alcohol; 0.6 mL/m (flow rate); rt=10.5 m; 240 nm; ee 99.0% by HPLC.

H-NMR (300 mHz, DMSO): δ 7.85 (2H, d, J=8.3 Hz), 7.27 (2H, d, J=8.3) 7.00 to 7.12 (3H, m), 4.85 (1H, d, J=5.1 Hz), 4.11 (1H, dd, J=3.0 Hz, J=10.2 Hz), 3.87 (1H, dd, J=3.1 Hz, J=10.2 Hz), 3.47 (1H, m), 2.08 (4H, q, J=7.3 Hz), 0.94 (9H, s), 0.56 (6H, t, J=7.3 Hz).

ES (+) MS: 436.2 [M+NH4], 441.1 [M+Na]
ES (−) MS: 417.2 [M−1].

Example 38

Preparation of racemic 3'-[3-chloro-4-(2-hydroxy-3,3-dimethylbutoxy)phenyl]-3'-[3-methyl-4-(carboxy)phenyl]pentane

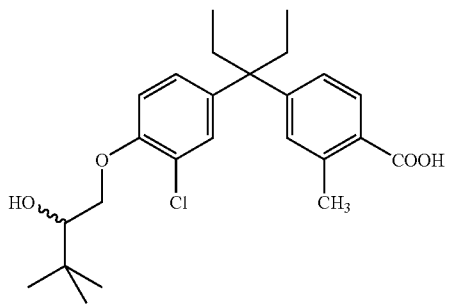

A. [E,Z]-3-[3-Chloro-4-(trifluoromethylsulfonyloxy)phenyl)-3-pentene

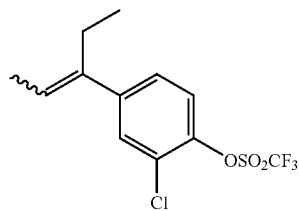

Using a procedure analogous to Example 1C, [E,Z]-3-(3-chloro-4-hydroxyphenyl)-3-pentene, triflic anhydride, and diisopropylethylamine are reacted at RT for 3 h to give the title compound as a yellow oil in a [E:Z] ratio of 9:1 (16.7 g, 98%). Chromatography over silica gel using 10% chloroform in hexane as the eluent provided 11.72 g (71.%) of purified material.

H-NMR (300 mHz, CDCl3): δ 7.01-7.39 (3H, m), 5.70 (0.9H, q, J=6.9 Hz), 5.53 (0.1H, q, J=6.9 Hz), 2.41 ((1.8H, q, J=7.6 Hz), 2.24 (0.2H, q, J=7.6 Hz), 1.74 (2.7H, d, J=7.6 Hz), 1.48 (0.3H, d, J=7.6 Hz), 0.91 (2.7H, t, J=7.6 Hz)), 0.89 (0.3H, t, J=7.6 Hz).

ES GC MS m/z 328.0; Calc. for C12H12ClF3O3S m/z 328.0148.

B. 3'-(4-hydroxy-3-methylphenyl)-3'-[3-chloro-4-(trifluoromethylsulfonyloxy)-phenyl]pentane

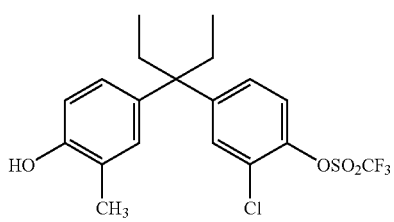

Using a procedure analogous to Example 35D, [E,Z]-3-[3-chloro-4-(trifluoromethylsulfonyloxy)phenyl]-3-pentene and o-cresol are reacted at RT overnight to give the title compound as a pale tan oil (4.29 g, 38%).

H-NMR (300 mHz, CDCl3): 6.5 to 7.3 (6H, m) 4.57 (1H, s), 2.21 (3H, s), 2.05 (4H, q, J=7.3 Hz), 0.62 (6H, t, J=7.3 Hz).

ES (−) MS m/z 435.1 [M−H].

C. 3'-[3-chloro-4-(2-oxo-3.3-dimethylbutoxy)-phenyl]-3'-[3-methyl-4-(trifluoromethylsulfonyloxy)phenyl]pentane Triflate Rearrangement Procedure.

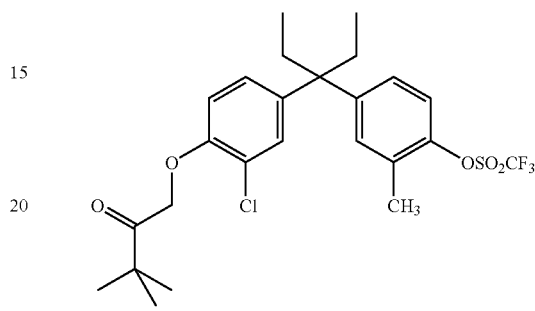

Using a procedure analogous to Example 35C, 3'-(3-chloro-4-hydroxyphenyl)-3'-[3-methyl-4-(trifluoromethylsulfonyloxy)phenyl]pentane, 1-chloropinacolone, anhydrous KI, and K2CO3 are reacted in acetonitrile to give the title compound (2.61 g, 53%) following chromatographies (30% to 50% chloroform/Hex; Hex to 10% EtOAc/Hex).

H-NMR (300 mHz, CDCl3): δ 7.15 (1H, d, J=2.3 Hz), 7.11 (1H, d, J=8.4 Hz), 7.04 (1H, d, J=2.3 Hz), 7.02 (1H, dd, J=2.3 Hz, J=8.4 Hz), 6.89 (1H, dd, J=8.6 Hz, J=2.3 Hz), 6.62 (1H, d, J=8.6 Hz), 4.91 (2H, s), 2.32 (3H, s), 2.03 (4H, q, J=7.2 Hz), 1.26 (9H, s), 0.60 (6H, t, J=7.2 Hz).

ES (+) MS m/z, [M+NH4]: 552.2.

Further NMR data: COSY data allowed the spin systems of the two aromatic rings to be grouped together. When the OCH2 was selectively excited, a NOE is observed with a resonance at 6.62δ which is ortho only coupled. When the aromatic methyl (at 2.32δ) was excited, a NOE is observed to a meta coupled proton at 7.04δ. These resonances are not part of the same spin system, requiring the OCH2 and aromatic methyl to be on different rings. Therefore the triflate has migrated during the reaction and the isolated product has the structure shown above. (HMBC data also supports this conclusion.)

D. 3'-[3-chloro-4-(2-oxo-3.3-dimethylbutoxy)phenyl]-3'-[3-methyl-4-(carbomethoxy)phenyl]pentane

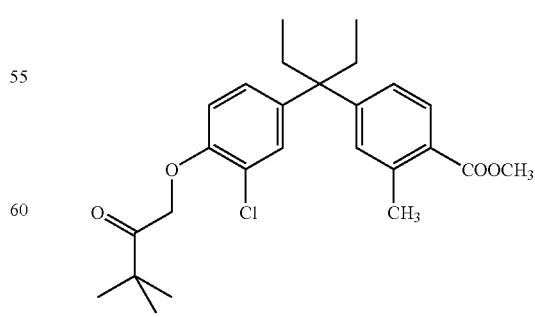

Using a procedure analogous to Example 35F, 3'-[3-chloro-4-(2-oxo-3.3-dimethylbutoxy)-phenyl]-3'-[3-methyl- 4-(trifluoromethylsulfonyl-oxy)phenyl]pentane, MeOH, dppb, DMSO, Et3N, and Pd(OAc)2 under an atmosphere of CO are reacted to provide the title compound as a colorless oil (938 mg, 73%).

H-NMR (300 mHz, CDCl3): δ 7.82 (1H, d, J=8.8 Hz), 7.20 (1H, d, J=2.3 Hz), 7.03-7.05 (2H, m), 6.92 (1H, dd, J=2.3 Hz, J=8.6 Hz), 6.63 (1H, d, J=8.6 Hz), 4.92 (2H, s), 3.89 (3H, s), 2.57 (3H, s), 2.08 (4H, q, J=7.3 Hz), 1.27 (9H, s), 0.63 (6H, t, J=7.3 Hz).

ES (+) MS m/z: 462.4 [M+NH4].

FAB (+) MS m/z [M+H]: 445.2; calc. m/z 445.1.

E. Racemic 3'-[3-chloro-4-(2-hydroxy-3,3-dimethyl-butoxy)phenyl]-3'-[3-methyl-4-(carbomethoxy)phenyl]pentane

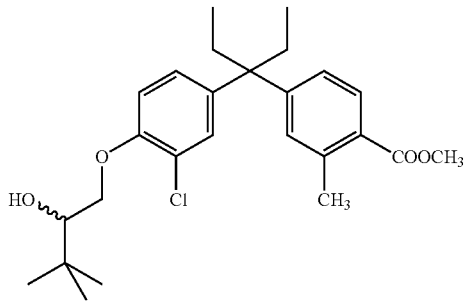

Using a procedure analogous to Example 35G, 3'-[3-chloro-4-(2-oxo-3,3-dimethylbutoxy)phenyl]-3'-[3-methyl-4-(carbomethoxy)phenyl]pentane was reduced by NaBH4 to provide the title compound as a colorless oil (735 mg, 98%).

H-NMR (300 mHz, CDCl3): δ 7.89 (1H, d, J=8.8 Hz), 7.13 (1H, d, J=1.78 Hz), 7.00 (2H, m), 6.93 (1H, dd, J=2.2 Hz, J=8.8 Hz), 6.80 (1H, d, J=8.8 Hz), (4.17 (1H, dd, J=2.6 Hz, J=9.0 Hz), 3.86 (1H, m), 3.85 (3H, s), 3.74 (1H, m), 2.60, (1H, d, J=3.0 Hz), 2.54 (3H, s), 2.06 (4H, q, J=7.3 Hz), 1.01 (9H, s), 0.61 (6H, t, J=7.3 Hz).

FAB (+) MS m/z [M+H]: 447.1; calc m/z 447.2.

IR (CHCl3): 1717 cm$^{-1}$

F. Racemic 3'-[3-chloro-4-(2-hydroxy-3,3-dimethyl-butoxy)phenyl]-3'-[3-methyl-4-(carboxy)phenyl]pentane

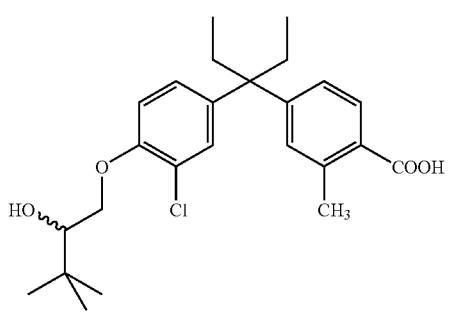

Using a procedure analogous to Example 35H&I, racemic 3'-[3-chloro-4-(2-hydroxy-3,3-dimethylbutoxy)phenyl]-3'-[3-methyl-4-(carbomethoxy)-phenyl]pentane was saponified by aqueous NaOH in EtOH to form the Na salt corresponding to the desired compound. After removal of the EtOH under reduced pressure, the residue containing the Na salt was dissolved in water and acidified in a manner analogous to the procedure of Example CDJ-3 to provide the title compound as a white solid (470 mg, 97%).

H-NMR (300 mHz, DMSO): δ 7.72 (1H, d, J=8.0 Hz), 7.00 to 7.10 (5H, m), 4.84 (1H, d, J=5.6 Hz), 4.09 (1H, dd, J=2.8 Hz, J=10.4 Hz), 3.85 (1H, dd, J=7.0 Hz, J=10.4 Hz), 3.45 (1H, m), 2.47 (3H, s), 2.06 (4H, q, J=7.3 Hz), 0.91 (9H, s), 0.55 (6H, t, J=7.3 Hz).

ES (+) MS m/z 450.2 [M+NH4], 455.2 [M+Na].

ES (−) MS m/z 431.1 [M−1].

IR (CHCl3): 1689 cm$^{-1}$.

Example 39

Preparation of Racemic 3'-[3-methyl-4-(2-hydroxy-3,3-dimethylbutoxy)phenyl]-3'-(3-chloro-4-carboxyphenyl)pentane

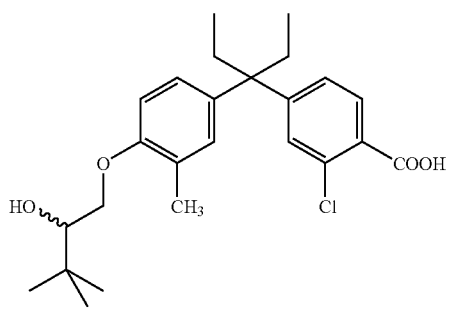

A.
[E,Z]-3-[3-Chloro-4-carbomethoxyphenyl]-3-pentene

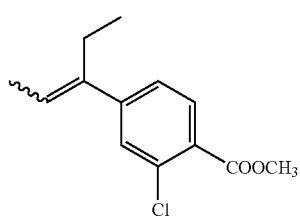

Using a procedure similar to Example 35F, a mixture of [E,Z]-3-[3-chloro-4-(trifluoromethylsulfonyloxy)phenyl)-3-pentene, MeOH, dppb, DMSO (instead of DMF), Et3N, and Pd(OAc)2 under an atmosphere of CO at 80° C. for 4 h are reacted to provide the title compound as a colorless liquid in a [E:Z] ratio of 9:1 (1.99 g, 92%).

H-NMR (300 mHz, CDCl3): δ 7.06-7.85 (3H, m), 5.85 (0.9H, q, J=6.9 Hz), 5.60 (0.1H, q, J=6.9 Hz), 3.94 (0.3H, s), 3.93 (2.7H, s), 2.50 (1.8H, q, J=7.6 Hz), 2.32 (0.2H, q, J=7.6 Hz), 1.82 (2.7H, d, J=7.6 Hz), 1.53 (0.3H, d, J=7.6 Hz), 0.97 (2.7H, t, J=7.6 Hz), 0.94 (0.3H, t, J=7.6 Hz).

IR (CHCl3): 1726 cm$^{-1}$

ES GC MS m/z 238.1, M+; Calc. C13H15ClO2 m/z 238.1

B. 3'-(4-hydroxy-3-methylphenyl)-3'-[3-chloro-4-carbomethoxyphenyl]pentane

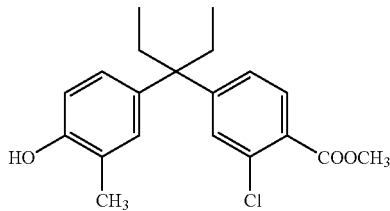

Using a procedure analogous to Example 35D, [E,Z]-3-[3-chloro-4-carbomethoxyphenyl)-3-pentene and o-cresol are reacted at RT overnight to give the title compound as a thick, pale yellow oil (3.54 g, 99%).

H-NMR (300 mHz, CDCl3): δ 7.74 (1H, d, J=8.2 Hz), 7.29 (1H, d, J=1.7 Hz), 7.08 (1H, dd, J=1.7 Hz, J=8.2 Hz), 6.81 (2H, m), 6.63 (1H, d, J=8.9 Hz), 3.91 (3H, s), 2.20 (3H, s), 2.09 (4H, q, J=7.3 Hz), 1.27 (9H, s), 0.70 (6H, t, J=7.3 Hz).
ES (+) MS m/z 347.1 [M+1].
IR (CHCl3): 1725 cm$^{-1}$.

C. 3'-[4-(2-oxo-3,3-trimethylbutoxy)-3-methyl-phenyl]-3'-(3-chloro-4-carbomethoxyphenyl)-pentane

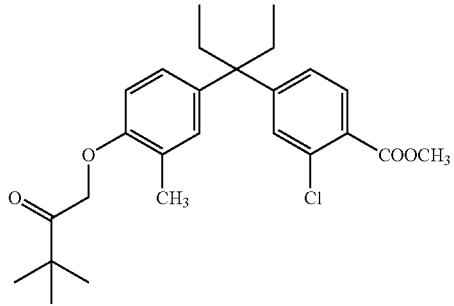

Using a procedure analogous to Example 35C, 3'-(4-hydroxy-3-methylphenyl)-3'-[3-chloro-4-carbomethoxyphenyl]pentane, 1-chloropinacolone, anhydrous KI, and K2CO3 are reacted in acetonitrile to give the title compound as a clear colorless oil (3.46 g, 90%).

H-NMR (300 mHz, CDCl3): δ 7.70 (1H, d, J=8.2 Hz), 7.28 (1H, d, J=1.8 Hz), 7.07 (1H, dd, J=1.8, J=8.2), 6.858-6.87 (2H, m), 6.50 (1H, d, J=9.2 Hz), 4.84 (2H, s), 3.91 (3H, s), 2.23 (3H, s), 2.05 (4H, q, J=7.3 Hz), 1.53 (9H, s), 0.61 (6H, t, J=7.3 Hz).
FAB(+) MS m/z [M+H]: 445.2 Calc. m/z 445.2.
IR (CHCl3): 1725 cm$^{-1}$.

D. Racemic 3'-[3-methyl-4-(2-hydroxy-3,3-dimethylbutoxy)phenyl]-3'-(3-chloro-4-carbomethoxyoxyphenyl)pentane

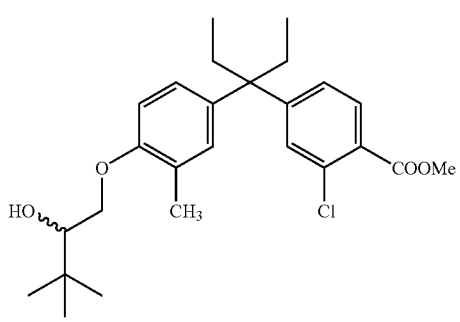

Using a procedure analogous to Example 35G, 3'-[4-(2-oxo-3,3-trimethylbutoxy)-3-methyl-phenyl]-3'-(3-chloro-4-carbomethoxyphenyl)-pentane was reduced by NaBH4 to provide the title compound as a colorless oil (2.75 g, 91%).

H-NMR (300 mHz, CDCl3): δ 7.75 (1H, d, J=8.8 Hz), 7.27 (1H, d, J=1.8 Hz), 7.16 (1H, d, J=2.0 Hz), 7.07 (1H, dd, J=1.8 Hz, J=8.8 Hz), 6.94 (1H, dd, J=2.0 Hz, J=8.8 Hz), 6.83 (1H, d, J=8.8 Hz), 4.18 (1H, dd, J=2.6 Hz, J=9.0 Hz), 3.92 (3H, s), 3.89 (1H, m), 3.74 (1H, m), 2.60, (1H, broad s), 2.06 (4H, q, J=7.3 Hz), 1.04 (9H, s), 0.63 (6H, t, J=7.3 Hz).
FAB(+) MS m/z [M+H]: 447.3; calc. m/z 447.2
IR (CHCl3): 1733 cm$^{-1}$

E. Racemic 3'-[3-methyl-4-(2-hydroxy-3,3-dimethylbutoxy)phenyl]-3'-(3-chloro-4-carboxyphenyl)pentane Using a procedure analogous to Example 35H, racemic 3'-[3-methyl-4-(2-hydroxy-3,3-dimethylbutoxy)phenyl]-3'-(3-chloro-4-carbomethoxyphenyl)pentane was saponified by aqueous NaOH in EtOH to form the Na salt corresponding to the desired compound. After removal of the EtOH under reduced pressure, the residue containing the Na salt was dissolved in water and acidified in a manner analogous to the procedure of Example 39I to provide the title compound as a white solid (1.84 g, 93%).

H-NMR (300 mHz, DMSO): δ 7.69 (1H, d, J=8.0 Hz), 7.10 to 7.20 (2H, m), 6.80 to 6.95 (3H, m), 4.78 (1H, d, J=5.6 Hz), 4.02 (1H, dd, J=2.8 Hz, J=10.4 Hz), 3.76 (1H, dd, J=7.0 Hz, J=10.4 Hz), 3.44 (1H, m), 2.10 (3H, s), 2.04 (4H, q, J=7.3 Hz), 0.93 (9H, s), 0.56 (6H, t, J=7.3 Hz).
ES (+) MS m/z 433.2 [M+H], 450.1 [M+NH4], 455.1 [M+Na].
ES (−) MS m/z 431.2 [M−H].
IR(CHCl3): 1701 cm$^{-1}$.

Example 40

Preparation of racemic 3'-[3-chloro-4-(2-hydroxy-3,3-dimethylbutoxy)phenyl]-3'-(3-chloro-4-carboxyphenyl)pentane

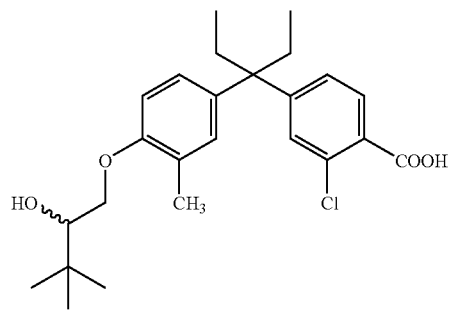

A. 3'-(4-hydroxy-3-chlorophenyl)-3'-(3-chloro-4-carbomethoxy-phenyl)pentane

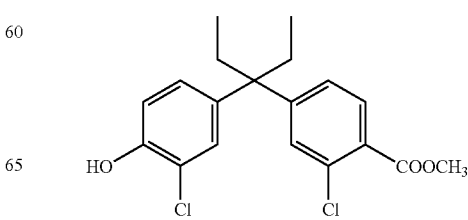

Using a procedure analogous to Example 35D, [E,Z]-3-[3-chloro-4-carbomethoxyphenyl]-3-pentene and o-chlorophenol are reacted (initially at RT overnight, then at 70° C. for 20 h, and finally at 90° C. overnight) to give the title compound as an oil (886 mg, 58%).

H-NMR (300 mHz, CDCl3): 6.90 to 7.76 (6H, m), 5.45 (1H, s), 3.93 (3H, s), 2.06 (4H, q, J=7.3 Hz), 0.64 (6H, t, J=7.3 Hz).

ES (+) MS m/z 367.0 [M+H].

IR (CHCl3): 1726 cm$^{-1}$

B. 3'-[4-(2-oxo-3,3-trimethylbutoxy)-3-chlorophenyl]-3'-(3-chloro-4-carbomethoxyphenyl)-pentane

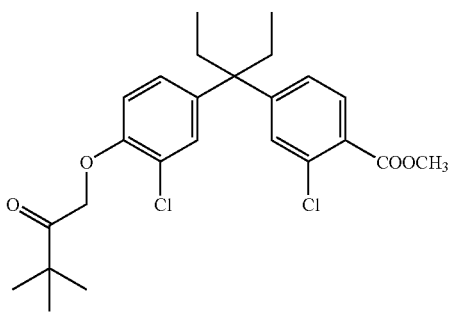

Using a procedure analogous to Example 35C, 3'-(4-hydroxy-3-chlorophenyl)-3'-(3-chloro-4-carbomethoxy-phenyl)pentane, 1-chloropinacolone, anhydrous KI, and K2CO3 are reacted in acetonitrile to give the title compound as a clear, nearly colorless oil (919 mg, 89%).

H-NMR (300 mHz, CDCl3): δ 7.72 (1H, d, J=8.2 Hz), 7.26 (1H, m), 7.17 (1H, d, J=2.3, 7.06 (1H, dd, J=1.8 Hz, J=8.2 Hz), 6.90 (1H, dd, J=8.7 Hz, J=2.3 Hz), 4.91 (2H, s), 3.92 (3H, s), 2.05 (4H, q, J=7.3 Hz), 1.26 (9H, s), 0.62 (6H, t, J=7.3 Hz).

ES (+) MS m/z 465.1 [M+H], 482.1 [M+NH4].

C. Racemic 3'-[3-chloro-4-(2-hydroxy-3,3-dimethylbutoxy)phenyl]-3'-(3-chloro-4-carbomethoxyphenyl) pentane

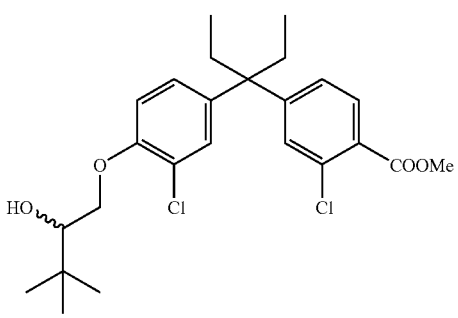

Using a procedure analogous to Example 35G, 3'-[4-(2-oxo-3,3-trimethylbutoxy)-3-chlorophenyl]-3'-(3-chloro-4-carbomethoxyphenyl)-pentane was reduced by NaBH4 to provide the title compound as a colorless oil (738 mg, 98%).

H-NMR (300 mHz, CDCl3): δ 7.89 (1H, d, J=8.8 Hz), 7.13 (1H, d, J=1.78 Hz), 7.00 (2H, m), 6.93 (1H, dd, J=2.2 Hz, J=8.8 Hz), 6.80 (1H, d, J=8.8 Hz), (4.17 (1H, dd, J=2.6 Hz, J=9.0 Hz), 3.86 (1H, m), 3.85 (3H, s), 3.74 (1H, m), 2.60, (1H, d, J=3.0 Hz), 2.06 (4H, q, J=7.3 Hz), 1.01 (9H, s), 0.61 (6H, t, J=7.3 Hz).

ES (+) MS m/z 489.2 (M+Na).

IR (CHCl3): 1717 cm$^{-1}$

D. Racemic 3'-[3-chloro-4-(2-hydroxy-3,3-dimethylbutoxy)phenyl]-3'-(3-chloro-4-carboxyphenyl)pentane Using a procedure analogous to Example 35H, racemic 3'-[3-methyl-4-(2-hydroxy-3,3-dimethylbutoxy)phenyl]-3'-(3-chloro-4-carbomethoxy-phenyl)pentane was saponified by aqueous NaOH in EtOH to form the Na salt corresponding to the desired compound. After removal of the EtOH under reduced pressure, the residue containing the Na salt was dissolved in water and acidified in a manner analogous to the procedure of Example 391 to provide the title compound as a white solid (517 mg, 94%).

H-NMR (300 mHz, DMSO): δ 7.74 (1H, d, J=8.0 Hz), 7.04 to 7.30 (5H, m), 4.88 (1H, d, J=5.6 Hz), 4.14 (1H, dd, J=2.8 Hz, J=10.4 Hz), 3.89 (1H, dd, J=7.0 Hz, J=10.4 Hz), 3.49 (1H, m), 2.04 (4H, q, J=7.3 Hz), 0.95 (9H, s), 0.58 (6H, t, J=7.3 Hz).

ES (+) MS m/z 475.2 [M+Na].

IR (CHCl3): 1701 cm$^{-1}$.

Example 41 and Example 42

Separation of optical isomers of 3'-[3-chloro-4-(2-hydroxy-3,3-dimethyl-butoxy)phenyl]-3'-(3-chloro-4-carboxyphenyl)pentane

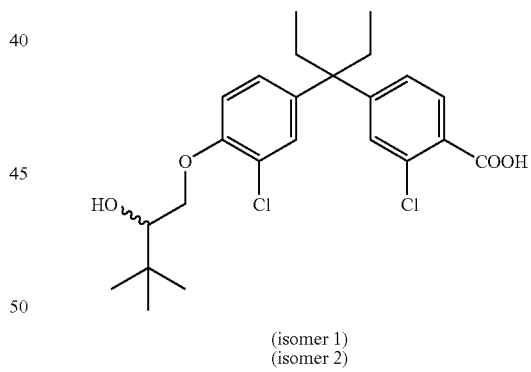

(isomer 1)
(isomer 2)

A racemic mixture 3'-[3-chloro-4-(2-hydroxy-3,3-dimethylbutoxy)-phenyl]-3'-(3-chloro-4-carboxyphenyl)pentane. (490 mg) is chromatographed with a ChiralpakAD column to give enantiomer 1, Example 41 (192 mg, 39%) and enantiomer 2, Example 42 (185 mg, 38%).

Enantiomer 1, Example 41

HPLC: Chiralpak AD (4.6×250 mm); 3:2 heptane:isopropyl alcohol with 0.1% TFA; 1.0 mL/m (flow rate); rt=7.8 m; 270 nm; ee 99.9% by HPLC.

H-NMR (300 mHz, DMSO): δ 7.74 (1H, d, J=8.0 Hz), 7.04 to 7.30 (5H, m), 4.88 (1H, d, J=5.6 Hz), 4.14 (1H, dd, J=2.8 Hz, J=10.4 Hz), 3.89 (1H, dd, J=7.0 Hz, J=10.4 Hz), 3.49 (1H, m), 2.04 (4H, q, J=7.3 Hz), 0.95 (9H, s), 0.58 (6H, t, J=7.3 Hz).
ES (+) MS m/z 475.2 [M+Na].

Enantiomer 2, Example 42

HPLC: Chiralpak AD (4.6×250 mm); 3:2 heptane:isopropyl alcohol with 0.1% TFA; 1.0 mL/m (flow rate); rt=10.6 m; 270 nm; ee 99.5% by HPLC.

H-NMR (300 mHz, DMSO): δ 7.74 (1H, d, J=8.0 Hz), 7.04 to 7.30 (5H, m), 4.88 (1H, d, J=5.6 Hz), 4.14 (1H, dd, J=2.8 Hz, J=10.4 Hz), 3.89 (1H, dd, J=7.0 Hz, J=10.4 Hz), 3.49 (1H, m), 2.04 (4H, q, J=7.3 Hz), 0.95 (9H, s), 0.58 (6H, t, J=7.3 Hz).
ES (+) MS m/z 475.1 [M+Na].

Example 43

Preparation of racemic 1-(4-{1-Ethyl-1-[4-(1H-tetrazol-5-yl)-phenyl]-propyl}-2-methyl-phenoxy)-3,3-dimethyl-butan-2-ol

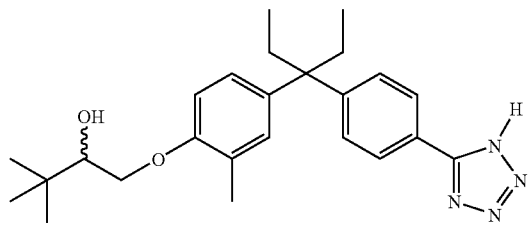

A. 3'-(4-Iodophenyl)-3'-pentanol.

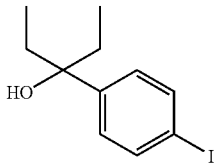

To ethyl, p-iodobenzoate (11.04 g, 40 mmol) in diethylether (100 mL) at −20° C. under nitrogen is added 1M ethylmagnesium bromide (91 mL, 91 mmol) dropwise with mechanical stirring, and the mixture is allowed to come to R.T. and stirred over night. The mixture is quenched with satd. sodium bicarbonate and triturated with diethylether six times. The organic layers are combined; washed with water; dried over anhydrous sodium sulfate; and evaporated under vacuum to give the title compound as an oil (10.4 g, 90%) which is used as is.

$^1$H NMR (400 mHz, CDCl$_3$), δ 7.64 (d, J=8.8 Hz, 2H), 7.11 (d, J=8.8 Hz, 2H), 1.74-1.85 (m, 4H), 0.75 (t, J=7.4 Hz, 6 h).

B. 1-{4-[1]-Ethyl-1-(4-iodophenyl)-propyl]}-2-methyl-phenol

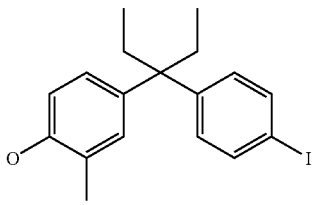

To 3'-(4-iodophenyl)-3'-pentanol (10.4 g, 36 mmol) and o-cresol (15.5 g, 143 mmol) in methylene chloride (5 mL) is added borontrifluoride etherate (0.96 mL, 7.2 mmol), and the mixture is allowed to stir at room temperature overnight. The mixture is quenched with satd. sodium bicarbonate, and extracted into diethylether. The organic phase is washed with water; dried over anhydrous sodium sulfate; and evaporated under vacuum. The residue is vacuum distilled (0.5 mm) to 80° C. to remove excess o-cresol, and the residue is partitioned between diethylether and water. The organic layer is dried over anhydrous sodium sulfate, and evaporated under vacuum to give the title compound as an oil (13 g, 95%) which is used as is.

$^1$H NMR (400 mHz, CDCl$_3$), δ 7.53 (d, J=8.8 Hz, 2H), 6.90 (d, J=8.8 Hz, 2H), 6.84 (s, 1H), 6.83 (d. J=8.9 Hz, 1H), 6.64 (d, J=8.9 Hz, 1H), 4.50 (s, 1H), 2.20 (s, 3H), 2.01 (q, J=7.2 Hz, 4H), 0.60 (t, J=7.2 Hz, 6H).

C. 1-{4-[1-Ethyl-1-(4-iodophenyl)-propyl]-2-methyl-phenoxy}-3,3-dimethyl-butan-2-one

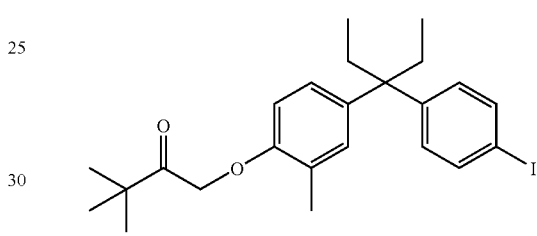

In a procedure analogous to Example 35C, 1-{4-[1-Ethyl-1-(4-iodophenyl)-propyl]}-2-methyl-phenol (13 g, 34 mmol) gave the title compound as an oil (13.9 g, 85%) which is used as is.

$^1$H NMR (400 mHz, CDCl$_3$), δ 7.53 (d, J=8.4 hz, 2H), 6.90 (d, J=8.4 Hz, 2H), 6.87 (s, 1H), 6.86 (d, J=8.8 hz, 1H), 6.48 (d, J=8.8 Hz, 1H), 4.83 (s, 2H), 2.23 (s, 3H), 2.01 (q, J=7.2 Hz, 4H), 1.25 (s, 9H).

D. 4-{1-[4-(3,3-Dimethyl-2-oxo-butoxy)-3-methyl-phenyl]-1-ethyl-propyl}-benzonitrile

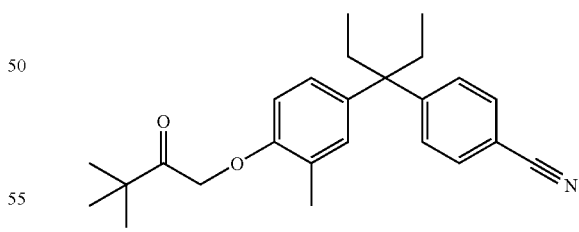

To a mixture of 1-{4-[1-ethyl-1-(4-iodo-phenyl)-propyl]-2-methyl-phenoxy}-3,3-dimethyl-butan-2-one (3.0 g 6.27 mmol) and DMF (30 mL) is added Zn(CN)$_2$ (0.44 g, 3.76 mmol), Pd$_2$(dba)$_3$ (0.29 g, 0.31 mmol), and DPPF (0.42 g, 0.75 mmol). The solution is heated at 100° C. overnight, diluted with Et$_2$O (200 mL), washed with 4:1:4 sat NH$_4$Cl: Conc. NH$_4$OH:water (100 mL), water (100 mL), brine (100 mL), dried MgSO$_4$, filtered and concentrated. The residue is purified by ISCO (10%-2-% EtOAc gradient) to furnish the title compound (1.1 g, 2.91 mmol, 46%).

¹H NMR (CDCl₃), δ 0.52-0.63 (m, 6H), 1.26 (s, 9H), 2.03-2.10 (m, 4H), 2.24 (s, 3H), 4.85 (s, 2H), 6.50 (d, J=9.4 Hz, 1H), 6.82-6.86 (m, 2H), 7.27 (d, J=8.4 Hz, 2H), 7.53 (d, J=8.9 Hz, 2H).

LC/MS (m/z): calcd. for $C_{25}H_{31}NO_2$ (M+H)⁺: 378.6; found: 395.3.

E 1-(4-{1-Ethyl-1-[4-(1H-tetrazol-5-yl)-phenyl]-propyl}-2-methyl-phenoxy)-3,3-dimethyl-butan-2-one

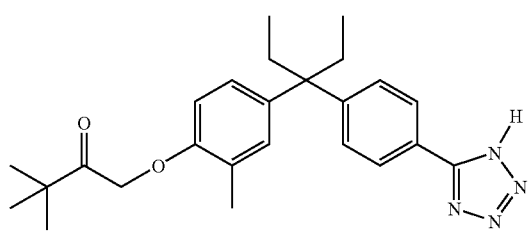

To a mixture of 4-{1-[4-(3,3-dimethyl-2-oxo-butoxy)-3-methyl-phenyl]-1-ethyl-propyl}-benzonitrile (0.50 g, 1.32 mmol), and DMF (5 mL) is added NaN₃ (0.26 g, 3.95 mmol) and Et₃N.HCl (0.54 g, 3.95 mmol). The slurry is heated at 110° C. overnight. The slurry is diluted with EtOAc (50 mL), washed with 1M HCl (40 mL) water (40 mL), brine (40 mL), dried over MgSO₄, filtered and concentrated. The residue is purified by ISCO (20%-40% [89% EtOAc: 10% MeOH: 1% ACOH] gradient) to furnish the title compound (0.37 g, 0.88 mmol, 66%).

¹H NMR (CDCl₃), δ 0.57-0.62 (m, 6H), 1.27 (s, 9H), 2.02-2.11 (m, 4H), 2.17 (s, 3H), 4.87 (s, 2H), 6.50 (d, J=9.4 Hz, 1H), 6.82-6.88 (m, 2H), 7.22-7.28 (m, 3H), 7.94 (d, J=7.9 Hz, 2H).

LC/MS (m/z): calcd. for $C_{25}H_{32}N_4O_2$ (M+H)⁺: 421.7; found: 421.2.

F. 1-(4-{1-Ethyl-1-[4-(1H-tetrazol-5-yl)-phenyl]-propyl}-2-methyl-phenoxy)-3,3-dimethyl-butan-2-ol To a mixture of 1-(4-{1-Ethyl-1-[4-(1H-tetrazol-5-yl)-phenyl]-propyl}-2-methyl-phenoxy)-3,3-dimethyl-butan-2-one (0.37 g, 0.88 mmol) and EtOH (5 mL) was added NaBH₄ (0.037 g, 0.97 mmol) and the solution stirred for 1 hour. The solids were removed by filtration and the solution concentrated. The residue was purified by ISCO (10-30 [89% EtOAc:10% MeOH:1% AcOH] gradient) to furnish the title compound (0.32 g, 0.76 mmol, 86%).

¹H NMR (CDCl₃), δ 0.59-0.64 (m, 6H), 1.02 (s, 9H), 2.05-2.12 (m, 4H), 2.13 (s, 3H), 3.75 (dd, J=2.8, 8.8 Hz, 1H), 3.89 (t, J=8.8 Hz, 1H), 4.10 (dd, J=2.8, 8.8 Hz, 1H), 6.68 (d, J=8.2 Hz, 1H), 6.85 (d, J=2.2 Hz, 1H), 6.92 (dd, J=2.2, 8.7 Hz, 1H), 7.31 (d, J=8.4 Hz, 2H), 8.01 (d, J=8.4 Hz, 2H).

LC/MS (m/z): calcd. for $C_{25}H_{34}N_4O_2$ (M+H)⁺: 423.7; found: 423.2.

Example 44 and Example 45

Separation of enantiomers of 1-(4-{1-Ethyl-1-[4-(1H-tetrazol-5-yl)-phenyl]-propyl}-2-methyl-phenoxy)-3,3-dimethyl-butan-2-ol

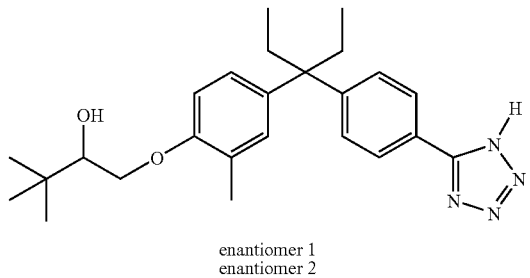

enantiomer 1
enantiomer 2

A racemic mixture of 1-(4-{1-Ethyl-1-[4-(1H-tetrazol-5-yl)-phenyl]-propyl}-2-methyl-phenoxy)-3,3-dimethyl-butan-2-ol (0.32 g) is chromatographed (CHIRALPAK ADH column, 0.1% TFA, 20% i-PrOH/Hept) to give enantiomer 1, (0.168 g, 0.40 mmol, 45%) and enantiomer 2, (0.150 g, 0.35 mmol, 41%).

Example 44, Enantiomer 1

Rt=7.7m

¹H NMR (CDCl₃), δ 0.57-0.67 (m, 6H), 1.02 (s, 9H), 2.05-2.12 (m, 4H), 2.14 (s, 3H), 3.74 (dd, J=2.2, 8.8 Hz, 1H), 3.89 (t, J=8.8 Hz, 1H), 4.10 (dd, J=2.2, 8.8 Hz, 1H), 6.69 (d, J=8.8 Hz, 1H), 6.86 (s, 1H), 6.93 (d, J=8.8 Hz, 1H), 7.31 (d, J=8.0 Hz, 2H), 7.99 (d, J=8.0 Hz, 2H). LC/MS (m/z): calcd. for $C_{25}H_{34}N_4O_2$ (M+H)⁺: 423.7; found: 423.3.

Example 45, enantiomer 2

Rt=11.6 m

¹H NMR (CDCl₃), δ 0.59-0.66 (m, 6H), 1.01 (s, 9H), 2.05-2.15 (m, 4H), 2.16 (s, 3H), 3.71 (dd, J=2.5, 8.7 Hz, 1H), 3.87 (t, J=9.0 Hz, 1H), 4.09 (dd, J=2.5, 9.0 Hz, 1H), 6.71 (d, J=8.8 Hz, 1H), 6.87 (d, J=1.7 Hz, 1H), 6.95 (dd, J=2.2, 8.5 Hz, 1H), 7.31 (d, J=8.2 Hz, 2H), 8.01 (d, J=8.2 Hz, 2H). LC/MS (m/z): calcd. for $C_{25}H_{34}N_4O_2$ (M+H)⁺: 423.7; found: 423.3.

Example 46

Preparation of epimer 1 of (D)-2-(4-{1-ethyl-1-[4-(2-hydroxy-1,3,3-trimethyl-butoxy)-3-methyl-phenyl]-propyl}-2-methyl-benzoylamino)-propionic acid

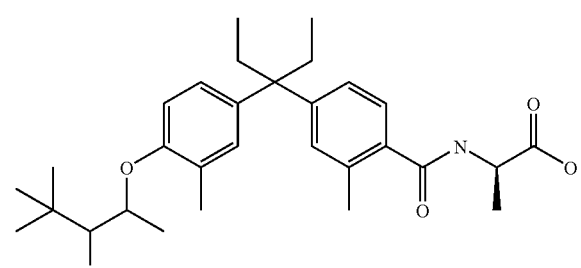

(Epimer 1, D-)

A. Preparation of epimer 1 of (D)-2-(4-{1-ethyl-1-[4-(2-hydroxy-1,3,3-trimethyl-butoxy) -3-methyl-phenyl]-propyl}-2-methyl-benzoylamino)-propionic acid methyl ester

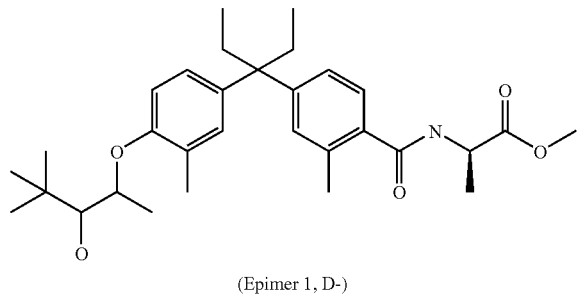

(Epimer 1, D-)

Using a procedure analogous to Example 5, isomer 1 of 4-{1-ethyl-1-[4-(2-hydroxy-1,3,3-trimethyl-butoxy)-3-methyl-phenyl]-propyl}-2-methyl-benzoic acid (0.55 g, 1.29 mmol). (D)-alananine methyl ester hydrochloride (198 mg, 1.42 mmol), EDCI (276 mg, 1.44 mmol), and 1-hydroxybenzotriazole hydrate (195 mg, 1.44 mmol) furnish the title compound (0.42 g, 0.82 mmol, 63%).

$^1$H NMR (CDCl$_3$), δ 0.62 (t, J=7.3 Hz, 6H), 0.97 (S, 9H), 1.35 (d, J=6.3 Hz, 3H), 1.51 (d, J=7.5 Hz, 3H), 2.06 (q, J=7.3 Hz, 4H), 2.14 (s, 3H), 2.43 (s, 3H), 3.18 (bs, 1H), 3.79 (s, 3H), 4.58 (q, J=6.3 Hz, 1H), 4.79 (m, 1H), 6.32 (d, J=8.1 Hz, 1H), 6.69 (d, J=8.3 Hz, 1H), 6.84-7.05 (m, 4H), 7.30 (d, J=8.3 Hz, 1H).

ES-MS (m/z): calcd. for C$_{31}$H$_{46}$NO$_5$ (M+H)$^+$: 511.7; found: 512.3.

B. Preparation of epimer 1 of (D)-2-(4-{1-ethyl-1-[4-(2-hydroxy-1,3,3-trimethyl-butoxy)-3-methyl-phenyl]-propyl}-2-methyl-benzoylamino)-propionic acid Using a procedure analogous to Example 2, epimer 1 of (D)-2-(4-{1-ethyl-1-[4-(2-hydroxy-1,3,3-trimethyl-butoxy)-3-methyl-phenyl]-propyl}-2-methyl-benzoylamino)-propionic acid methyl ester (0.42 g, 0.82 mmol) and LiOH give the title compound (0.41 g, 0.82 mmol, 100%).

$^1$H NMR (CDCl$_3$), δ 0.62 (t, J=7.5 Hz, 6H), 0.97 (S, 9H), 1.36 (d, J=6.2 Hz, 3H), 1.57 (d, J=7.0 Hz, 3H), 2.06 (q, J=7.5 Hz, 4H), 2.14 (s, 3H), 2.44 (s, 3H), 3.19 (d, J=0.9 Hz, 1H), 4.58 (dq, J=6.2, 0.9 Hz, 1H), 4.74-4.82 (m, 1H), 6.28 (d, J=7.0 Hz, 1H), 6.69 (d, J=8.8 Hz, 1H), 6.84-7.06 (m, 4H), 7.31 (d, J=7.9 Hz, 1H). ES-MS (m/z): calcd. for C$_{31}$H$_{46}$NO$_5$ (M+H)$^+$: 511.7; found: 512.3.).

ES-MS (m/z): calcd for C$_{30}$H$_{42}$NO$_5$ (M–H)$^-$: 496.7; found: 496.3.

Example 47

Preparation of epimer 1 of (L)-2-(4-{1-Ethyl-1-[4-(2-hydroxy-1,3,3-trimethyl-butoxy)-3-methyl-phenyl]-propyl}-2-methyl-benzoylamino)-propionic acid

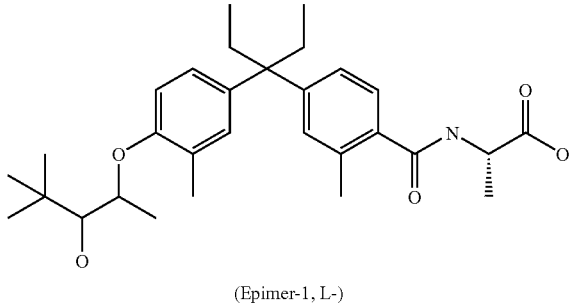

(Epimer-1, L-)

A. Preparation of epimer 1 of (L)-2-(4-{1-ethyl-1-[4-(2-hydroxy-1,3,3-trimethyl-butoxy)-3-methyl-phenyl]-propyl}-2-methyl-benzoylamino)-propionic acid methyl ester

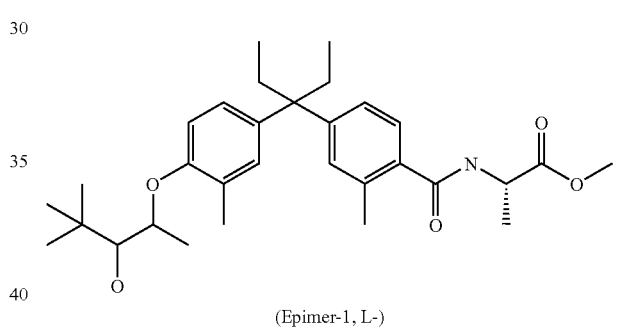

(Epimer-1, L-)

Using the procedure analogous to Example 46A, isomer 1 of 4-{1-ethyl-1-[4-(2-hydroxy-1,3,3-trimethyl-butoxy)-3-methyl-phenyl]-propyl}-2-methyl-benzoic acid (0.55 g, 1.29 mmol) and (L)-alananine methyl ester hydrochloride (198 mg, 1.42 mmol) furnish the title compound (0.56 g, 1.09 mmol, 85%).

$^1$H NMR (CDCl$_3$), δ 0.62 (t, J=7.2 Hz, 6H), 0.97 (s, 9H), 1.36 (d, J=6.1 Hz, 3H), 1.51 (d, J=7.4 Hz, 3H), 2.06 (q, J=7.2 Hz, 4H), 2.15 (s, 3H), 2.43 (s, 3H), 3.18 (bs, 1H), 3.79 (s, 3H), 4.58 (dq, J=6.1, 0.9 Hz, 1H), 4.79 (m, 1H), 6.32 (d, J=7.3 Hz, 1H), 6.69 (d, J=8.5 Hz, 1H), 6.84-7.05 (m, 4H), 7.30 (d, J=8.3 Hz, 1H).

ES-MS (m/z): calcd. for C$_{31}$H$_{46}$NO$_5$ (M+H)$^+$: 511.7; found: 512.3.

B. Preparation of epimer 1 of (L)-2-(4-{1-Ethyl-1-[4-(2-hydroxy-1,3,3-trimethyl-butoxy)-3-methyl-phenyl]-propyl}-2-methyl-benzoylamino)-propionic acid Using a procedure analogous to Example 46B, epimer 1 of (D)-2-(4-{1-ethyl-1-[4-(2-hydroxy-1,3,3-trimethyl-butoxy)-3-methyl-phenyl]-propyl}-2-methyl-benzoylamino)-propionic acid methyl ester (0.56 g, 1.09 mmol) gives the title compound (0.54 g, 1.09 mmol, 100%).

¹H NMR (CDCl₃), δ 0.62 (t, J=7.0 Hz, 6H), 0.97 (S, 9H), 1.36 (d, J=6.1 Hz, 3H), 1.57 (d, J=7.4 Hz, 3H), 2.06 (q, J=7.0 Hz, 4H), 2.14 (s, 3H), 2.44 (s, 3H), 3.19 (d, J=1.3 Hz, 1H), 4.59 (q, J=6.1, Hz, 1H), 4.74-4.82 (m, 1H), 6.29 (d, J=7.0 Hz, 1H), 6.69 (d, J=8.8 Hz, 1H), 6.84-7.07 (m, 4H), 7.31 (d, J=8.4 Hz, 1H).

ES-MS (m/z): calcd for C₃₀H₄₂NO₅ (M–H)⁻: 496.7; found: 496.3.

Example 48

Preparation of epimer 2 of (D)-2-(4-{1-ethyl-1-[4-(2-hydroxy-1,3,3-trimethyl-butoxy)-3-methyl-phenyl]-propyl}-2-methyl-benzoylamino)-propionic acid

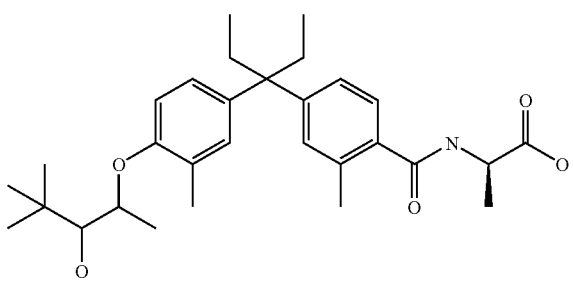

(Epimer-2, D-)

A. Preparation of epimer 2 of (D)-2-(4-{1-ethyl-1-[4-(2-hydroxy-1,3,3-trimethyl-butoxy)-3-methyl-phenyl]-propyl}-2-methyl-benzoylamino)-propionic acid methyl ester

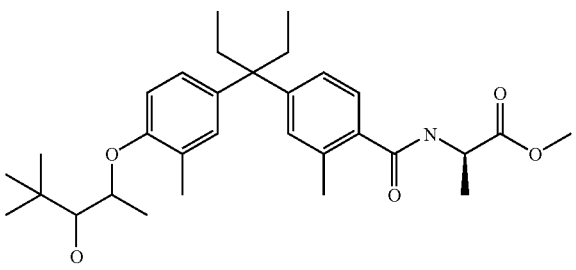

(Epimer-2, D-)

Using the procedure analogous to Example 46A, isomer 2 of 4-{1-ethyl-1-[4-(2-hydroxy-1,3,3-trimethyl-butoxy)-3-methyl-phenyl]-propyl}-2-methyl-benzoic acid (0.50 g, 1.17 mmol) and (D)-alananine methyl ester hydrochloride (180 mg, 1.29 mmol) furnish the title compound (0.47 g, 0.92 mmol, 79%). ¹H NMR) & ES-MS (m/z): identical to that of Example 47A.

B. Preparation of epimer 2 of (D)-2-(4-{1-ethyl-1-[4-(2-hydroxy-1,3,3-trimethyl-butoxy)-3-methyl-phenyl]-propyl}-2-methyl-benzoylamino)-propionic acid Using a procedure analogous to Example 46B, from epimer 2 of (D)-2-(4-{1-ethyl-1-[4-(2-hydroxy-1,3,3-trimethyl-butoxy)-3-methyl-phenyl]-propyl}-2-methyl-benzoylamino)-propionic acid methyl ester (0.47 g, 0.92 mmol) to give the title compound (0.39 g, 0.79 mmol, 86%). ¹H NMR & ES-MS: identical to that of Example 47B.

Example 49

Preparation of epimer 2 of (L)-2-(4-{1-Ethyl-1-[4-(2-hydroxy-1,3,3-trimethyl-butoxy)-3-methyl-phenyl]-propyl}-2-methyl-benzoylamino)-propionic acid

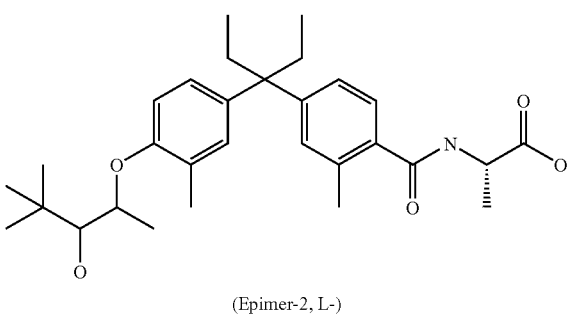

(Epimer-2, L-)

A. Preparation of epimer 2 of (L)-2-(4-{1-ethyl-1-[4-(2-hydroxy-1,3,3-trimethyl-butoxy)-3-methyl-phenyl]-propyl}-2-methyl-benzoylamino)-propionic acid methyl ester

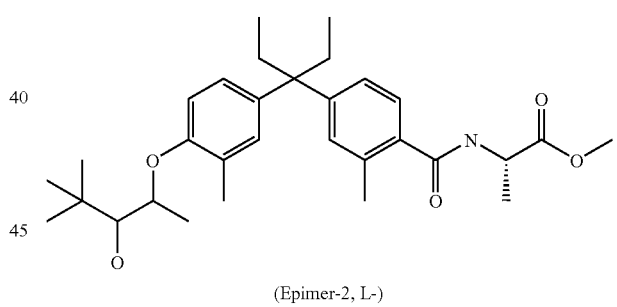

(Epimer-2, L-)

Using the procedure analogous to Example 46A, isomer 2 of 4-{1-ethyl-1-[4-(2-hydroxy-1,3,3-trimethyl-butoxy)-3-methyl-phenyl]-propyl}-2-methyl-benzoic acid (0.50 g, 1.17 mmol) and (L)-alananine methyl ester hydrochloride (180 mg, 1.29 mmol) furnish the title compound (0.47 g, 0.92 mmol, 79%). ¹H NMR) & ES-MS (m/z): identical to that of Example 46A.

B. Preparation of epimer 2 of (L)-2-(4-{1-ethyl-1-[4-(2-hydroxy-1,3,3-trimethyl-butoxy)-3-methyl-phenyl]-propyl}-2-methyl-benzoylamino)-propionic acid Using a procedure analogous to Example 24B, epimer 2 of (L)-2-(4-{1-ethyl-1-[4-(2-hydroxy-1,3,3-trimethyl-butoxy)-3-methyl-phenyl]-propyl}-2-methyl-benzoylamino)-propionic acid methyl ester (0.47 g, 0.92 mmol) give the title compound (0.44 g, 0.88 mmol, 96%). $^1$H NMR & ES-MS: identical to that of Example 46B.

Example 50

Preparation of enantiomer 1 of 5-(4-{1-ethyl-1-[4-(2-hydroxy-3,3-dimethyl-butoxy)-3-methyl-phenyl]-propyl}-2-methyl-benzyl)-thiazolidine-2,4-dione

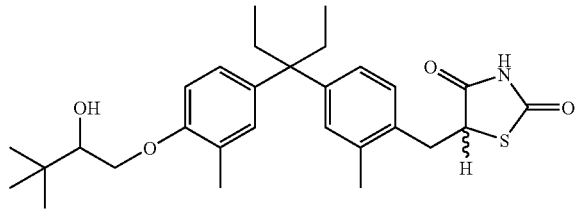

A. Enantiomer 1 of 4-{1-ethyl-1-[4-(2-hydroxy-3,3-dimethyl-butoxy)-3-methyl-phenyl]-propyl}-N-methoxy-2,N-dimethyl-benzamide

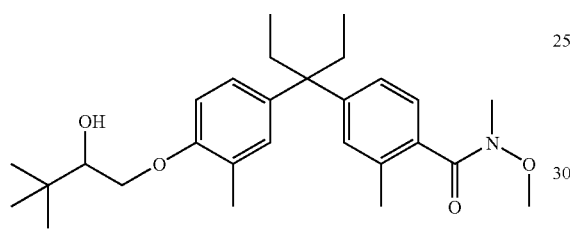

To a mixture of enantiomer 1 of 4-{1-ethyl-1-[4-(2-hydroxy-3,3-dimethyl-butoxy)-3-methyl-phenyl]-propyl}-2-methyl-benzoic acid (1.11 g, 2.69 mmol) and DMF (5 mL) is added hydroxylamine hydrochloride (0.29 g, 2.96 mmol), EDCI (0.57 g, 2.96 mmol), HOBt (0.40 g, 2.96 mmol), and NEt$_3$ (1.65 mL, 11.84 mmol). The mixture is stirred at ambient temperature overnight, diluted with EtOAc (40 mL), washed with 1M HCl (40 mL), water (40 mL), brine (40 mL), dried over MgSO$_4$, filtered and concentrated.

The residue is purified by ISCO (10%-40% EtOAc gradient) to furnish the title compound (1.0 g, 2.19 mmol, 81%).

$^1$H NMR (CDCl$_3$), δ 0.57-0.64 (m, 6H), 1.02 (s, 9H), 2.02-2.10 (m, 4H), 2.17 (s, 3H), 2.29 (s, 3H), 3.28 (bs, 3H), 3.53 (bs, 1H), 3.71 (dd, J=2.7, 8.8 Hz, 1H), 3.86 (t, J=8.8 Hz, 1H), 4.10 (dd, J=2.7, 8.8 Hz, 1H), 6.70 (d, J=8.6 Hz, 1H), 6.86 (d, J=2.0 Hz, 1H), 6.94 (dd, J=2.2, 8.1 Hz, 1H), 6.97-7.02 (m, 3H), 7.14 (d, J=8.4 Hz, 1H). LC/MS (m/z): calcd. for C$_{28}$H$_{41}$NO$_4$ (M+H)$^+$: 456.7; found: 456.2.

B. Enantiomer 1 of 4-{1-ethyl-1-[4-(2-hydroxy-3,3-dimethyl-butoxy)-3-methyl-phenyl]-propyl}-2-methyl-benzaldehyde

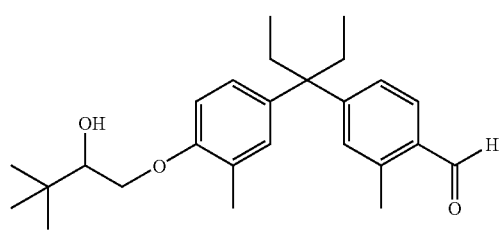

To a mixture of enantiomer 1 of 4-{1-ethyl-1-[4-(2-hydroxy-3,3-dimethyl-butoxy)-3-methyl-phenyl]-propyl}-N-methoxy-2,N-dimethyl-benzamide (1.0 g, 2.42 mmol) and THF (10 mL) is added 1M in THF LAH (2.5 mL, 2.55 mmol) with cooling.

THF (5 mL) was added and the solution stirred for 1 hour. The solution is diluted with Et$_2$O (100 mL) and washed with 1M HCl (50 mL). The aqueous phase is extracted with Et$_2$O (50 mL). The combined organic layers are washed with 1M HCl (50 mL), brine (50 mL), dried over MgSO$_4$, filtered and concentrated to furnish the title compound (0.64 g, 1.61 mmol, 67%).

$^1$H NMR (CDCl$_3$), δ 0.59-0.66 (m, 6H), 1.02 (s, 9H), 2.05-2.15 (m, 4H), 2.18 (s, 3H), 2.62 (s, 3H), 3.71 (dd, J=1.9, 9.1 Hz, 1H), 3.86 (t, J=9.1 Hz, 1H), 4.10 (dd, J=1.9, 9.1 Hz, 1H), 6.72 (d, J=8.2 Hz, 1H), 6.87 (s, 1H), 6.93 (d, J=8.7 Hz, 1H), 7.06 (s, 1H), 7.17 (d, J=8.2 Hz, 1H) 7.67 (dd, J=1.7, 8.0, 1H), 10.20 (s, 1H).

LC/MS (m/z): calcd. for C$_{26}$H$_{36}$O$_3$ (M+H)$^+$: 397.7; found: N/A.

C. Enantiomer 1 of 5-(4-{1-ethyl-1-[4-(2-hydroxy-3,3-dimethyl-butoxy)-3-methyl-phenyl]-propyl}-2-methyl-benzylidene)-thiazolidine-2,4-dione

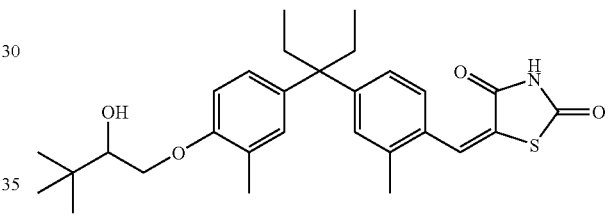

To a mixture of enantiomer 1 of 4-{1-Ethyl-1-[4-(2-hydroxy-3,3-dimethyl-butoxy)-3-methyl-phenyl]-propyl}-2-methyl-benzaldehyde (0.64 g, 1.61 mmol) and toluene (20 mL) is added 90% 2,4-thiazolidinedione (0.25 g, 1.94 mmol), and piperidine acetate (0.04 g, 0.24 mmol). The solution is heated to a reflux overnight and the water removed by a Dean-Stark trap. The solution is diluted with EtOAc (60 mL), washed with water (50 mL), saturated NaHCO$_3$ (50 mL), dried over MgSO$_4$, filtered and concentrated. Purified by ISCO (20%-50% EtOAc gradient) to furnish the title compound (0.75 g, 1.51 mmol, 94%).

$^1$H NMR (CDCl$_3$), δ 0.60-0.67 (m, 6H), 1.03 (s, 9H), 2.04-2.13 (m, 4H), 2.19 (s, 3H), 2.42 (s, 3H), 2.50 (d, J=2.0 Hz, 1H), 3.72 (d, J=8.8 Hz, 1H), 3.86 (t, J=8.9 Hz, 1H), 4.10 (dd, J=2.7, 9.4 Hz, 1H), 6.72 (d, J=8.1 Hz, 1H), 6.88 (d, J=1.7 Hz, 1H), 6.94 (dd, J=2.3, 8.7 Hz, 1H), 7.08 (s, 1H), 7.11 (dd, J=1.8, 8.4 Hz, 1H), 7.33 (d, J=8.4, 1H), 8.06 (s, 1H), 8.97 (bs, 1H).

LC/MS (m/z): calcd. for C$_{29}$H$_{37}$NO$_4$S (M+H)$^+$: 494.5; found: 494.2.

D. Enantiomer 1 of 5-(4-{1-ethyl-1-[4-(2-hydroxy-3,3-dimethyl-butoxy)-3-methyl-phenyl]-propyl}-2-methyl-benzyl)-thiazolidine-2,4-dione To a mixture of enantiomer 1 of 5-(4-{1-Ethyl-1-[4-(2-hydroxy-3,3-dimethyl-butoxy)-3-methyl-phenyl]-propyl}-2-methyl-benzylidene)-thiazolidine-2,4-dione (0.35 g, 0.71 mmol) and MeOH (10 mL) is added Mg (0.17 g, 7.1 mmol).

The solution is heated at a reflux for 4 hours. The solution is filtered thru Celite®, rinsed with MeOH (2 mL), and the solution concentrated. The residue is purified by ISCO (15%-30% EtOAc gradient) to furnish the title compound (0.13 g, 0.26 mmol, 37%).

$^1$H NMR (CDCl$_3$), δ 0.57-0.65 (m, 6H), 1.02 (s, 9H), 2.01-2.10 (m, 4H), 2.19 (s, 3H), 2.31 (s, 3H), 2.50 (d, J=2.6 Hz, 1H), 2.97-3.06 (m, 1H), 3.65 (dd, J=3.8, 14.5 Hz, 1H), 3.69-3.75 (m, 1H), 3.87 (t, J=8.8 Hz, 1H), 4.10 (dd, J=2.7, 9.3 Hz, 1H), 4.52 (dd, J=3.8, 11.2 Hz, 1H), 6.70 (dd, J=2.3, 8.5 Hz, 1H), 6.87-7.04 (m, 5H), 8.56 (bs, 1H).

LC/MS (m/z): calcd. for C$_{29}$H$_{39}$NO$_4$S (M+H)$^+$: 496.6; found: 496.2.

Example 51

Preparation of enantiomer 2 of 5-(4-{1-ethyl-1-[4-(2-hydroxy-3,3-dimethyl-butoxy)-3-methyl-phenyl]-propyl}-2-methyl-benzyl)-thiazolidine-2,4-dione

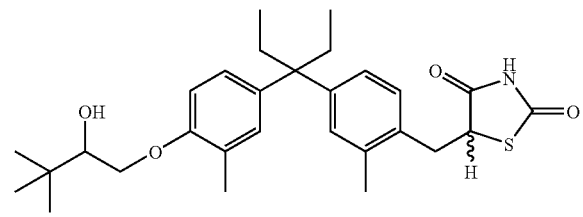

A. Enantiomer 2 of 4-{1-ethyl-1-[4-(2-hydroxy-3,3-dimethyl-butoxy)-3-methyl-phenyl]-propyl}-N-methoxy-2,N-dimethyl-benzamide

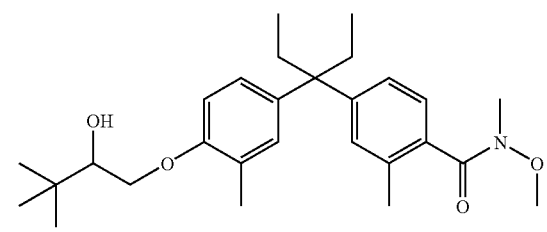

To mixture of enantiomer 2 of 4-{1-ethyl-1-[4-(2-hydroxy-3,3-dimethyl-butoxy)-3-methyl-phenyl]-propyl}-2-methyl-benzoic acid (0.70 g, 1.70 mmol) and DMF (5 mL) is added hydroxylamine hydrochloride (0.18 g, 1.87 mmol), EDCI (0.33 g, 1.87 mmol), HOBt (0.23 g, 1.87 mmol), and NEt$_3$ (0.95 mL, 6.79 mmol). The mixture is stirred at ambient temperature overnight, diluted with EtOAc (40 mL), washed with 1M HCl (40 mL), water (40 mL), brine (40 mL), dried over MgSO$_4$, filtered and concentrated to furnish the title compound (0.76 g, 2.19 mmol, 81%).

$^1$H NMR (CDCl$_3$), δ 0.57-0.64 (m, 6H), 1.02 (s, 9H), 2.01-2.10 (m, 4H), 2.17 (s, 3H), 2.28 (s, 3H), 3.28 (bs, 3H), 3.54 (bs, 1H), 3.71 (dd, J=2.6, 8.8 Hz, 1H), 3.86 (t, J=8.8 Hz, 1H), 4.10 (dd, J=2.6, 8.8 Hz, 1H), 6.70 (d, J=8.3 Hz, 1H), 6.86 (d, J=2.2 Hz, 1H), 6.94 (dd, J=2.2, 8.6 Hz, 1H), 6.97-7.02 (m, 3H), 7.13 (d, J=8.3 Hz, 1H). LC/MS (m/z): calcd. for C$_{28}$H$_{41}$NO$_4$ (M+H)$^+$: 456.7; found: 456.3.

B. Enantiomer 2 of 4-{1-Ethyl-1-[4-(2-hydroxy-3,3-dimethyl-butoxy)-3-methyl-phenyl]-propyl}-2-methyl-benzaldehyde

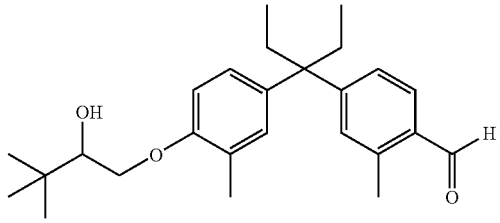

To a mixture of enantiomer 2 of 4-{1-ethyl-1-[4-(2-hydroxy-3,3-dimethyl-butoxy)-3-methyl-phenyl]-propyl}-N-methoxy-2,N-dimethyl-benzamide (0.76 g, 1.75 mmol) and THF (20 mL) is added 1M LAH in THF (1.75 mL, 1.75 mmol) with cooling, and the solution stirred for 1 hour. The solution is diluted with Et$_2$O (100 mL) and washed with 1M HCl (50 mL). The aqueous phase is extracted with Et$_2$O (50 mL). The combined organic layers are washed with 1M HCl (50 mL), brine (50 mL), dried over MgSO$_4$, filtered and concentrated to furnish the title compound (0.48 g, 1.21 mmol, 73%).

$^1$H NMR (CDCl$_3$), δ 0.60-0.65 (m, 6H), 1.02 (s, 9H), 2.07-2.14 (m, 4H), 2.18 (s, 3H), 2.62 (s, 3H), 3.58-3.74 (m, 1H), 3.87 (t, J=8.9 Hz, 1H), 4.10 (dd, J=2.6, 9.2 Hz, 1H), 6.72 (d, J=8.6 Hz, 1H), 6.87 (d, J=2.5, 8.6, 1H), 7.06 (s, 1H), 7.17 (dd, J=1.8, 8.2 Hz, 1H), 7.67 (d, J=8.4, 1H), 10.20 (s, 1H).

LC/MS (m/z): calcd. for C$_{26}$H$_{36}$O$_3$ (M+H)$^+$: 397.7; found: 397.3.

C. Enantiomer 2 of 5-(4-{1-Ethyl-1-[4-(2-hydroxy-3,3-dimethyl-butoxy)-3-methyl-phenyl]-propyl}-2-methyl-benzylidene)-thiazolidine-2,4-dione

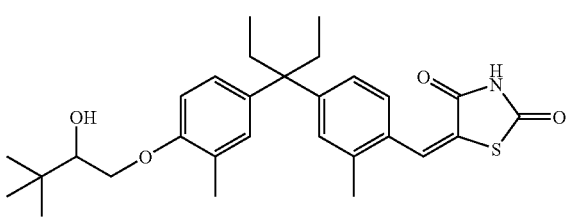

To a mixture of enantiomer 2 of 4-{1-ethyl-1-[4-(2-hydroxy-3,3-dimethyl-butoxy)-3-methyl-phenyl]-propyl}-2-methyl-benzaldehyde (048 g, 1.21 mmol) and toluene (15 mL) is added 90% 2,4-thiazolidinedione (0.19 g, 1.45 mmol), and piperidine acetate (0.03 g, 0.18 mmol). The solution is heated to a reflux overnight and the water removed by a Dean-Stark trap. The solution is diluted with EtOAc (60 mL), washed with water (50 mL), brine (50 mL), dried over MgSO$_4$, filtered and concentrated. Purified by ISCO (20%-40% EtOAc gradient) to furnish the title compound (0.50 g, 1.00 mmol, 83%).

$^1$H NMR (CDCl$_3$), δ 0.60-0.67 (m, 6H), 1.03 (s, 9H), 2.05-2.12 (m, 4H), 2.19 (s, 3H), 2.42 (s, 3H), 2.51 (d, J=2.5 Hz, 1H), 3.70-3.75 (m, 1H), 3.88 (t, J=8.8 Hz, 1H), 4.10 (dd, J=2.7, 9.2 Hz, 1H), 6.72 (d, J=8.3 Hz, 1H), 6.88 (d, J=1.8 Hz, 1H), 6.94 (dd, J=2.2, 8.6 Hz, 1H), 7.08 (s, 1H), 7.11 (dd, J=1.8, 8.0 Hz, 1H), 7.33 (d, J=8.0, 1H), 8.06 (s, 1H), 9.02 (bs, 1H).

LC/MS (m/z): calcd. for $C_{29}H_{37}NO_4S$ $(M+H)^+$: 494.5; found: 494.2.

D. Enantiomer 2 of 5-(4-{1-Ethyl-1-[4-(2-hydroxy-3,3-dimethyl-butoxy)-3-methyl-phenyl]-propyl}-2-methyl-benzyl)-thiazolidine-2,4-dione To a mixture of enantiomer 2 of 5-(4-{1-Ethyl-1-[4-(2-hydroxy-3,3-dimethyl-butoxy)-3-methyl-phenyl]-propyl}-2-methyl-benzylidene)-thiazolidine-2,4-dione (example Rupp-7) (0.25 g, 0.50 mmol) and MeOH (10 mL) is added Mg (0.12 g, 5.04 mmol). The solution is heated at a reflux for 4 hours. The solution is filtered thru Celite®, rinsed with MeOH (2 mL), and the solution concentrated. The residue is purified by ISCO (15%-30% EtOAc gradient) to furnish the title compound (0.084 g, 0.17 mmol, 34%).

$^1$H NMR (CDCl$_3$), δ 0.56-0.63 (m, 6H), 1.02 (s, 9H), 2.00-2.10 (m, 4H), 2.18 (s, 3H), 2.31 (s, 3H), 2.51 (d, J=2.1 Hz, 1H), 2.97-3.06 (m, 1H), 3.65 (dd, J=3.9, 14.7 Hz, 1H), 3.69-3.75 (m, 1H), 3.86 (t, J=8.9 Hz, 1H), 4.09 (dd, J=2.7, 9.4 Hz, 1H), 4.52 (dd, J=3.8, 11.2 Hz, 1H), 6.70 (d, J=8.5 Hz, 1H), 6.86-7.03 (m, 5H), 8.56 (bs, 1H). LC/MS (m/z): calcd. for $C_{29}H_{39}NO_4S$ $(M+H)^+$: 496.6; found: 496.2.

Example 52 and 53

Enantiomer 1 and 2 of [(4-{1-Ethyl-1-[4-(2-hydroxy-1,3,3-trimethyl-butoxy)-3-methyl-phenyl]-propyl}-2-methyl-benzoyl)-methyl-amino]-acetic acid

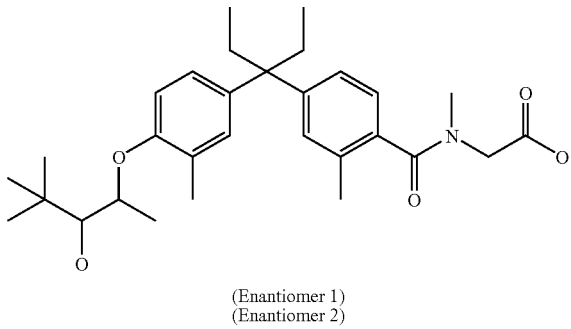

(Enantiomer 1)
(Enantiomer 2)

A. Racemic [(4-{1-Ethyl-1-[4-(2-hydroxy-1,3,3-trimethyl-butoxy)-3-methyl-phenyl]-propyl}-2-methyl-benzoyl)-methyl-amino]-acetic acid methyl ester

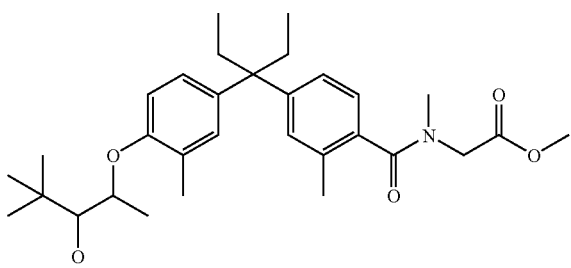

Using a procedure analogous to Example 46A, from racemic 4-{1-ethyl-1-[4-(2-hydroxy-1,3,3-trimethyl-butoxy)-3-methyl-phenyl]-propyl}-2-methyl-benzoic acid (1.46 g, 3.43 mmol) and sascoine methyl ester hydrochloride (0.52 g, 3.76 mmol) to give the title compound (1.74 g, 3.40 mmol, 99%).

$^1$H NMR (CDCl$_3$), δ 0.58-0.65 (m, 6H), 0.97 (s, 6H), 1.02 (s, 3H), 1.33 (d, J=6.2 Hz, 1H), 1.36 (d, J=6.2 Hz, 2H), 2.00-2.10 (m, 4H), 2.14 (s, 3H), 2.25 (s, 1H), 2.33 (s, 2H), 2.57 (d, J=9.6 Hz, 0.33H), 2.58 (d, J=9.6 Hz, 0.66H), 2.89 (s, 3H), 3.18 (dd, J=9.6, 1.3 Hz, 1H), 3.69 (s, 1H), 3.79 (s, 2H), 3.91 (s, 0.66H), 4.32 (bs, 1.34H), 4.59 (dq, J=6.2, 1.3 Hz, 1H), 6.69 (d, J=8.3 Hz, 1H), 6.84-7.11 (m, 5H).

ES-MS (m/z): calcd for $C_{31}H_{45}NO_5$ $(M+H)^+$: 512.7; found: 512.3.

B. Separation of enantiomers of [(4-{1-ethyl-1-[4-(2-hydroxy-1,3,3-trimethyl-butoxy)-3-methyl-phenyl]-propyl}-2-methyl-benzoyl)-methyl-amino]-acetic acid methyl ester A racemic mixture of [(4-{1-ethyl-1-[4-(2-hydroxy-1,3,3-trimethyl-butoxy)-3-methyl-phenyl]-propyl}-2-methyl-benzoyl)-methyl-amino]-acetic acid methyl ester (1.73 g), is chromatographed (HPLC: ChiralPak AD, 0.1% TFA in iPrOH:Hept=5:95) to give enantiomer 1 (0.636 g, 38%, rt=21.8 m) and enantiomer 2 (0.72 g, 42%, rt=26.7 m).

(Enantiomer 1)

HPLC: ChiralPak AD, 0.1% TFA in iPrOH:Hept=5:95; 0.6 mL/m (flow rate); rt=21.8 m; @ 240 nm;

NMR & LC/MS: equivalent to the racemate.

(Enantiomer 2)

HPLC: ChiralPak AD, 0.1% TFA in iPrOH:Hept=5:95; 0.60 mL/m (flow rate); rt=26.7 m; @240 nm;

NMR & LC/MS: equivalent to the racemate

C. Enantiomer 1 of [(4-{1-Ethyl-1-[4-(2-hydroxy-1,3,3-trimethyl-butoxy)-3-methyl-phenyl]-propyl}-2-methyl-benzoyl)-methyl-amino]-acetic acid Using a procedure analogous to Example 46B, enantiomer 1 of [(4-{1-ethyl-1-[4-(2-hydroxy-1,3,3-trimethyl-butoxy)-3-methyl-phenyl]-propyl}-2-methyl-benzoyl)-methyl-amino]-acetic acid methyl ester (0.63 g, 1.24 mmol) gives the title compound (0.58 g, 1.16 mmol, 93%).

$^1$H NMR (CDCl$_3$), δ 0.58-0.65 (m, 6H), 0.98 (s, 9H), 1.36 (d, J=6.2 Hz, 3H), 2.06 (q, J=7.1 Hz, 4H), 2.14 (s, 3H), 2.25 (s, 0.9H), 2.31 (s, 2.1H), 2.93 (s, 3H), 3.16 (bs, 1H), 3.18 (d, J=1.3 Hz, 1H), 3.95 (s, 1H), 4.35 (s, 1H), 4.59 (q, J=6.2 Hz, 1H), 6.68-7.11 (m, 6H).

ES-MS (m/z): calcd for $C_{30}H_{42}NO_5$ $(M-H)^-$: 496.7; found: 496.3.

D. Enantiomer 2 of [(4-{1-Ethyl-1-[4-(2-hydroxy-1,3,3-trimethyl-butoxy)-3-methyl-phenyl]-propyl}-2-methyl-benzoyl)-methyl-amino]-acetic acid Using a procedure analogous to Example 46B, enantiomer 2 of [(4-{1-ethyl-1-[4-(2-hydroxy-1,3,3-trimethyl-butoxy)-3-methyl-phenyl]-propyl}-2-methyl-benzoyl)-methyl-amino]-acetic acid methyl ester (0.72 g, 1.41 mmol) gives the title compound (0.64 g, 1.28 mmol, 91%). $^1$H NMR & ES-MS (m/z): identical to enantiomer 1 of [(4-{1-Ethyl-1-[4-(2-hydroxy-1,3,3-trimethyl-butoxy)-3-methyl-phenyl]-propyl}-2-methyl-benzoyl)-methyl-amino]-acetic acid.

Example 54

Preparation of 3'-[4-(3-oxo-4,4-dimethylpentyl)-3-methylphenyl]-3'-[4-carboxyl-3-methylphenyl]pentane

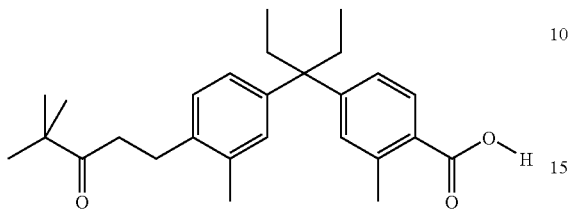

A. 3'-[4-benzyloxy-3-methylphenyl]-3'-[4-methoxycarbonyl-3-methylphenyl]pentane

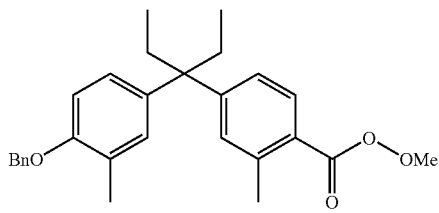

Using a procedure analogous to Example 1E, 3'-[4-benzyloxy-3-methylphenyl]-3'-[4-trifluoromethanesulfonyloxy-3-methylphenyl]pentane gives the title compound (30 g, 77%).

$^1$H NMR 300 MHz (DMSO-d$_6$): δ 0.54 (t, J=6.9 Hz, 6H), 2.05 (q, J=6.9 Hz, 4H), 2.12 (s, 3H), 2.47 (s, 3H), 3.78 (s, 3H), 5.06 (s, 2H), 6.91 (m, 3H), 7.05 (d, J=8.41 Hz, 1H), 7.11 (s, 1H), 7.29-7.47 (m, 5H), 7.72 (d, J=8.05, 1H).

B. 3'-[4-benzyloxy-3-methylphenyl]-3'-[4-hydroxymethyl-3-methylphenyl]pentane

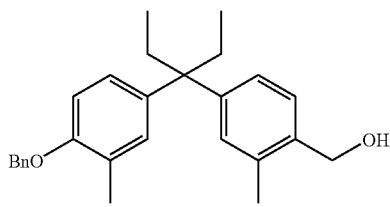

Using a procedure analogous to Example 13B, 3'-[4-benzyloxy-3-methylphenyl]-3'-[4-methoxycarbonyl-3-methylphenyl]pentane gives the title compound (6.0 g, quant).

$^1$H NMR 400 MHz (DMSO-d$_6$): δ 0.54 (t, J=7.2 Hz, 6H), 2.02 (q, J=7.2 Hz, 4H), 2.12 (s, 3H), 2.17 (s, 3H), 4.42 (d, J=6.0 Hz, 2H), 4.94 (t, J=5.6 Hz, 1H), 5.05 (s, 2H), 6.87-6.94 (m, 5H), 7.19 (d, J=8.0 Hz, 1H), 7.31 (d, J=7.6 Hz, 1H), 7.38 (t, J=7.2 Hz, 2H), 7.44 (d, J=7.2 Hz, 2H).

High Res. FAB-MS: 388.2397; calc. for C$_{27}$H$_{32}$O$_2$: 388.2402.

C. 3'-[4-(3-oxo-4,4-dimethylpentyl)-3-methylphenyl]-3'-[4-benzyloxy-3-methylphenyl]pentane

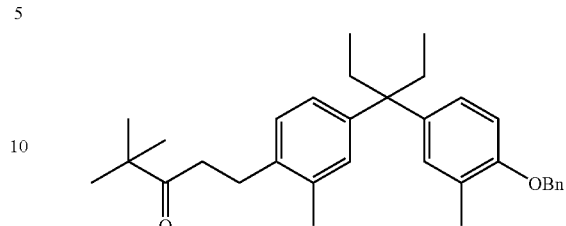

To a 0° C. mixture of 3'-[4-benzyloxy-3-methylphenyl]-3'-[4-hydroxymethyl-3-methylphenyl]pentane (6.0 g, 15.4 mmol) and Et$_2$O (40 ml) is added PBr$_3$ (1.6 ml, 17.0 mmol). The reaction is stirred for 2 h and allowed to warm to RT. The reaction is diluted with Et$_2$O, washed with minimal amount of water, brine, Na$_2$SO$_4$ dried, concentrated, and azeotrope to dryness with toluene. The resulting residue is dissolved in THF (4 ml) and cooled to −78° C. to afford the bromide/THF solution. In a separate flask is charged with 1M LiHMDS (31 ml, 30.8 mmol), cooled to −78 C, and added pinacolone (3.9 ml, 30.8 mmol). The reaction is stirred for 1.5 h, warmed to −55 C and transferred (via syringe) to the −78° C. solution of bromide/THF. The reaction is allowed to warm to RT and stirred for 16 h. The reaction is diluted with Et2O and washed with 1N HCl. The organic layer is Na2SO4 dried and chromatographed (70% CHCl3/Hex) to give the title compound (5.2 g, 71%).

$^1$H NMR 400 MHz (DMSO-d$_6$): δ 0.48 (t, J=7.6 Hz, 6H), 0.97 (s, 9H), 1.93 (q, J=7.2 Hz, 4H), 2.05 (s, 3H), 2.13 (s, 3H), 2.60 (t, J=8.0 Hz, 2H), 2.69 (t, J=8.4 Hz, 2H), 4.98 (d, J=4.4 Hz, 2H), 6.77-6.84 (m, 5H), 6.90 (d, J=8.0 Hz, 1H), 7.24-7.26 (m, 1H), 7.32 (t, J=7.2 Hz, 2H), 7.38 (d, J=7.2 Hz, 2H).

D. 3'-[4-(3-oxo-4,4-dimethylpentyl)-3-methylphenyl]-3'-[4-hydroxy-3-methylphenyl]pentane

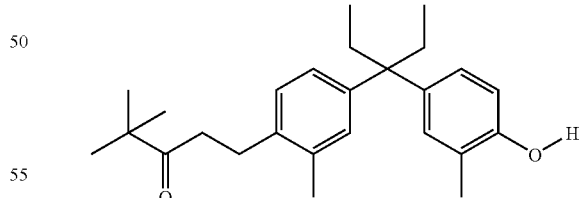

Using a procedure analogous to Example 6D, 3'-[4-(3-oxo-4,4-dimethylpentyl)-3-methylphenyl]-3'-[4-benzyloxy-3-methylphenyl]pentane gives the title compound (3.1 g, 74%).

$^1$H NMR 400 MHz (DMSO-d$_6$): δ 0.51 (t, J=6.8 Hz, 6H), 1.03 (s, 9H), 1.96 (q, J=7.2 Hz, 4H), 2.03 (s, 3H), 2.19 (s, 3H), 2.66 (t, J=6.4 Hz, 2H), 2.74 (t, J=6.4 Hz, 2H), 6.61 (d, J=8.0 Hz, 1H), 6.73 (dd, J=2.0 Hz, J=8.0 Hz, 2H), 6.83-6.86 (m, 2H), 6.95 (d, J=8.0 Hz, 1H), 8.97 (s, J=8.0 Hz, 1H).

E. 3'-[4-(3-oxo-4,4-dimethylpentyl)-3-methylphenyl]-3'-[4-(trifluoromethylsulfonyloxy)-3-methylphenyl]pentane

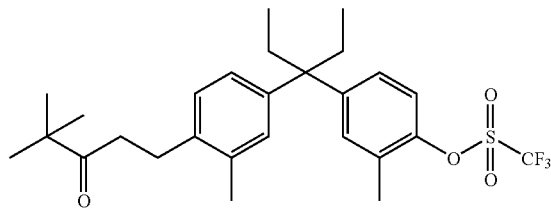

Using a procedure analogous to Example 1C, 3'-[4-(3-oxo-4,4-dimethylpentyl)-3-methylphenyl]-3'-[4-hydroxy-3-methylphenyl]pentane gives the title compound (4.2 g, quant).

$^1$H NMR 400 MHz (DMSO-$d_6$): δ 0.53 (t, J=7.2 Hz, 6H), 1.03 (s, 9H), 2.05 (q, J=7.2 Hz, 4H), 2.21 (s, 3H), 2.27 (s, 3H), 2.66 (t, J=8.4 Hz, 2H), 2.74 (t, J=8.0 Hz, 2H), 6.84 (dd, J=1.6 Hz, J=6.4 Hz, 1H), 6.91 (s, 1H), 7.00 (d, J=7.6 Hz, 1H), 7.07 (dd, J=2.0 Hz, J=6.4 Hz, 1H), 7.21-7.24 (m, 2H).

ES-MS: 530.25 (M+NH4).

F. 3'-[4-(3-oxo-4,4-dimethylpentyl)-3-methylphenyl]-3'-[4-(methoxycarboxyl)-3-methylphenyl]pentane

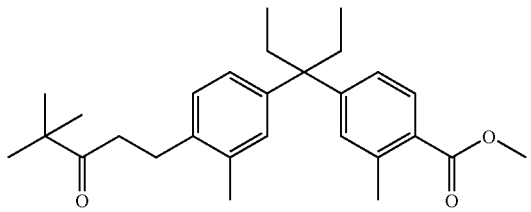

Using a procedure analogous to Example 1E, 3'-[4-(3-oxo-4,4-dimethylpentyl)-3-methylphenyl]-3'-[4-(trifluoromethylsulfonyloxy)-3-methylphenyl]pentane gives the title compound as a white foam (2.1 g, 67%).

$^1$H NMR 400 MHz (DMSO-$d_6$): δ 0.53 (t, J=7.2 Hz, 6H), 1.03 (s, 9H), 2.07 (q, J=7.2 Hz, 4H), 2.20 (s, 3H), 2.46 (s, 3H), 2.69 (t, J=7.6 Hz, 2H), 2.75 (t, J=6.4 Hz, 2H), 3.78 (s, 3H), 6.84 (d, J=8.4 Hz, 1H), 6.88 (s, 1H), 6.98 (d, J=8.0 Hz, 1H), 7.03 (dd, J=1.6 Hz, J=6.8 Hz, 1H), 7.08 (s, 1H), 7.70 (d, J=8.4 Hz, 1H).

High Res ES(+)MS m/z: 440.3167; calc. for $C_{28}H_{38}O_3$+NH$_4$: 440.3165

G. 3'-[4-(3-oxo-4,4-dimethylpentyl)-3-methylphenyl]-3'-[4-carboxyl-3-methylphenyl]pentane Using a procedure analogous to Example 2, 3'-[4-(3-oxo-4,4-dimethylpentyl)-3-methylphenyl]-3'-[4-(methoxycarboxyl)-3-methylphenyl]pentane gives the title compound as a white foam (1.5 g, 97%).

$^1$H NMR 300 MHz (DMSO-$d_6$): δ 0.54 (t, J=7.0 Hz, 6H), 1.03 (s, 9H), 2.07 (q, J=6.6 Hz, 4H), 2.20 (s, 3H), 2.46 (s, 3H), 2.68 (d, J=7.0 Hz, 2H), 2.73 (d, J=5.9 Hz, 2H), 6.85-6.90 (m, 2H), 6.99-7.06 (m, 3H), 7.72 (d, J=8.4 Hz, 1H).

High Res ES(+)MS m/z: 426.3003; calc. for $C_{27}H_{36}O_3$+NH$_4$: 426.3008

Example 55

Preparation of racemic 3'-[4-(3-hydroxy-4,4-dimethylpentyl)-3-methylphenyl]-3'-[4-carboxyl-3-methylphenyl]pentane

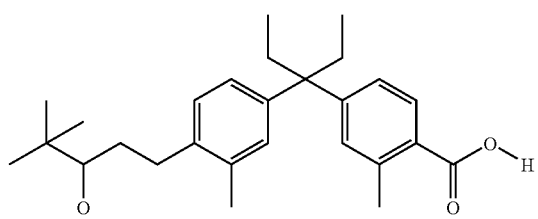

Using a procedure analogous to Example 1D, 3'-[4-(3-oxo-4,4-dimethylpentyl)-3-methylphenyl]-3'-[4-carboxyl-3-methylphenyl]pentane gives the title compound as a white foam (1.5 g, quant).

$^1$H NMR 300 MHz (DMSO-$d_6$): δ 0.54 (t, J=7.3 Hz, 6H), 0.80 (s, 9H), 1.30-1.36 (m, 1H), 1.58-1.64 (m, 1H), 2.07 (q, J=6.9 Hz, 4H), 2.20 (s, 3H), 2.47 (s, 3H), 2.74-2.82 (m, 1H), 2.99-3.04 (m, 1H), 4.41 (d, J=6.2, 1H), 6.85-6.89 (m, 2H), 7.02-7.08 (m, 3H), 7.72 (d, J=8.0 Hz, 1H),

High Res ES(+)MS m/z: 428.3145; calc. for $C_{27}H_{38}O_3$+NH$_4$: 428.3165

Compounds of the Invention—Salts, Stereoisomers, & Prodrugs

Salts of the compounds represented by formulae (I) are an additional aspect of the invention. The skilled artisan will also appreciate that the family of compounds of formulae I include acidic and basic members and that the present invention includes pharmaceutically acceptable salts thereof.

In those instances where the compounds of the invention possess acidic or basic functional groups various salts may be formed which are more water soluble and physiologically suitable than the parent compound. Representative pharmaceutically acceptable salts, include but are not limited to, the alkali and alkaline earth salts such as lithium, sodium, potassium, ammonium, calcium, magnesium, aluminum, zinc, and the like. Salts are conveniently prepared from the free acid by treating the acid in solution with a base or by exposing the acid to an ion exchange resin. For example, a carboxylic acid substituent on the compound of Formula I may be selected as —CO$_2$H and salts may be formed by reaction with appropriate bases (e.g., NaOH, KOH) to yield the corresponding sodium and potassium salt.

Included within the definition of pharmaceutically acceptable salts are the relatively non-toxic, inorganic and organic base addition salts of compounds of the present invention, for example, ammonium, quaternary ammonium, and amine cations, derived from nitrogenous bases of sufficient basicity to form salts with the compounds of this invention (see, for example, S. M. Berge, et al., "Pharmaceutical Salts," *J. Phar. Sci.*, 66: 1-19 (1977)). Moreover, the basic group(s) of the compound of the invention may be reacted with suitable organic or inorganic acids to form salts such as acetate, benzenesulfonate, benzoate, bicarbonate, bisulfate, bitartrate, borate, bromide, camsylate, carbonate, chloride, choline, clavulanate, citrate, chloride, chloroprocaine, choline, diethanolamine, dihydrochloride, diphosphate, edetate, edisylate, estolate, esylate, ethylenediamine, fluoride, fumarate, gluceptate, gluconate, glutamate, glycolylarsanilate, hexylresorcinate, hydrabamine, bromide, chloride, hydrobromide, hydrochloride, hydroxynaphthoate, iodide, isothionate, lactate, lactobionate, laurate, malate, maleate, malseate, mandelate, meglumine, mesylate, mesviate, methylbromide, methylnitrate, methylsulfate, mucate, napsylate, nitrate, oleate, oxalate, palmitate, pamoate, pantothenate, phosphate, polygalacturonate, procane, salicylate, stearate, subacetate, succinate, sulfate, tannate, tartrate, teoclate, tosylate, trifluoroacetate, trifluoromethane sulfonate, and valerate.

Certain compounds of the invention may possess one or more chiral centers and may thus exist in optically active forms. Likewise, when the compounds contain an alkenyl or alkenylene group there exists the possibility of cis- and trans-isomeric forms of the compounds. The R— and S— isomers and mixtures thereof, including racemic mixtures as well as mixtures of cis- and trans-isomers, are contemplated by this invention. Additional asymmetric carbon atoms can be present in a substituent group such as an alkyl group. All such isomers as well as the mixtures thereof are intended to be included in the invention. If a particular stereoisomer is desired, it can be prepared by methods well known in the art by using stereospecific reactions with starting materials which contain the asymmetric centers and are already resolved or, alternatively by methods which lead to mixtures of the stereoisomers and subsequent resolution by known methods. For example, a chiral column may be used such as those sold by Daicel Chemical Industries identified by the trademarks:

CHIRALPAK AD, CHIRALPAK AS, CHIRALPAK OD, CHIRALPAK OJ,
CHIRALPAK OA, CHIRALPAK OB, CHIRALPAK OC, CHIRALPAK OF,
CHIRALPAK OG, CHIRALPAK OK, and
CHIRALPAK CA-1.

By another conventional method, a racemic mixture may be reacted with a single enantiomer of some other compound. This changes the racemic form into a mixture of diastereomers. These diastereomers, because they have different melting points, different boiling points, and different solubilities can be separated by conventional means, such as crystallization.

Compounds of the Invention—Salts, Stereoisomers, & Prodrugs:

Salts of the compounds represented by formulae (I) are an additional aspect of the invention. The skilled artisan will also appreciate that the family of compounds of formulae I include acidic and basic members and that the present invention includes pharmaceutically acceptable salts thereof.

In those instances where the compounds of the invention possess acidic or basic functional groups various salts may be formed which are more water soluble and physiologically suitable than the parent compound. Representative pharmaceutically acceptable salts, include but are not limited to, the alkali and alkaline earth salts such as lithium, sodium, potassium, ammonium, calcium, magnesium, aluminum, zinc, and the like. Salts are conveniently prepared from the free acid by treating the acid in solution with a base or by exposing the acid to an ion exchange resin. For example, a carboxylic acid substituent on the compound of Formula I may be selected as —$CO_2H$ and salts may be formed by reaction with appropriate bases (e.g., NaOH, KOH) to yield the corresponding sodium and potassium salt.

Included within the definition of pharmaceutically acceptable salts are the relatively non-toxic, inorganic and organic base addition salts of compounds of the present invention, for example, ammonium, quaternary ammonium, and amine cations, derived from nitrogenous bases of sufficient basicity to form salts with the compounds of this invention (see, for example, S. M. Berge, et al., "Pharmaceutical Salts," *J. Phar.* *Sci.*, 66: 1-19 (1977)). Moreover, the basic group(s) of the compound of the invention may be reacted with suitable organic or inorganic acids to form salts such as acetate, benzenesulfonate, benzoate, bicarbonate, bisulfate, bitartrate, borate, bromide, camsylate, carbonate, chloride, choline, clavulanate, citrate, chloride, chloroprocaine, choline, diethanolamine, dihydrochloride, diphosphate, edetate, edisylate, estolate, esylate, ethylenediamine, fluoride, fumarate, gluceptate, gluconate, glutamate, glycolylarsanilate, hexylresorcinate, hydrabamine, bromide, chloride, hydrobromide, hydrochloride, hydroxynaphthoate, iodide, isothionate, lactate, lactobionate, laurate, malate, maleate, malseate, mandelate, meglumine, mesylate, mesviate, methylbromide, methylnitrate, methylsulfate, mucate, napsylate, nitrate, oleate, oxalate, palmitate, pamoate, pantothenate, phosphate, polygalacturonate, procane, salicylate, stearate, subacetate, succinate, sulfate, tannate, tartrate, teoclate, tosylate, trifluoroacetate, trifluoromethane sulfonate, and valerate.

Certain compounds of the invention may possess one or more chiral centers and may thus exist in optically active forms. Likewise, when the compounds contain an alkenyl or alkenylene group there exists the possibility of cis- and trans-isomeric forms of the compounds. The R- and S-isomers and mixtures thereof, including racemic mixtures as well as mixtures of cis- and trans-isomers, are contemplated by this invention.

Additional asymmetric carbon atoms can be present in a substituent group such as an alkyl group. All such isomers as well as the mixtures thereof are intended to be included in the invention. If a particular stereoisomer is desired, it can be prepared by methods well known in the art by using stereospecific reactions with starting materials which contain the asymmetric centers and are already resolved or, alternatively by methods which lead to mixtures of the stereoisomers and subsequent resolution by known methods. For example, a chiral column may be used such as those sold by Daicel Chemical Industries identified by the trademarks:

CHIRALPAK AD, CHIRALPAK AS, CHIRALPAK OD, CHIRALPAK OJ,
CHIRALPAK OA, CHIRALPAK OB, CHIRALPAK OC, CHIRALPAK OF,
CHIRALPAK OG, CHIRALPAK OK, and
CHIRALPAK CA-1.

By another conventional method, a racemic mixture may be reacted with a single enantiomer of some other compound. This changes the racemic form into a mixture of diastereomers. These diastereomers, because they have different melting points, different boiling points, and different solubilities can be separated by conventional means, such as crystallization.

The present invention is also embodied in mixtures of compounds of formulae I.

Prodrugs are derivatives of the compounds of the invention which have chemically or metabolically cleavable groups and become by solvolysis or under physiological conditions the compounds of the invention which are pharmaceutically active in vivo.

Derivatives of the compounds of this invention have activity in both their acid and base derivative forms, but the acid derivative form often offers advantages of solubility, tissue compatibility, or delayed release in a mammalian organism (see, Bundgard, H., *Design of Prodrugs*, pp. 7-9, 21-24, Elsevier, Amsterdam 1985). Prodrugs include acid derivatives well known to practitioners of the art, such as, for example, esters prepared by reaction of the parent acidic compound with a suitable alcohol, or amides prepared by reaction of the parent acid compound with a suitable amine. Simple aliphatic or aromatic esters derived from acidic groups pendent on the compounds of this invention are preferred prodrugs. In some cases it is desirable to prepare double ester type prodrugs such as (acyloxy)alkyl esters or ((alkoxycarbonyl)oxy)alkyl esters. Particularly preferred esters to use as prodrugs are; methyl, ethyl, propyl, isopropyl, n-butyl, isobutyl, tert-butyl, morpholinoethyl, and N,N-diethylglycolamido.

N,N-diethylglycolamido ester prodrugs may be prepared by reaction of the sodium salt of a compound of Formula (I) (in a medium such as dimethylformamide) with 2-chloro-N, N-diethylacetamide (available from Aldrich Chemical Co., Milwaukee, Wis. USA; Item No. 25,099-6).

Morpholinylethyl ester prodrugs may be prepared by reaction of the sodium salt of a compound of Formula (I) (in a medium such as dimethylformamide) 4-(2-chloroethyl)morpholine hydrochloride (available from Aldrich Chemical Co., Milwaukee, Wis. USA, Item No. C5,220-3).

Morpholinylethyl ester prodrugs may be prepared by reaction of the sodium salt of a compound of Formula I (in a medium such as dimethylformamide) 4-(2-chloroethyl)morpholine hydrochloride (available from Aldrich Chemical Co., Milwaukee, Wis. USA, Item No. C5,220-3). The prodrugs, for example, may be prepared by reaction of the sodium salt for a compound of Formula I with;

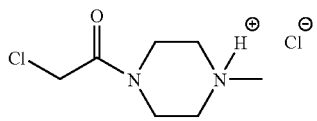

and sodium iodide to provide the ester prodrug pendent group

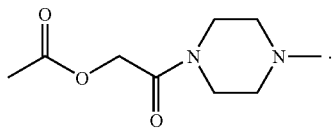

Also, lower alkyl (viz., $C_1$-$C_8$) ester prodrugs may be prepared by conventional means such as reacting the sodium or potassium salt (derived by forming the salt of any acidic compound of the invention, viz., reaction of a base such as KOH with an acidic group such as —$CO_2H$) of a compound of Formula I with an alkyl iodide such as methyl iodide, ethyl iodide, n-propyl iodide, isopropyl iodide. Typical ester prodrug substituents are

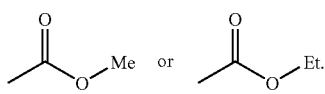

Pharmaceutical Formulations Containing the Novel Compounds of the Invention:

Pharmaceutical formulations of the invention are prepared by combining (e.g., mixing) a therapeutically effective amount of the compound of the invention (compounds of Formula I) together with a pharmaceutically acceptable carrier or diluent. The present pharmaceutical formulations are prepared by known procedures using well-known and readily available ingredients.

In making the compositions of the present invention, the compounds of Formula I will usually be admixed with a carrier, or diluted by a carrier, or enclosed within a carrier which may be in the form of a capsule, sachet, paper or other container. When the carrier serves as a diluent, it may be a solid, semi-solid or liquid material which acts as a vehicle, or can be in the form of tablets, pills, powders, lozenges, elixirs, suspensions, emulsions, solutions, syrups, aerosols (as a solid or in a liquid medium), or ointment, containing, for example, up to 10% by weight of the compound. The compounds of the present invention are preferably formulated prior to administration.

The compounds of the invention may also be delivered by suitable formulations contained in a transderm patch. Alternatively, the compounds of the invention may be delivered to a patient by sublingual administration.

For the pharmaceutical formulations any suitable carrier known in the art can be used. In such a formulation, the carrier may be a solid, liquid, or mixture of a solid and a liquid. Solid form formulations include powders, tablets and capsules. A solid carrier can be one or more substances which may also act as flavoring agents, lubricants, solubilisers, suspending agents, binders, tablet disintegrating agents and encapsulating material.

Tablets for oral administration may contain suitable excipients such as calcium carbonate, sodium carbonate, lactose, calcium phosphate, together with disintegrating agents, such as maize, starch, or alginic acid, and/or binding agents, for example, gelatin or acacia, and lubricating agents such as magnesium stearate, stearic acid, or talc.

In powders the carrier is a finely divided solid which is in admixture with the finely divided Active ingredient. In tablets the compound of Formula I is mixed with a carrier having the necessary binding properties in suitable proportions and compacted in the shape and size desired. The powders and tablets preferably contain from about 1 to about 99 weight percent of the compound which is the novel compound of this invention.

Suitable solid carriers are magnesium carbonate, magnesium stearate, talc, sugar lactose, pectin, dextrin, starch, gelatin, tragacanth, methyl cellulose, sodium carboxymethyl cellulose, low melting waxes, and cocoa butter.

Sterile liquid form formulations include suspensions, emulsions, syrups and elixirs.

The compounds of the invention may be dissolved or suspended in a pharmaceutically acceptable carrier, such as sterile water, sterile organic solvent or a mixture of both. The compounds can often be dissolved in a suitable organic solvent, for instance aqueous propylene glycol. Other compositions can be made by dispersing the finely divided compounds of the invention in aqueous starch or sodium carboxymethyl cellulose solution or in a suitable oil.

Methods of Using the Compounds of the Invention:

Generic disease states benefited by treatment with the compounds of Formula I include, but are not limited to:

disease states characterized by abnormal calcium regulation disease states characterized by abnormal cell proliferation disease states characterized by abnormal cell differentiation disease states characterized by abnormal immune response disease states characterized by abnormal dermatological conditions disease states characterized by neurodegenerative condition disease states characterized by inflammation disease states characterized by vitamin D sensitivity disease states characterized by hyperproliferative disorders.

Specific disease states benefited by treatment of the compounds of Formula I and II include, but are not limited to:

Acne
Actinic keratosis
Alopecia
Alzheimer's disease
Bone maintenance in zero gravity
Bone fracture healing
Breast cancer
Chemoprovention of Cancer
Crohn's disease
Colon cancer
Type I diabetes
Host-graft rejection
Hypercalcemia
Type II diabetes
Leukemia
Multiple sclerosis
Myelodysplastic syndrome
Insufficient sebum secretion
Osteomalacia
Osteoporosis
Insufficient dermal firmness
Insufficient dermal hydration
Psoriatic arthritis
Prostate cancer
Psoriasis
Renal osteodystrophy
Rheumatoid arthritis
Scleroderma
Skin cancer
Systemic lupus erythematosus
Skin cell protection from Mustard vesicants
Ulcerative colitis
Vitiligo
Wrinkles Particularly preferred is the treatment of psoriasis and osteoporosis by administration to a mammal (including a human) of a therapeutically effective amount of compounds of Formulae I. By "pharmaceutically effective amount" it is meant that quantity of pharmaceutical agent corresponding to formulae I which prevents, removes or reduces the deleterious effects of a disease state in mammals, including humans.

The specific dose of a compound administered according to this invention to obtain therapeutic or prophylactic effects will, of course, be determined by the particular circumstances surrounding the case, including, for example, the compound administered, the route of administration and the condition being treated. Typical daily doses will contain a pharmaceutically effective amount typically in the range of from about 0.0001 mg/kg/day to about 50 mg/kg/day of body weight of an active compound of this invention. Preferably the dose of compounds of the invention will be from 0.0001 to 5 mg/kg/day of body weight.

Preferably compounds of the invention (e.g., per Formula I) or pharmaceutical formulations containing these compounds are in unit dosage form for administration to a mammal. The unit dosage form can be a capsule or tablet itself, or the appropriate number of any of these. The quantity of Active ingredient in a unit dose of composition may be varied or adjusted from about 0.0001 to about 1000 milligrams or more according to the particular treatment involved. It may be appreciated that it is necessary to make routine variations to the dosage depending on the age and condition of the patient. Dosage will also depend on the route of administration. The compounds of the invention may be administered by a variety of routes including oral, aerosol, rectal, transdermal, sublingual, subcutaneous, intravenous, intramuscular, and intranasal. Particularly preferred is the treatment of psoriasis with an ointment type formulation containing the compounds of the invention. The ointment formulation may be applied as needed, typically from one to 6 times daily.

Treatment of psoriasis is preferably done with topical application by a formulation in the form of a cream, oil, emulsion, paste or ointment containing a therapeutically effective amount of a compound defined by Formula (I), and in particular those compounds set out in Tables 1 or 2 or those compounds identified as "AA" to "BQ", supra. The formulation for topical treatment contains from 0.5 to 0.00005 weight percent, preferably from 0.05 to 0.0005 weight percent, and most preferably from 0.025 to 0.001 of a compound defined by formula (I).

For example, two semisolid topical preparations useful as vehicles for VDR modulators in treatment and prevention of psoriasis are as follows:

Polyethylene Glycol Ointment USP (p. 2495)
Prepare Polyethylene Glycol Ointment as Follows:

| | |
|---|---|
| Polyethylene Glycol 3350 | 400 g. |
| Polyethylene Glycol 400 | 600 g. |
| To make | 1000 g. |

Heat the two ingredients on a water bath to 65 C. Allow to cool, and stir until congealed. If a firmer preparation is desired, replace up to 100 g of the polyethylene glycol 400 with an equal amount of polyethylene glycol 3350.

Hydrophilic Ointment USP (p. 1216)
Prepare Hydrophilic Ointment as Follows:

| | |
|---|---|
| Methylparaben | 0.25 g. |
| Propylparaben | 0.15 g. |
| Sodium Lauryl Sulfate | 10 g. |
| Propylene Glycol | 120 g. |
| Stearyl Alcohol | 250 g. |
| White Petrolatum | 250 g. |
| Purified Water | 370 g. |
| To make about | 1000 g. |

The Stearyl Alcohol and White Petrolatum are melted on a steam bath, and warmed to about 75 C. The other ingredients, previously dissolved in the water are added, warmed to 75 C, and the mixture stirred until it congeals.

For each of the above formulations the compound of formula (I) is added during the heating step in an amount that is from 0.5 to 0.00005 weight percent, preferably from 0.05 to 0.0005 weight percent, and most preferably from 0.025 to 0.001 weight percent of the total ointment weight. (Source: —United States Pharmacopoeia 24, United States Pharmacopeial Convention, 1999)

Conventional therapy for osteoporosis includes; (i) estrogens, (ii) androgens, (iii) calcium supplements, (iv) vitamin D metabolites, (v) thiazide diuretics, (vi) calcitonin, (vii) bisphosphonates, (viii) SERMS, and (ix) fluorides (see, Harrison's Principles of Internal Medicine, $13^{th}$ edition, 1994, published by McGraw Hill Publ., ISBN 0-07-032370-4, pgs. 2172-77; the disclosure of which is incorporated herein by reference.). Any one or combination of these conventional therapies may be used in combination with the method of treatment using compounds of Formulae I as taught herein. For example, in a method of treating osteoporosis, the vitamin D receptor modulator compounds of the invention (e.g., as defined by formula I) may be administered separately or simultaneously with a conventional therapy. Alternatively, the vitamin D receptor modulator compounds of the invention may be combined with conventional therapeutic agents in a formulation for treatment of osteoporosis such as set out below:

A formulation for treating osteoporosis comprising:

Ingredient (A1): a vitamin D receptor modulator represented by formula (I), or a pharmaceutically acceptable salt or aliphatic ester prodrug derivative thereof;

Ingredient (B1):
one or more co-agents that are conventional for treatment osteoporosis selected from the group consisting of:
  a. estrogens,
  b. androgens,
  c. calcium supplements,
  d. vitamin D metabolites,
  e. thiazide diuretics,
  f. calcitonin,
  g. bisphosphonates,
  h. SERMS, and
  i. fluorides.

Ingredient (C1): optionally, a carrier or diluent.

Typically useful formulations are those wherein the weight ratio of (A1) to (B1) is from 10:1 to 1:1000 and preferably from 1:1 to 1:100.

Combination Therapy for Psoriasis:

Conventional therapy for psoriasis includes topical glucocorticoids, salicylic acid, crude coal tar, ultraviolet light, and methotrexate (see, Harrison's Principles of Internal Medicine, 13$^{th}$ edition, 1994, published by McGraw Hill Publ., ISBN 0-07-032370-4, pgs. 2172-77). Any one or combination of these conventional therapies may be used in combination with the method of treatment using compounds of Formulae I as taught herein. For example, in a method of treating osteoporosis, the vitamin D receptor modulator compounds of the invention (e.g., as defined by formula I) may be topically administered separately or simultaneously with a conventional therapy. Alternatively, the vitamin D receptor modulator compounds of the invention may be combined with conventional therapeutic agents in a topically applied formulation for treatment of osteoporosis such as set out below:

A formulation for treating osteoporosis comprising:

Ingredient (A2): a vitamin D receptor modulator represented by formula (I), or a pharmaceutically acceptable salt or aliphatic ester prodrug derivative thereof;

Ingredient (B2):
one or more co-agents that are conventional for treatment osteoporosis selected from the group consisting of:
  a. topical glucocorticoids,
  b. salicylic acid, or
  c. crude coal tar.

Ingredient (C2): optionally, a carrier or diluent.

Typically useful formulations are those wherein the weight ratio of (A2) to (B2) is from 1:10 to 1:100000 and preferably from 1:100 to 1:10000.

Experimental Results:

TABLE 3

Summary of Experimental Results

| Test Cmpd.[1] | RXR-VDR heterodimer[2] $EC_{50}$ (nM) | VDR $EC_{50}$ (nM) (Caco-2 cells)[3] | OCN Promoter[4] $EC_{50}$ (nM) | Mouse Hypercal[5] µg/Kg/d |
|---|---|---|---|---|
| Ex. 1 | | | 21 | |
| Ex. 3A | 149/51 | 1261 | 15/18 | 1000 |
| Ex. 3B | 396/292 | 2869 | 57/83 | 3000 |
| Ex. 4A | | | 3 | |
| Ex. 4B | | | 15 | |
| Ex. 5 | | 3000 | 42 | 100 |
| Ex 6 | 20/1 | 300 | 0.3 | 10 |
| Ex. 7 | | 63 | 4 | |
| Ex. 8 | 1 | 35 | 4/1 | 100 |
| Ex. 9 | 4 | 4 | 7/6 | |
| Ex. 10Da | 218/25 | 538 | 8/46 | |
| Ex. 10Db | 86 | 935 | 15 | |
| Ex. 11 | 186 | 1011 | 7 | 3000 |
| Ex. 12 | 562/206 | 1261 | 20/25 | 4000 |
| Ex. 12a | 67 | 651 | 1 | 300 |
| Ex. 12b | 335/55 | 960 | 13/23 | 300 |
| Ex. 13 | 22/30 | 1009 | 89/167 | 3000 |
| Ex. 14 | | | 306 | 3000 |
| Ex. 15A | 229/17 | 662 | 35/43 | 1500 |
| Ex. 15B | | | 163 | |
| Ex. 16 | | | 35 | >5000 |
| Ex. 17 | 275/101 | 990 | 56/15 | >3000 |
| Ex. 18 | 38/4 | 430 | 1/3 | 1000 |
| Ex. 19 | 96/12 | 613 | 12/16 | 2000 |
| Ex. 20B | 9/3 | 101 | 0.8/0.2 | 300 |
| Ex. 21 | 226/77 | 935 | 8/27 | 6000 |
| Ex. 22 | 80/23 | 467 | 7/3 | 1000 |
| Ex. 23 | 283/230 | 805 | 13/40 | 3000 |
| Ex. 24 | 3 | 368 | 0.2 | |
| Ex. 25A | 8/2 | 340 | 0.4 | <300 |
| Ex. 25B | 83/25 | 982 | 2/3 | 1000 |
| Ex. 26 | 6/67 | 651 | 1 | 300 |
| Ex. 27 | 335/55 | 960 | 13/23 | 300 |
| Ex. 28 | 171/337 | 72 | 106/84 | |
| Ex. 29 | 93/60 | 958 | 2/11 | 3000 |
| Ex. 30 | 101/48 | 698 | 1/3 | 1000 |
| Ex. 31 | 19/33 | 410 | 1 | 3000 |
| Ex. 32 | 89/9 | 345 | 4/1 | 1000 |
| Ex. 33 | 1/55 | 418 | 3/1 | <300 |
| Ex. 34 | 15/5 | 303 | 9/1 | <300 |
| Ex. 35 | | | 27 | |
| Ex. 36 | 242/293 | 698 | 135/37 | >300 |
| Ex. 37 | 60 | 698 | 12 | 1000 |
| Ex. 38 | 266/137 | 863 | 41 | |
| Ex. 39 | 302/204 | 979 | 74/61 | |
| Ex. 40 | 138 | 694 | 70 | |
| Ex. 41 | 523 | | 421 | |
| Ex. 42 | 56/316 | 1227 | 98/19 | |
| Ex. 44 | 0.4 | | 0.1 | <300 |
| Ex. 45 | 2 | | 0.7 | 300 |
| Ex. 46 | 6 | 400 | 2/3 | 3000 |
| Ex. 47 | 59 | 816 | 22/6 | 3000 |
| Ex. 48 | 44 | 433 | 9/4 | <1000 |
| Ex. 49 | 92 | 859 | 14/40 | |
| Ex. 50 | 10 | 83 | 0.2 | 300 |
| Ex. 51 | 4 | | 1.4 | 300 |
| Ex. 52 | 81 | 813 | 4 | >3000 |
| Ex. 53 | 236/210 | | 12/34 | >3000 |
| Ex. 54 | 396 | | 119 | >3000 |
| Ex. 55 | 9 | 920 | 6 | |
| AA | 5.02 | 16 | 5 | 0.06 |
| BB | 10.32 | 169.81 | 8.24 | 20 |
| CC | 2427.7 | | >1000 | |
| DD | 109.44 | | 31.1 | 1000 |
| EE | 429.99 | 891.16 | 341.25 | 1000 |
| FF | 3 | 57 | | |

TABLE 4

Summary of Experimental Results

| Test Cmpd.[1] | Kera. Prolif. IC$_{50}$ (nM) | IL-10. IC$_{50}$ (nM) |
|---|---|---|
| Ex. 1 | | |
| Ex. 3A | | |
| Ex. 3B | | |
| Ex. 4A | | |
| Ex. 4B | | |
| Ex. 5 | 375 | |
| Ex 6 | 2 | 55 |
| Ex. 7 | 18 | |
| Ex. 8 | 330 | |
| Ex. 9 | 985 | |
| Ex. 10Da | 1000 | |
| Ex. 10Db | 1000 | |
| Ex. 11 | 308 | 478 |
| Ex. 12 | | |
| Ex. 12a | 4 | 52 |
| Ex. 12b | | |
| Ex. 13 | | |
| Ex. 14 | | |
| Ex. 15A | 117 | |
| Ex. 15B | | |
| Ex. 16 | | |
| Ex. 17 | 1000 | |
| Ex. 18 | 1000 | 47 |
| Ex. 19 | 82 | 142 |
| Ex. 20B | 3 | 4 |
| Ex. 21 | 223 | 1050 |
| Ex. 22 | 4 | 39 |
| Ex. 23 | 40 | 27 |
| Ex. 24 | | |
| Ex. 25A | 1105 | 40 |
| Ex. 25B | 26 | 158 |
| Ex. 26 | 4 | 52 |
| Ex. 27 | | |
| Ex. 28 | 240 | |
| Ex. 29 | 49 | 153 |
| Ex. 30 | 20 | 123 |
| Ex. 31 | 21 | 295 |
| Ex. 32 | 1000 | 106 |
| Ex. 33 | 6 | 19 |
| Ex. 34 | 25 | 45 |
| Ex. 35 | 40 | |
| Ex. 36 | 139 | |
| Ex. 37 | 55 | 229 |
| Ex. 38 | | |
| Ex. 39 | 508 | |
| Ex. 40 | 1000 | |
| Ex. 41 | | |
| Ex. 42 | 50 | |
| Ex. 44 | 28 | 6 |
| Ex. 45 | 32 | 15 |
| Ex. 46 | 21 | 33 |
| Ex. 47 | 1000 | |
| Ex. 48 | 1000 | |
| Ex. 49 | 1000 | |
| Ex. 50 | 3 | 4 |
| Ex. 51 | 26 | 19 |
| Ex. 52 | 52 | 154 |
| Ex. 53 | 224 | |
| Ex. 54 | | |
| Ex. 55 | | |
| AA | 120 | 1.2 |
| BB | 10 | 28 |
| CC | | |
| DD | 1060 | |
| EE | | |
| FF | 103 | 0.5 |

Explanation of Table 5 and 6 Column Numerical Superscripts:

1. Test Compound numbers refer to the products of the corresponding Example Nos. that is, compounds within the scope of the invention. For example, the number "Ex. 2" refers to the compound, 3'-[4-(2-hydroxy-3,3-dimethylbutoxy)-3-methylphenyl]-3'-[5-methoxycarbonyl-4-methylthiophen-2-yl]pentane, prepared in Example 2. The control experiments are done with the double letter coded compounds identified as follows:

"AA"=1α,25-dihydroxyvitamin D$_3$

"BB"=3-(4-{1-Ethyl-1-[4-(2-hydroxy-3,3-dimethyl-butoxy)-3-methyl-phenyl]-propyl}-2-methyl-phenoxy)-propane-1,2-diol "CC"=1-(4-{1-[4-(3,3-Dimethyl-2-oxo-butoxy)-3-methyl-phenyl]-cyclohexyl}-2-methyl-phenoxy)-3,3-dimethyl-butan-2-one "DD"=compound represented by the formula:

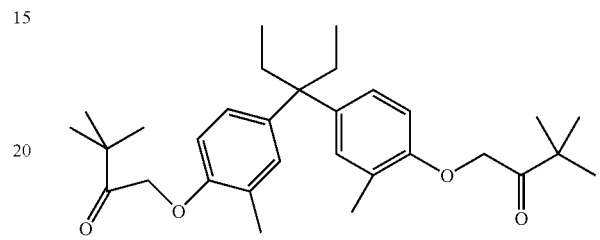

"EE"=compound represented by the formula:

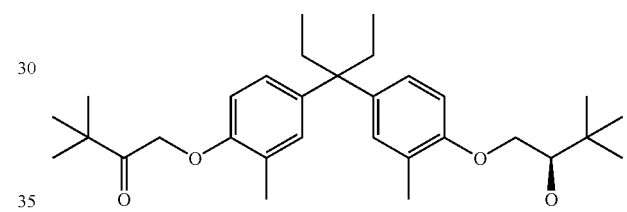

"FF"-=calcipotriol (structural formula below):

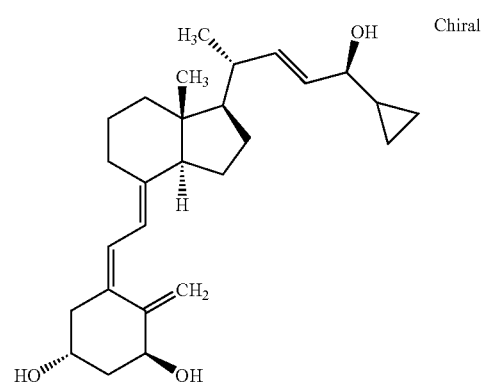

2. The RXR-VDR heterodimerization (SaOS-2 cells) test is described in the "Assay" section of the Description, infra.

3. The VDR CTF (Caco-2 cells) test is described in the "Assay" section of the Description, infra.

4. The OCN Promoter test is described in the "Assay" section of the Description, infra.

5. The Mouse Hypercalcemia test is described in the "Assay" section of the Description, infra.

6. The keratinocyte proliferation assay is described in the "Assay" section of the Description, infra.

7. The IL-10 induction assay is described in the "Assay" section of the Description, infra.

Assay Methods

Use of the Assay Methods:

The evaluation of the novel compounds of the invention for osteoporosis and other related diseases is done using a plurality of test results. The use of multiple assays is necessary since the combined properties of (i) high activity for the vitamin D receptor, and (ii) prevention of hypercalcemia must be achieved to have utility for the methods of treating diseases, which are also, aspects of this invention. Some of the tests described below are believed related to other tests and measure related properties of compounds. Consequently, a compound may be considered to have utility in the practice of the invention if is meets most, if not all, of the acceptance criteria for the above described tests.

The evaluation of the novel compounds of the invention for psoriasis is done using the Keratinocyte Proliferation Assay in combination with other assays that measure inhibition of IL-2 production and stimulation of IL-10 production in peripheral blood mononuclear cells (PBMCs).

Brief Description, Utility and Acceptance Criteria for the Assay Methods:

1. The RXR-VDR heterodimerAssay:

This assay provides the VDR activity of a test compound. It is desirable to have low EC50 values for a compound in this assay. The lower the EC50 value, the more active the compound will be as a VDR agonist. Desired assay results are EC50 values less than or equal to 600 nM. Preferred assay results are less than 250 nM, and most preferably less than 150 nM.

2. The Caco-2 cell Co-transfection Assay:

The Caco-2 cell assay is an indicator for the undesirable condition of hypercalcemia. This co-transfection assay is a surrogate assay for in vivo calcemic activity of VDR ligands. It is desirable to have high EC50 values for a test compound in this assay. The higher the EC50 values for a compound the less calcemic it will be in vivo. Desired assay results are EC50 greater than or equal to 300 mM. Preferred assay results are greater than 1000 nM.

3. The OCN (osteocalcin) Promoter Assay

The OCN Promoter Assay is an indicator and marker for osteoporosis. Desired assay results are EC50 less than or equal to 325 nM. Preferred assay results are less than 50 nM.

4. The Mouse Hypercalcemia Assay

The Mouse Hypercalcemia Assay is a six day hypercalcemia test for toxicity and selectivity. Acceptable test results are levels greater than 300 μg/kg/day. Preferred assay results are levels greater than 1000 μg/kg/day.

5. The Keratinocyte Proliferation Assay

This Assay is indicative for the treatment of psoriasis. An acceptable test result is IC50 value of less than or equal to 300 nM. Preferred assay results are IC50 values of less than 100 nM.

6. The IL-10 Induction Assay

This is an in vitro efficacy assay for psoriasis, abscess and adhesion. Psoriasis involves both keratinocytes and immune cells. IL-10 is a unique cytokine because it is anti-inflammatory and immunosuppressive. This assay tells us whether a VDRM is able to function as an agonist in PBMCs (primary blood mononuclear cells) or not. A lower EC50 value is desirable in this assay since a compound with a lower EC50 value will be a better agonist in PBMCs. An acceptable test result is an EC50 value of less than 200 nM. Preferred assay results are EC50 values of less than 100 nM.

7. Other Compound Assay Standards

An alternative measure of the therapeutic index (bone efficacy vx. Hypervcalcemia) of compounds of the invention for treatment of osteoporosis is a numerical ratio calculated as follows:

> Dose Threshold needed to induce hypercalcemia divided by Dose Threshold needed for bone efficacy An alternative measure of the therapeutic index (in vivo keratinocyte proliferation vs. hypercalcemia) of compounds of the invention for treatment of psoriasis is a numerical ratio calculated as follows:

> Dose Threshold needed to induce hypercalcemia divided by Dose Threshold needed to induce keratinocyte proliferation For the above ratios, Dose Thresholds are determined from dose response curve data.

Details of the Assay Methods:

(1) Materials and Method for RXR-VDR Heterodimerization Assay:

Transfection Method:
  FuGENE 6 Transfection Reagent (Roche Cat # 1 814 443)
Growth Media:
  D-MEM High Glucose (Gibco BRL Cat # 11054-020), 10% FBS, 1% antibiotic-antimycotic (Ab-Am)
FBS heat inactivated (Gibco BRL Cat # 10092-147)
Ab-Am (Gibco BRL Cat # 15240-062)

Cells:
  Grow SaOs-2 cells in T-152 cm$^2$ culture flasks in growth media.
  Keep the density at 5-6×10$^5$ cells/ml
  Passage cells 1:3 twice a week
  Add Trypsin EDTA (Gibco BRL Cat # 25300-020) and incubate
  Resuspend cells in plating media and transfer into growth media.

Wash Media:
  HBSS Low Glucose Without Phenol Red (Gibco BRL Cat # 14175-095), 1% Ab-Am Plating Media:
  D-MEM Low Glucose Without Phenol Red (Gibco BRL Cat # 11054-020), 1% Ab-Am
  D-MEM
  Stripped FBS (Hyclone Cat# SH30068.03 Lot # AHM9371)
  Ab-Am Transfection/Treatment Media:
  D-MEM Low Glucose Without Phenol Red only T-152 cm$^2$ culture flask:
  Use Corning Coastar T-152 cm$^2$ culture flask (Cat # 430825) to grow the cells Flat well Plates:
  Use well plate to plate cells
  Use Deep well plate sterile to make up treatment media.

Luciferase Assay Reagent:
  Use Steady-Glo Luciferase Reagent from Promega (Cat # E2550) Consists of:
a. E2533 Assay Substrate, lypholized product and
b. E2543 Assay Buffer.
  Thaw at room temperature
  Store DAY 1: Cell Plating:
Cell Harvesting
Aspirate media from culture flask, rinse cells with HBSS and aspirate.
Add trypsin and incubate.
When cells appear detached, resuspend cells in growth media.
Transfer into a new flask with fresh growth media for passaging the cells.
Plate well plates and two extra plates D. Cell Count
Mix the cell suspension using pipette
Use Hematocytometer to count the cells
Load cell suspension onto the hemocytometer chamber
Count cells.

Plate seeding:
Use plating media 10% Stripped FBS in D-MEM Low Glucose, Without Phenol Red, 1% Ab-Am
Plate 14 plates @ 165 µl/well.
In sterile flask add cell suspension to plating media.
Mix.
Add cells/well.
Place the cells in the incubator.
Cells should be about 75% confluent prior to transfection.

Step 1: DNA and Media
Add plain DMEM media to tubes for mixing the DNA
Add the Reporter gene pFR-LUC
Add the Gal4—RXR-DEF and VP16-VDR-LBD Step 2: FuGENE and Media
Prepare plain DMEM media in a ubes for mixing FuGENE
Add FuGENE 6 Transfection Reagent
Incubate Step 3: FuGENE, DNA and Media Complex
Add FuGENE Media complex from step 2 to DNA Media complex from step 1
Incubate Step 4: FuGENE, DNA and Media Complex to-well plate
Add FuGENE-DNA-Media complex from step 3 to each plate
Incubate.

Day 3: Dosing

Treatment Preparation

Allow for transfection time
Make a stock solution of the compounds in DMSO Vortex until all the compounds has been dissolved.
Further dilute in D-MEM (Low Glucose—With out Phenol Red)
Add compounds in quadruplicate to give final volume Incubate.

Day 4: Luciferase Assay

Read the plates after drug treatment
Remove part of media from all the wells and leave remainder
Add Steady-Glo Luciferase Reagent mixture/wells
Incubate
Count each well using a Luminescence counter, Top Count NXT by Packard
  Set a delay between plates to reduce the background.

(2) Materials and Method for The Caco-2 Cell Assay:
  Caco-2 cells, grown in phenol red free, DMEM (Invitrogen, Carlsbad, Calif.) containing 10% charcoal-stripped FCS (Hyclone, Logan, Utah), were transfected with Fugene 6 reagent (Roche Diagnostics, Indianapolis, Ind.). Cells (5000/well) were plated 18 h before transfection in a 96 well plate. The Cells were transfected with Gal4-responsive reporter pFRLuc (150 ng, Stratagene, La Jolla Calif.) and the receptor expression vector pGal4-VDR-LBD (10 ng), along with Fugene 6 reagent (0.2 µl/well). The DNA-Fugene complex was formed by incubating the mixture for 30 min at room temperature. The cells were transfected in triplicate for 5 h, and treated with various concentrations of VDR ligands (form 0.01 nM to 10,000 nM concentration range) 18 h post-transfection. The luciferase activity was quantified using Steady-Glo reagent kit (Promega, Madison, Wis.) as per manufacturer's specifications.

(3) Materials and Method for The OCN Promoter Assay:
  The activation of osteocalcin by VDR ligands was evaluated in a rat osteoblast-like cell line RG-15 (ROS 17/2.8) stably expressing rat osteocalcin promoter fused with luciferase reporter gene. The stable cell lines were established as reported before (Activation of Osteocalcin Transcription involves interaction of protein kinase A- and Protein kinase C-dependent pathways. Boguslawski, G., Hale, L. V., Yu, X.-P., Miles, R. R., Onyia, J. E., Santerre R. F., Chandrasekhar, S. J. Biol. Chem. 275, 999-1006, 2000). Confluent RG-15 cells maintained in DMEM/F-12 medium (3:1) containing 5% FBS, 300 □g/ml G418 and at 37° C. under 5% $CO_2$/95% air atmosphere were trypsinized (0.25% trypsin) and plated into white opaque 96-well cell culture plates (25000 cells/well). After 24 hr, cells (in DMEM/F-12 medium+2% FBS) were treated with various concentrations of compounds, dissolved in DMSO. The final DMSO concentration remained at 0.01% (v/v). After 48 hr treatment, the medium was removed, cells were lysed with 50 □l of lysis buffer (From Luciferase reporter assay system, Roche Diagnostics, Indianapolis, Ind.) and assayed for luciferase activity using the Luciferase Reporter Gene Assay kit from Boehringer Mannheim as per manufacturer's specifications.

(4) Materials and Method for the Mouse Hypercalcemia Assay:
  Weanling, virus-antibody-free, five to six weeks old female DBF mice (Harlan, Indianapolis, Ind.) are used for all the studies. Animals are allowed to acclimate to local vivarium conditions for 2 days. Mice are maintained on a 12 hr light/dark cycle at 22° C. with ad lib access to food (TD 5001 with 1.2% Ca and 0.9% P, Teklad, Madison, Wis.) and water. The animals then are divided into groups with 4-5 mice per group. Different doses of test compounds prepared in 10% Ethanol and 90% sesame oil are administered to mice orally via gavage for 6 days. 1α-25(OH)$_2$D$_3$ 0.5 µg/kg/d was also given to one group of mice as the positive control. Serum ionized calcium is evaluated at 6 hours after the last dosing under isoflurane anesthesia by Ciba-Corning Ca++/PH Analyzer, (Model 634, Chiron Diagnostics Corp., East Walpole, Mass.). Raw data of group differences is assessed by analysis of variance (ANOVA) using Fisher's protected least significant difference (PLSD) where the significance level was P<0.05.

(5) The Keratinocyte Proliferation Assay:

KERtr cells (Human skin keratinocyte transformed with a retrovirus vector, obtained from ATCC) were plated in 96-well flat-bottomed plates (3000 cells/well) in 100 □l keratinocyte serum free medium supplemented with bovine pituitary extract in the absence of EGF (Life Technologies, Rockville, Md.) and incubated at 37° C. for two days. The cells were treated with various concentrations of VDR ligands (ten-fold serial dilution from 10,000 nM to 0.1 nM in triplicate), dissolved in 100 □l keratinocyte serum free medium supplemented with bovine pituitary extract in the absence of EGF and incubated at 37° C. for 72 hr. BrdU (5-bromo-2'-deoxyuridine) incorporation was analyzed as a measure of DNA replication (Cell proliferation ELISA kit, Roche Diagnostics, Indianapolis, Ind.) and absorbance was measured at 405 nm. Potency values ($IC_{50}$) values were determined as the concentration (nM) of compound that elicited a half-maximal response.

(6) Materials and Method for human IL-10 Induction Assay:
Isolation of peripheral blood mononuclear cells (PBMCs):
- A. Collect 50 ml of human blood and dilute with media, RPMI-1640.
- B. Prepare sterile tubes with ficol.
- C. Add diluted blood to tubes.
- D. Centrifuge.
- E. Discard the top layer and collect the cells from middle layer.
- F. Divide all cells into four tubes and add media.
- G. Centrifuge.
- H. Aspirate off media and resuspend.
- I. Collect all cells
- J. Centrifuge. at 1200 rpm for 10 minutes.
- K. Resuspend in RPMI-1640 with 2% FBS and count cells
Stimulation of PBMC:
- L. Prepare TPA in DMSO.
- M. Dissolve PHA in water.
- N. Plate TPA/PHA treated PBMCs in well plates.
- O. Incubate.
Treatment:
- P. Prepare all compound dilutions in plain RPMI-1640 media.
- Q. Add diluted compound.
- R. Incubate.
Sample Collection and assay:
- S. Remove all the cells by centrifugation and assay the supernatant for IL-10 by immunoassay.
1) T. Perform IL-10 assay using anti-human IL-10 antibody coated beads, as described by the manufacturer (Linco Research Inc., St. Charles, Mo.).

We claim:
1. A compound or a pharmaceutically acceptable salt represented by the formula:

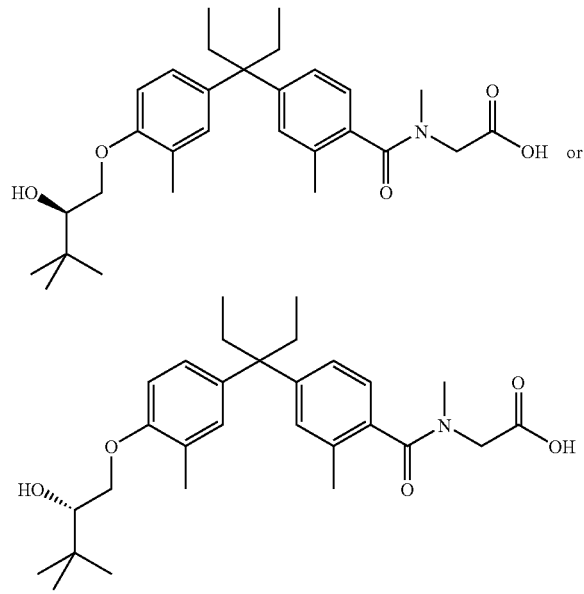

or a mixture thereof.

2. The salt derivative of a compound of claim 1 wherein the salt is sodium or potassium.

3. A pharmaceutical formulation comprising a compound of claim 1, or a pharmaceutically acceptable salt thereof, together with a pharmaceutically acceptable carrier or diluent.

4. A formulation according to claim 3 for treating osteoporosis comprising:
Ingredient (A1): a vitamin D receptor modulator of claim 1, or a pharmaceutically acceptable salt thereof;
Ingredient (B1):
one or more co-agents selected from the group consisting of:
- a. estrogens,
- b. androgens,
- c. calcium supplements,
- d. vitamin D metabolites,
- e. thiazide diuretics,
- f. calcitonin,
- g. bisphosphonates,
- h. SERMS, and
- i. fluorides.

5. The formulation of claim 3 wherein the weight ratio of (A1) to (B1) is from 10:1 to 1:1000.

6. A formulation according to claim 3 for treating psoriasis comprising:
Ingredient (A2): a vitamin D receptor modulator of claim 1;
Ingredient (B2):
one or more co-agents that are conventional for treatment psoriasis selected from the group consisting of:
- a. topical glucocorticoids,
- b. salicylic acid,
- c. crude coal tar, 7. The formulation of claim 6 wherein the weight ratio of (A2) to (B2) is from 1:10 to 1:100000.

8. A compound according to claim 1 represented by the formula:

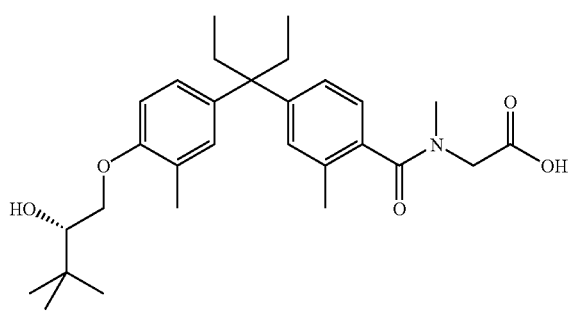

or a pharmaceutically acceptable salt thereof.

9. A compound represented by the formula:

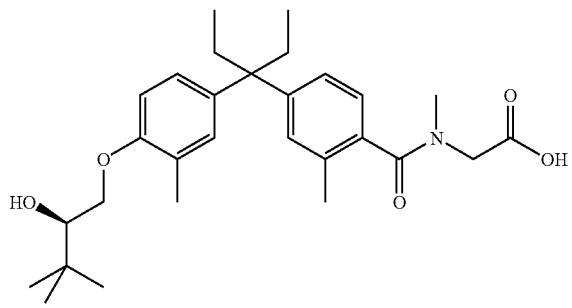

or a pharmaceutically acceptable salt thereof.

10. A compound represented by the formula:

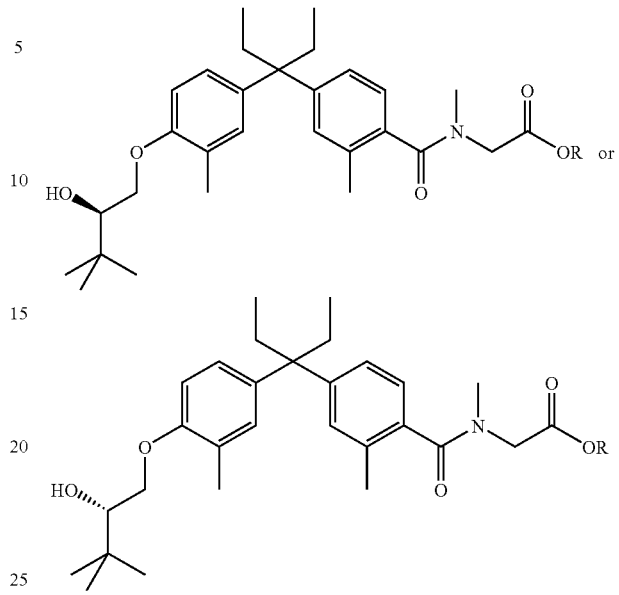

or a mixture thereof,
wherein R is methyl, ethyl, propyl, isopropyl, n-butyl, isobutyl, tert-butyl, morpholinoethyl, and N,N, diethylglycolamide.

11. A pharmaceutical formulation according to claim 3 provided for oral administration.

12. A method of treating osteoporosis by administration to a mammal a compound according to claim 1 or a pharmaceutically acceptable salt thereof.

13. A method according to claim 12 comprising administrating a dose between 0.0001 mg/kg/day to 5 mg/kg/day of body weight.

14. A method of treating a mammal to alleviate the pathological effects of at least one of: osteoporosis, leukemia, and psoriasis.

* * * * *